US008603359B2

(12) United States Patent
Kubo et al.

(10) Patent No.: US 8,603,359 B2
(45) Date of Patent: Dec. 10, 2013

(54) FOUR-RING COMPOUND HAVING A PLURALITY OF $CF_2O$ BONDING GROUPS, LIQUID CRYSTAL COMPOSITION AND LIQUID CRYSTAL DISPLAY DEVICE

(75) Inventors: Takahiro Kubo, Ichihara (JP); Yasuyuki Goto, Tokyo (JP)

(73) Assignees: JNC Corporation, Tokyo (JP); JNC Petrochemical Corporation, Tokyo (JP)

( * ) Notice: Subject to any disclaimer, the term of this patent is extended or adjusted under 35 U.S.C. 154(b) by 0 days.

(21) Appl. No.: 13/490,159

(22) Filed: Jun. 6, 2012

(65) Prior Publication Data

US 2012/0313041 A1 Dec. 13, 2012

(30) Foreign Application Priority Data

Jun. 8, 2011 (JP) ................. 2011-128240

(51) Int. Cl.
*C09K 19/06* (2006.01)
*C09K 19/52* (2006.01)
*C09K 19/30* (2006.01)
*C09K 19/12* (2006.01)
*C09K 19/00* (2006.01)
*C09K 19/02* (2006.01)
*C07C 41/00* (2006.01)
*C07C 43/02* (2006.01)
*C07C 43/20* (2006.01)
*C07F 15/00* (2006.01)

(52) U.S. Cl.
USPC ............. 252/299.6; 252/299.01; 252/299.63; 252/299.66; 428/1.1; 349/182; 568/300; 568/579; 568/626; 568/630; 568/631; 568/642; 568/643; 568/645

(58) Field of Classification Search
USPC ............... 252/299.01, 299.6, 299.63, 299.66; 428/1.1; 349/182; 568/300, 579, 626, 568/630, 631, 642, 643, 645
See application file for complete search history.

(56) References Cited

U.S. PATENT DOCUMENTS

| 5,262,085 | A | 11/1993 | Bartmann et al. |
| 5,858,270 | A | 1/1999 | Matsui et al. |
| 6,007,740 | A | 12/1999 | Andou et al. |
| 7,501,164 | B2 * | 3/2009 | Saito .............................. 428/1.1 |
| 2008/0017830 | A1 | 1/2008 | Takeda |
| 2009/0302273 | A1 | 12/2009 | Tanaka |
| 2011/0193022 | A1 | 8/2011 | Tanaka |

FOREIGN PATENT DOCUMENTS

GB 2229438 A 9/1990

* cited by examiner

*Primary Examiner* — Geraldina Visconti
(74) *Attorney, Agent, or Firm* — Hogan Lovells US LLP

(57) ABSTRACT

A liquid crystal compound having a high stability to heat, light or the like, a high clearing point, a low minimum temperature of a liquid crystal phase, a small viscosity, a suitable optical anisotropy, a large dielectric anisotropy, a suitable elastic constant and an excellent compatibility with other liquid crystal compounds, and a liquid crystal composition including this compound, and a liquid crystal display device containing this composition. A compound represented by formula (1):

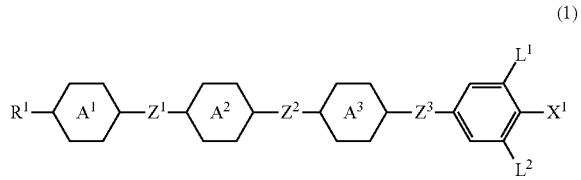

(1)

for example, $R^1$ is alkyl having 1 to 10 carbons; ring $A^1$, ring $A^2$ and ring $A^3$ are 1,4-cyclohexylene, 1,4-phenylene or 1,4-phenylene in which at least one of hydrogen has been replaced by fluorine; $Z^1$ is a single bond, and $Z^2$ and $Z^3$ are —$CF_2O$— or —$OCF_2$—; $X^1$ is fluorine; and $L^1$ and $L^2$ are fluorine.

19 Claims, No Drawings

FOUR-RING COMPOUND HAVING A PLURALITY OF CF$_2$O BONDING GROUPS, LIQUID CRYSTAL COMPOSITION AND LIQUID CRYSTAL DISPLAY DEVICE

This is a Non-Provisional application, which claims priority to Japanese Patent Application No. 2012-109346, filed on May 11, 2012 and Japanese Patent Application No. 2011-128240, filed on June 8, 2011; the contents of which are all herein incorporated by this reference in their entireties. All publications, patents, patent applications, databases and other references cited in this application, all related applications referenced herein, and all references cited therein, are incorporated by reference in their entirety as if restated here in full and as if each individual publication, patent, patent application, database or other reference were specifically and individually indicated to be incorporated by reference.

BACKGROUND OF THE INVENTION

1. Technical Field

The invention relates to a liquid crystal compound, a liquid crystal composition and a liquid crystal display device. More specifically, it relates to a four-ring compound having a plurality of CF$_2$O bonding groups, a composition including this compound and having a nematic phase, and a liquid crystal display device containing this composition.

2. Technical Background

A liquid crystal display device is widely used for the display of personal computers, televisions and so forth. This device utilizes optical anisotropy, dielectric anisotropy and so forth of a liquid crystal compound. The operating modes of this liquid crystal display device are known, such as a PC (phase change) mode, a TN (twisted nematic) mode, a STN (super twisted nematic) mode, a BTN (bistable twisted nematic) mode, an ECB (electrically controlled birefringence) mode, an OCB (optically compensated bend) mode, an IPS (in-plane switching) mode, a VA (vertical alignment) mode and a PSA (polymer sustained alignment).

A liquid crystal composition having suitable physical properties has been used for such a liquid crystal display device. It is desirable that a liquid crystal compound included in this composition should have physical properties shown in the following items (1) to (8), in order to further improve the characteristics of the liquid crystal display device.

(1) high stability to heat, light or the like,
(2) high clearing point,
(3) low minimum temperature of a liquid crystal phase,
(4) small viscosity ($\eta$),
(5) suitable optical anisotropy ($\Delta n$),
(6) large dielectric anisotropy ($\Delta \epsilon$),
(7) suitable elastic constant (K), and
(8) excellent compatibility with other liquid crystal compounds.

The effect of the physical properties of the liquid crystal compound on the characteristics of the device is as follows. A compound having a high stability to heat, light or the like, as described item (1), increases the voltage holding ratio of the device, as a result of which the service life of the device is increased. A compound having a high clearing point, as described in items (2), increases the temperature range in which the device can be used. A compound having a low minimum temperature of a liquid crystal phase such as a nematic phase and a smectic phase, especially of a nematic phase, as described in item (3), also increases the temperature range in which the device can be used. A compound having a small viscosity, as described in item (4), decreases the response time of the device.

A compound having a suitable optical anisotropy, as described in item (5), improves the contrast of the device. A compound having a large optical anisotropy or a small optical anisotropy, that is to say a suitable optical anisotropy, is necessary according to the design of the device. A compound having a large optical anisotropy is suitable when the response time is decreased by decreasing the cell gap of the device. A compound having a large dielectric anisotropy, as described in item (6), decreases the threshold voltage of the device, as a result of which the electric power consumption of the device is decreased.

In regard to the item (7), a compound having a large elastic constant decreases the response time of the device. A compound having a small elastic constant decreases the threshold voltage of the device. Thus, a suitable elastic constant is necessary according to the characteristics that should be improved. A compound having an excellent compatibility with other liquid crystal compounds is desirable as described in item (8). This is because the physical properties of the composition are adjusted by mixing liquid crystal compounds having different physical properties.

A variety of liquid crystal compounds having a large dielectric anisotropy have been prepared until now. This is because excellent physical properties which are not possessed by conventional compounds are expected. This is because a new compound is expected to possess a suitable balance between two physical properties which are required for the preparation of a liquid crystal composition. Compounds having CF$_2$O bonding group is described in Patent documents Nos. 1 to 4. However, each compound does not have a sufficiently large dielectric anisotropy, and thus a liquid crystal composition including this compound does not seem to satisfy threshold voltage that is necessary for commercial devices.

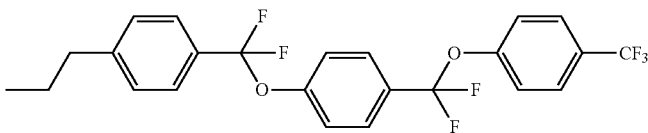

(S-1)

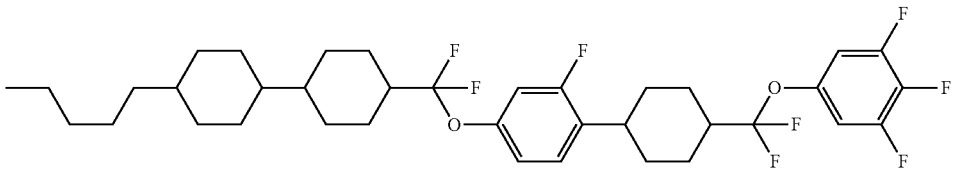

(S-2)

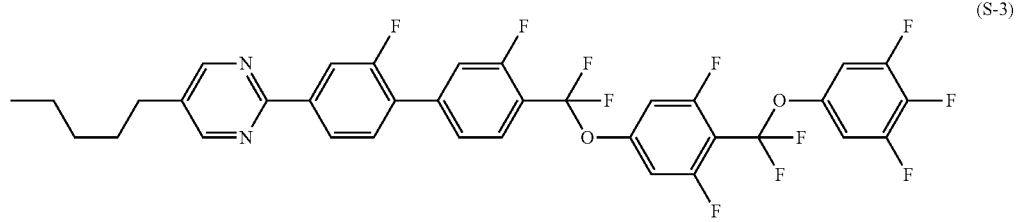

(S-3)

A three-ring compound having two CF₂O bonding groups, the compound (S-1), is shown in Patent document No. 5. However, this compound does not have a sufficiently high clearing point. Five-ring compounds having two CF₂O bonding groups, the compounds (S-2) and (S-3), are shown in Patent documents Nos. 6 and 7. However, these compounds do not have a sufficiently small viscosity.

In view of these situations, a compound with excellent physical properties and a suitable balance concerning the physical properties (1) to (8) described above has been expected to be developed.

PATENT DOCUMENT

Patent document No. 1: WO 1996-11897 A.
Patent document No. 2: JP H10-204016 A (1998).
Patent document No. 3: GB 2229438 A.
Patent document No. 4: DE 4023106 A.
Patent document No. 5: JP 2008-015286 A.
Patent document No. 6: US 2009-0302273 A.
Patent document No. 7: WO 2010-047260 A.

SUMMARY OF THE INVENTION

Subject to be Solved by the Invention

The first subject of the invention is to provide a liquid crystal compound having a high stability to heat, light or the like, a high clearing point, a low minimum temperature of a liquid crystal phase, a small viscosity, a suitable optical anisotropy, a large dielectric anisotropy, a suitable elastic constant, an excellent compatibility with other liquid crystal compounds. The subject is to provide a compound having an especially small viscosity. The subject is to provide a compound having an especially large dielectric anisotropy. The second subject is to provide a liquid crystal composition including this compound and having a high maximum temperature of a nematic phase, a low minimum temperature of a nematic phase, a small viscosity, a suitable optical anisotropy, a large dielectric anisotropy and a suitable elastic constant. The subject is to provide a liquid crystal composition having a suitable balance regarding at least two of the physical properties. The third subject is to provide a liquid crystal display device containing this composition and having a wide temperature range in which the device can be used, a short response time, a large voltage holding ratio, a large contrast ratio and a long service life.

Means for Solving the Subject

The invention concerns a compound represented by formula (1), a liquid crystal composition including this compound, and a liquid crystal display device containing this composition.

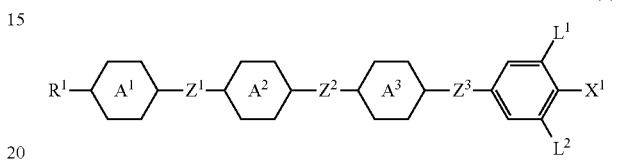

(1)

In formula (1),
R¹ is hydrogen, halogen or alkyl having 1 to 20 carbons, and in the alkyl, at least one of —CH₂— may be replaced by —O— or —S—, and at least one of —(CH₂)₂— may be replaced by —CH=CH—, and in the groups, at least one of hydrogen may be replaced by halogen;
ring A¹, ring A² and ring A³ are independently 1,4-cyclohexylene, 1,4-phenylene, 1,4-phenylene in which at least one of hydrogen has been replaced by halogen, tetrahydropyran-2,5-diyl, 1,3-dioxane-2,5-diyl, pyrimidine-2,5-diyl or pyridine-2,5-diyl;
Z¹, Z² and Z³ are independently a single bond, —(CH₂)₂—, —CH=CH—, —C≡C—, —COO—, —OCO—, —CF₂O—, —OCF₂—, —CH₂O—, —OCH₂—, —CF=CF—, —(CH₂)₄—, —(CH₂)₂CF₂O—, —(CH₂)₂OCF₂—, —CF₂O(CH₂)₂—, —OCF₂(CH₂)₂—, —CH=CH—(CH₂)₂— or —(CH₂)₂—CH=CH—, and at least two of Z¹, Z² and Z³ are —CF₂O— or —OCF₂—;
L¹ and L² are independently hydrogen or halogen, and at least one of L¹ and L² is halogen; and
X¹ is hydrogen, halogen, —C≡N, —N=C=S, —SF₅ or alkyl having 1 to 10 carbons, and in the alkyl, at least one of —CH₂— may be replaced by —O— or —S—, and at least one of —(CH₂)₂— may be replaced by —CH=CH—, and in the groups, at least one of hydrogen may be replaced by halogen.

Effect of the Invention

The first advantage of the invention is a liquid crystal compound having a high stability to heat, light or the like, a high clearing point, a low minimum temperature of a liquid crystal phase, a small viscosity, a suitable optical anisotropy, a large dielectric anisotropy, a suitable elastic constant, an excellent compatibility with other liquid crystal compounds. The advantage is a compound having an especially small viscosity. The advantage is a compound having an especially large dielectric anisotropy. The second advantage is a liquid crystal composition including this compound and having a high maximum temperature of a nematic phase, a low minimum temperature of a nematic phase, a small viscosity, a suitable optical anisotropy, a large dielectric anisotropy and a suitable elastic constant. The advantage is a liquid crystal composition having a suitable balance regarding at least two of the physical properties. The third advantage is a liquid crystal display device containing this composition and having a wide temperature range in which the device can be used, a short response time, a large voltage holding ratio, a large contrast ratio and a long service life.

EMBODIMENTS TO CARRY OUT THE INVENTION

Usage of the terms in this specification is as follows. A liquid crystal compound is a generic term for a compound having a liquid crystal phase such as a nematic phase or a smectic phase, and also for a compound having no liquid crystal phases but useful as a component of a liquid crystal composition. The terms, a liquid crystal compound, a liquid crystal composition and a liquid crystal display device may be abbreviated to a compound, a composition and a device, respectively. A liquid crystal display device is a generic term for a liquid crystal display panel and a liquid crystal display module. A clearing point is the transition temperature between a liquid crystal phase and an isotropic phase in a liquid crystal compound. The minimum temperature of a liquid crystal phase is the transition temperature between solids and a liquid crystal phase (a smectic phase, a nematic phase and so forth) in a liquid crystal compound. The maximum temperature of a nematic phase is the transition temperature between a nematic phase and an isotropic phase in a liquid crystal composition, and may be abbreviated to the maximum temperature. The minimum temperature of a nematic phase may be abbreviated to the minimum temperature. A compound represented by formula (1) may be abbreviated to the compound (1). This abbreviation may apply to a compound represented by formula (2) or the like. In formulas (1) to (14), the symbol $A^1$, $B^1$, $C^1$ or the like surrounded by a hexagonal shape corresponds to ring $A^1$, ring $B^1$, ring $C^1$ or the like, respectively. A plurality of $R^1$ were described in the same or different formulas. Two groups represented by arbitrary two of $R^1$ may be the same or different in these compounds. The same rule applies to symbols such as ring $A^1$ and $Z^1$. The amount of a compound, which is expressed as a percentage, means a weight percentage (% by weight) based on the total weight of the composition.

The expression "at least one of 'A' may be replaced by 'B'" means that the position of one 'A' is arbitrary when the number of 'A' is one, and that the positions of 'A' can also be selected without restriction when the numbers of 'A' are two or more. The expression "at least one of A may be replaced by B, C or D" includes cases where arbitrary A has been replaced by B, and arbitrary A has been replaced by C, and arbitrary A has been replaced by D, and also cases where a plurality of A are replaced by at least two of B, C and/or D. For example, "alkyl in which at least one of —$CH_2$— may be replaced by —O— or —CH═CH—" includes alkyl, alkenyl, alkoxy, alkoxyalkyl, alkoxyalkenyl and alkenyloxyalkyl. Incidentally, it is undesirable that two successive —$CH_2$— should be replaced by —O— to give —O—O—. It is also undesirable that —$CH_2$— of a methyl moiety (—$CH_2$—H) in alkyl and so forth should be replaced by —O— to give —O—H.

The invention includes the contents described in the following items 1 to 19.

Item 1. A compound represented by formula (1).

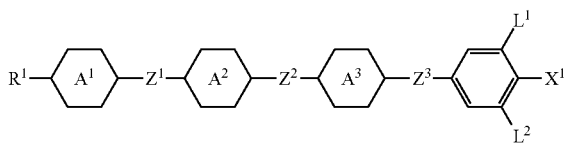

(1)

In formula (1),
$R^1$ is hydrogen, halogen or alkyl having 1 to 20 carbons, and in the alkyl, at least one of —$CH_2$— may be replaced by —O— or —S—, and at least one of —$(CH_2)_2$— may be replaced by —CH═CH—, and in the groups, at least one of hydrogen may be replaced by halogen;
ring $A^1$, ring $A^2$ and ring $A^3$ are independently 1,4-cyclohexylene, 1,4-phenylene, 1,4-phenylene in which at least one of hydrogen has been replaced by halogen, tetrahydropyran-2,5-diyl, 1,3-dioxane-2,5-diyl, pyrimidine-2,5-diyl or pyridine-2,5-diyl;
$Z^1$, $Z^2$ and $Z^3$ are independently a single bond, —$(CH_2)_2$—, —CH═CH—, —CF═CF—, —C≡C—, —COO—, —OCO—, —$CF_2O$—, —$OCF_2$—, —$CH_2O$—, —$OCH_2$—, —$(CH_2)_4$—, —$(CH_2)_2CF_2O$—, —$(CH_2)_2OCF_2$—, —$CF_2O(CH_2)_2$—, —$OCF_2(CH_2)_2$—, —CH═CH—$(CH_2)_2$— or —$(CH_2)_2$—CH═CH—, and at least two of $Z^1$, $Z^2$ and $Z^3$ are —$CF_2O$— or —$OCF_2$—;
$L^1$ and $L^2$ are independently hydrogen or halogen, and at least one of $L^1$ and $L^2$ is halogen; and
$X^1$ is hydrogen, halogen, —C≡N, —N═C═S, —$SF_5$ or alkyl having 1 to 10 carbons, and in the alkyl, at least one of —$CH_2$— may be replaced by —O— or —S—, and at least one of —$(CH_2)_2$— may be replaced by —CH═CH—, and in the groups, at least one of hydrogen may be replaced by halogen.

Item 2. The compound according to item 1, wherein in formula (1) according to item 1, any one of $Z^1$, $Z^2$ and $Z^3$ is a single bond.

Item 3. The compound according to item 1, wherein the compound is represented by any one of formulas (1-2) to (1-4).

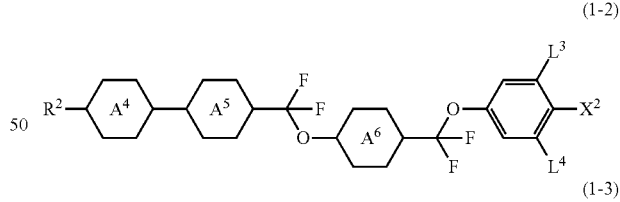

(1-2)

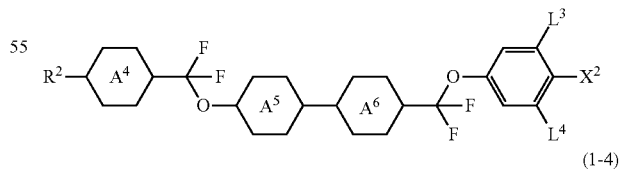

(1-3)

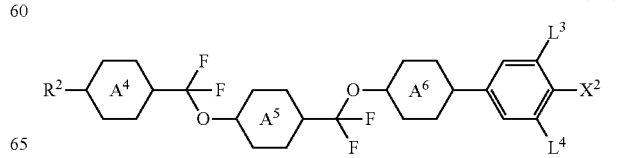

(1-4)

In formulas (1-2) to (1-4), $R^2$ is alkyl having 1 to 15 carbons, and in the alkyl, at least one of —$CH_2$— may be replaced by —O— or —S—, and at least one of —$(CH_2)_2$— may be replaced by —CH═CH—, and in the groups, at least one of hydrogen may be replaced by fluorine; ring $A^4$, ring $A^5$ and ring $A^6$ are independently 1,4-cyclohexylene, 1,4-phenylene, 1,4-phenylene in which at least one of hydrogen has been replaced by halogen, tetrahydropyran-2,5-diyl or 1,3-dioxane-2,5-diyl; $L^3$ and $L^4$ are independently hydrogen or fluorine, and at least one of $L^3$ and $L^4$ is fluorine; and $X^2$ is fluorine or alkyl having 1 to 10 carbons, and in the alkyl, at least one of —$CH_2$— may be replaced by —O— or —S—, and at least one of —$(CH_2)_2$— may be replaced by —CH═CH—, and in the groups, at least one of hydrogen may be replaced by fluorine.

Item 4. The compound according to item 1, wherein the compound is represented by any one of formulas (1-2-1) to (1-4-1).

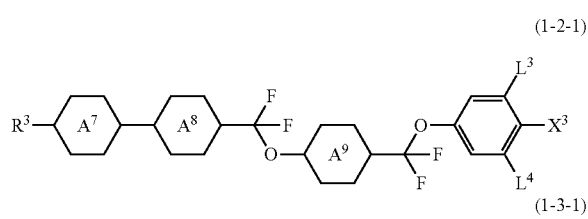
(1-2-1)

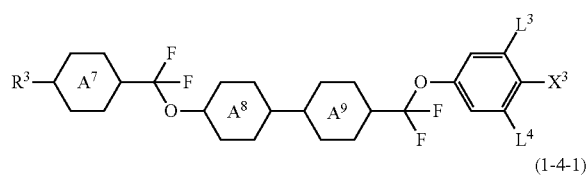
(1-3-1)

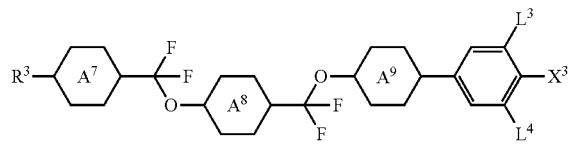
(1-4-1)

In formulas (1-2-1) to (1-4-1), $R^3$ is alkyl having 1 to carbons, and in the alkyl, at least one of —$CH_2$— may be replaced by —O—, and at least one of —$(CH_2)_2$— may be replaced by —CH═CH—; ring $A^7$, ring $A^8$ and ring $A^9$ are independently 1,4-cyclohexylene, 1,4-phenylene, 2-fluoro-1,4-phenylene, 2,6-difluoro-1,4-phenylene, tetrahydropyran-2,5-diyl or 1,3-dioxane-2,5-diyl; $L^3$ and $L^4$ are independently hydrogen or fluorine, and at least one of $L^3$ and $L^4$ is fluorine; and $X^3$ is fluorine, —$CF_3$ or —$OCF_3$.

Item 5. The compound according to item 1, wherein the compound is represented by any one of formulas (1-2-1-1) to (1-2-1-8), formulas (1-3-1-1) to (1-3-1-8) and formulas (1-4-1-1) to (1-4-1-8)

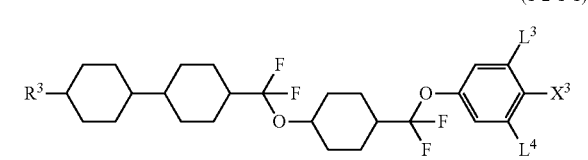
(1-2-1-1)

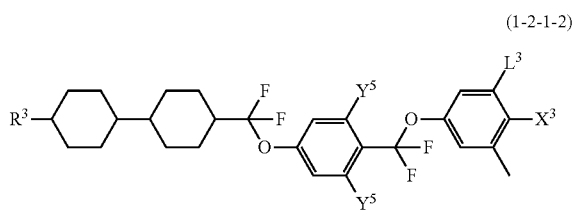
(1-2-1-2)

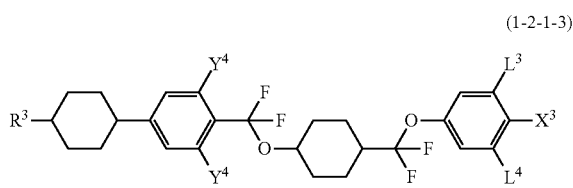
(1-2-1-3)

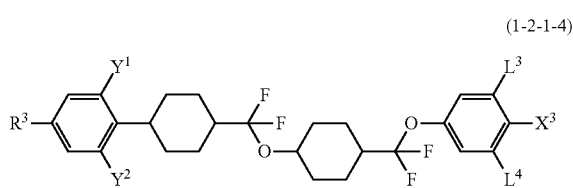
(1-2-1-4)

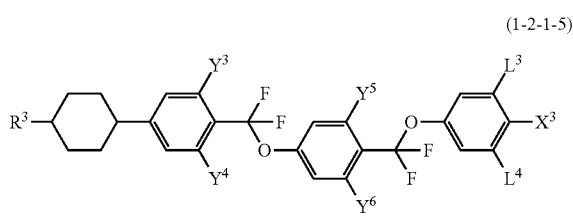
(1-2-1-5)

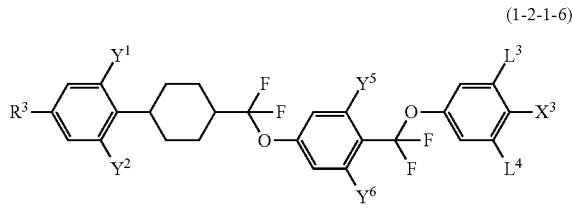
(1-2-1-6)

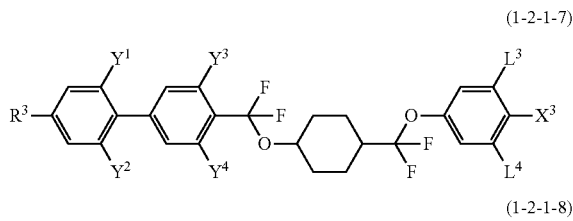
(1-2-1-7)

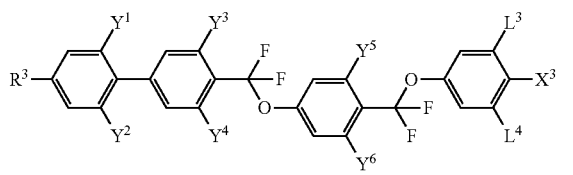
(1-2-1-8)

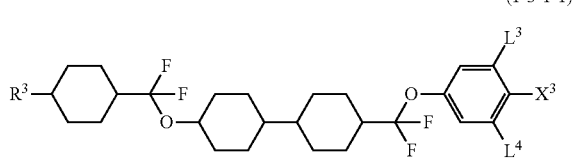
(1-3-1-1)

(1-3-1-2)
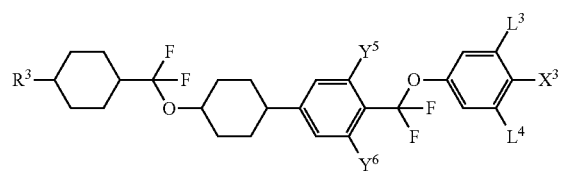

(1-3-1-3)
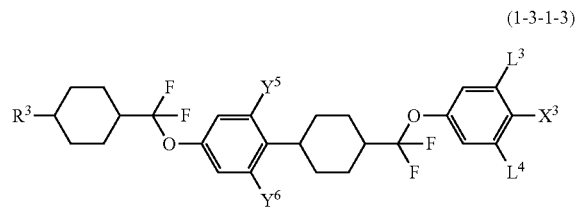

(1-3-1-4)
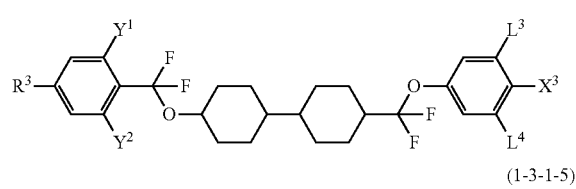

(1-3-1-5)
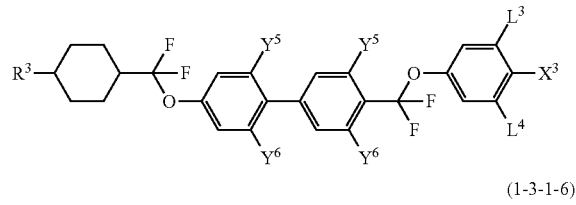

(1-3-1-6)
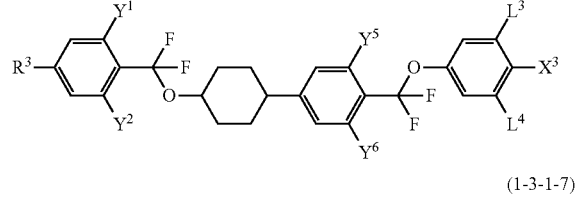

(1-3-1-7)
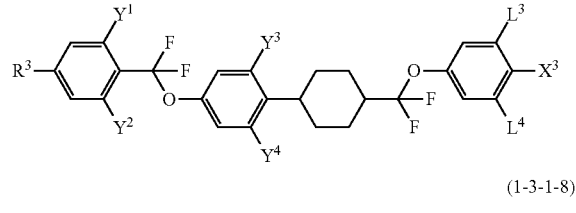

(1-3-1-8)
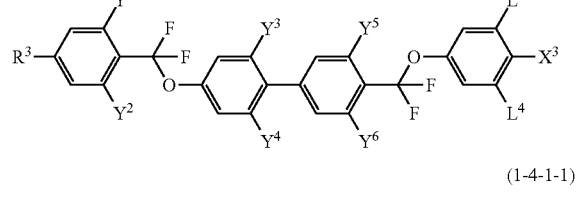

(1-4-1-1)
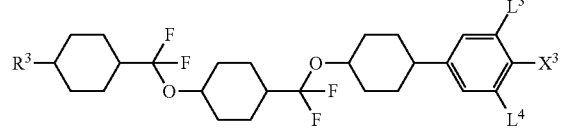

(1-4-1-2)
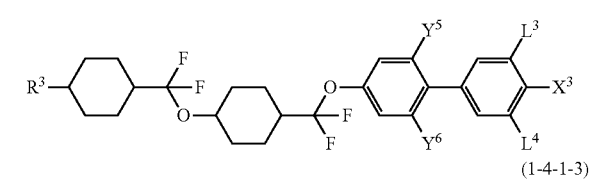

(1-4-1-3)
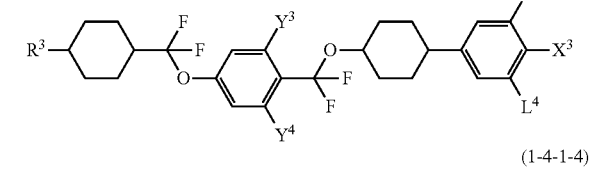

(1-4-1-4)
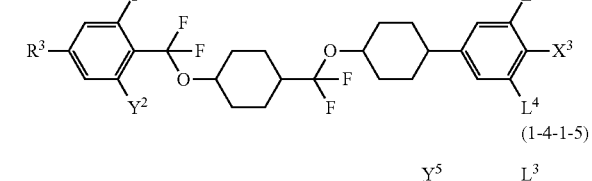

(1-4-1-5)
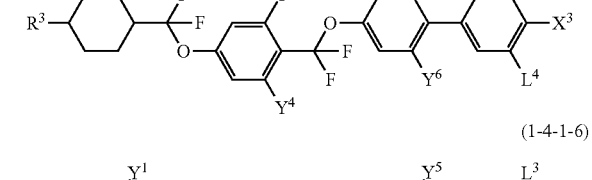

(1-4-1-6)
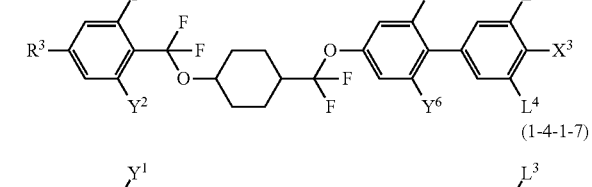

(1-4-1-7)
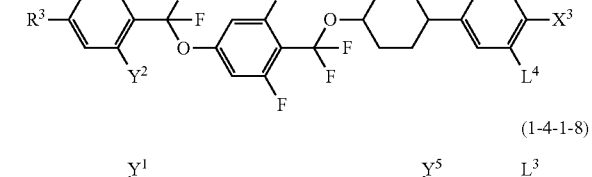

(1-4-1-8)
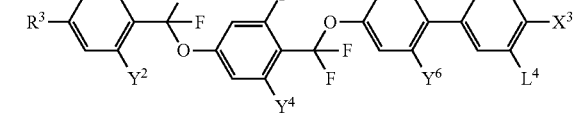

In formulas (1-2-1-1) to (1-2-1-8), formulas (1-3-1-1) to (1-3-1-8) and formulas (1-4-1-1) to (1-4-1-8), $R^3$ is alkyl having 1 to 10 carbons, and in the alkyl, at least one of —$CH_2$— may be replaced by —O—, and at least one of —$(CH_2)_2$— may be replaced by —CH=CH—; $Y^1$, $Y^2$, $Y^3$, $Y^4$, $Y^5$ and $Y^6$ are independently hydrogen or fluorine; $L^3$ and $L^4$ are independently hydrogen or fluorine, and at least one of $L^3$ and $L^4$ is fluorine; and $X^3$ is fluorine, —$CF_3$ or —$OCF_3$.

Item 6. The compound according to item 5, wherein in formulas (1-2-1-1) to (1-2-1-8) according to item 5, $R^3$ is alkyl having 1 to 10 carbons, alkoxy having 1 to 9 carbons or alkenyl having 2 to 10 carbons; $Y^1$, $Y^2$, $Y^3$, $Y^4$, $Y^5$ and $Y^6$ are independently hydrogen or fluorine; $L^3$ and $L^4$ are independently hydrogen or fluorine, and at least one of $L^3$ and $L^4$ is fluorine; and $X^3$ is fluorine, —$CF_3$ or —$OCF_3$.

Item 7. The compound according to item 5, wherein in formulas (1-3-1-1) to (1-3-1-8) according to item 5, $R^3$ is alkyl having 1 to 10 carbons, alkoxy having 1 to 9 carbons or alkenyl having 2 to 10 carbons; $Y^1, Y^2, Y^3, Y^4, Y^5$ and $Y^6$ are independently hydrogen or fluorine; $L^3$ and $L^4$ are independently hydrogen or fluorine, and at least one of $L^3$ and $L^4$ is fluorine; and $X^3$ is fluorine, —$CF_3$ or —$OCF_3$.

Item 8. The compound according to item 5, wherein in formulas (1-4-1-1) to (1-4-1-8) according to item 5, $R^3$ is alkyl having 1 to 10 carbons, alkoxy having 1 to 9 carbons or alkenyl having 2 to 10 carbons; $Y^1, Y^2, Y^3, Y^4, Y^5$ and $Y^6$ are independently hydrogen or fluorine; $L^3$ and $L^4$ are independently hydrogen or fluorine, and at least one of $L^3$ and $L^4$ is fluorine; and $X^3$ is fluorine, —$CF_3$ or —$OCF_3$.

Item 9. The compound according to item 1, wherein the compound is represented by any one of formulas (1-2-1-8-1) and (1-2-1-2-1).

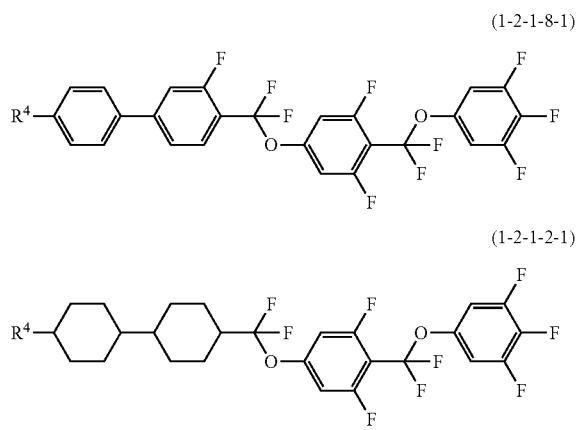

(1-2-1-8-1)

(1-2-1-2-1)

In formula (1-2-1-8-1) and formula (1-2-1-2-1), $R^4$ is alkyl having 1 to 10 carbons.

Item 10. A liquid crystal composition including at least one of compounds according to any one of items 1 to 9.

Item 11. The liquid crystal composition according to item 10, further including at least one compound selected from the group of compounds represented by formulas (2) to (4).

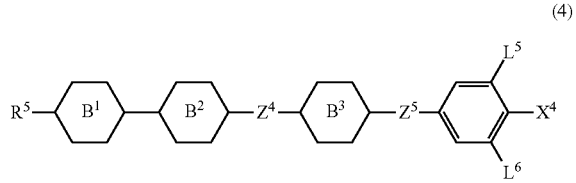

(2)

(3)

(4)

In formulas (2) to (4), $R^5$ is alkyl having 1 to 10 carbons or alkenyl having 2 to 10 carbons, and in the alkyl and the alkenyl, at least one of hydrogen may be replaced by fluorine, and at least one of —$CH_2$— may be replaced by —O—;

$X^4$ is fluorine, chlorine, —$OCF_3$, —$OCHF_2$, —$CF_3$, —$CHF_2$, —$CH_2F$, —$CF=F_2$, —$OCF_2CHF_2$ or —$OCF_2CHFCF_3$;

ring $B^1$, ring $B^2$ and ring $B^3$ are independently 1,4-cyclohexylene, 1,4-phenylene, 2-fluoro-1,4-phenylene, 2,6-difluoro-1,4-phenylene, tetrahydropyran-2,5-diyl, 1,3-dioxane-2,5-diyl or pyrimidine-2,5-diyl;

$Z^4$ and $Z^5$ are independently a single bond, —$(CH_2)_2$—, —$CH=CH$—, —$C\equiv C$—, —$COO$—, —$CF_2O$—, —$OCF_2$—, —$CH_2O$— or —$(CH_2)_4$—, and $Z^4$ and $Z^5$ are not simultaneously —$CF_2O$— or —$OCF_2$—; and $L^5$ and $L^6$ are independently hydrogen or fluorine.

Item 12. The liquid crystal composition according to item 10, further including at least one compound selected from the group of compounds represented by formula (5).

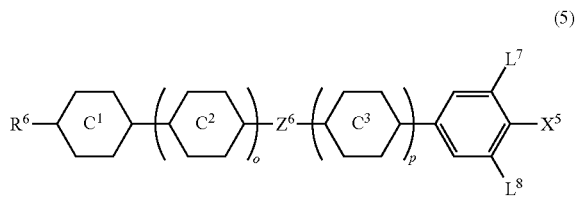

(5)

In formula (5), $R^6$ is alkyl having 1 to 10 carbons or alkenyl having 2 to 10 carbons, and in the alkyl and the alkenyl, at least one of hydrogen may be replaced by fluorine, and at least one of —$CH_2$— may be replaced by —O—;

$X^5$ is —$C\equiv N$ or —$C\equiv C$—$C\equiv N$;

ring $C^1$, ring $C^2$ and ring $C^3$ are independently 1,4-cyclohexylene, 1,4-phenylene in which at least one of hydrogen may be replaced by fluorine, tetrahydropyran-2,5-diyl, 1,3-dioxane-2,5-diyl or pyrimidine-2,5-diyl;

$Z^6$ is a single bond, —$(CH_2)_2$—, —$C\equiv C$—, —$COO$—, —$CF_2O$—, —$OCF_2$— or —$CH_2O$—;

$L^7$ and $L^8$ are independently hydrogen or fluorine; and o is 0, 1 or 2, p is 0 or 1, the sum of o and p is 0, 1, 2 or 3.

Item 13. The liquid crystal composition according to item 10, further including at least one compound selected from the group of compounds represented by formulas (6) to (11).

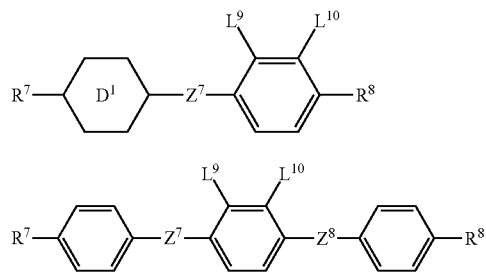

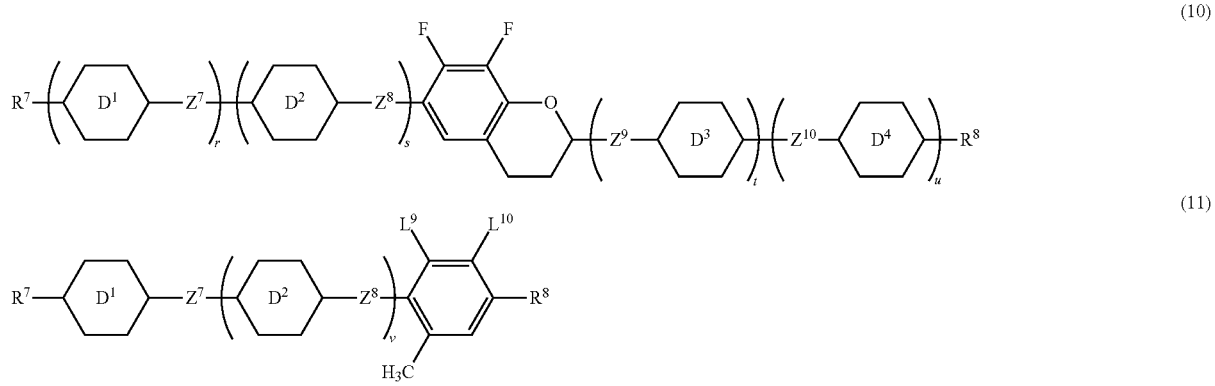

In formulas (6) to (11), $R^7$ and $R^8$ are independently alkyl having 1 to 10 carbons or alkenyl having 2 to 10 carbons, and in the alkyl and the alkenyl, at least one of hydrogen may be replaced by fluorine, and at least one of —$CH_2$— may be replaced by —O—;

ring $D^1$, ring $D^2$, ring $D^3$ and ring $D^4$ are independently 1,4-cyclohexylene, 1,4-cyclohexenylene, 1,4-phenylene in which at least one of hydrogen may be replaced by fluorine, tetrahydropyran-2,5-diyl or decahydronaphthalene-2,6-diyl;

$Z^7$, $Z^8$, $Z^9$ and $Z^{10}$ are independently a single bond, —$(CH_2)_2$—, —COO—, —$CH_2O$—, —$OCF_2$— or —$OCF_2(CH_2)_2$—;

$L^9$ and $L^{10}$ are independently fluorine or chlorine; and q, r, s, t, u and v are independently 0 or 1, and the sum of r, s, t and u is 1 or 2.

Item 14. The liquid crystal composition according to item 10, further including at least one compound selected from the group of compounds represented by formulas (12) to (14).

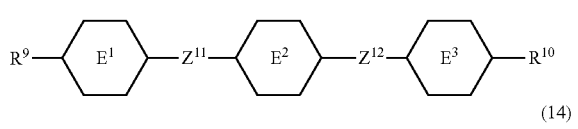

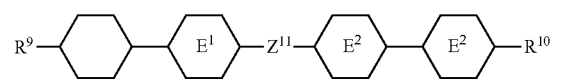

In formulas (12) to (14), $R^9$ and $R^{10}$ are independently alkyl having 1 to 10 carbons or alkenyl having 2 to 10 carbons, and in the alkyl and the alkenyl, at least one of —$CH_2$— may be replaced by —O—;

ring $E^1$, ring $E^2$ and ring $E^3$ are independently 1,4-cyclohexylene, 1,4-phenylene, 2-fluoro-1,4-phenylene, 2,5-difluoro-1,4-phenylene or pyrimidine-2,5-diyl; and $Z^{11}$ and $Z^{12}$ are independently a single bond, —$(CH_2)_2$—, —CH=CH—, —C≡C— or —COO—.

Item 15. The liquid crystal composition according to item 11, further including at least one compound selected from the group of compounds represented by formulas (12) to (14) according to item 14.

Item 16. The liquid crystal composition according to item 13, further including at least one compound selected from the group of compounds represented by formulas (12) to (14) according to item 14.

Item 17. The liquid crystal composition according to item 10, further including at least one optically active compound and/or at least one polymerizable compound.

Item 18. The liquid crystal composition according to item 10, further including at least one antioxidant and/or at least one ultraviolet light absorber.

Item 19. A liquid crystal display device containing the liquid crystal composition according to any one of items 10 to 18.

The compound, the liquid crystal composition and the liquid crystal display device of the invention will be explained in this order.

1-1. The Compound (1)

The compound (1) of the invention and desirable examples of the compound (1) will be explained. Desirable examples of the terminal group, the ring structure, the bonding group and the substituent of the compound (1) can be applied to the sub-formulas of the compound (1).

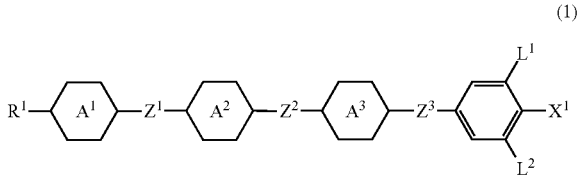

(1)

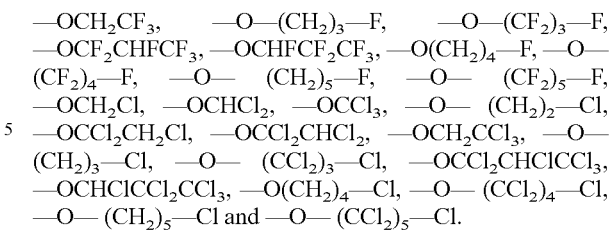

In formula (1), $R^1$ is hydrogen, halogen or alkyl having 1 to 20 carbons, and in the alkyl, at least one of —$CH_2$— may be replaced by —O— or —S—, and at least one of —$(CH_2)_2$— may be replaced by —CH=CH—, and in the groups, at least one of hydrogen may be replaced by halogen.

Examples of such $R^1$ are alkyl, alkoxy, alkoxyalkyl, alkoxyalkoxy, alkylthio, alkylthioalkoxy, alkenyl, alkenyloxy, alkenyloxyalkyl, alkoxyalkenyl and alkenylthio. These groups are a straight-chain or a branched chain, and do not include a cyclic group such as cyclohexyl. In the groups, a straight chain is preferable to a branched chain. The branched chain is also desirable when $R^1$ is optically active.

A desirable configuration of —CH=CH— in the alkenyl depends on the position of the double bond. The trans-configuration is preferable in the alkenyl having the double bond in the odd position, such as —CH=$CHCH_3$, —CH=$CHC_2H_5$, —CH=$CHC_3H_7$, —CH=$CHC_4H_9$, —$C_2H_4$CH=$CHCH_3$ and —$C_2H_4$CH=$CHC_2H_5$. The cis-configuration is preferable in the alkenyl having the double bond in the even position, such as —$CH_2$CH=$CHCH_3$, —$CH_2$CH=$CHC_2H_5$ and —$CH_2$CH=$CHC_3H_7$. An alkenyl compound having a desirable configuration has a high clearing point or a wide temperature range of a liquid crystal phase. For detailed explanation, see Mol. Cryst. Liq. Cryst., 1985, 131, 109 and Mol. Cryst. Liq. Cryst., 1985, 131, 327.

Examples of the alkyl are —$CH_3$, —$C_2H_5$, —$C_3H_7$, —$C_4H_9$, —$C_5H_{11}$, —$C_6H_{13}$, —$C_7H_{15}$, —$C_8H_{17}$, —$C_9H_{19}$, —$C_{10}H_{21}$, —$C_{11}H_{23}$, —$C_{12}H_{25}$, —$C_{13}H_{27}$, —$C_{14}H_{29}$ and —$C_{15}H_{31}$.

Examples of the alkoxy are —$OCH_3$, —$OC_2H_5$, —$OC_3H_7$, —$OC_4H_9$, —$OC_5H_{11}$, —$OC_6H_{13}$, —$OC_7H_{15}$, —$OC_8H_{17}$, —$OC_9H_{19}$, —$OC_{10}H_{21}$, —$OC_{11}H_{23}$, —$OC_{12}H_{25}$, —$OC_{13}H_{27}$ and —$OC_{14}H_{29}$.

Examples of the alkoxyalkyl are —$CH_2OCH_3$, —$CH_2OC_2H_5$, —$CH_2OC_3H_7$, —$(CH_2)_2$—$OCH_3$, —$(CH_2)_2$—$OC_2H_5$, —$(CH_2)_2$—$OC_3H_7$, —$(CH_2)_3$—$OCH_3$, —$(CH_2)_4$—$OCH_3$ and —$(CH_2)_5$—$OCH_3$.

Examples of the alkenyl are —CH=$CH_2$, —CH=$CHCH_3$, —$CH_2$CH=$CH_2$, —CH=$CHC_2H_5$, —$CH_2$CH=$CHCH_3$, —$(CH_2)_2$—CH=$CH_2$, —CH=$CHC_3H_7$, —$CH_2$CH=$CHC_2H_5$, —$(CH_2)_2$—CH=$CHCH_3$ and —$(CH_2)_3$—CH=$CH_2$.

Examples of the alkenyloxy are —$OCH_2$CH=$CH_2$, —$OCH_2$CH=$CHCH_3$ and —$OCH_2$CH=$CHC_2H_5$.

Examples of the alkyl in which at least one of hydrogen has been replaced by halogen are —$CH_2F$, —$CHF_2$, —$CF_3$, —$(CH_2)_2$—F, —$CF_2CH_2F$, —$CF_2CHF_2$, —$CH_2CF_3$, —$CF_2CF_3$, —$(CH_2)_3$—F, —$(CF_2)_3$—F, —$CF_2CHFCF_3$, —$CHFCF_2CF_3$, —$(CH_2)_4$—F, —$(CF_2)_4$—F, —$(CH_2)_5$—F, —$(CF_2)_5$—F, —$CH_2Cl$, —$CHCl_2$, —$CCl_3$, —$(CH_2)_2$—Cl, —$CCl_2CH_2Cl$, —$CCl_2CHCl_2$, —$CH_2CCl_3$, —$CCl_2CCl_3$, —$(CH_2)_3$—Cl, —$(CCl_2)_3$—Cl, —$CCl_2CHClCCl_3$, —$CHClCCl_2CCl_3$, —$(CH_2)_4$—Cl, —$(CCl_2)_4$—Cl, —$(CH_2)_5$—Cl and —$(CCl_2)_5$—Cl.

Examples of the alkoxy in which at least one of hydrogen has been replaced by halogen are —$OCH_2F$, —$OCHF_2$, —$OCF_3$, —O—$(CH_2)_2$—F, —$OCF_2CH_2F$, —$OCF_2CHF_2$, —$OCH_2CF_3$, —O—$(CH_2)_3$—F, —O—$(CF_2)_3$—F, —$OCF_2CHFCF_3$, —$OCHFCF_2CF_3$, —O$(CH_2)_4$—F, —O—$(CF_2)_4$—F, —O—$(CH_2)_5$—F, —O—$(CF_2)_5$—F, —$OCH_2Cl$, —$OCHCl_2$, —$OCCl_3$, —O—$(CH_2)_2$—Cl, —$OCCl_2CH_2Cl$, —$OCCl_2CHCl_2$, —$OCH_2CCl_3$, —O—$(CH_2)_3$—Cl, —O—$(CCl_2)_3$—Cl, —$OCCl_2CHClCCl_3$, —$OCHClCCl_2CCl_3$, —O$(CH_2)_4$—Cl, —O—$(CCl_2)_4$—Cl, —O—$(CH_2)_5$—Cl and —O—$(CCl_2)_5$—Cl.

Examples of the alkenyl in which at least one of hydrogen has been replaced by halogen are —CH=CHF, —CH=$CF_2$, —CF=CHF, —CH=$CHCH_2F$, —CH=$CHCF_3$, —$(CH_2)_2$—CH=$CF_2$, —$CH_2$CH=$CHCF_3$, —CH=$CHCF_2CF_3$, —CH=CHCl, —CH=$CCl_2$, —CCl=CHCl, —CH=$CHCH_2Cl$, —CH=$CHCCl_3$, —$(CH_2)_2$—CH=$CCl_2$, —$CH_2$CH=$CHCCl_3$ and —CH=$CHCCl_2CCl_3$.

Desirable examples of $R^1$ are alkyl having 1 to 15 carbons and alkenyl having 2 to 15 carbons. More desirable examples of $R^1$ are —$CH_3$, —$C_2H_5$, —$C_3H_7$, —$C_4H_9$, —$C_5H_{11}$, —$C_6H_{13}$, —$C_7H_{15}$, —$C_8H_{17}$, —$C_9H_{19}$, —$C_{10}H_{21}$, —$C_{11}H_{23}$, —$C_{12}H_{25}$, —$C_{13}H_{27}$, —$C_{14}H_{29}$, —$C_{15}H_{31}$, —CH=$CH_2$, —CH=$CHCH_3$, —$CH_2$CH=$CH_2$, —CH=$CHC_2H_5$, —$CH_2$CH=$CHCH_3$, —$(CH_2)_2$—CH=$CH_2$, —CH=$CHC_3H_7$, —$CH_2$CH=$CHC_2H_5$, —$(CH_2)_2$—CH=$CHCH_3$ and —$(CH_2)_3$—CH=$CH_2$.

In formula (1), ring $A^1$, ring $A^2$ and ring $A^3$ are independently 1,4-cyclohexylene, 1,4-phenylene, 1,4-phenylene in which at least one of hydrogen has been replaced by halogen, tetrahydropyran-2,5-diyl, 1,3-dioxane-2,5-diyl, pyrimidine-2,5-diyl or pyridine-2,5-diyl.

Desirable examples of ring $A^1$, ring $A^2$ and ring $A^3$ are 1,4-cyclohexylene, 1,4-phenylene, 1,4-phenylene in which at least one of hydrogen has been replaced by halogen, tetrahydropyran-2,5-diyl and 1,3-dioxane-2,5-diyl. There are cis and trans configurations concerning 1,4-cyclohexylene. The trans configuration is preferable in view of a high maximum temperature. Desirable examples of 1,4-phenylene in which at least one of hydrogen has been replaced by halogen are the groups (R-1) to (R-18).

(R-1)

(R-2)

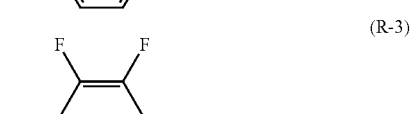

(R-3)

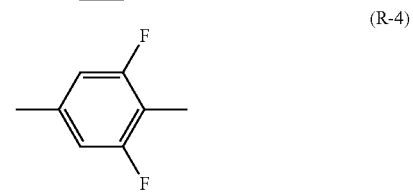

(R-4)

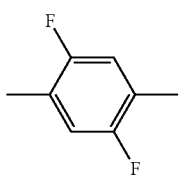 (R-5)

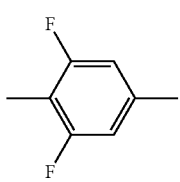 (R-6)

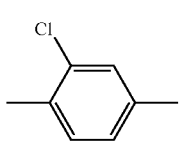 (R-7)

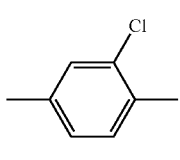 (R-8)

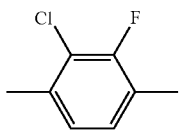 (R-9)

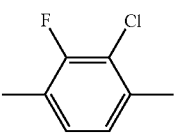 (R-10)

 (R-11)

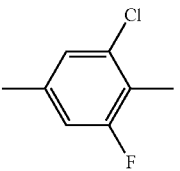 (R-12)

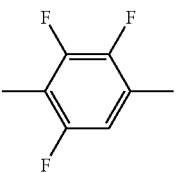 (R-13)

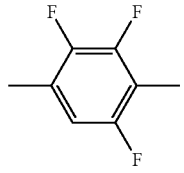 (R-14)

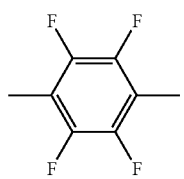 (R-15)

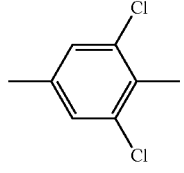 (R-16)

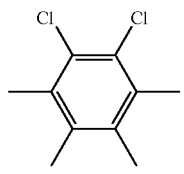 (R-17)

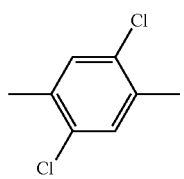 (R-18)

2-Fluoro-1,4-phenylene is asymmetric. Fluorine in the lateral position is located in the side of the right-terminal group (facing left; R-1) or in the side of the left-terminal group (facing right; R-2). Desirable 2-fluoro-1,4-phenylene is facing right. 2,6-Difluoro-1,4-phenylene (R-4 and R-6) is also asymmetric. Desirable 2,6-difluoro-1,4-phenylene is facing right (R-4). In the other groups, a group, facing right, is preferable when it is asymmetric.

Further desirable examples of 1,4-phenylene in which at least one of hydrogen has been replaced by halogen are 2-fluoro-1,4-phenylene and 2,6-difluoro-1,4-phenylene.

More desirable examples of ring $A^1$, ring $A^2$ and ring $A^3$ are 1,4-cyclohexylene, 1,4-phenylene, 2-fluoro-1,4-phenylene, 2,6-difluoro-1,4-phenylene, tetrahydropyran-2,5-diyl and 1,3-dioxane-2,5-diyl. Most desirable examples of ring $A^1$, ring $A^2$ and ring $A^3$ are 1,4-cyclohexylene, 1,4-phenylene, 2-fluoro-1,4-phenylene and 2,6-difluoro-1,4-phenylene.

In formula (1), $Z^1$, $Z^2$ and $Z^3$ are independently a single bond, —(CH$_2$)$_2$—, —CH=CH—, —CF=CF—, —C≡C—, —COO—, —OCO—, —CF$_2$O—, —OCF$_2$—, —CH$_2$O—, —OCH$_2$—, —(CH$_2$)$_4$—, —(CH$_2$)$_2$CF$_2$O—, —(CH$_2$)$_2$OCF$_2$—, —CF$_2$O(CH$_2$)$_2$—, —OCF$_2$(CH$_2$)$_2$—, —CH=CH—(CH$_2$)$_2$— or —(CH$_2$)$_2$—CH=CH—, and at least two of $Z^1$, $Z^2$ and $Z^3$ are —CF$_2$O— or —OCF$_2$—. The expression "at least two are —CF$_2$O— or —OCF$_2$—" means that the compound must have two —CF$_2$O—, or two —OCF$_2$—, or both —CF$_2$O— and —OCF$_2$—.

Desirable examples of $Z^1$, $Z^2$ and $Z^3$ are a single bond, —(CH$_2$)$_2$—, —CH=CH—, —CF=CF—, —C≡C—, —COO—, —CF$_2$O—, —OCF$_2$—, —(CH$_2$)$_4$—, —CH═CH—(CH$_2$)$_2$— and —(CH$_2$)$_2$—CH═CH—. More desirable examples of Z$^1$, Z$^2$ and Z$^3$ are a single bond, —CF$_2$O— and —OCF$_2$—. A desirable combination of Z$^1$, Z$^2$ and Z$^3$ is that two of Z$^1$, Z$^2$ and Z$^3$ are —CF$_2$O— and the other is a single bond.

In formula (1), L$^1$ and L$^2$ are independently hydrogen or halogen, and at least one of L$^1$ and L$^2$ is halogen. A desirable combination of L$^1$ and L$^2$ is that one of L$^1$ and L$^2$ is hydrogen, and the other is fluorine. A more desirable combination of L$^1$ and L$^2$ is that both L$^1$ and L$^2$ are fluorine.

In formula (1), X$^1$ is hydrogen, halogen, —C≡N, —N═C═S, —SF$_5$ or alkyl having 1 to 10 carbons, and in the alkyl, at least one of —CH$_2$— may be replaced by —O— or —S—, and at least one of —(CH$_2$)$_2$— may be replaced by —CH═CH—, and in the groups, at least one of hydrogen may be replaced by halogen. Examples of alkyl in which at least one of —CH$_2$— (or —(CH$_2$)$_2$—) has been replaced by —O— or —S-(or —CH═CH—) are alkoxy, alkoxyalkyl, alkoxyalkoxy, alkylthio, alkylthioalkoxy, alkenyl, alkenyloxy, alkenyloxyalkyl, alkoxyalkenyl and alkenylthio. In the alkyl and in these groups, at least one of hydrogen may be replaced by halogen.

Examples of the alkyl in which at least one of hydrogen has been replaced by halogen are —CH$_2$F, —CHF$_2$, —CF$_3$, —(CH$_2$)$_2$—F, —CF$_2$CH$_2$F, —CF$_2$CHF$_2$, —CH$_2$CF$_3$, —CF$_2$CF$_3$, —(CH$_2$)$_3$—F, —(CF$_2$)$_3$—F, —CF$_2$CHFCF$_3$, —CHFCF$_2$CF$_3$, —(CH$_2$)$_4$—F, —(CF$_2$)$_4$—F, —(CH$_2$)$_5$—F, —(CF$_2$)$_5$—F, —CH$_2$Cl, —CHCl$_2$, —CCl$_3$, —(CH$_2$)$_2$—Cl, —CCl$_2$CH$_2$Cl, —CCl$_2$CHCl$_2$, —CH$_2$CCl$_3$, —CCl$_2$CCl$_3$, —(CH$_2$)$_3$—Cl, —(CCl$_2$)$_3$—Cl, —CCl$_2$CHClCCl$_3$, —CHClCCl$_2$CCl$_3$, —(CH$_2$)$_4$—Cl, —(CCl$_2$)$_4$—Cl, —(CH$_2$)$_5$—Cl and —(CCl$_2$)$_5$—Cl.

Examples of the alkoxy in which at least one of hydrogen has been replaced by halogen are —OCH$_2$F, —OCHF$_2$, —OCF$_3$, —O—(CH$_2$)$_2$—F, —OCF$_2$CH$_2$F, —OCF$_2$CHF$_2$, —OCH$_2$CF$_3$, —O—(CH$_2$)$_3$—F, —O—(CF$_2$)$_3$—F, —OCF$_2$CHFCF$_3$, —OCHFCF$_2$CF$_3$, —O(CH$_2$)$_4$—F, —O—(CF$_2$)$_4$—F, —O—(CH$_2$)$_5$—F, —O—(CF$_2$)$_5$—F, —OCH$_2$Cl, —OCHCl$_2$, —OCCl$_3$, —O—(CH$_2$)$_2$—Cl, —OCCl$_2$CH$_2$Cl, —OCCl$_2$CHCl$_2$, —OCH$_2$CCl$_3$, —O—(CH$_2$)$_3$—Cl, —O—(CCl$_2$)$_3$—Cl, —OCCl$_2$CHClCCl$_3$, —OCHClCCl$_2$CCl$_3$, —O(CH$_2$)$_4$—C, —O—(CCl$_2$)$_4$—Cl, —O—(CH$_2$)$_5$—Cl and —O—(CCl$_2$)$_5$—Cl.

Examples of the alkenyl in which at least one of hydrogen has been replaced by halogen are —CH═CHF, —CH═CF$_2$, —CF═CHF, —CH═CHCH$_2$F, —CH═CHCF$_3$, —(CH$_2$)$_2$CH═CF$_2$, —CH$_2$CH═CHCF$_3$, —CH═CHCF$_2$CF$_3$, —CH═CHCl, —CH═CCl$_2$, —CCl═CHCl, —CH═CHCH$_2$Cl, —CH═CHCCl$_3$, —(CH$_2$)$_2$—CH═CCl$_2$, —CH$_2$CH═CHCCl$_3$ and —CH═CHCCl$_2$CCl$_3$.

Desirable examples of X$^1$ are hydrogen, fluorine, chlorine, —C≡N, —N═C═S, —SF$_5$, —CH$_3$, —C$_2$H$_5$, —C$_3$H$_7$, —C$_4$H$_9$, —C$_5$H$_{11}$, —C$_6$H$_{13}$, —C$_7$H$_{15}$, —C$_8$H$_{17}$, —C$_9$H$_{19}$, —C$_{10}$H$_{21}$, —CH$_2$F, —CHF$_2$, —CF$_3$, —(CH$_2$)$_2$—F, —CF$_2$CH$_2$F, —CF$_2$CHF$_2$, —CH$_2$CF$_3$, —CF$_2$CF$_3$, —(CH$_2$)$_3$—F, —(CF$_2$)$_3$—F, —CF$_2$CHFCF$_3$, —CHFCF$_2$CF$_3$, —(CH$_2$)$_4$—F, —(CF$_2$)$_4$—F, —(CH$_2$)$_5$—F, —(CF$_2$)$_5$—F, —OCH$_3$, —OC$_2$H$_5$, —OC$_3$H$_7$, —OC$_4$H$_9$, —OC$_5$H$_{11}$, —OCH$_2$F, —OCHF$_2$, —OCF$_3$, —O—(CH$_2$)$_2$—F, —OCF$_2$CH$_2$F, —OCF$_2$CHF$_2$, —OCH$_2$CF$_3$, —O—(CH$_2$)$_3$—F, —O—(CF$_2$)$_3$—F, —OCF$_2$CHFCF$_3$, —OCHFCF$_2$CF$_3$, —O(CH$_2$)$_4$—F, —O—(CF$_2$)$_4$—F, —O—(CH$_2$)$_5$—F, —O—(CF$_2$)$_5$—F, —CH═CH$_2$, —CH═CHCH$_3$, —CH$_2$CH═CH$_2$, —CH═CHC$_2$H$_5$, —CH$_2$CH═CHCH$_3$, —(CH$_2$)$_2$—CH═CH$_2$, —CH═CHC$_3$H$_7$, —CH$_2$CH═CHC$_2$H$_5$, —(CH$_2$)$_2$—CH═CHCH$_3$, —(CH$_2$)$_3$—CH═CH$_2$, —CH═CHF, —CH═CF$_2$, —CF═CHF, —CH═CHCH$_2$F, —CH═CHCF$_3$, —(CH$_2$)$_2$—CH═CF$_2$, —CH$_2$CH═CHCF$_3$ and —CH═CHCF$_2$CF$_3$.

More desirable examples of X$^1$ are fluorine, chlorine, —C≡N, —CF$_3$, —CHF$_2$, —CH$_2$F, —OCF$_3$, —OCHF$_2$ and —OCH$_2$F. Most desirable examples of X$^1$ are fluorine, —CF$_3$ and —OCF$_3$. A compound where X$^1$ is fluorine is desirable in view of a small viscosity. A compound where X$^1$ is —CF$_3$ is desirable in view of a large dielectric anisotropy. A compound where X$^1$ is —OCF$_3$ is desirable in view of an excellent compatibility.

1-2. Physical Properties of the Compound (1)

In the compound (1), physical properties such as a clearing point, optical anisotropy and dielectric anisotropy can be arbitrary adjusted by a suitable combination of the kinds of R$^1$, ring A$^1$, ring A$^2$, ring A$^3$, Z$^1$, Z$^2$, Z$^3$, X$^1$, L$^1$ and L$^2$. The compound (1) may also contain isotopes such as $^2$H (deuterium) and $^{13}$C in a larger amount than the amount of the natural abundance, since there are no major differences in physical properties of the compound. Main effects of the kinds of R$^1$ and so forth on the physical properties of the compound (1) will be explained below.

When the left-terminal group R$^1$ is a straight chain, the temperature range of a liquid crystal phase is wide and the viscosity is small. When R$^1$ is a branched chain, the compatibility with other liquid crystal compounds is excellent. A compound in which R$^1$ is optically active is useful as a chiral dopant. A reverse twisted domain which will occur in a liquid crystal display device can be prevented by the addition of this compound to a composition. A compound in which R$^1$ is not optically active is useful as a component of a composition. A desirable configuration depends on the position of the double bond when R$^1$ is alkenyl. An alkenyl compound having a desirable configuration has a high maximum temperature or a wide temperature range of a liquid crystal phase.

When all of ring A$^1$, ring A$^2$ and ring A$^3$ are 1,4-cyclohexylene, the clearing point is high and the viscosity is small. When at least one of ring A$^1$, ring A$^2$ and ring A$^3$ is 1,4-phenylene or 1,4-phenylene in which at least one of hydrogen has been replaced by halogen, the optical anisotropy is relatively large and the orientational order parameter is relatively large. When all of ring A$^1$, ring A$^2$ and ring A$^3$ are 1,4-phenylene, 1,4-phenylene in which at least one of hydrogen has been replaced by halogen or a combination of them, the optical anisotropy is especially large.

When the bonding group Z$^1$, Z$^2$ or Z$^3$ is a single bond, —(CH$_2$)$_2$—, —CH═CH—, —CF$_2$O—, —OCF$_2$—, —CH$_2$O—, —OCH$_2$—, —CF═CF—, —(CH$_2$)$_3$—O—, —O—(CH$_2$)$_3$—, —(CH$_2$)$_2$—CF$_2$O—, —OCF$_2$—(CH$_2$)$_2$— or —(CH$_2$)$_4$—, the viscosity is small. When the bonding group is a single bond, —(CH$_2$)$_2$—, —CF$_2$O—, —OCF$_2$— or —CH═CH—, the viscosity is smaller. When the bonding group is —CH═CH—, the temperature range of a liquid crystal phase is wide and the elastic constant (K) is large. When the bonding group is —C≡C—, the optical anisotropy is large. When Z$^1$, Z$^2$ or Z$^3$ is a single bond, —(CH$_2$)$_2$— or —(CH$_2$)$_4$—, the chemical stability is high.

When the right-terminal group X$^1$ is fluorine, chlorine, —C≡N, —N═C═S, —SF$_5$, —CF$_3$, —CHF$_2$, —CH$_2$F, —OCF$_3$, —OCHF$_2$ or —OCH$_2$F, the dielectric anisotropy is large. When X$^1$ is —C≡N, —N═C═S or alkenyl, the optical anisotropy is large. When X$^1$ is fluorine, —CF$_3$ or alkyl, the chemical stability is high.

When both L$^1$ and L$^2$ are fluorine, and X$^1$ is fluorine, chlorine, —C≡N, —N═C═S, —SF$_5$, —CF$_3$, —CHF$_2$, —CH$_2$F, —OCF$_3$, —OCHF$_2$ or —OCH$_2$F, the dielectric anisotropy is large. The chemical stability is high, the temperature range of a liquid crystal phase is wide, and the dielectric anisotropy is large, when L is fluorine and $X^1$ is —$CF_3$, or when both $L^1$ and $L^2$ are fluorine and $X^1$ is —$CF_3$, or when all of $L^1$, $L^2$ and $X^1$ are fluorine.

As described above, a compound having objective physical properties can be obtained by a suitable selection of the kinds of ring structures, terminal groups, bonding groups and so forth. Accordingly, the compound (1) is useful as the component of a liquid crystal composition for use in a liquid crystal display device having a mode such as PC, TN, STN, ECB, OCB, IPS or VA.

1-3. Desirable Compounds

Desirable examples of the compound (1) are the compounds (1-2) to (1-4) as described in item 3. More desirable examples are the compounds (1-2-1) to (1-4-1) as described in item 4. Further desirable examples are the compounds (1-2-1-1) to (1-2-1-8), the compounds (1-3-1-1) to (1-3-1-8) and the compounds (1-4-1-1) to (1-4-1-8) as described in item 5. The compounds (1-2-1-1) to (1-2-1-8) are desirable in view of a small viscosity, a large optical anisotropy or a larger dielectric anisotropy. The compounds (1-3-1-1) to (1-3-1-8) are desirable in view of a large optical anisotropy or a larger dielectric anisotropy. The compounds (1-4-1-1) to (1-4-1-8) are desirable in view of a large dielectric anisotropy or an excellent compatibility. Most desirable examples are the compounds (1-2-1-8-1). and (1-2-1-2-1) as described in item 9.

1-4. Preparation of the Compound (1)

The method for synthesizing the compound (1) will be explained. The compound (1) can be prepared by a suitable combination of methods in synthetic organic chemistry. Methods of introducing objective terminal groups, rings and bonding groups into starting materials are described in books such as "Organic Syntheses" (John Wiley & Sons, Inc.), "Organic Reactions" (John Wiley & Sons, Inc.), "Comprehensive Organic Synthesis" (Pergamon Press) and "Shin Jikken Kagaku Kouza" (New Experimental Chemistry Course, in English; Maruzen Co., Ltd., Japan).

1-4-1. Formation of the Bonding Group

Examples of the formation of the bonding group in the compound (1) are shown in the following schemes. In these schemes, $MSG^1$ (or $MSG^2$) is a monovalent organic group having at least one ring. Monovalent organic groups represented by a plurality of the $MSG^1$ (or $MSG^2$) may be the same or different. The compounds (1A) to (1G) correspond to the compound (1).

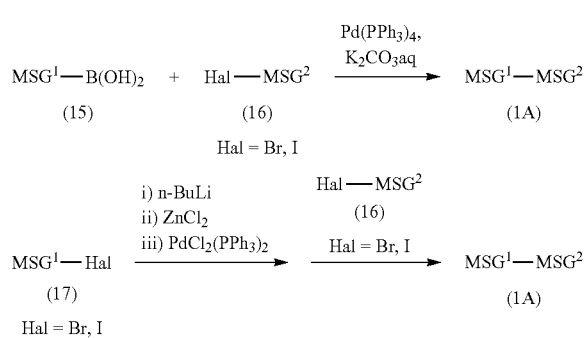

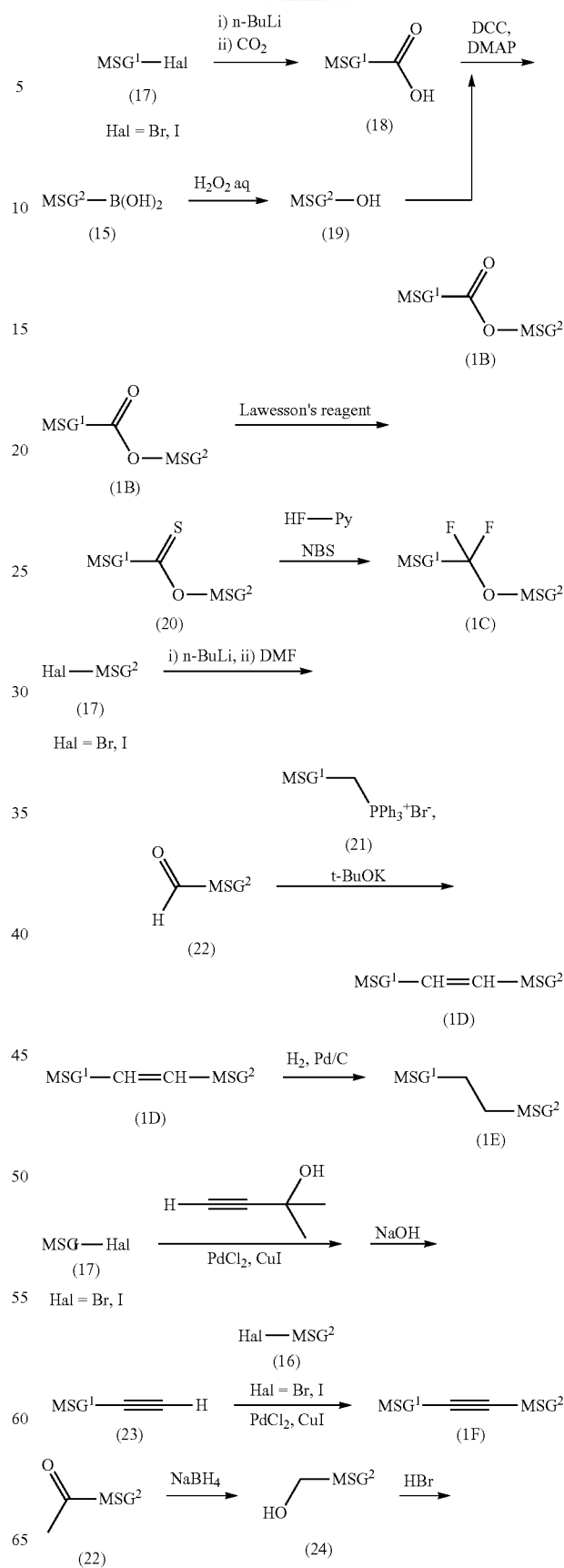

-continued

MSG¹—OH, (19)

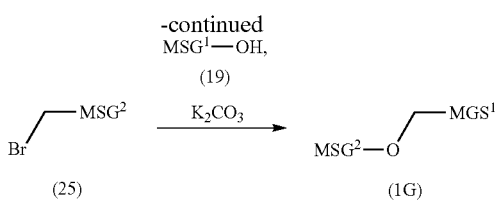

(I) Formation of a Single Bond

The compound (1A) is prepared by the reaction of the arylboronic acid (15) with the compound (16) prepared by known methods, in the presence of a catalyst such as tetrakis (triphenylphosphine)palladium in an aqueous solution of a carbonate. This compound (1A) is also prepared by the reaction of the compound (17) prepared by known methods with n-butyllithium and then with zinc chloride, and then by the reaction with the compound (16) in the presence of a catalyst such as dichlorobis(triphenylphosphine)palladium.

(II) Formation of —COO— and —OCO—

The carboxylic acid (18) is prepared by the reaction of the compound (17) with n-butyllithium and then with carbon dioxide. Dehydration of the compound (18) and the phenol (19) prepared by known methods, in the presence of DDC (1,3-dicyclohexylcarbodiimide) and DMAP (4-dimethylaminopyridine) gives the compound (1B) having —COO—. The compound having —OCO— is also prepared by this method.

(III) Formation of —CF$_2$O— and —OCF$_2$—

The treatment of the compound (1B) with a thionating agent such as Lawesson's reagent gives the compound (20). The compound (20) is fluorinated with a hydrogen fluoride-pyridine complex and NBS (N-bromdsuccinimide) to give the compound (1C) having —CF$_2$O—. See M. Kuroboshi et al., Chem. Lett., 1992, 827. The compound (1C) is also prepared by the fluorination of the compound (20) with (diethylamino)sulfur trifluoride (DAST). See W. H. Bunnelle et al., J. Org. Chem. 1990, 55, 768. The compound having —OCF$_2$— is also prepared by this method. These bonding groups can also be formed according to the method described in Peer. Kirsch et al., Angew. Chem. Int. Ed. 2001, 40, 1480.

(IV) Formation of —CH=CH—

The compound (17) is treated with n-butyllithium, and then reacted with a formamide such as N,N-dimethylformamide (DMF) to give the aldehyde (22). The phosphonium salt (21) prepared by known methods is treated with a base such as potassium tert-butoxide, and the resulting phosphorus ylide is allowed to react with the aldehyde (22) to give the compound (1D). Since the cis-isomer is formed depending on the reaction conditions, the cis-isomer is isomerized to the trans-isomer by known methods as requested.

(V) Formation of —(CH$_2$)$_2$—

The compound (1E) is prepared by the hydrogenation of the compound (1D) in the presence of a catalyst such as palladium on carbon.

(VI) Formation of —C≡C—

The reaction of the compound (17) with 2-methyl-3-butyn-2-ol in the presence of a catalyst of dichloropalladium and a copper halide, followed by the deprotection of the product under basic conditions gives the compound (23). The compound (1F) is prepared by the reaction of the compound (23) with the compound (16) in the presence of a catalyst of dichlorobistriphenylphosphinepalladium and a copper halide.

(VII) Formation of —CH$_2$O— and —OCH$_2$—

The compound (22) is reduced with a reducing agent such as sodium borohydride to give the compound (24). The compound (24) is halogenated with hydrobromic acid or the like, giving the compound (25). The compound (25) is allowed to react with the compound (19) in the presence of potassium carbonate or the like, giving the compound (1G).

1-4-2. Formation of rings A¹, A² and A³

Starting materials are commercially available, or methods are well known for the preparation of rings, such as 1,4-cyclohexylene, 1,4-phenylene, 2-fluoro-1,4-phenylene, 2,3-difluoro-1,4-phenylene, 2,5-difluoro-1,4-phenylene, 2,6-difluoro-1,4-phenylene, 2,3,5,6-tetrafluoro-1,4-phenylene, tetrahydropyran-2,5-diyl, 1,3-dioxane-2,5-diyl, pyrimidine-2,5-diyl and pyridine-2,5-diyl.

1-4-3. Synthetic Example

Examples for the synthesis of the compound (1) are as follows. The dehydrative condensation of the carboxylic acid (30) and the alcohol (31) in the presence of DCC and DMAP gives the ester (32). The ester (32) is allowed to react with a thionating agent such as Lawesson's reagent to give thion-O-ester (33). The product is fluorinated with a hydrogen fluoride-pyridine complex and NBS to give the compound (34). The compound (34) is allowed to react with n-butyllithium, and then with carbon dioxide to give the carboxylic acid (35). The dehydrative condensation of the carboxylic acid (35) and the phenol (36) in the presence of DCC and DMAP gives the ester (37). The ester (37) is allowed to react with a thionating agent such as Lawesson's reagent to give thion-O-ester (38). The compound (1) is prepared by the fluorination of this compound with a hydrogen fluoride-pyridine complex and NBS.

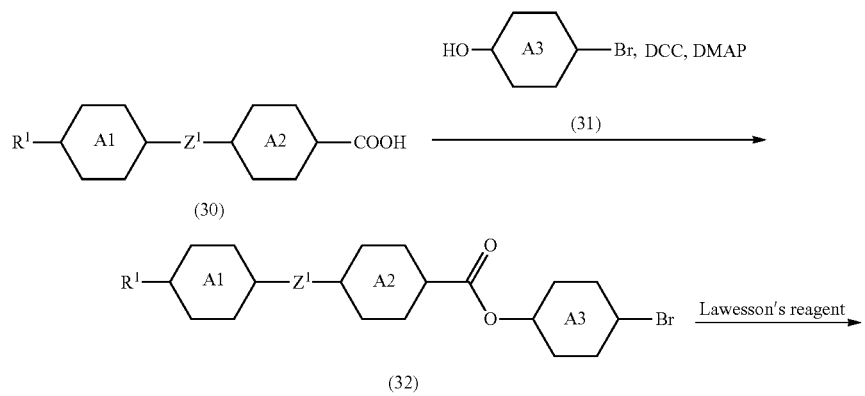

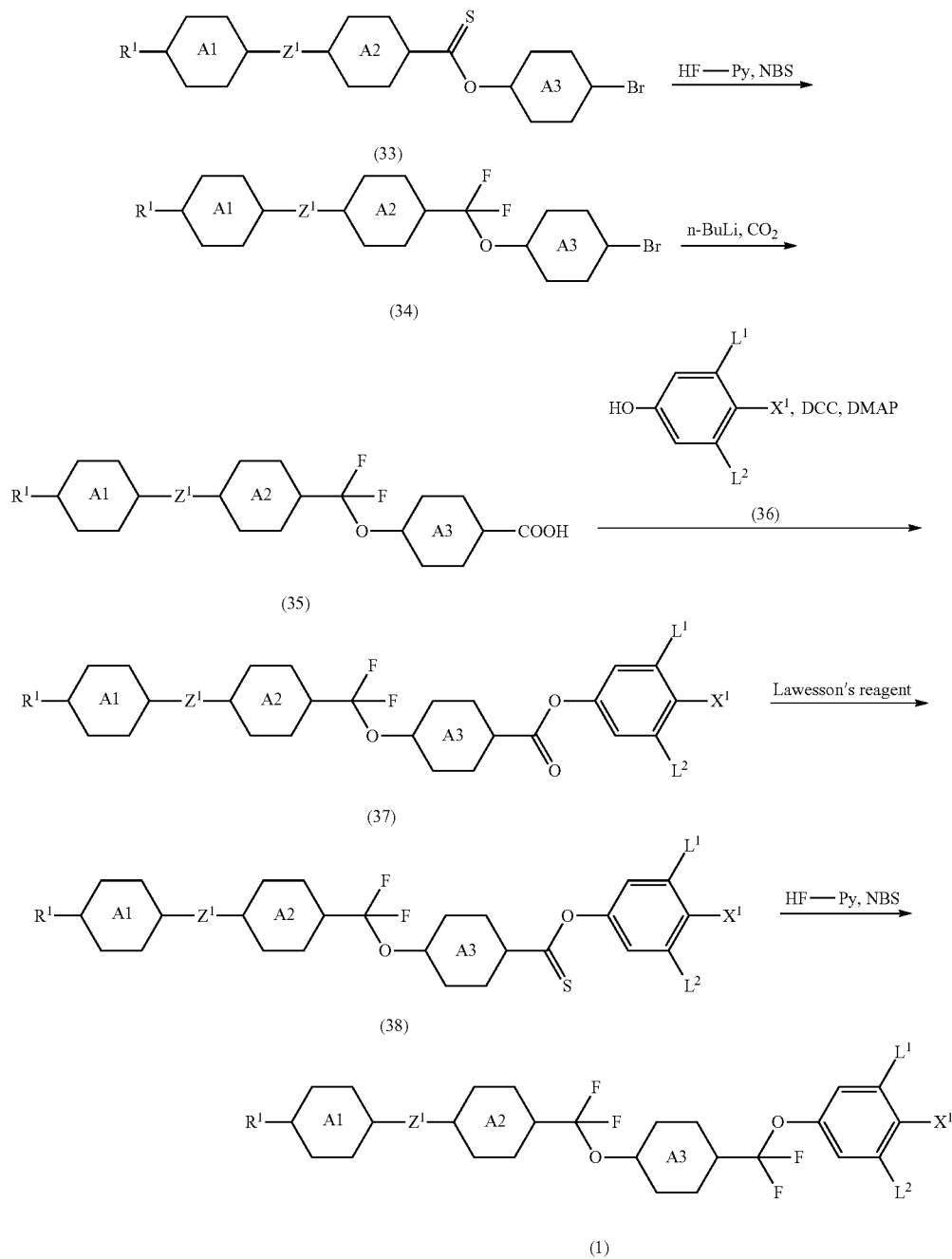

In these compounds, the definitions of $R^1$, ring $A^1$, ring $A^2$, ring $A^3$, $Z^1$, $L^1$, $L^2$ and $X^1$ are just the same as described previously.

The compound (1) where ring $A^3$ is 1,4-cyclohexylene can be prepared by the following method.

The dehydrative condensation of the carboxylic acid (30) and the compound (39) in the presence of DCC and DMAP gives the ester (40). The reaction of the ester (40) with a thionating agent such as Lawesson's reagent, followed by the fluorination with a hydrogen fluoride-pyridine complex and NBS gives the compound (41). The deprotection of the compound (41) using formic acid gives the ketone (42). The ketone (42) was allowed to react with a phosphine ylide generated by the treatment of a phosphonium salt with potassium t-butoxide to give the compound (43). The compound (43) is treated with hydrochloric acid to give the aldehyde (44). The oxidation of the aldehyde (44) in the presence of sodium chlorite, 2-methyl-2-butene and sodium hydrogenphosphate gives the carboxylic acid (45). The dehydrative condensation of the carboxylic acid (45) and the phenol (36) in the presence of DCC and DMAP gives the ester (46). The compound (1) is prepared by the reaction of the ester (46) with a thionating agent such as Lawesson's reagent, and then by the fluorination with a hydrogen fluoride-pyridine complex and NBS.

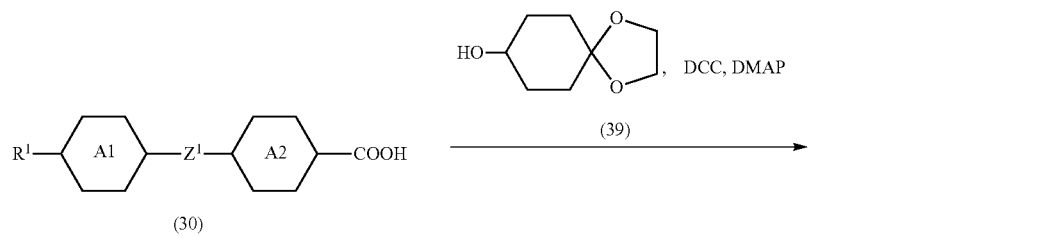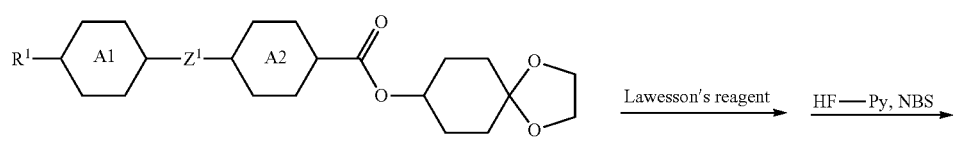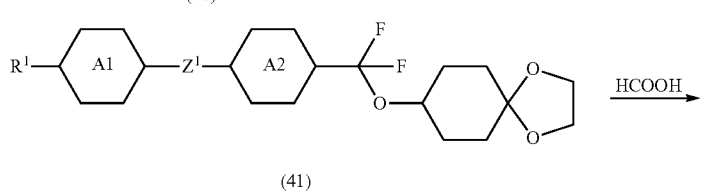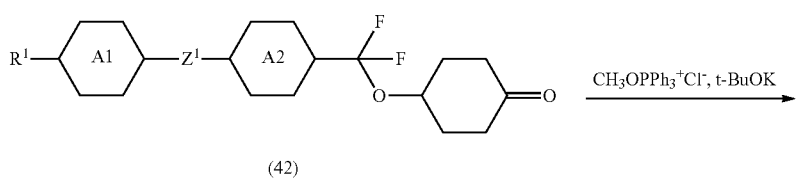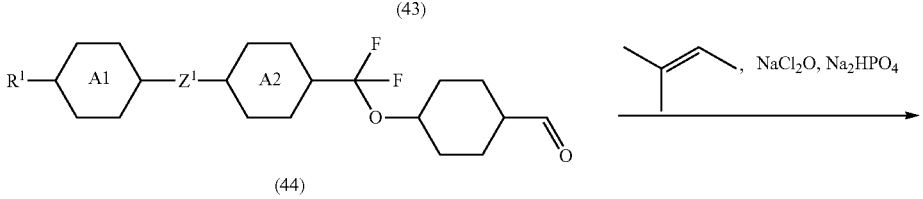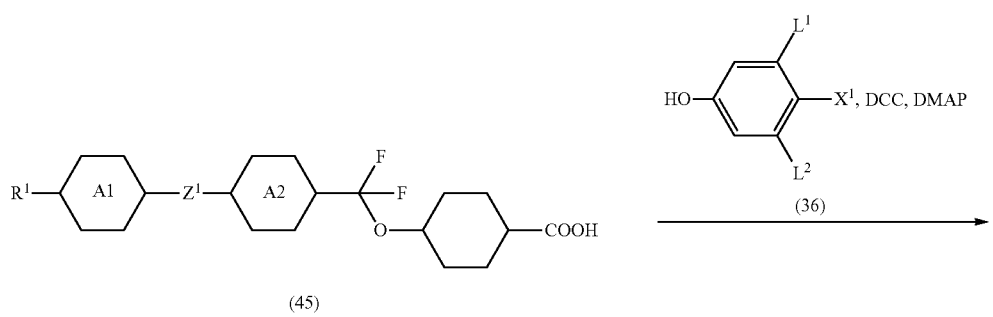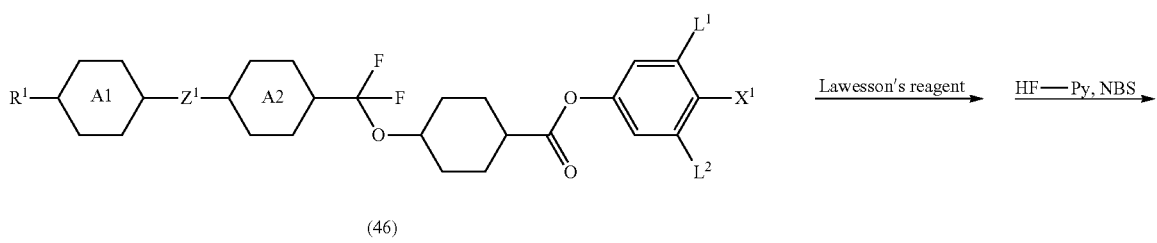

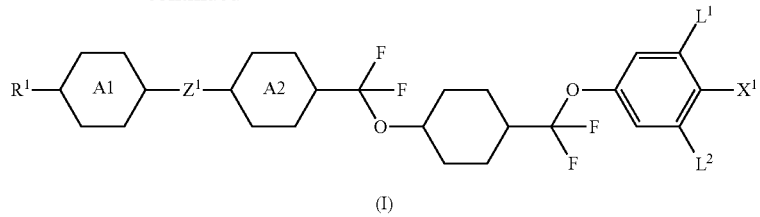

(I)

In these compounds, the definitions of $R^1$, ring $A^1$, ring $A^2$, $Z^1$, $L^1$, $L^2$ and $X^1$ are just the same as described previously.

The compound (1) where ring $A^3$ is 1,4-phenylene or 1,4-phenylene in which at least one of hydrogen has been replaced by fluorine can be prepared by the following method.

The carboxylic acid (30) is allowed to react with an alkanedithiol and trifluoromethanesulfonic acid to give the dithianylium salt (47) according to the method described in P. Kirsch et al., Angew. Chem. Int. Ed., 2001, 40, 1480. The dithianylium salt (47) is allowed to react with the phenol (48), and then with $Et_3N_3HF$, and to treat with bromine to give the compound (49). The compound (49) is allowed to react with n-butyllithium, and then with dibromodifluoromethane to give the compound (50) according to the method described in U.S. Pat. No. 6,231,785 B1. The compound (1) is prepared by the reaction of the compound (50) with the phenol (36) in the presence of a base such as potassium carbonate.

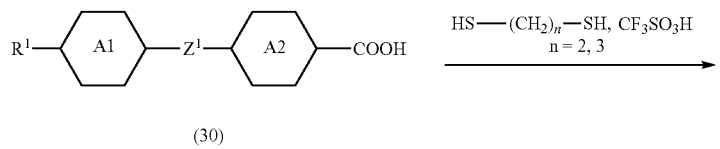

(30)

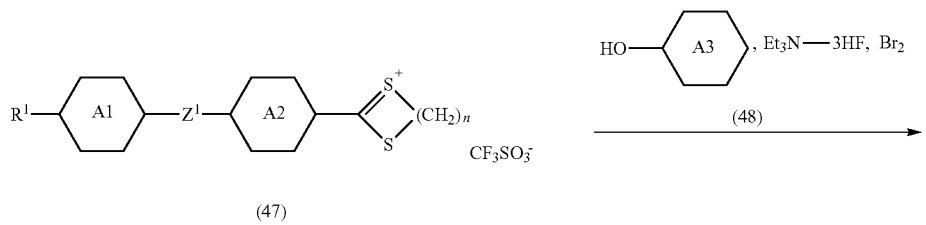

(47)

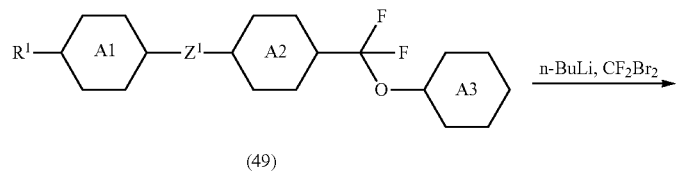

(49)

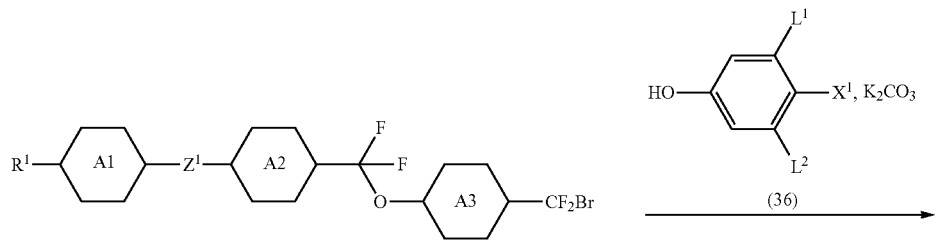

(50)

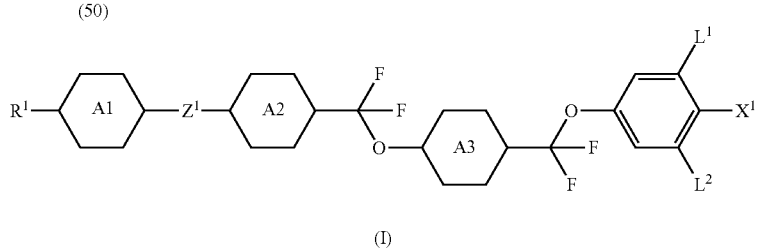

(I)

In these compounds, the definitions of $R^1$, ring $A^1$, ring $A^2$, $Z^1$, $L^1$, $L^2$ and $X^1$ are just the same as described previously, and ring $A^3$ is 1,4-phenylene or 1,4-phenylene in which at least one of hydrogen has been replaced by fluorine.

2. The Composition (1)

The liquid crystal composition (1) of the invention will be explained. The composition (1) includes at least one of the compound (1) as a component A. The composition (1) may include two or more of the compound (1). The component of the liquid crystal compounds may be the compound (1) alone. It is desirable that the composition (1) should include at least one of the compound (1) in the range of 1% to 99% by weight in order to exhibit excellent physical properties. More desirable ratio is in the range of 5% to 60% by weight. The composition (1) may include the compound (1) andavariety of liquid crystal compounds that are not described in this specification.

A desirable composition includes a compound selected from the components B, C, D and E, which will be shown below. When the composition (1) is prepared, the component can be selected in consideration of, for example, the dielectric anisotropy of the compound (1). The composition in which the component is suitably selected has a high maximum temperature of a nematic phase, a low minimum temperature of a nematic phase, a small viscosity, a suitable optical anisotropy, a large dielectric anisotropy and a suitable elastic constant.

The component B is the compounds (2) to (4). The component C is the compound (5). The component D is the compounds (6) to (11). The component E is the compounds (12) to (14). These components will be explained in this order.

The component B is a compound having halogen or a fluorine-containing group in the right terminal. Desirable examples of the component B include the compounds (2-1) to (2-16), the compounds (3-1) to (3-112) and the compounds (4-1) to (4-54). Incidentally, in formulas (3) and (4), both $Z^4$ and $Z^5$ are not —CF$_2$O— and/or —OCF$_2$—. This means that the component B does not include a compound where both $Z^4$ and $Z^5$ are —CF$_2$O—, a compound where both $Z^4$ and $Z^5$ are —OCF$_2$—, and a compound where one is —CF$_2$O— and the other is —OCF$_2$—.

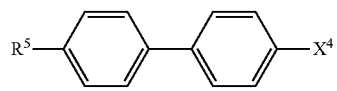

(2-1)

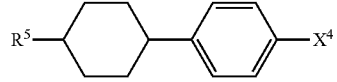

(2-2)

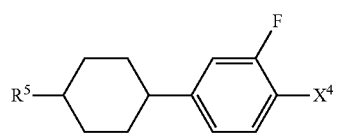

(2-3)

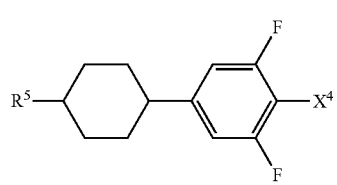

(2-4)

-continued

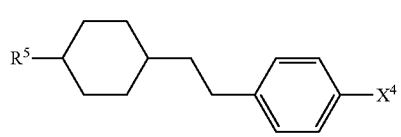

(2-5)

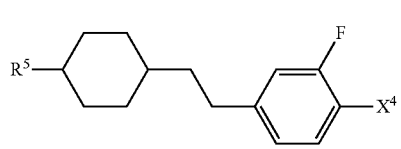

(2-6)

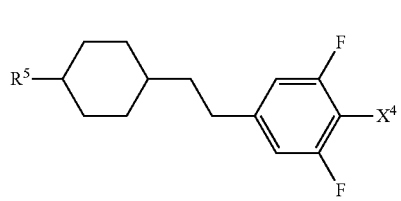

(2-7)

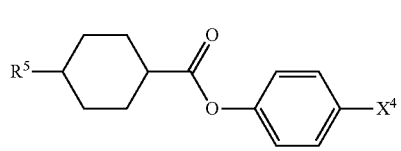

(2-8)

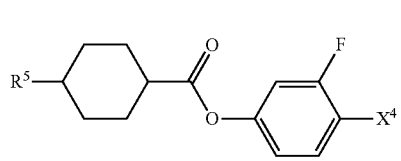

(2-9)

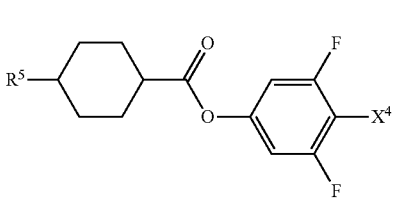

(2-10)

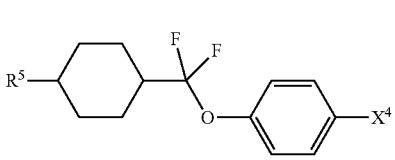

(2-11)

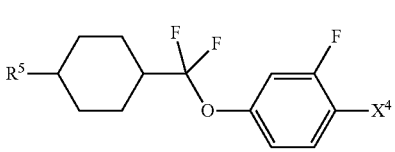

(2-12)

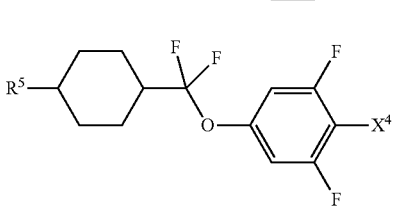

(2-13)

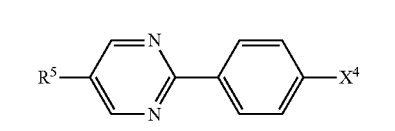

(2-14)

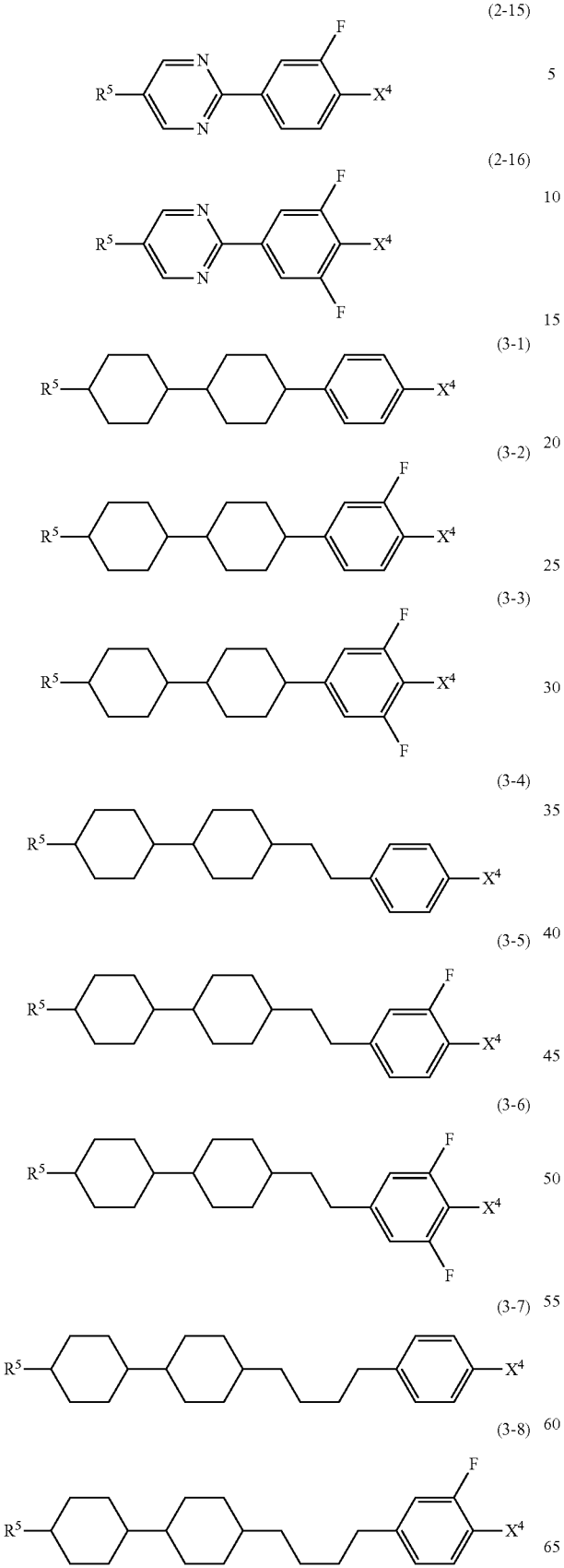
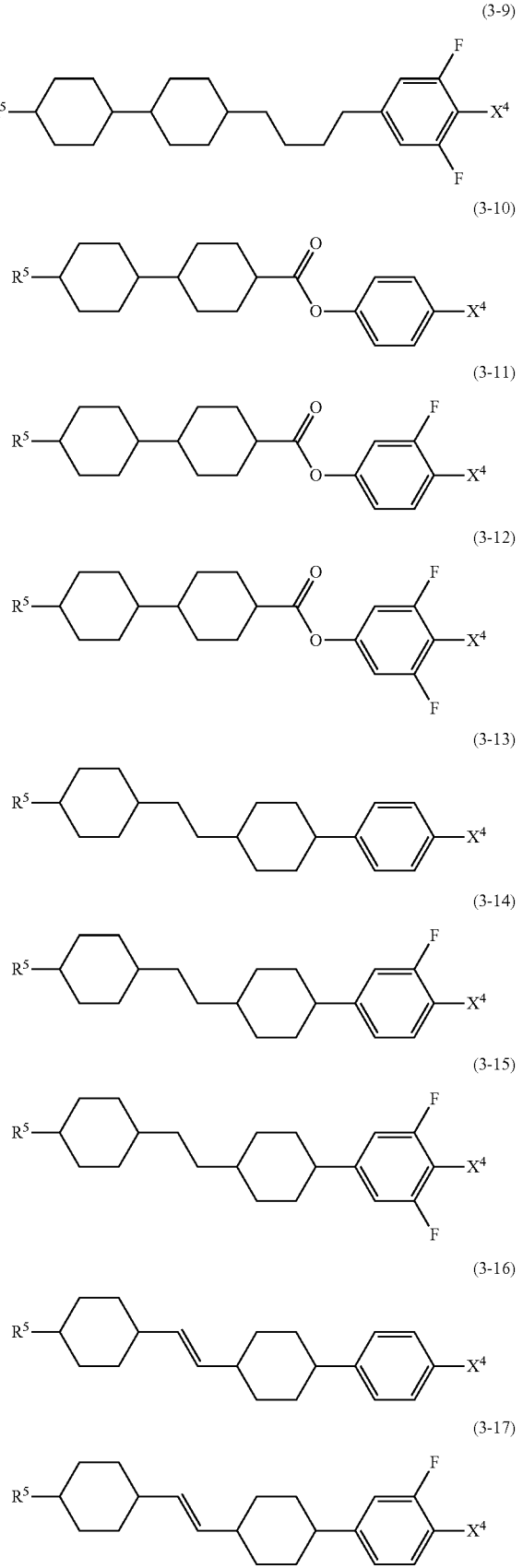

(3-18) 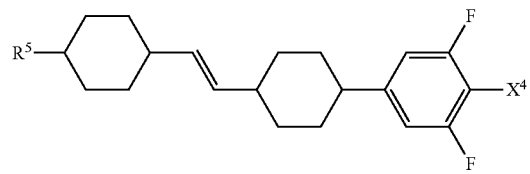
(3-19) 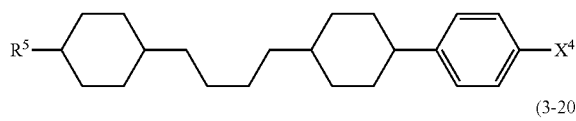
(3-20) 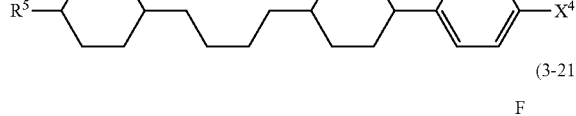
(3-21) 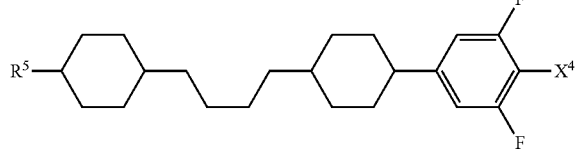
(3-22) 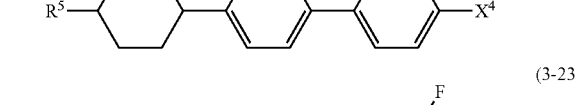
(3-23) 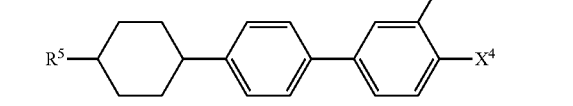
(3-24) 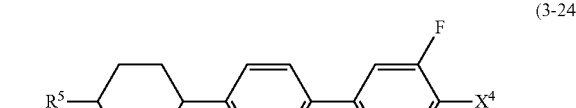
(3-25) 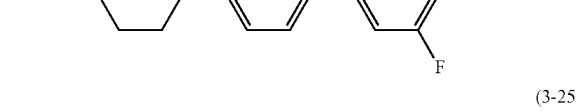
(3-26) 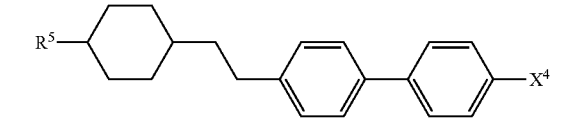
(3-27) 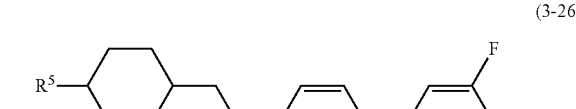
(3-28) 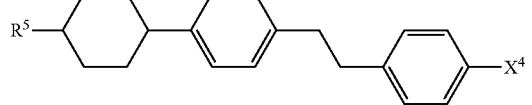
(3-29) 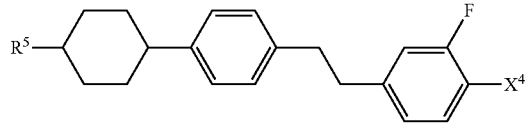
(3-30) 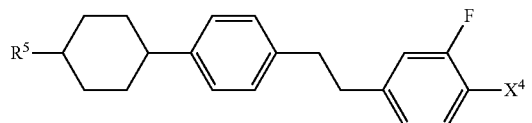
(3-31) 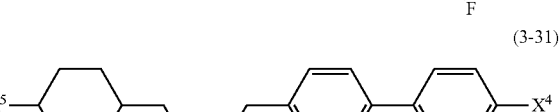
(3-32) 
(3-33) 
(3-34) 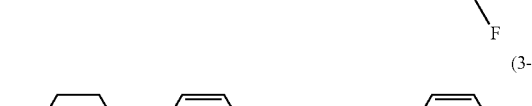
(3-35) 
(3-36) 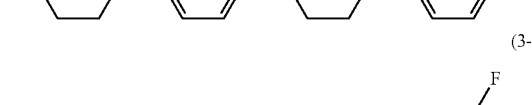
(3-37) 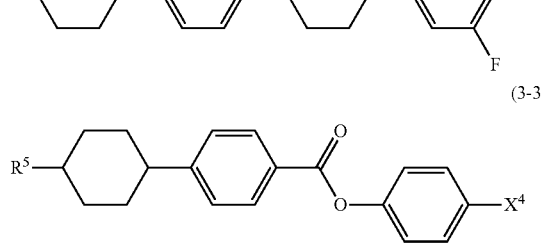

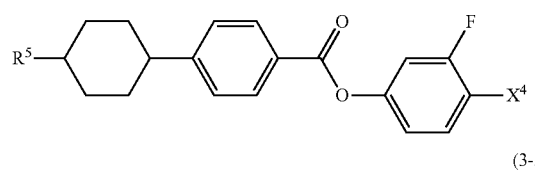
(3-38)
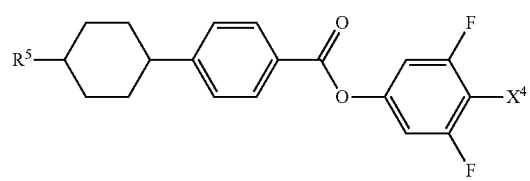
(3-39)
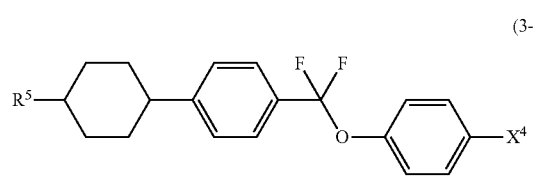
(3-40)
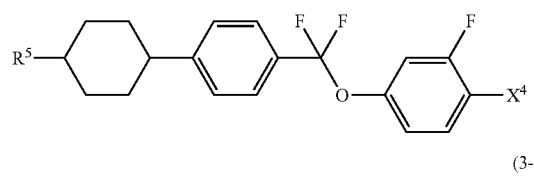
(3-41)
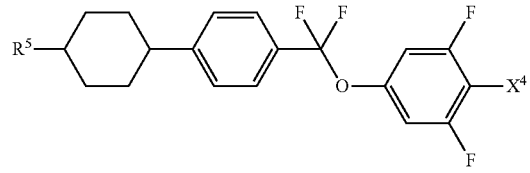
(3-42)
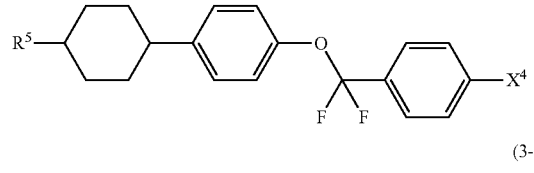
(3-43)
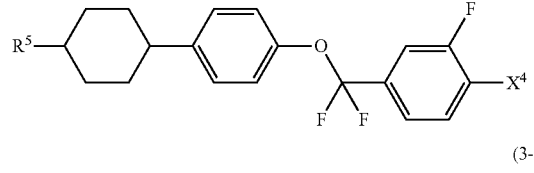
(3-44)
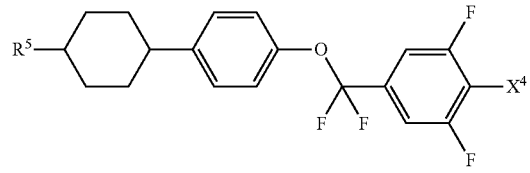
(3-45)
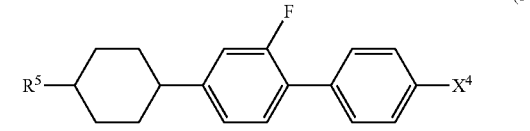
(3-46)
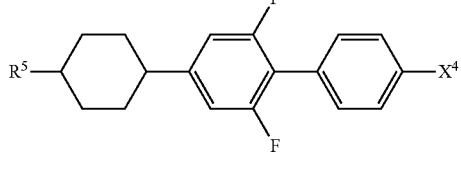
(3-47)
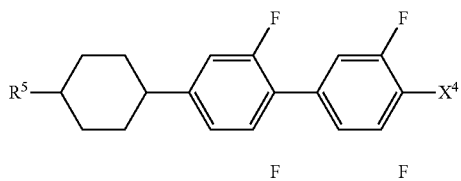
(3-48)
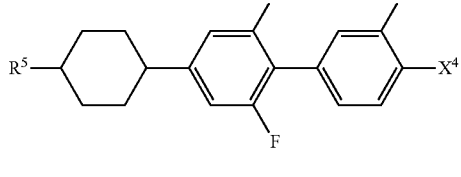
(3-49)
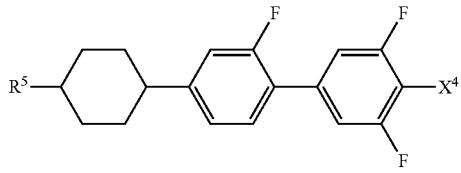
(3-50)
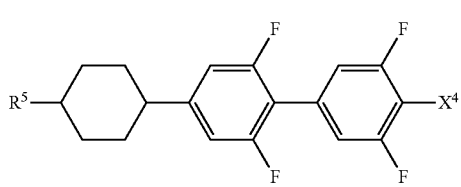
(3-51)
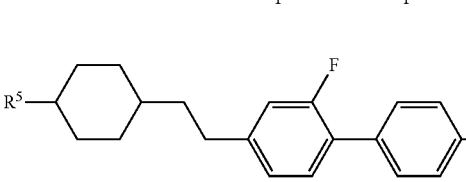
(3-52)
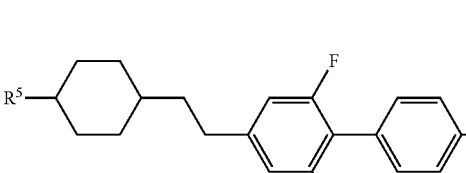
(3-53)
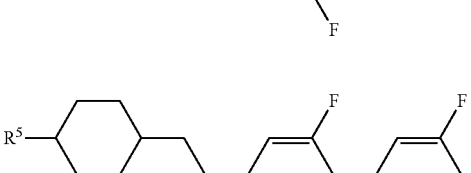
(3-54)
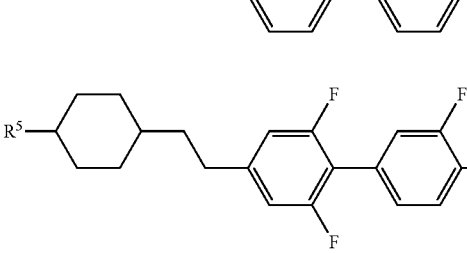
(3-55)

(3-56)
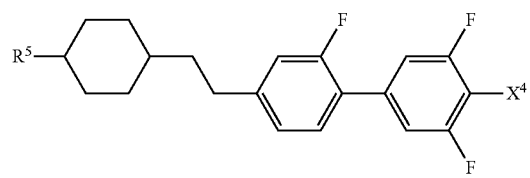
(3-57)
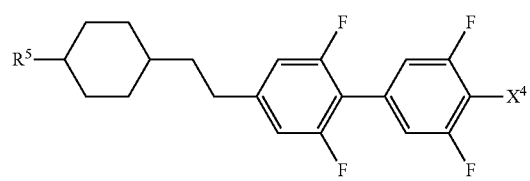
(3-58)
(3-59)
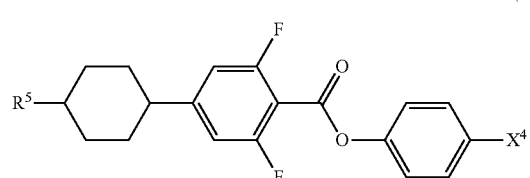
(3-60)
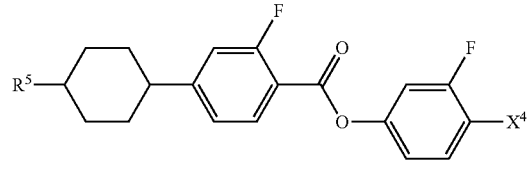
(3-61)
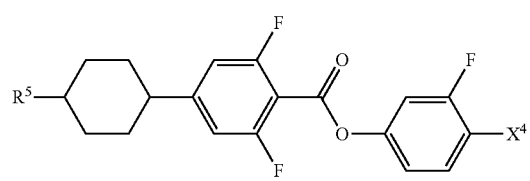
(3-62)
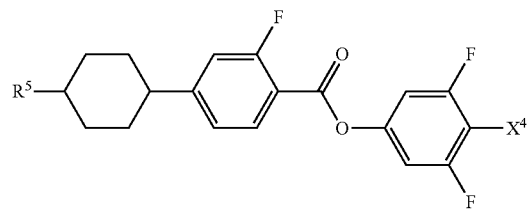
(3-63)
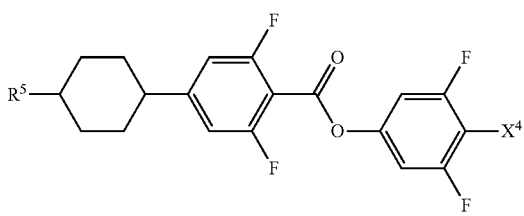
(3-64)
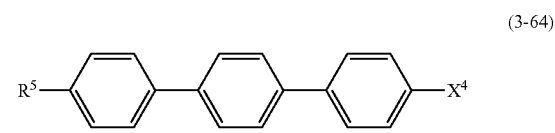
(3-65)
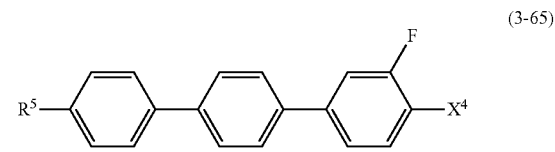
(3-66)
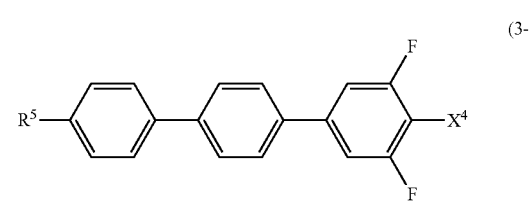
(3-67)
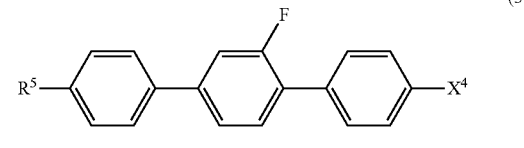
(3-68)
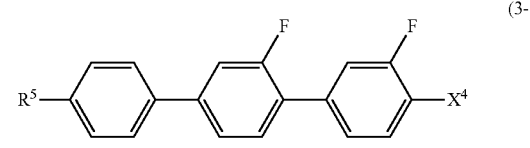
(3-69)
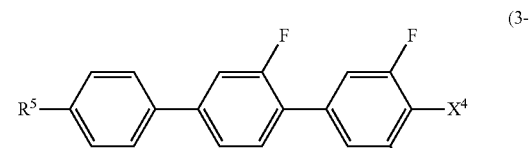
(3-70)
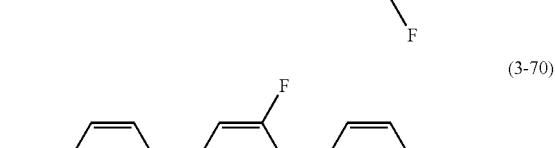
(3-71)
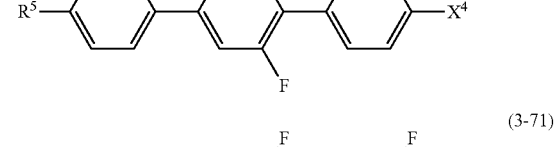

(3-72) through (3-88): chemical structure diagrams (3-89) 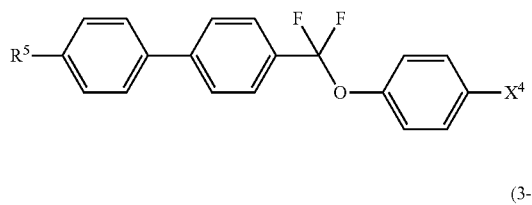
(3-90) 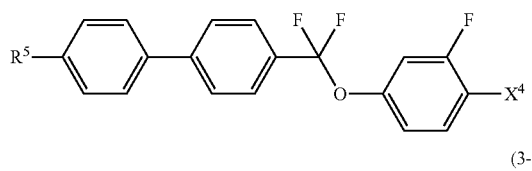
(3-91) 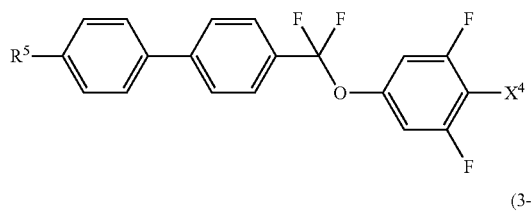
(3-92) 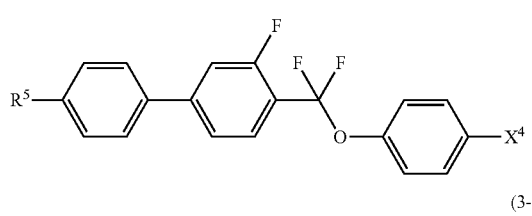
(3-93) 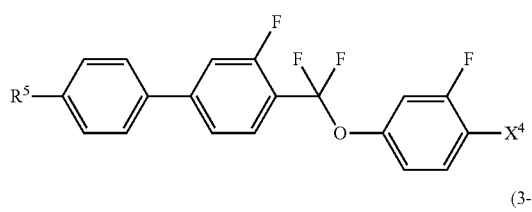
(3-94) 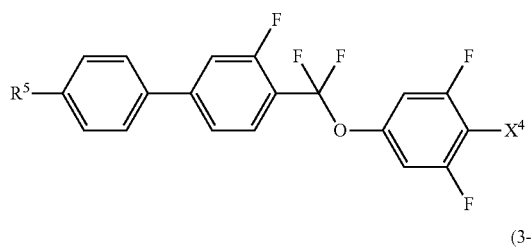
(3-95) 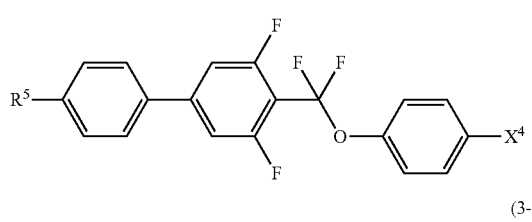
(3-96) 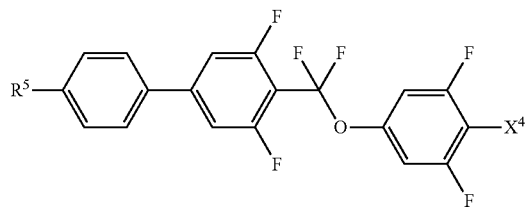
(3-97) 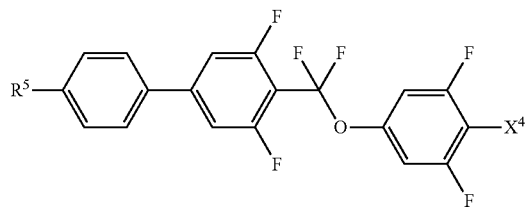
(3-98) 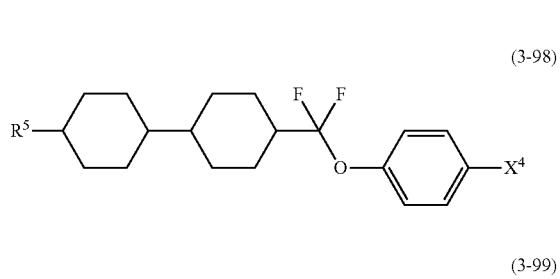
(3-99) 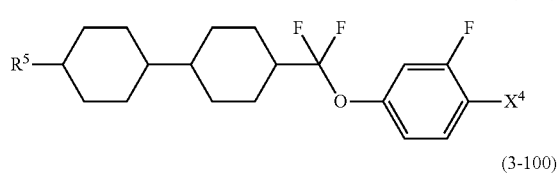
(3-100) 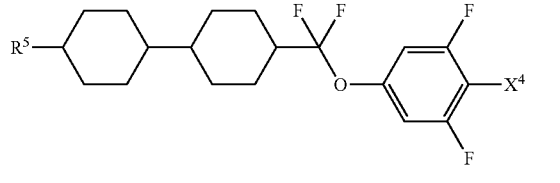
(3-101) 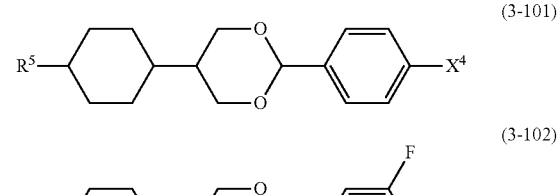
(3-102) 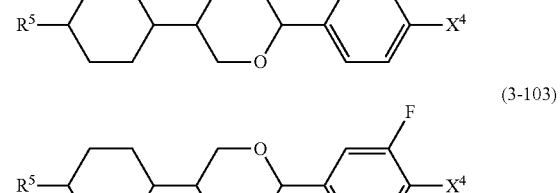
(3-103) 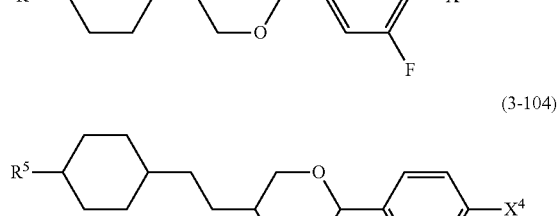
(3-104) 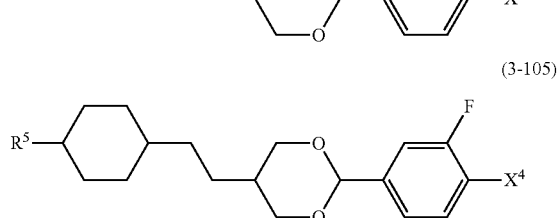
(3-105) 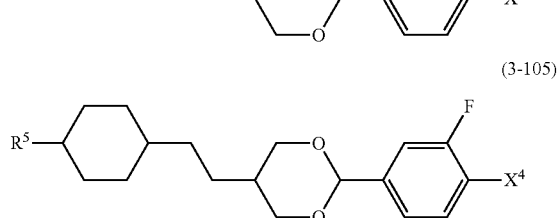

(3-106) 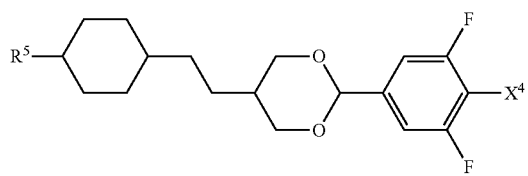
(3-107) 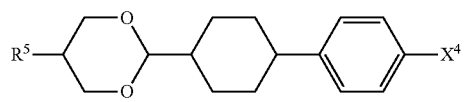
(3-108) 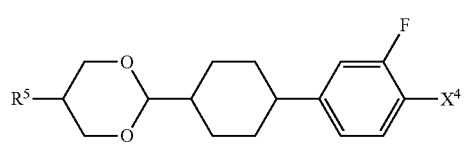
(3-109) 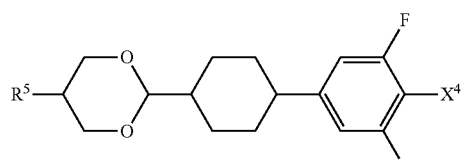
(3-110) 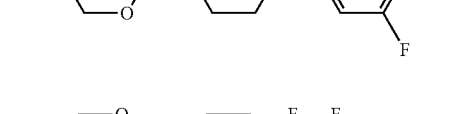
(3-111) 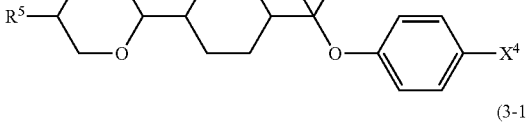
(3-112) 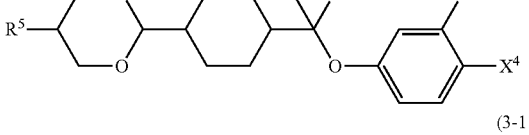
(4-1) 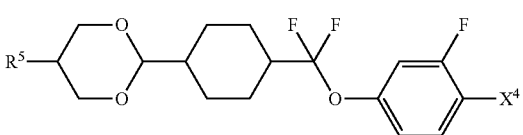
(4-2) 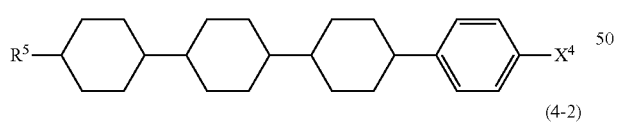
(4-3) 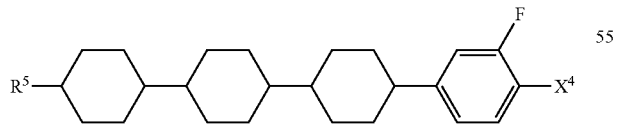
(4-4) 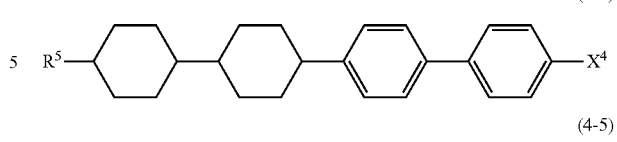
(4-5) 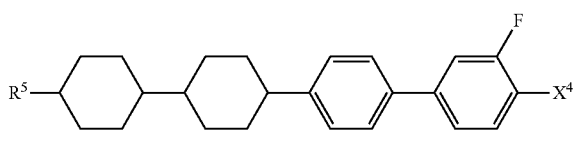
(4-6) 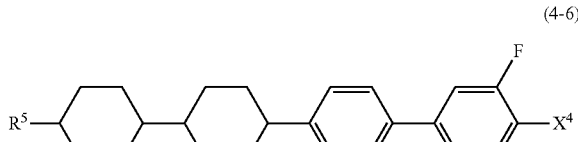
(4-7) 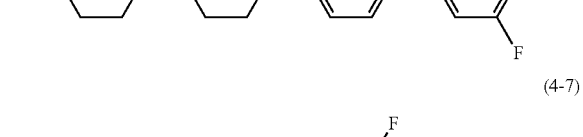
(4-8) 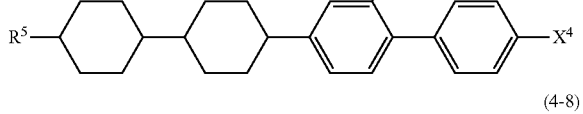
(4-9) 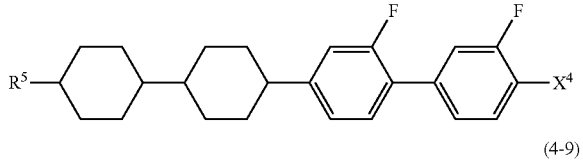
(4-10) 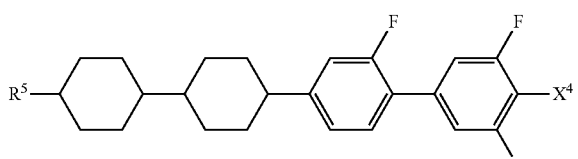
(4-11) 
(4-12) 

(4-13) 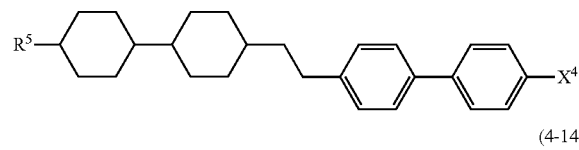
(4-14) 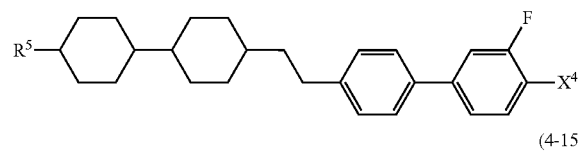
(4-15) 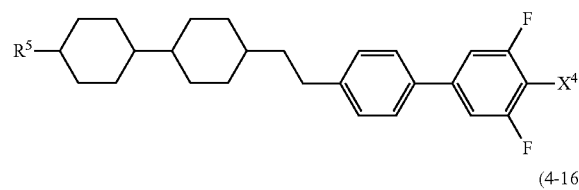
(4-16) 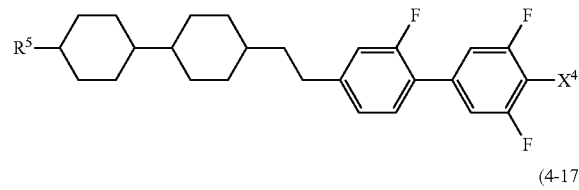
(4-17) 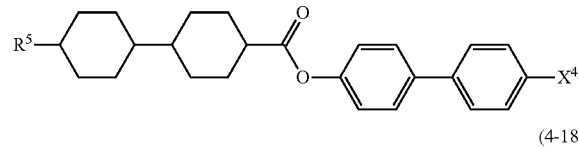
(4-18) 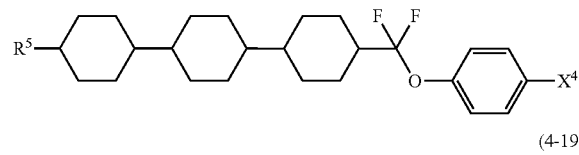
(4-19) 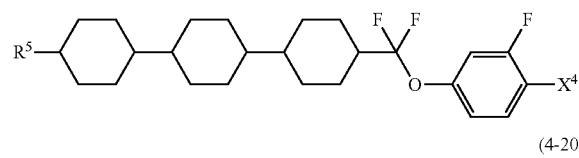
(4-20) 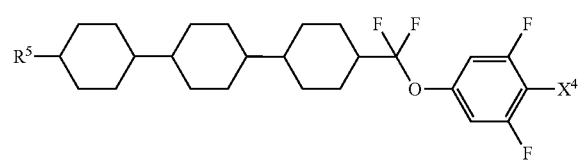
(4-21) 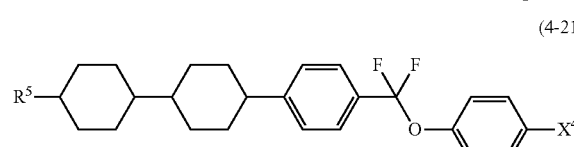
(4-22) 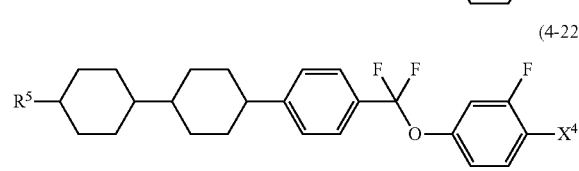
(4-23) 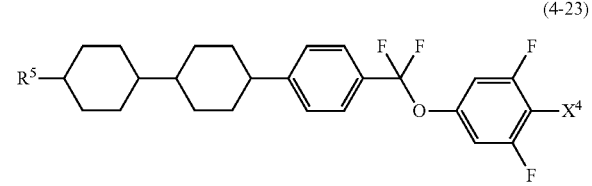
(4-24) 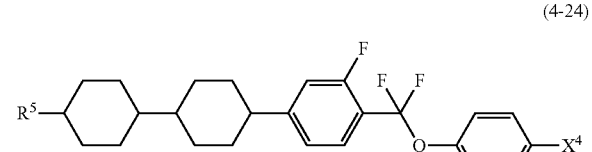
(4-25) 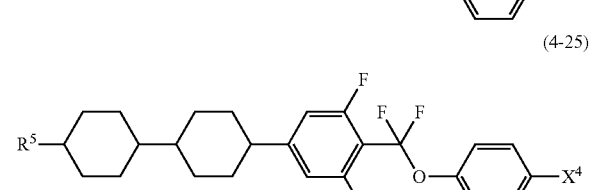
(4-26) 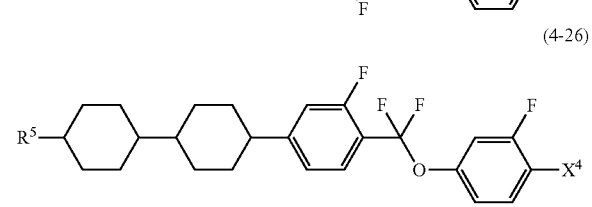
(4-27) 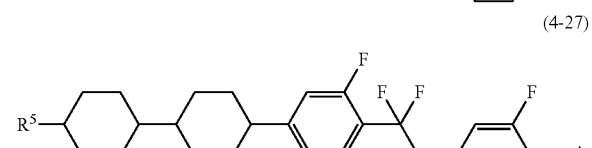
(4-28) 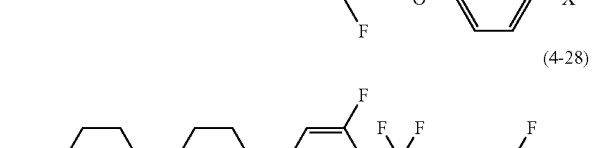
(4-29) 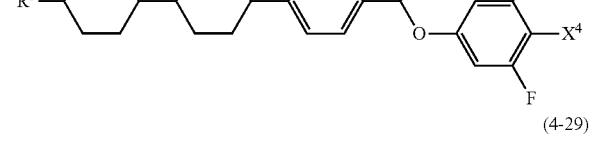
(4-30) 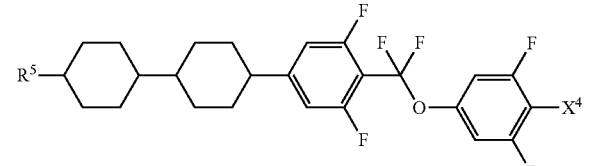
(4-31) 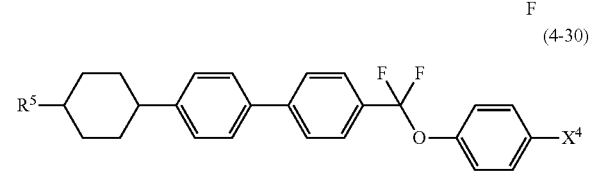

(4-32) 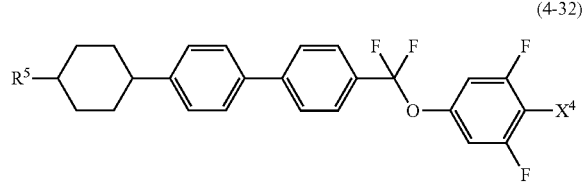
(4-33) 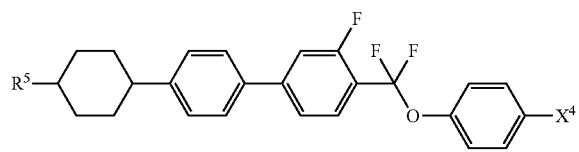
(4-34) 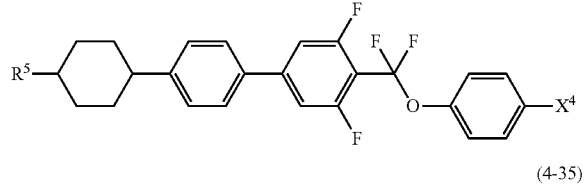
(4-35) 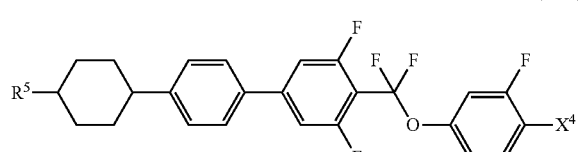
(4-36) 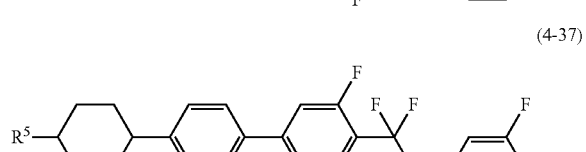
(4-37) 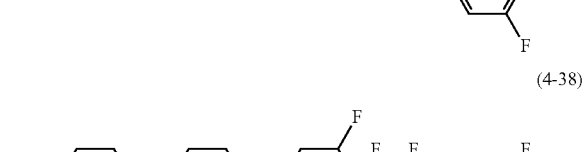
(4-38) 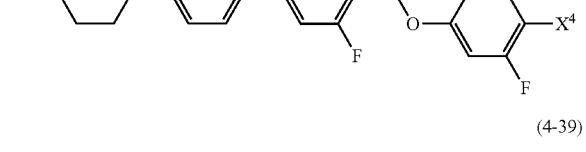
(4-39)
(4-40) 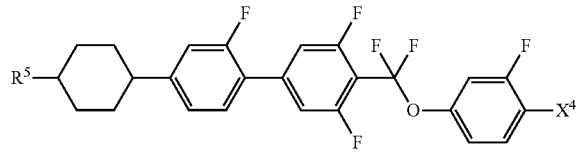
(4-41) 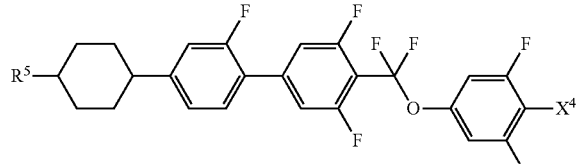
(4-42) 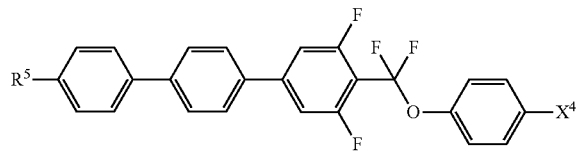
(4-43) 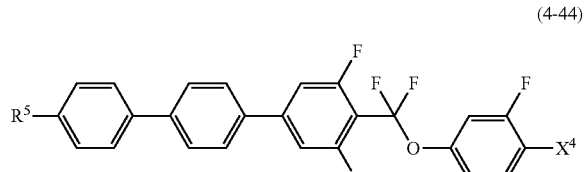
(4-44) 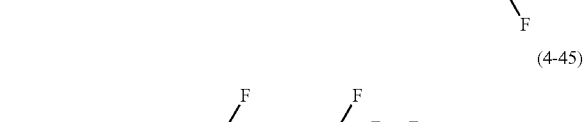
(4-45) 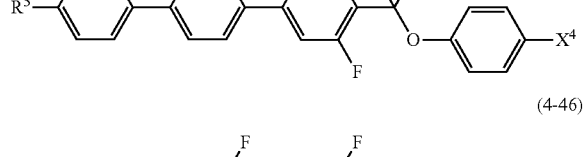
(4-46) 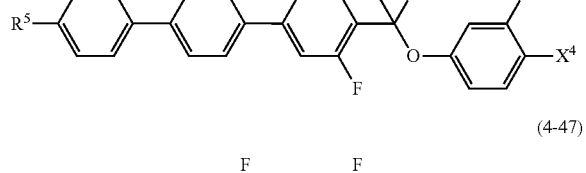
(4-47)

In these compounds (the component B), the definitions of R⁵ and X⁴ are just the same as described previously.

The component B is used for the preparation of a composition for use in a TFT mode or a PSA mode, since the dielectric anisotropy is positive and the stability to heat, light or the like is quite excellent. The content of the component B is suitably in the range of 1% to 99% by weight, preferably in the range of 10% to 97% by weight, more preferably in the range of 40% to 95% by weight, based on the total weight of the composition. In this composition, the viscosity can be adjusted by further addition of the compounds (12) to (14) (the component E).

The component C is the compound (5) where the right-terminal group is —C≡N or —C≡C—C≡N. Desirable examples of the component C include the compounds (5-1) to (5-64).

(5-11) 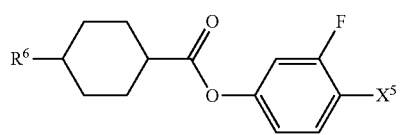
(5-12) 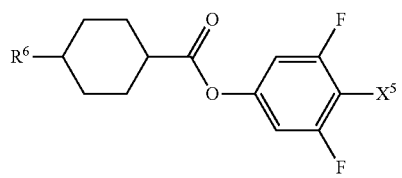
(5-13) 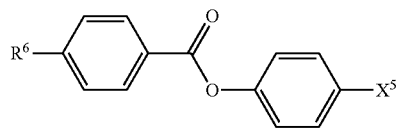
(5-14) 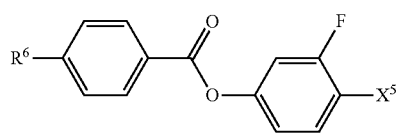
(5-15) 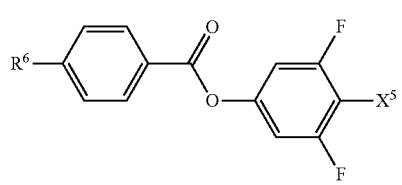
(5-16) 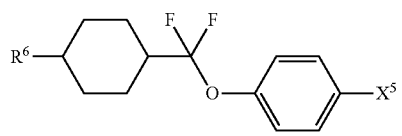
(5-17) 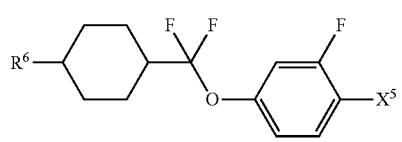
(5-18) 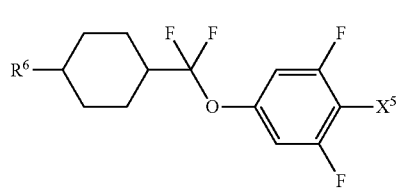
(5-19) 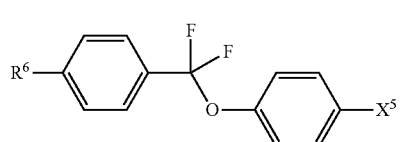
(5-20) 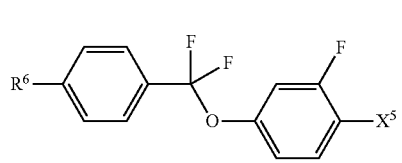
(5-21) 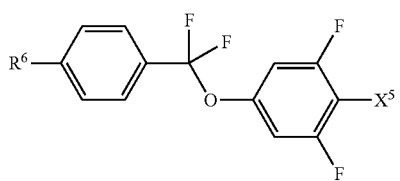
(5-22) 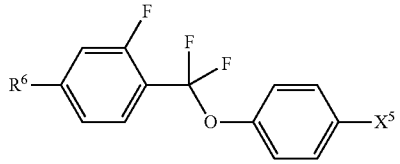
(5-23) 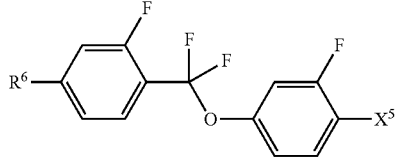
(5-24) 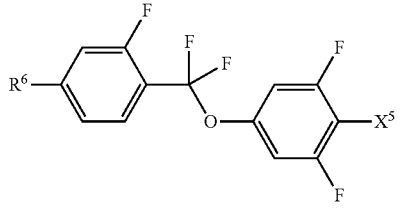
(5-25) 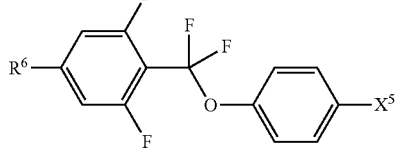
(5-26) 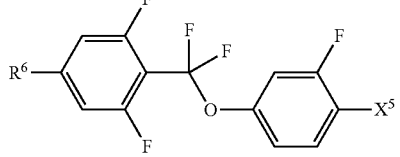
(5-27) 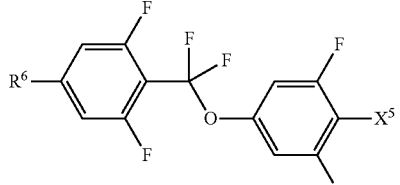
(5-28) 
(5-29) 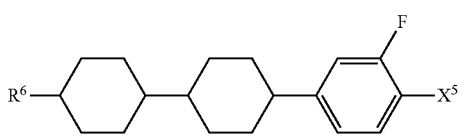

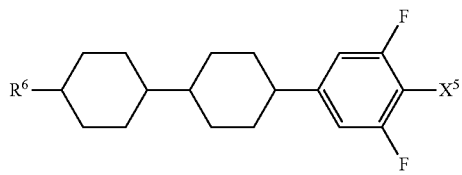 (5-30)
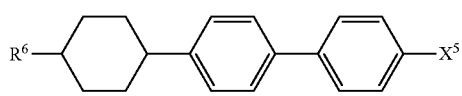 (5-31)
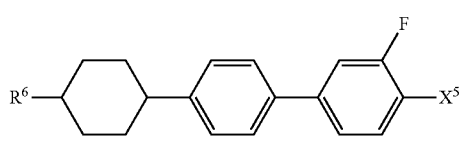 (5-32)
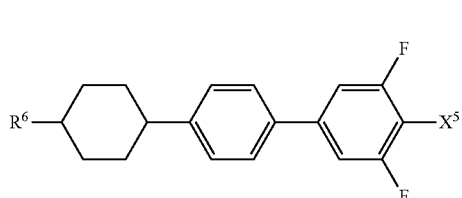 (5-33)
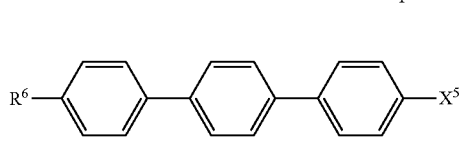 (5-34)
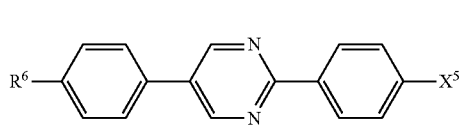 (5-35)
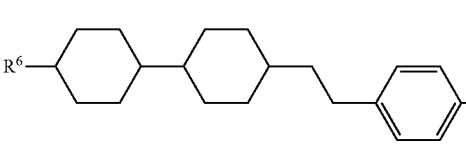 (5-36)
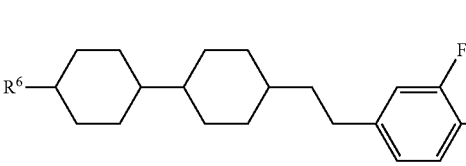 (5-37)
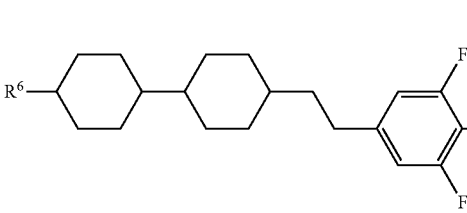 (5-38)
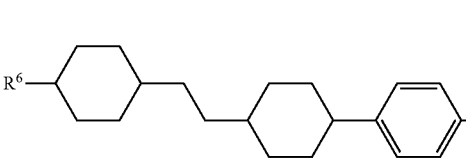 (5-39)
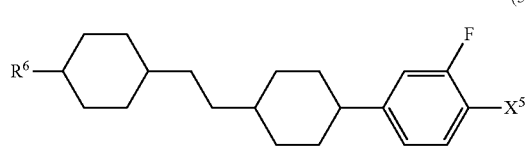 (5-40)
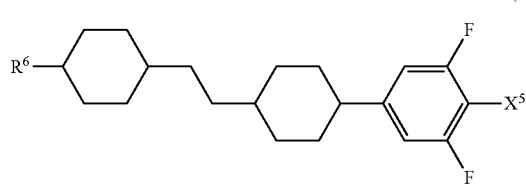 (5-41)
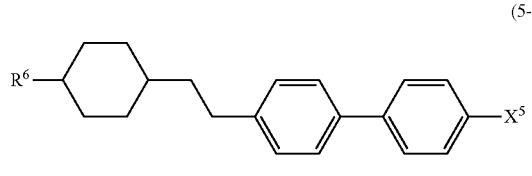 (5-42)
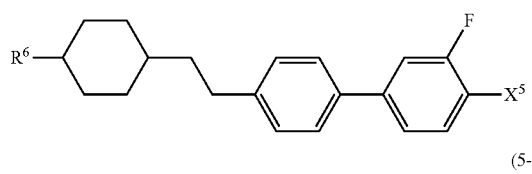 (5-43)
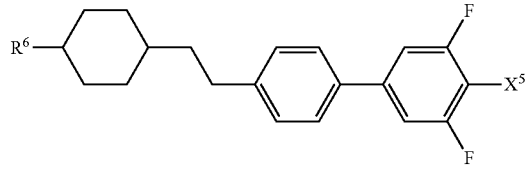 (5-44)
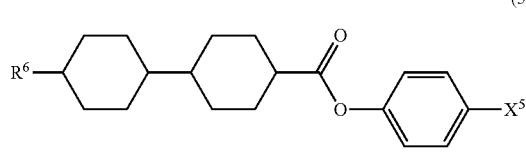 (5-45)
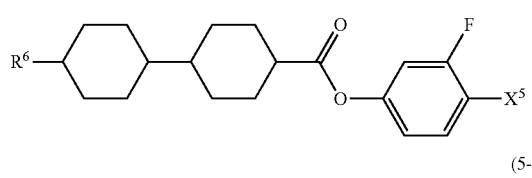 (5-46)
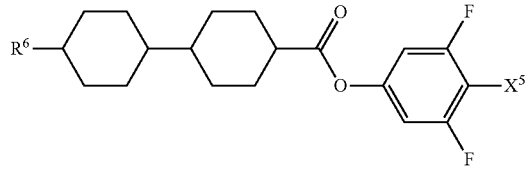 (5-47)
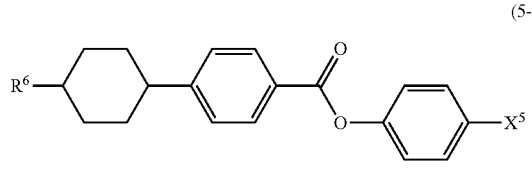 (5-48)

-continued (5-49)
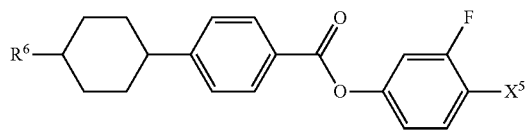

(5-50)
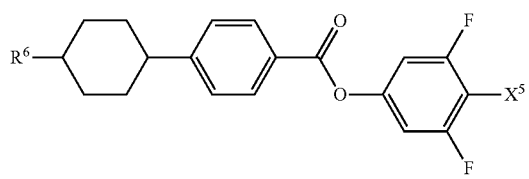

(5-51)
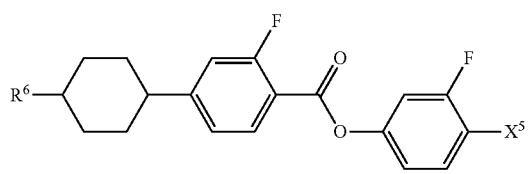

(5-52)
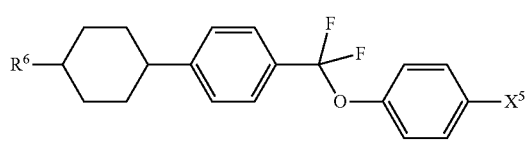

(5-53)
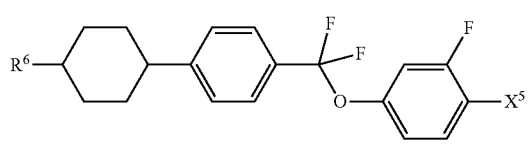

(5-54)
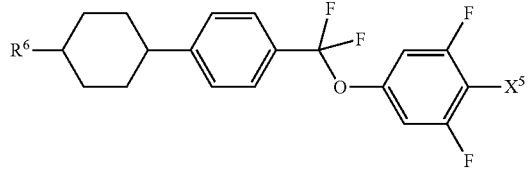

(5-55)
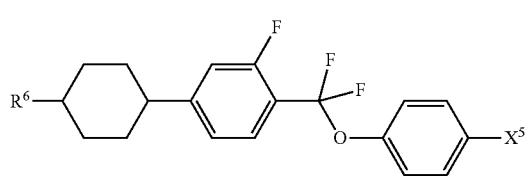

(5-56)
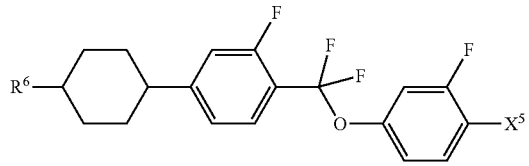

-continued (5-57)
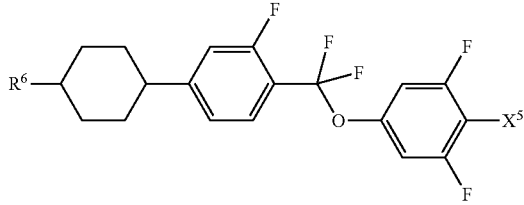

(5-58)
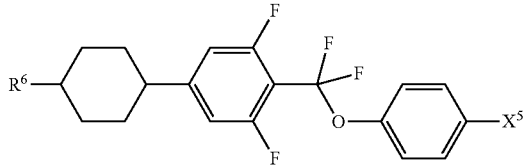

(5-59)
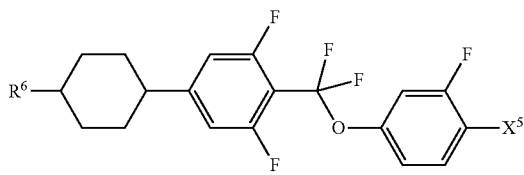

(5-60)
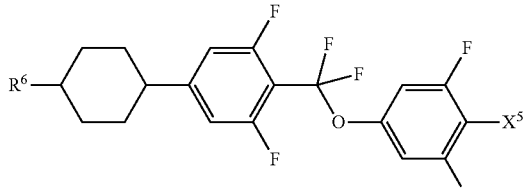

(5-61)
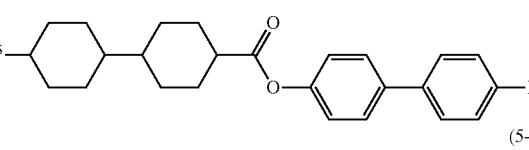

(5-62)
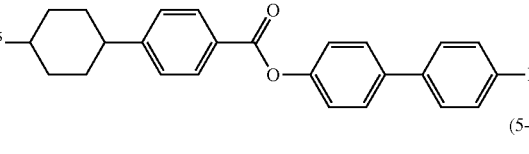

(5-63)
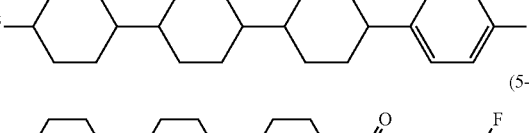

(5-64)
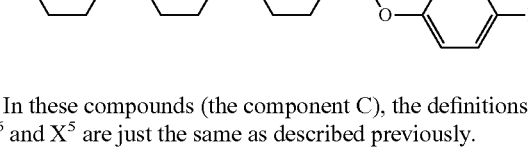

In these compounds (the component C), the definitions of $R^6$ and $X^5$ are just the same as described previously.

The component C is mainly used for the preparation of a composition for use in a STN mode, a TN mode or a PSA mode, since the dielectric anisotropy is positive and its value is large. The dielectric anisotropy of the composition can be increased by the addition of the component C. The component C has the effect of increasing the temperature range of a liquid crystal phase, adjusting the viscosity and adjusting the optical anisotropy. The component C is useful for adjusting the voltage-transmission curve of a device.

The content of the component C is suitably in the range of 1% to 99% by weight, preferably in the range of 10 to 97% by weight, more preferably 40% to 95% by weight, based on the total weight of the composition, in the preparation of a composition for use in a STN mode or a TN mode. In this composition, the temperature range of a liquid crystal phase, the viscosity, the optical anisotropy, the dielectric anisotropy or the like can be adjusted by the addition of the component E.

The component D is the compounds (6) to (11). These compounds have a benzene ring that is substituted with two halogens in the lateral positions, such as 2,3-difluoro-1,4-phenylene. Desirable examples of the component D include the compounds (6-1) to (6-6), the compounds (7-1) to (7-15), the compound (8-1), the compounds (9-1) to (9-3), the compounds (10-1) to (10-11) and the compounds (11-1) to (11-10).

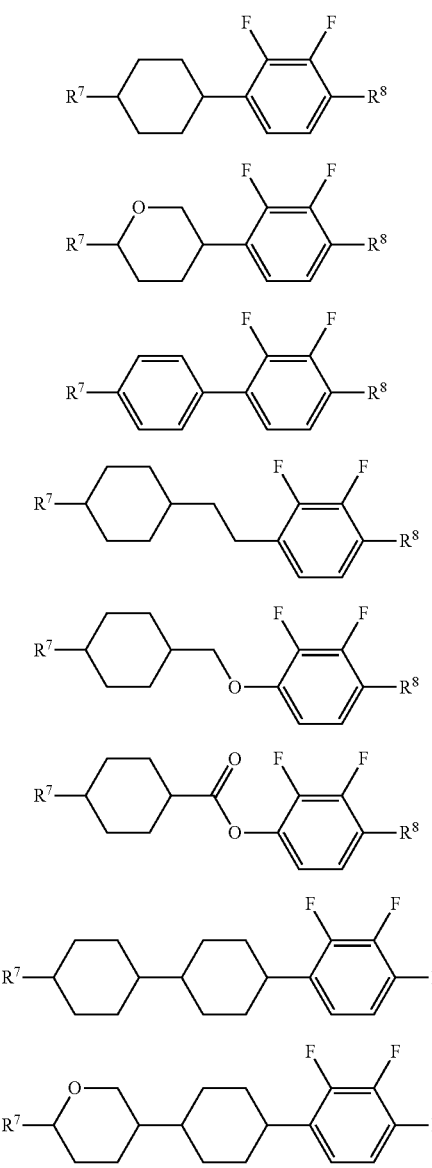

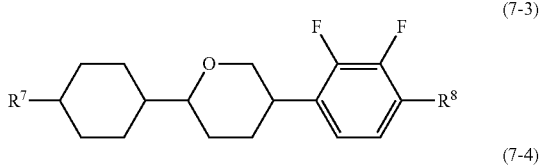

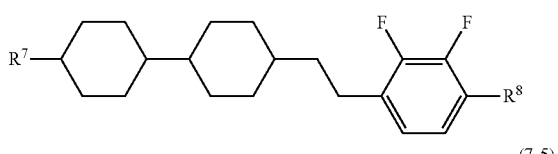

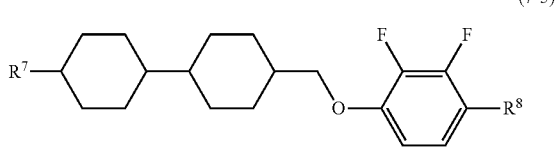

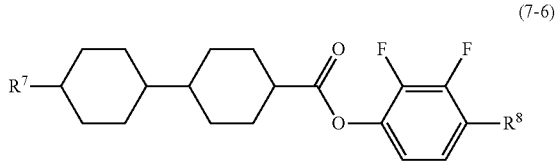

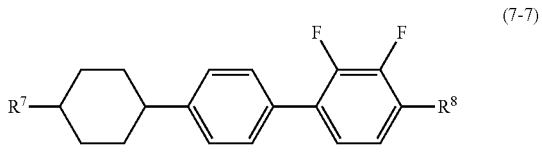

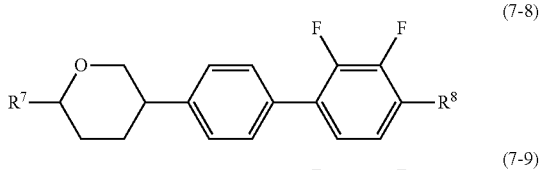

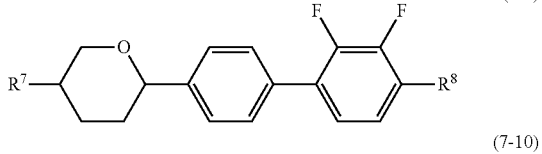

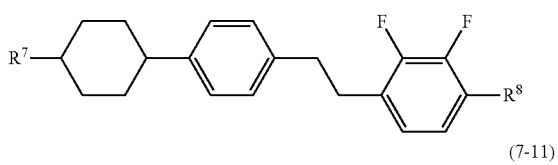

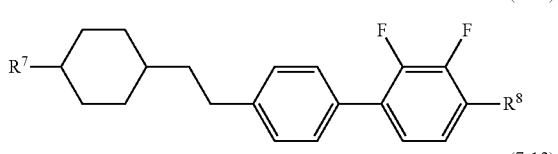

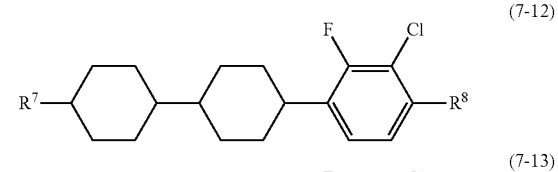

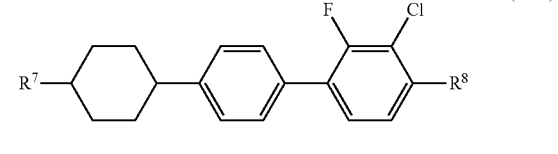

(7-14)
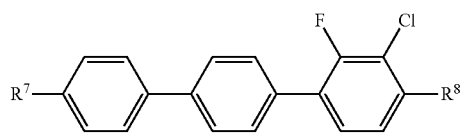
(7-15)
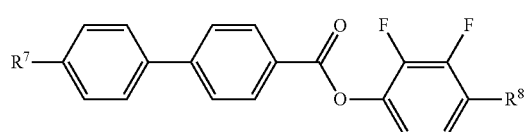
(8-1)
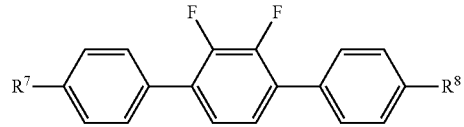
(9-1)
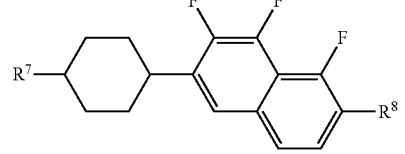
(9-2)
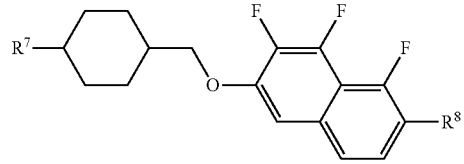
(9-3)
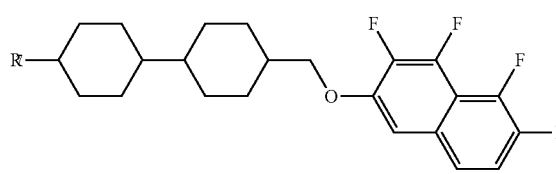
(10-1)
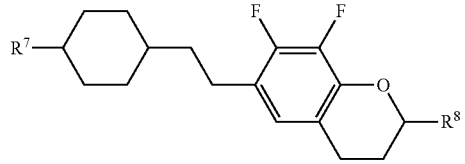
(10-2)
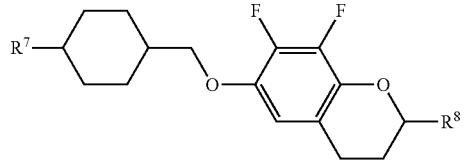
(10-3)
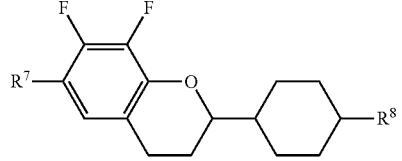
(10-4)
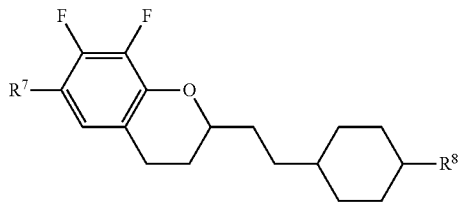
(10-5)
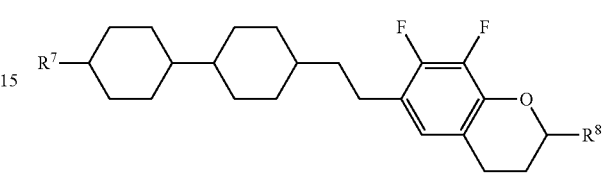
(10-6)
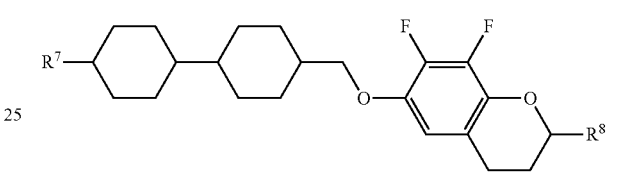
(10-7)
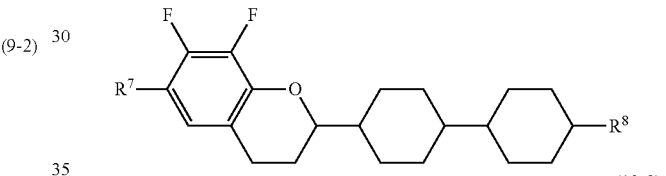
(10-8)
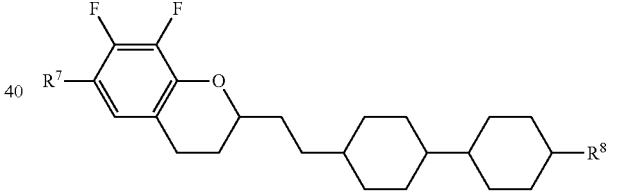
(10-9)
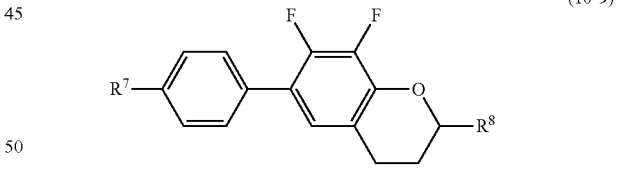
(10-10)
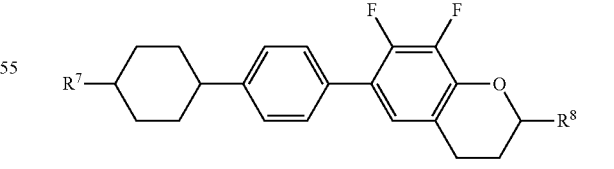
(10-11)
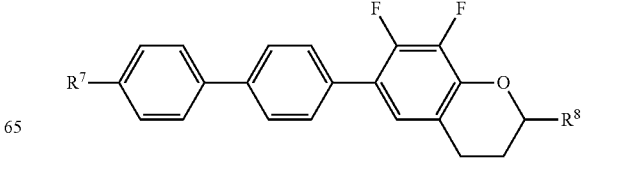

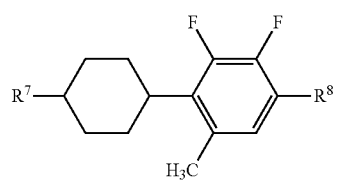

(11-1)

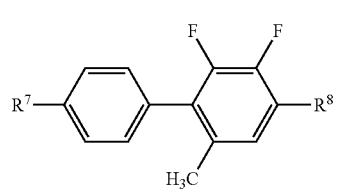

(11-2)

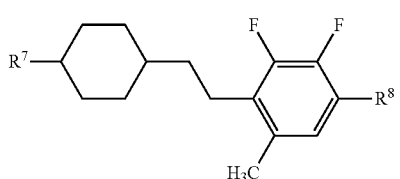

(11-3)

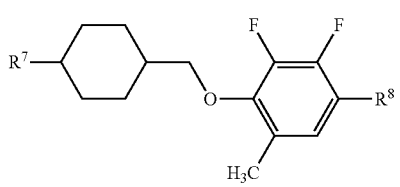

(11-4)

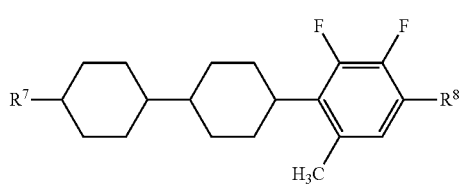

(11-5)

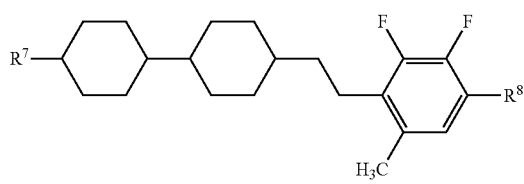

(11-6)

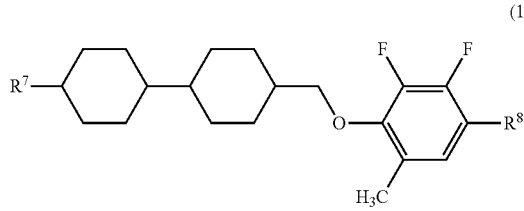

(11-7)

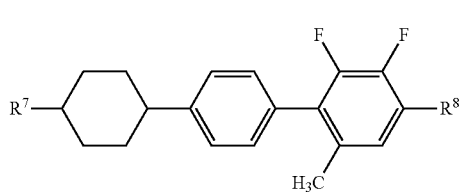

(11-8)

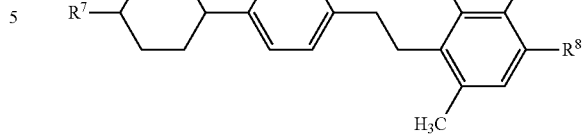

(11-9)

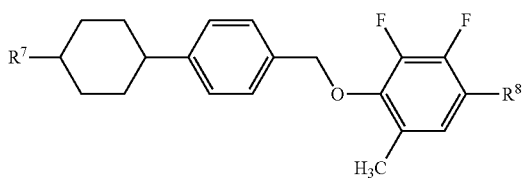

(11-10)

In these compounds (the component D), the definitions of $R^7$ and $R^8$ are just the same as described previously.

The component D is a compound in which the dielectric anisotropy is negative. The component D is mainly used for the preparation of a composition for use in a VA mode or a PSA mode. As the content of the component D is increased, the dielectric anisotropy of the composition increases. However, the viscosity increases. Thus, it is desirable that the content should decrease as long as the required value of the threshold voltage is satisfied. Accordingly, the content is preferably 40% by weight or more in order to ensure adequate voltage drive, in consideration that the absolute value of the dielectric anisotropy is about 5.

In the component D, the compound (6) is mainly effective in adjusting the viscosity, adjusting the optical anisotropy or adjusting the dielectric anisotropy, since it is a two-ring compound. The compounds (7) and (8) are effective in increasing the maximum temperature, increasing the optical anisotropy or increasing the dielectric anisotropy, since it is a three-ring compound. The compounds (9) to (11) are effective in increasing the dielectric anisotropy.

The content of the component D is preferably 40% by weight or more, and more preferably in the range of 50% to 95% by weight, based on the total weight of the composition, in the preparation of a composition for use in a VA mode or a PSA mode. The elastic constant of the composition can be adjusted and the voltage-transmission curve of a device can be adjusted by the addition of the component D. It is desirable that the content of the component D should 30% by weight or less based on the total weight of the composition when the component D is added to a composition having positive dielectric anisotropy The component E is a compound where two terminal groups are alkyl or the like. Desirable examples of the component E include the compounds (12-1) to (12-11), the compounds (13-1) to (13-19) and the compounds (14-1) to (14-6).

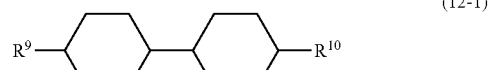

(12-1)

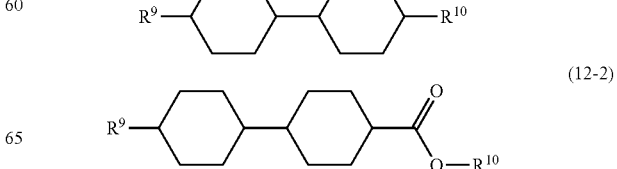

(12-2)

-continued (12-3), (12-4), (12-5), (12-6), (12-7), (12-8), (12-9), (12-10), (12-11), (13-1), (13-2), (13-3), (13-4), (13-5), (13-6), (13-7), (13-8), (13-9), (13-10), (13-11), (13-12), (13-13), (13-14), (13-15)

-continued

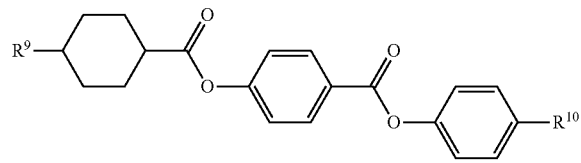
(13-16)

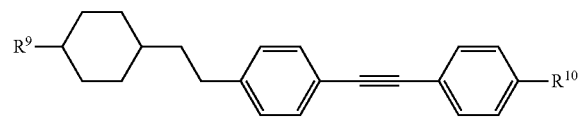
(13-17)

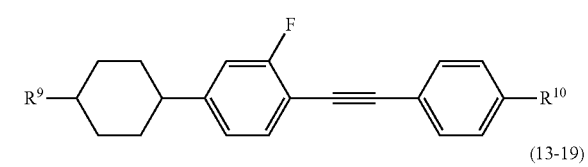
(13-18)

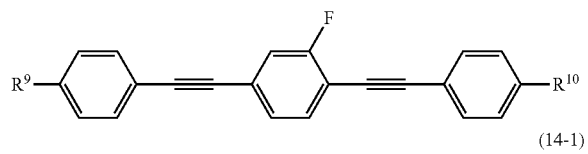
(13-19)

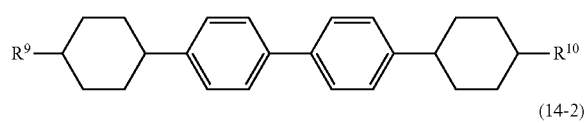
(14-1)

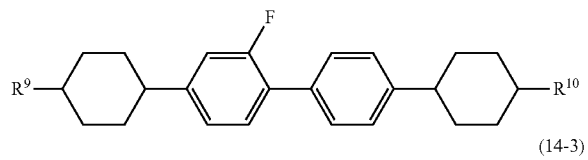
(14-2)

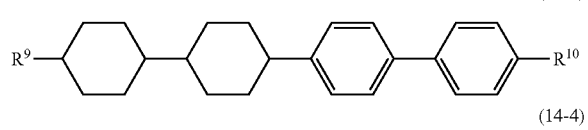
(14-3)

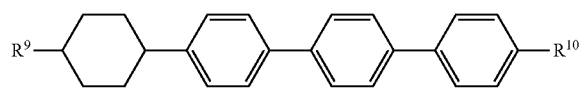
(14-4)

-continued

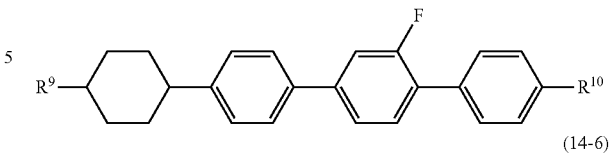
(14-5)

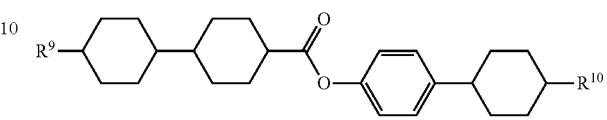
(14-6)

In these compounds (component E), the definitions of $R^9$ and $R^{10}$ are just the same as described previously.

The component E is close to neutral, since the absolute value of the dielectric anisotropy is small. The compound (12) is mainly effective in adjusting the viscosity or adjusting the optical anisotropy. The compounds (13) and (14) are effective in increasing the temperature range of a nematic phase that is caused by an increase in the maximum temperature, or adjusting the optical anisotropy.

As the content of the component E is increased, the viscosity of the composition decreases. However, the dielectric anisotropy decreases. Thus, it is desirable that the content should increase as long as the required value of the dielectric anisotropy is satisfied. Accordingly, the content of the component E is preferably 30% by weight or more, and more preferably 40% by weight or more based on the total weight of the composition, in the preparation of a composition for use in a VA mode or a PSA mode.

The preparation of the composition (1) is carried out according to known methods such as the mutual dissolution of necessary components at a high temperature. An additive may be added to the composition depending on its intended use. Examples of the additive are an optically active compound, a polymerizable compound, a polymerization initiator, an antioxidant, an ultraviolet light absorber and so forth. These kinds of additives are known to a person skilled in the art, and have been described in the literature.

The composition (1) may further include at least one optically active compound. A known chiral dopant can be added as an optically active compound. The chiral dopant is effective in inducing a helical structure in liquid crystals, giving a necessary twist angle and thus preventing a reverse twist. Desirable examples of the chiral dopant include the following optically active compounds (Op-1) to (Op-13).

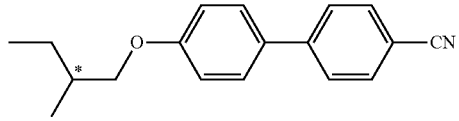
(Op-1)

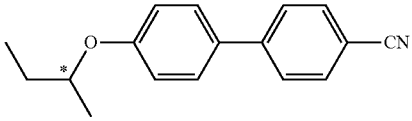
(Op-2)

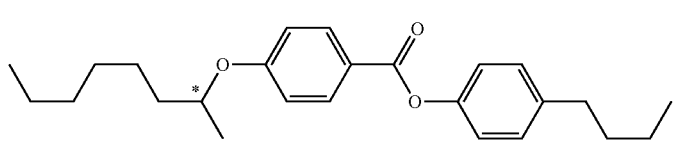
(Op-3)

-continued
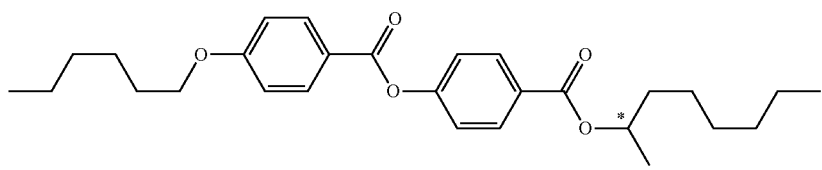
(Op-4)
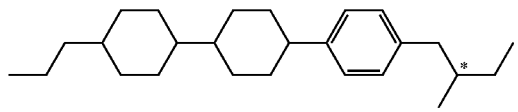
(Op-5)
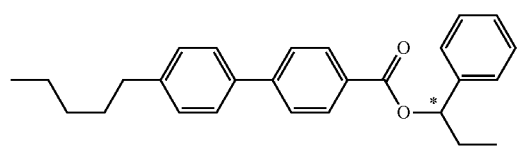
(Op-6)
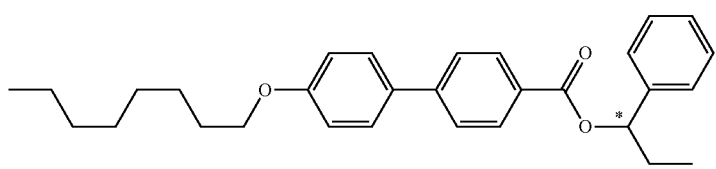
(Op-7)
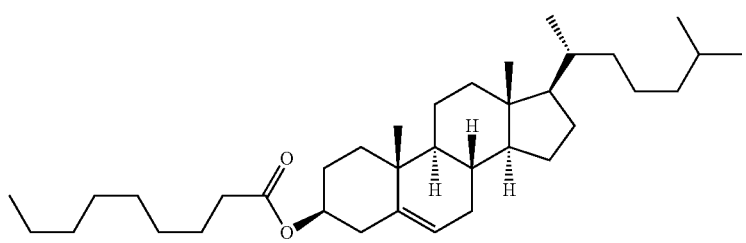
(Op-8)
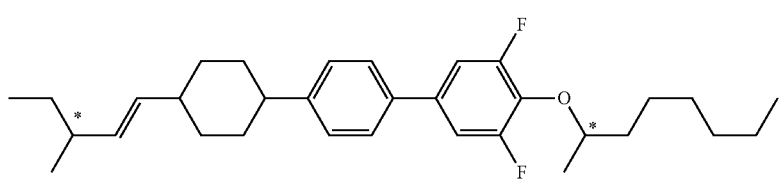
(Op-9)
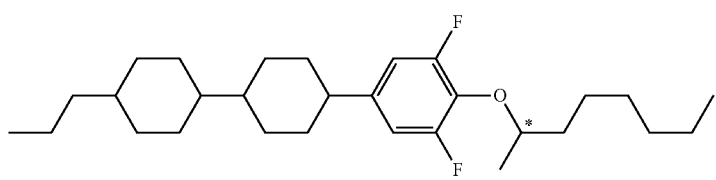
(Op-10)
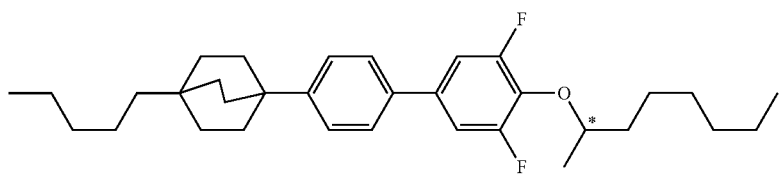
(Op-11)
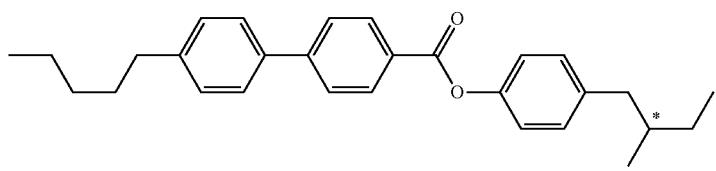
(Op-12)

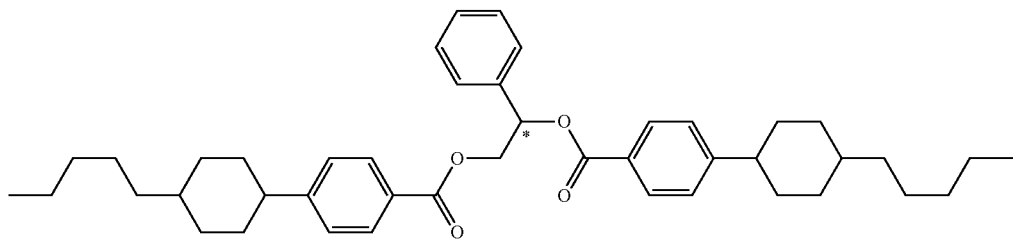
(Op-13)

A helical pitch is adjusted by the addition of an optically active compound to the composition (1). It is desirable to adjust the helical pitch to the range of 40 to 200 micrometers in a composition for use in a TFT mode and a TN mode. It is desirable to adjust the helical pitch to the range of 6 to 20 micrometers in a composition for use in a STN mode. It is desirable to adjust the helical pitch to the range of 1.5 to 4 micrometers in a composition for use in a BTN mode. Two or more optically active compounds may be added for the purpose of adjusting the temperature dependence of the helical pitch.

The composition (1) can be used for use in a PSA mode by the addition of a polymerizable compound. Examples of the polymerizable compound include acrylates, methacrylates, vinyl compounds, vinyloxy compounds, propenyl ethers, epoxy compounds (oxiranes, oxetanes) and vinyl ketones. The polymerizable compound is polymerized on irradiation with ultraviolet light or the like, preferably in the presence of a suitable initiator such as a photopolymerization initiator. Suitable conditions for the polymerization, and a suitable type and a suitable amount of the initiator are known to a person skilled in the art and are described in the literature.

The antioxidant is effective in maintaining a large voltage holding ratio. Desirable examples of the antioxidant include 2,6-di-tert-butyl-4-alkylphenol. The ultraviolet light absorber is effective for preventing a decrease in the maximum temperature. Desirable examples of the ultraviolet light absorber include a benzophenone derivative, a benzoate derivative and a triazole derivative. A light stabilizer such as an amine having steric hindrance is also desirable.

The composition (1) can be used for use in a GH mode by the addition of a dichroic dye such as a merocyanine, styryl, azo, azomethine, azoxy, quinophthalone, anthraquinone or tetrazine compound.

3. Liquid Crystal Display Device

The composition (1) can be used for a liquid crystal display device having an operating mode such as a PC mode, a TN mode, a STN mode, an OCB mode or a PSA mode, which is driven by means of an AM (active matrix) mode. The composition (1) can also be used for a liquid crystal display device having an operating mode such as a PC mode, a TN mode, a STN mode, an OCB mode, a VA mode or an IPS mode, which is driven by means of a PM (passive matrix) mode. These liquid crystal display devices having the AM mode and the PM mode can be applied to any type of a reflection type, a transmission type, and a semi-transmission type.

The composition (1) can be used for a nematic curvilinear aligned phase (NCAP) device containing a composition microencapsulated, and a polymer dispersed-liquid crystal display device (PDLCD) having a three-dimensional network polymer formed in the liquid crystal composition, and a polymer network-liquid crystal display device (PNLCD).

EXAMPLES

The invention will be explained in more detail based on examples. It will be apparent to those skilled in the art that various modifications and variations can be made in the invention and specific examples provided herein without departing from the spirit or scope of the invention. Thus, it is intended that the invention covers the modifications and variations of this invention that come within the scope of any claims and their equivalents. The following examples are for illustrative purposes only and are not intended, nor should they be interpreted to limit the scope of the invention.

1-1. Examples of the Compound (1)

The compound (1) was prepared by the procedures described below. Compounds prepared herein were identified by means of NMR analysis and so forth. Physical properties of the compounds were measured by the methods described below.

NMR Analysis

A model DRX-500 apparatus (made by Bruker BioSpin Corporation) was used for measurement. In the measurement of $^1$H-NMR, a sample was dissolved in a deuterated solvent such as $CDCl_3$, and the measurement was carried out under the conditions of room temperature, 500 MHz and the accumulation of 16 scans. Tetramethylsilane (TMS) was used as the internal standard. In the measurement of $^{19}$F-NMR, $CFCl_3$ was used as the internal standard, and the accumulation of 24 scans was performed. In the explanation of the nuclear magnetic resonance spectra, the symbols s, d, t, q, quin, sex, m and br stand for a singlet, a doublet, a triplet, a quartet, a quintet, a sextet, a multiplet and line-broadening, respectively.

Sample for Measurement

A liquid crystal compound itself was used as a sample when the phase structure and the transition temperature were measured. A composition prepared by mixing the compound and mother liquid crystals was used as a sample when physical properties such as the maximum temperature of a nematic phase, viscosity, optical anisotropy, dielectric anisotropy were measured.

When a sample in which a compound was mixed with mother liquid crystals was used, the measurement was carried out according to the following method. The sample was prepared by mixing 15% by weight of the compound and 85% by weight of the mother liquid crystals. Extrapolated values were calculated from the measured values of the sample by means of an extrapolation method represented by the following equation, and their values were reported. [Extrapolated value]=(100×[Measured value of sample]−[% by weight of mother liquid crystals]×[Measured value of mother liquid crystals])/[% by weight of compound].

When crystals (or a smectic phase) deposited at 25° C. even at this ratio of the compound to the mother liquid crystals, the ratio of the compound to the mother liquid crystals was changed in the order of (10% by weight: 90% by weight), (5% by weight: 95% by weight) and (1% by weight: 99% by weight). The physical properties of the sample were measured at the ratio in which the crystals (or the smectic phase) did not deposit at 25° C. Incidentally, the ratio of the compound to the mother liquid crystals is (15% by weight: 85% by weight), unless otherwise noted.

The following mother liquid crystals (i) were used as mother liquid crystals. The ratio of each component is expressed as a percentage by weight.

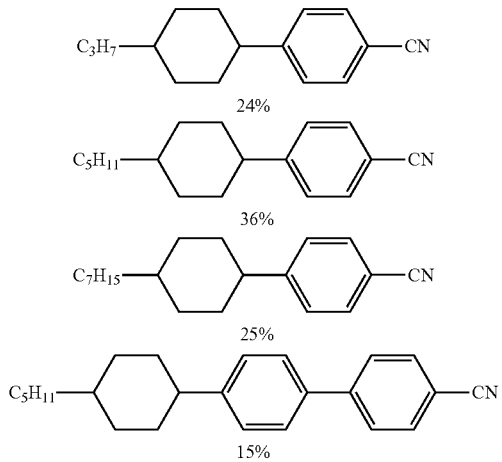

Measurement Method

The physical properties of compounds were measured according to the following methods. Most were methods described in the JEITA standards (JEITA-ED-2521B) which was deliberated and established by Japan Electronics and Information Technology Industries Association (abbreviated to JEITA), or the modified methods. No TFT was attached to a TN device used for measurement.

(1) Phase Structure

A sample was placed on a hot plate of a melting point apparatus (Hot Stage Model FP-52 made by Mettler Toledo International Inc.) equipped with a polarizing microscope, and the phase conditions and their changes were observed with the polarizing microscope while the sample was heated at the rate of 3° C. per minute, and the kinds of phases were specified.

(2) Transition temperature (° C.)

A sample was heated and then cooled at the rate of 3° C. per minute using a Perkin-Elmer differential scanning calorimeter, a DSC-7 System or a Diamond DSC System. The starting point of an endothermic peak or an exothermic peak caused by the phase change of the sample was obtained by means of the extrapolation, and thus the transition temperature was determined. The transition temperature of a compound from solid to a liquid crystal phase such as a smectic phase or a nematic phase may be abbreviated to "the minimum temperature of a liquid crystal phase". The transition temperature of a compound from a liquid crystal phase to liquid may be abbreviated to "a clearing point".

The symbol C stood for crystals, which were expressed as $C_1$ and $C_2$ when the kinds of crystals were distinguishable. The symbols S and N stood for a smectic phase and a nematic phase, respectively. When a smectic A phase, a smectic B phase, a smectic C phase or a smectic F was distinguishable in the smectic phases, it was expressed as $S_A$, $S_B$, $S_C$ or $S_F$, respectively. The symbol I stood for a liquid (isotropic). Transition temperatures were expressed as, for example, "C 50.0 N 100.0 Iso", which means that the transition temperature from crystals to a nematic phase was 50.0° C., and the transition temperature from the nematic phase to a liquid was 100.0° C.

(3) Compatibility at Low Temperatures

Samples were prepared by mixing a compound with mother liquid crystals so that the ratio of the compound became 20% by weight, 15% by weight, 10% by weight, 5% by weight, 3% by weight and 1% by weight, and placed in glass vials. After these glass vials had been kept in a freezer at −10° C. or −20° C. for a certain period of time, they were observed as to whether or not crystals (or a smectic phase) had deposited.

(4) Maximum Temperature of a Nematic Phase ($T_{NI}$ or NI; ° C.)

A sample was placed on a hot plate in a melting point apparatus equipped with a polarizing microscope and was heated at the rate of 1° C. per minute. The temperature was measured when part of the sample began to change from a nematic phase to an isotropic liquid. A higher limit of the temperature range of a nematic phase may be abbreviated to "the maximum temperature." The symbol $T_{NI}$ means that the sample was a mixture of a compound and mother liquid crystals. The symbol NI means that the sample was a mixture of a compound and the component B and so forth.

(5) Minimum Temperature of a Nematic Phase (Tc; ° C.)

A sample having a nematic phase was kept in freezers at temperatures of 0° C., −10° C., −20° C., −30° C. and −40° C. for 10 days, and then the liquid crystal phases were observed. For example, when the sample maintained the nematic phase at −20° C. and changed to crystals or a smectic phase at −30° C., $T_C$ was expressed as ≤−20° C. A lower limit of the temperature range of a nematic phase may be abbreviated to "the minimum temperature."

(6) Viscosity (Bulk Viscosity; η; Measured at 20° C.; mPa·s)

An E-type viscometer was used for measurement.

(7) Viscosity (Rotational Viscosity; γ1; Measured at 25° C.; mPa·s)

Measurement was carried out according to the method described in M. Imai, et al., Molecular Crystals and Liquid Crystals, Vol. 259, 37 (1995). A sample was poured into a TN device in which the twist angle was 0 degrees and the distance between the two glass substrates (cell gap) was 5 micrometers. A voltage with an increment of 0.5 volt in the range of 16 to 19.5 volts was applied stepwise to the device. After a period of 0.2 second with no voltage, a voltage was applied repeatedly under the conditions of only one rectangular wave (rectangular pulse; 0.2 second) and of no voltage (2 seconds) The peak current and the peak time of the transient current generated by the applied voltage were measured. The value of rotational viscosity was obtained from the measured values and the calculating equation (8) on page 40 of the paper presented by M. Imai, et al. The value of dielectric anisotropy necessary for this calculation was obtained by use of the device that had been used for the measurement of rotational viscosity, according to the method that will be described below.

(8) Optical Anisotropy (Refractive Index Anisotropy; Δn; Measured at 25° C.)

Measurement was carried out using an Abbe refractometer with a polarizing plate attached to the ocular, using light at a wavelength of 589 nanometers. The surface of the main prism was rubbed in one direction, and then a sample was placed on the main prism. The refractive index (n∥) was measured when the direction of the polarized light was parallel to that of the rubbing. The refractive index (n⊥) was measured when the direction of polarized light was perpendicular to that of the rubbing. The value of the optical anisotropy (Δn) was calculated from the equation: Δn=n∥−n⊥.

(9) Dielectric Anisotropy (Δ∈; measured at 25° C.)

A sample was poured into a TN device in which the distance between the two glass substrates (cell gap) was 9 micrometers and the twist angle was 80 degrees. Sine waves (10 V, 1 kHz) were applied to this device, and the dielectric constant (∈∥) in a major axis direction of liquid crystal molecules was measured after 2 seconds. Sine waves (0.5 V, 1 kHz) were applied to the device and the dielectric constant (∈⊥) in a minor axis direction of the liquid crystal molecules was measured after 2 seconds. The value of dielectric anisotropy was calculated from the equation: Δ∈=∈∥−∈⊥.

(10) Elastic Constant (K; Measured at 25° C.; pN)

A LCR meter Model HP 4284-A made by Yokokawa Hewlett-Packard, Ltd. was used for measurement. A sample was poured into a homogeneous device in which the distance between the two glass substrates (cell gap) was 20 micrometers. An electric charge of 0 volts to 200 volts was applied to the cell, and the electrostatic capacity and the applied voltage were measured. The measured values of the electric capacity (C) and the applied voltage (V) were fitted to the equation (2.98) and the equation (2.101) in page 75 of the "Ekisho Debaisu Handobukku" (Liquid Crystal Device Handbook, in English; The Nikkan Kogyo Shimbun, Ltd., Japan) and the values of $K_{11}$ and $K_{33}$ were obtained from the equation (2.99). Next, the value of $K_{22}$ was calculated from the equation (3.18) in page 171 and the values of $K_{11}$ and $K_{33}$ thus obtained. The elastic constant was an average value of $K_{11}$, $K_{22}$ and $K_{33}$.

(11) Threshold Voltage (Vth; Measured at 25° C.; V)

Measurement was carried out with an LCD evaluation system Model LCD-5100 made by Otsuka Electronics Co., Ltd. The light source was a halogen lamp. A sample was poured into a TN device having a normally white mode, in which the distance between the two glass substrates (cell gap) was about 4.45/An (micrometers) and the twist angle was 80 degrees. Voltage to be applied to the device (32 Hz, rectangular waves) was stepwise increased in 0.02 V increments from 0 V up to 10 V. During the increase, the device was irradiated with light in the perpendicular direction, and the amount of light passing through the device was measured. A voltage-transmittance curve was prepared, in which the maximum amount of light corresponded to 100% transmittance and the minimum amount of light corresponded to 0% transmittance. The threshold voltage was voltage at 90% transmittance.

(12) Voltage Holding Ratio (VHR-1; Measured at 25° C.; %)

A TN device used for measurement had a polyimide-alignment film, and the distance between the two glass substrates (cell gap) was 5 micrometers. A sample was poured into the device, and then the device was sealed with an adhesive curable on irradiation with ultraviolet light. A pulse voltage (60 microseconds at 5 V) was applied to the device and the device was charged. A decreasing voltage was measured for 16.7 milliseconds with a high-speed voltmeter, and the area A between a voltage curve and a horizontal axis in a unit cycle was obtained. The area B was an area without the decrease. The voltage holding ratio was a percentage of the area A to the area B.

(13) Voltage Holding Ratio (VHR-2; Measured at 80° C.; %)

A TN device used for measurement had a polyimide-alignment film, and the distance between the two glass substrates (cell gap) was 5 micrometer. A sample was poured into the device, and then the device was sealed with an adhesive curable on irradiation with ultraviolet light. A pulse voltage (60 microseconds at 5 V) was applied to the TN device and the device was charged. A decreasing voltage was measured for 16.7 milliseconds with a high-speed voltmeter and the area A between a voltage curve and a horizontal axis in a unit cycle was obtained. The area B was an area without the decrease. The voltage holding ratio was a percentage of the area A to the area B.

Materials

Solmix A-11 (registered trademark) was a mixture of ethanol (85.5%), methanol (13.4%) and isopropanol (1.1%), and was available from Japan Alcohol Trading Co., Ltd. Tetrahydrofuran may be abbreviated to THF.

Example 1

Preparation of the Compound (No. 5)

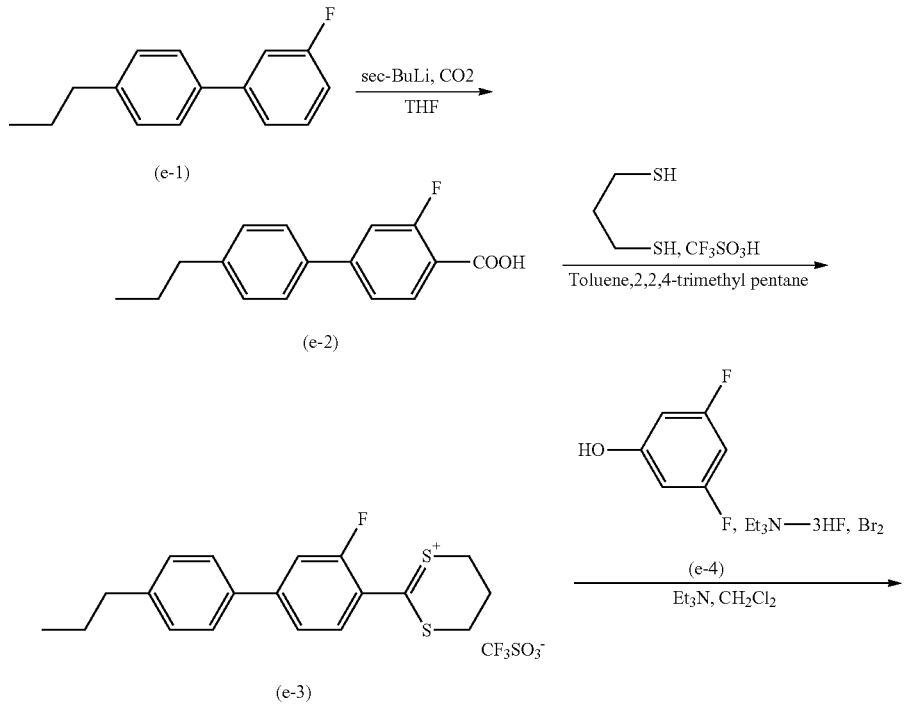

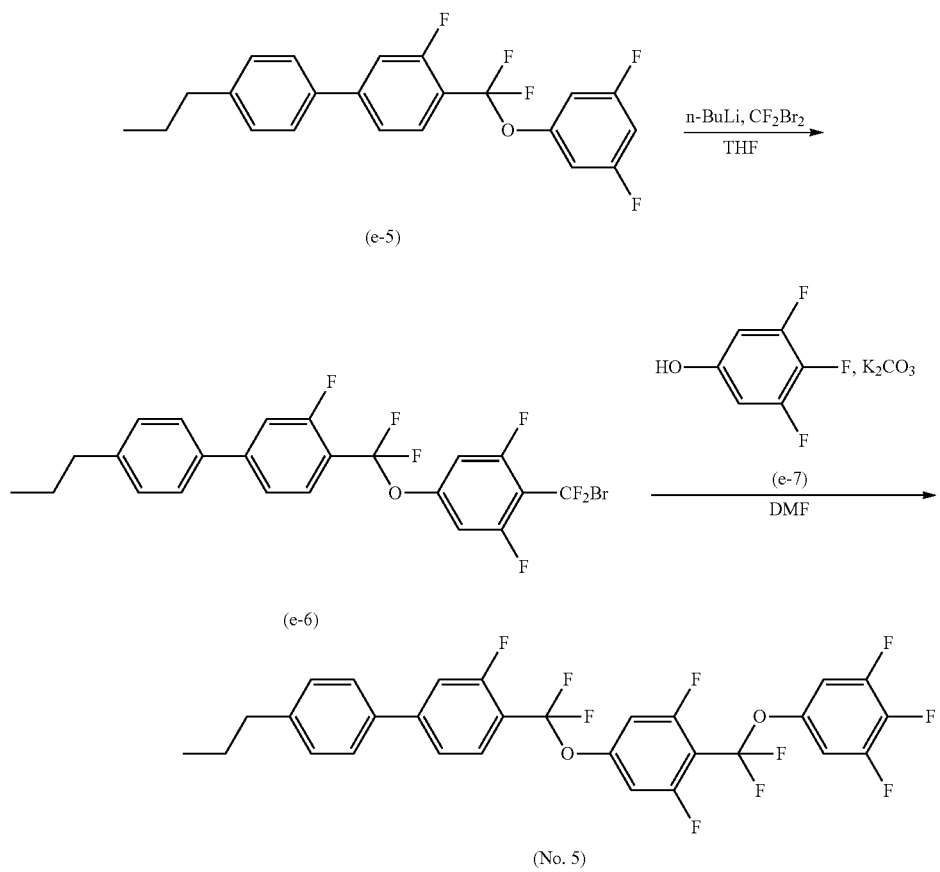

First Step:

The compound (e-1) (30.00 g) and THF (150 ml) were placed in a reaction vessel under an atmosphere of nitrogen, and the mixture was cooled to −74° C. sec-Butyllithium (1.07 M; n-hexane solution; 157.0 ml) was added dropwise in the temperature range of −74° C. to −70° C., and the stirring was continued for another 60 minutes. Dry ice (12.32 g) was added in the temperature range of −75° C. to −70° C., and the stirring was continued for another 60 minutes while the mixture was allowed to warm to 25° C. The reaction mixture was poured into ice-water, and the aqueous layer was extracted with toluene. The combined organic layers were washed with brine, and then dried over anhydrous magnesium sulfate. The solution was concentrated under reduced pressure, and the residue was washed with heptane to give the compound (e-2) (28.31 g; 78.3%).

Second Step:

The compound (e-2) (28.31 g), 2,2,4-trimethylpentane (60.0 ml) and toluene (60.0 ml) were placed in a reaction vessel under an atmosphere of nitrogen, and the mixture was heated to 60° C. Propanedithiol (12.1 ml) was added dropwise and the stirring was continued for another 90 minutes. Trifluoromethanesulfonic acid (36.18 g) was added slowly. The mixture was stirred at 60° C. for 60 minutes, and then at 110° C. for 120 minutes. The reaction mixture was cooled to 25° C., and was concentrated under reduced pressure. The products were purified by recrystallization from t-butyl methyl ether to give the dithianylium salt (e-3) (43.99 g; 83.5%)

Third Step:

3,5-Difluorophenol (e-4) (14.29 g), triethylamine (16.6 ml) and dichloromethane (150 ml) were placed in a reaction vessel under an atmosphere of nitrogen, and the mixture was cooled to −70° C. The dithianylium salt (e-3) (43.99 g) in a dichloromethane (300 ml) solution was slowly added dropwise. After 60 minutes of stirring, a hydrogen fluoride-triethylamine complex (44.8 ml) was added dropwise, and the stirring was continued for another 30 minutes. Bromine (23.5 ml) was slowly added, and the stirring was continued for another 60 minutes. The reaction mixture was warmed to 25° C., and poured into ice-water. Sodium hydrogencarbonate was added slowly to the mixture to neutralize. The organic layer was washed successively with water, a saturated aqueous solution of sodium hydrogencarbonate and water, and then dried over anhydrous magnesium sulfate. The solution was concentrated under reduced pressure, and the residue was purified by silica gel chromatography (heptane: toluene=5:1 by volume) to give the compound (e-5) (25.79 g; 71.8%).

Fourth Step:

The compound (e-5) (25.79 g) and THF (130 ml) were placed in a reaction vessel under an atmosphere of nitrogen, and the mixture was cooled to −74° C. n-Butyllithium (1.57 M; n-hexane solution; 50.2 ml) was added dropwise in the temperature range of −74° C. to −70° C., and the stirring was continued for another 60 minutes. Dibromodifluoromethane (16.55 g) in a THF (40.0 ml) solution was added dropwise in the temperature range of −75° C. to −70° C., and the stirring was continued for another 60 minutes while the mixture was allowed to warm to 25° C. The reaction mixture was poured into ice-water, and the aqueous layer was extracted with toluene. The combined organic layers were washed with brine, and then dried over anhydrous magnesium sulfate. The solution was concentrated under reduced pressure, and the residue was purified by silica gel chromatography (heptane) to give the compound (e-6) (23.06 g; 67.3%).

Fifth Step:

3,4,5-Trifluorophenol (e-7) (7.87 g), potassium carbonate (18.66 g) and DMF (50 ml) were placed in a reaction vessel under an atmosphere of nitrogen, and the mixture was heated to 90° C. and stirred for 0.5 hour. The compound (e-6) (23.06 g) in a DMF (50 ml) solution was added dropwise, and the stirring was continued at 90° C. for another 1 hour. The reaction mixture was cooled to 25° C., and poured into water, and the aqueous layer was extracted with toluene. The combined organic layers were washed with water, and then dried over anhydrous magnesium sulfate. The solution was concentrated under reduced pressure, and the residue was purified by silica gel chromatography (heptane). The product was further purified by recrystallization from a mixed solvent of heptane and Solmix A-11 (1:1 by volume) to give the compound (No. 5) (3.15 g; 12.1%).

$^1$H-NMR ($\delta$ ppm; CDCl$_3$): 7.72 (dd, 1H), 7.52 (d, 2H), 7.46 (dd, 1H), 7.41 (dd, 1H), 7.30 (d, 2H), 7.00-6.96 (m, 4H), 2.65 (t, 2H), 1.69 (q, 2H) and 0.98 (t, 3H).

The physical properties of the compound (No. 5) were as follows. Transition temperature: C 67.8 N 76.9 I. $T_{NI}$=65.0° C.; $\eta$=58.5 mPa·s; $\Delta$n=0.150; and $\Delta\epsilon$=39.0.

Example 2

Preparation of the Compound (No. 31)

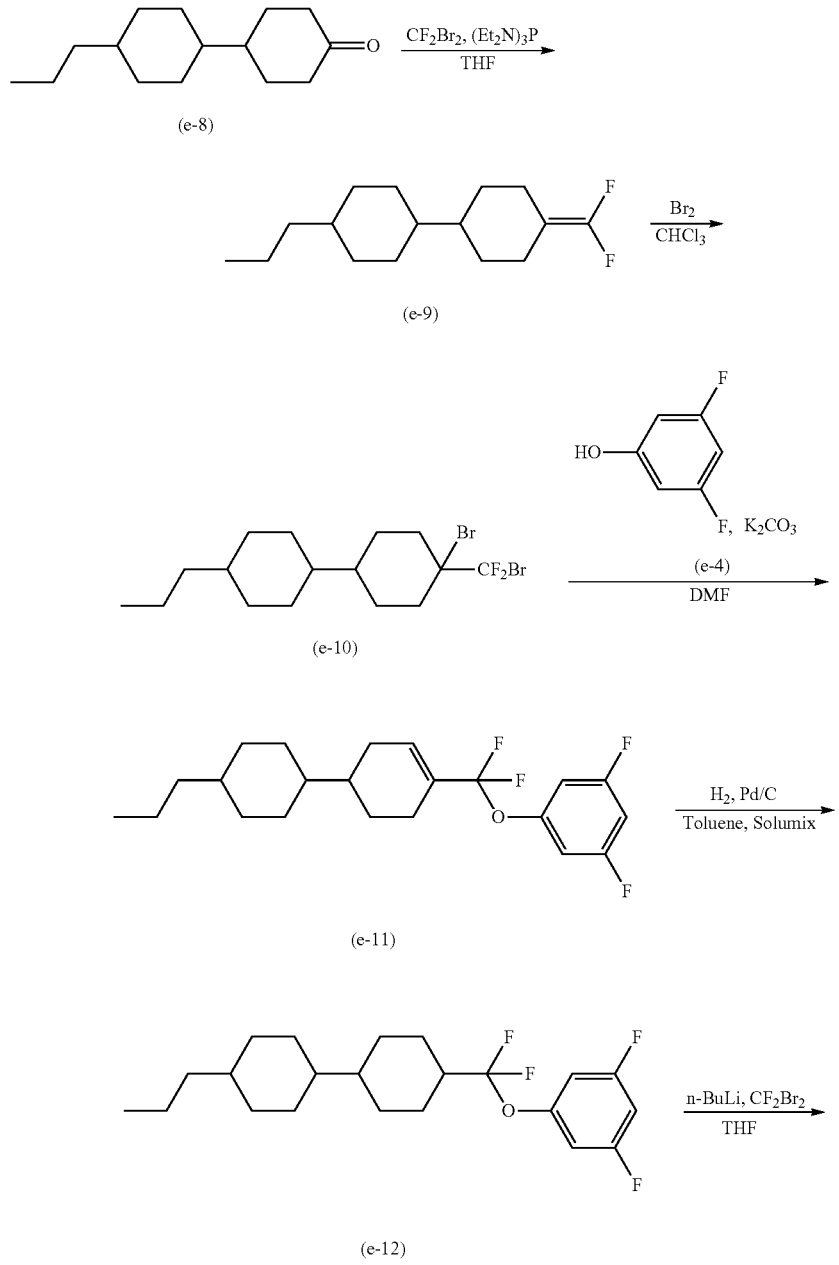

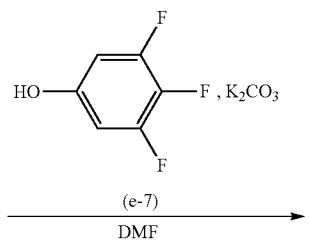
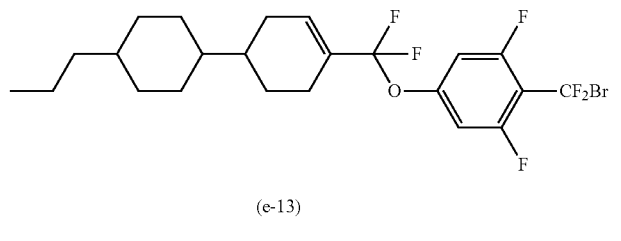

(e-13)

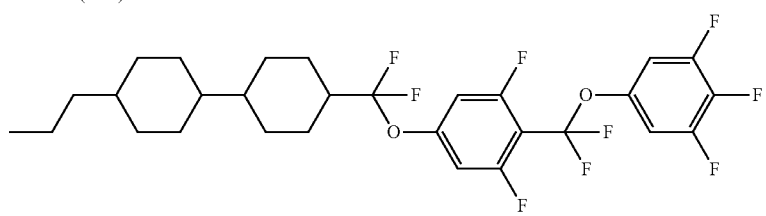

(No. 31)

First Step:

Dibromodifluoromethane (28.31 g) and THF (60 ml) were placed in a reaction vessel under an atmosphere of nitrogen. N,N,N',N',N'',N''-Hexaethylphosphinetriamine (68.97 g) in a THF (140 ml) solution was added dropwise under the conditions that the reaction temperature did not exceed 30° C., and the stirring was continued at 0° C. for another 1 hour. The compound (e-8) (20.00 g) in a THF (50 ml) solution was added dropwise under the conditions that the reaction temperature did not exceed 30° C., and the stirring was continued at 25° C. for another 20 hours. The reaction mixture was poured into water, and the aqueous layer was extracted with heptane. The combined organic layers were washed with water, 3N-hydrochloric acid and water, and then dried over anhydrous magnesium sulfate. The solution was concentrated under reduced pressure, and the residue was purified by silica gel chromatography (heptane) to give the compound (e-9) (19.37 g; 84.0%).

Second Step:

The compound (e-9) (19.37 g) and chloroform (100 ml) were placed in a reaction vessel under an atmosphere of nitrogen, and the mixture was cooled to −30° C. Bromine (12.68 g) in a chloroform (20 ml) solution was added dropwise in the temperature range of −34° C. to −20° C., and the stirring was continued for another 1 hour. The reaction mixture was warmed to 25° C. and poured into water, and the aqueous layer was extracted with heptane. The combined organic layers were washed with water, an aqueous solution of sodium thiosulfate and water, and then dried over anhydrous magnesium sulfate. The solution was concentrated under reduced pressure, and the residue was purified by silica gel chromatography (heptane) to give the compound (e-10) (29.08 g; 92.5%).

Third Step:

3,5-Difluorophenol (e-4) (9.55 g), potassium carbonate (19.31 g) and DMF (100 ml) were placed in a reaction vessel under an atmosphere of nitrogen, and the mixture was stirred at 115° C. for 0.5 hour. The compound (e-10) (29.08 g) in a DMF (60 ml) solution was added dropwise, and the stirring was continued at 115° C. for another 1 hour. The reaction mixture was cooled to 25° C., and poured into water, and the aqueous layer was extracted with toluene. The combined organic layers were washed with water, and then dried over anhydrous magnesium sulfate. The solution was concentrated under reduced pressure, and the residue was purified by silica gel chromatography (heptane). The product was further purified by recrystallization from a mixed solvent of heptane and Solmix A-11 (1:1 by volume) to give the compound (e-11) (15.91 g; 59.2%).

Fourth Step:

The compound (e-11) (15.91 g) was dissolved in a mixed solvent of toluene (150 ml) and Solmix A-11 (150 ml), to which Pd/C (0.40 g) was added, and the mixture was stirred at room temperature under a hydrogen atmosphere until hydrogen absorption had ceased. After the completion of the reaction, Pd/C was filtered off, and then the solvent was distilled off. The residue was purified by silica gel chromatography (heptane), and then purified by recrystallization from a mixed solvent of heptane and Solmix A-11 (1:1 by volume) to give the compound (e-12) (11.58 g; 72.4%).

Fifth Step:

The compound (e-12) (11.58 g) and THF (60 ml) were placed in a reaction vessel under an atmosphere of nitrogen, and the mixture was cooled to −74° C. n-Butyllithium (1.67 M; n-hexane solution; 21.5 ml) was added dropwise in the temperature range of −74° C. to −70° C., and the stirring was continued for another 60 minutes. Dibromodifluoromethane (7.54 g) in a THF (20.0 ml) solution was added dropwise in the temperature range of −75° C. to −70° C., and the stirring was continued for another 60 minutes while the mixture was allowed to warm to 25° C. The reaction mixture was poured into ice-water, and the aqueous layer was extracted with toluene. The combined organic layers were washed with brine, and then dried over anhydrous magnesium sulfate. The solution was concentrated under reduced pressure, and the residue was purified by silica gel chromatography (heptane) to give the compound (e-13) (14.77 g; 95.7%).

Sixth Step:

3,4,5-Trifluorophenol (e-7) (3.82 g), potassium carbonate (11.88 g) and DMF (50 ml) were placed in a reaction vessel under an atmosphere of nitrogen, and the mixture was stirred at 90° C. for 0.5 hour. The compound (e-13) (14.77 g) in a DMF (50 ml) solution was added dropwise, and the stirring was continued at 90° C. for another 1 hour. The reaction mixture was cooled to 25° C., and poured into water, and the aqueous layer was extracted with toluene. The combined organic layers were washed with water, and then dried over anhydrous magnesium sulfate. The solution was concentrated under reduced pressure, and the residue was purified by silica gel chromatography (heptane). The product was further purified by recrystallization from a mixed solvent of heptane and Solmix A-11 (1:1 by volume) to give the compound (No. 31) (8.45 g; 50.6%).

$^1$H-NMR (δ ppm; CDCl$_3$): 6.96 (dd, 2H), 6.85 (d, 2H), 2.03-1.96 (m, 3H), 1.86-1.84 (m, 2H), 1.77-1.70 (m, 4H), 1.37-1.23 (m, 4H), 1.15-1.13 (m, 3H), 1.10-0.94 (m, 6H) and 0.89-0.82 (m, 5H).

The physical properties of the compound (No. 31) were as follows. Transition temperature: C 76.8 N 168.3 I. $T_{NI}$=121.7° C.; η=57.1 mPa·s; Δn=0.110; and Δ∈=24.1.

Example 3

Preparation of the Compound (No. 3)

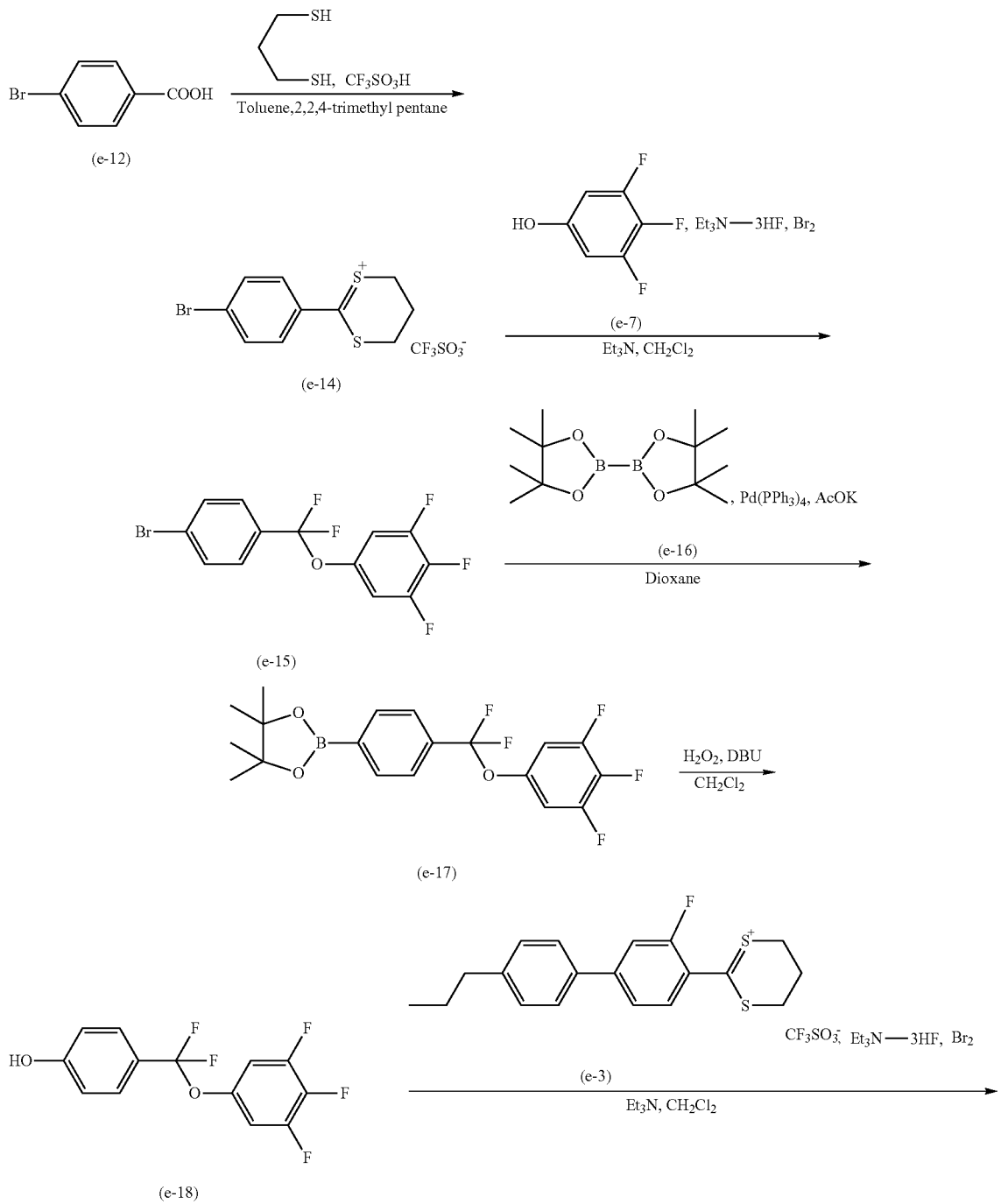

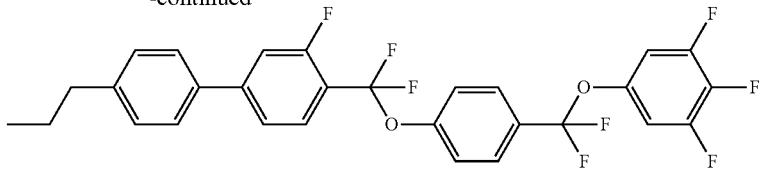

(No. 3)

First Step:

The compound (e-13) (75.00 g), 2,2,4-trimethylpentane (150.0 ml) and toluene (150.0 ml) were placed in a reaction vessel under an atmosphere of nitrogen, and the mixture was heated to 60° C. Propanedithiol (41.2 ml) was added dropwise, and the mixture was stirred for 90 minutes. Trifluoromethanesulfonic acid (123.20 g) was added slowly. The mixture was stirred at 60° C. for 60 minutes, and then stirred at 110° C. for 120 minutes. The reaction mixture was cooled to 25° C., and concentrated under reduced pressure. The residue was purified by recrystallization from t-butyl methyl ether to give the dithianylium salt (e-14) (78.38 g; 49.6%).

Second Step:

3,4,5-Trifluorophenol (e-7) (8.39 g), triethylamine (8.6 ml) and dichloromethane (70 ml) were placed in a reaction vessel under an atmosphere of nitrogen, and the mixture was cooled to −70° C. The dithianylium salt (e-14) (20.00 g) in a dichloromethane (140 ml) solution was slowly added dropwise. After 60 minutes of stirring, a hydrogen fluoride-pyridine complex (23.2 ml) was added dropwise, and the mixture was stirred for 30 minutes. Bromine (12.2 ml) was added slowly, and the mixture was stirred for 60 minutes. The reaction mixture was warmed to 25° C., and poured into ice-water. Sodium hydrogencarbonate was added slowly to the mixture to neutralize. The organic layer was washed successively with water, a saturated aqueous solution of sodium hydrogencarbonate and water, and then dried over anhydrous magnesium sulfate. The solution was concentrated under reduced pressure, and the residue was purified by silica gel chromatography (heptane) to give the compound (e-15) (8.87 g; 53.2%).

Third Step:

The compound (e-15) (8.87 g), bis(pinacolato)diborane (e-16) (7.02 g), tetrakistriphenylphosphine (0.44 g), potassium acetate (7.40 g) and 1,4-dioxane (40 ml) were placed in a reaction vessel under an atmosphere of nitrogen, and the mixture was heated to reflux for 3 hours. The reaction mixture was cooled to 25° C., and poured into water, and then aqueous layer was extracted with toluene. The combined organic layers were washed with water, and then dried over anhydrous magnesium sulfate. The solution was concentrated under reduced pressure, and the residue was purified by silica gel chromatography (by volume, heptane: ethyl acetate=20:1) to give the compound (e-17) (9.45 g; 93.9%).

Fourth Step:

The compound (e-17) (9.45 g), 1,8-diazabicyclo[5.4.0]undec-7-ene (DBU) (0.36 g) and dichloromethane (40 ml) were placed in a reaction vessel under an atmosphere of nitrogen. Hydrogen peroxide (30%; aqueous solution; 5.35 g) was slowly added dropwise. After 2 hours of stirring, the reaction mixture was poured into water, and aqueous layer was extracted with dichloromethane (10 ml) twice. The combined organic layers were washed successively with water and a saturated aqueous solution of sodium thiosulfate, and then dried over anhydrous magnesium sulfate. The anhydrous magnesium sulfate was filtered off, and the solution itself was used for the next reaction.

Fifth Step:

The compound (e-18) in a dichloromethane solution and triethylamine (3.6 ml) were placed in a reaction vessel under an atmosphere of nitrogen, and the mixture was cooled to −70° C. The dithianylium salt (e-3) (9.45 g), which was prepared according to the method described in Example 1, in a dichloromethane (70 ml) solution was slowly added dropwise. After 60 minutes of stirring, a hydrogen fluoride-pyridine complex (9.6 ml) was added dropwise, and the mixture was stirred for 30 minutes. Bromine (5.0 ml) was added slowly, and the mixture was stirred for 60 minutes. The reaction mixture was warmed to 25° C., and poured into ice-water. Sodium hydrogencarbonate was added slowly to the mixture to neutralize. The organic layer was washed successively with water, a saturated aqueous solution of sodium hydrogencarbonate and water, and then dried over anhydrous magnesium sulfate. The solution was concentrated under reduced pressure, and the residue was purified by silica gel chromatography (heptane). The product was further purified by recrystallization from a mixed solvent of heptane and Solmix A-11 (by volume, 1:1) to give the compound (No. 3) (4.68 g). The yield based on the compound (e-17) was 35.9%.

$^1$H-NMR (δ ppm; CDCl$_3$): 7.78 (dd, 1H), 7.74 (d, 2H), 7.55 (d, 2H), 7.48-7.42 (m, 4H), 7.32 (d, 2H), 7.00-6.97 (m, 2H), 2.68 (t, 2H), 1.75-1.68 (m, 2H) and 1.00 (t, 3H).

The physical properties of the compound (No. 3) were as follows. Transition temperature: C 83.5 N 111.6 I. $T_{NI}$=88.4° C.; η=46.0 mPa·s; Δn=0.164; and Δ∈=32.2.

Example 4

Preparation of the Compound (No. 1)

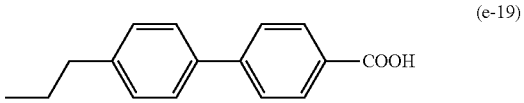

(e-19)

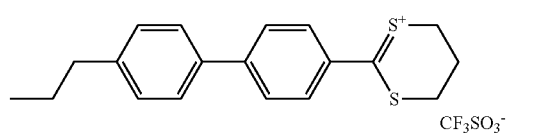

(e-20)

-continued

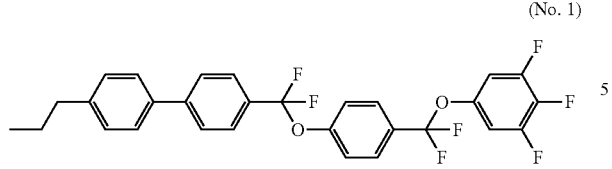
(No. 1)

The compound (e-20) was prepared using the compound (e-19) instead of the compound (e-2) in the procedure of Example 1. The compound (No. 1) was obtained using the compound (e-20) instead of the compound (e-3) in the procedure of Example 3.

$^1$H-NMR (δ ppm; CDCl$_3$): 7.79 (d, 2H), 7.72-7.69 (m, 4H), 7.54 (d, 2H), 7.41 (d, 2H), 7.29 (d, 2H), 7.00-6.95 (m, 2H), 2.65 (t, 2H), 1.73-1.65 (m, 2H) and 0.98 (t, 3H).

The physical properties of the compound (No. 1) were as follows. Transition temperature: C 123.7 N 139.6 I. $T_{NI}$=107.7° C.; η=34.6 mPa·s; Δn=0.177; and Δ∈=26.1. Incidentally, the sample for measurement was prepared from 5% by weight of the compound (No. 1) and 95% by weight of the mother liquid crystals (i). This is because crystals deposited at the normal ratio (15% by weight:85% by weight).

Example 5

Preparation of the Compound (No. 29)

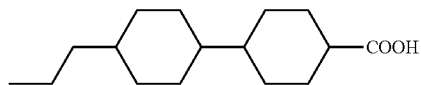
(e-21)

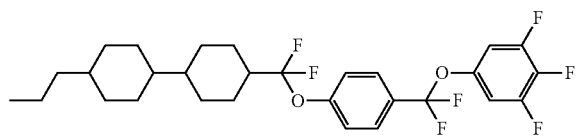
(No. 29)

The compound (No. 29) was obtained using the compound (e-21) instead of the compound (e-19) in the procedure of Example 4.

$^1$H-NMR (δ ppm; CDCl$_3$): 7.65 (d, 2H), 7.27 (d, 2H), 6.97-6.93 (m, 2H), 2.06-1.98 (m, 3H), 1.86-1.84 (m, 2H), 1.77-1.71 (m, 4H), 1.41-1.25 (m, 6H), 1.16-0.96 (m, 7H) and 0.89-0.82 (t, 3H).

The physical properties of the compound (No. 29) were as follows. Transition temperature: C 68.3 N 190.0 I. $T_{NI}$=147.7° C.; η=50.2 mPa·s; Δn=0.117; and Δ∈=17.5.

Example 6

Preparation of the Compound (No. 90)

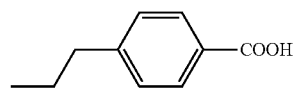
(e-22)

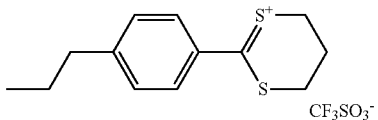
(e-23)

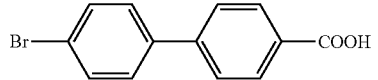
(e-24)

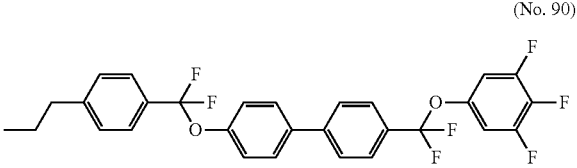
(No. 90)

The compound (e-23) was prepared using the compound (e-22) instead of the compound (e-2) in the procedure of Example 1.

The compound (No. 90) was obtained using the compound (e-23) instead of the compound (e-3) and using the compound (e-24) instead of the compound (e-13) in the procedure of example 3.

$^1$H-NMR (δ ppm; CDCl$_3$): 7.76 (d, 2H), 7.69-7.66 (m, 4H), 7.60 (d, 2H), 7.38 (d, 2H), 7.30 (d, 2H), 7.00-6.97 (m, 2H), 2.66 (t, 2H), 1.71-1.64 (m, 2H) and 0.96 (t, 3H).

The physical properties of the compound (No. 90) were as follows. Transition temperature: C 99.4 S$_C$ 117.2 S$_A$ 126.8 N 144.7 I. $T_{NI}$=106.7° C.; η=36.6 mPa·s; Δn=0.177; and Δ∈=26.1.

Incidentally, the sample for measurement was prepared from 10% by weight of the compound (No. 90) and 90% by weight of the mother liquid crystals (i). This is because crystals deposited at the normal ratio (15% by weight:85% by weight).

Example 7

Preparation of the Compound (No. 99)

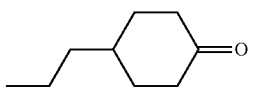
(e-25)

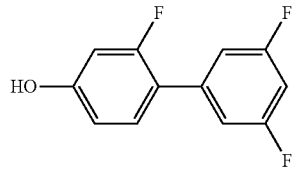
(e-26)

-continued (No. 99)

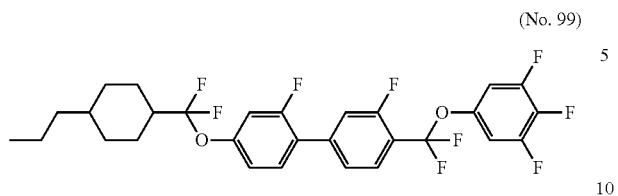

The compound (No. 99) was obtained using the compound (e-26) instead of the compound (e-4) and using the compound (e-25) instead of the compound (e-8) in the procedure of Example 1.

$^1$H-NMR (δ ppm; CDCl$_3$): 7.39 (dd, 1H), 7.19 (d, 2H), 7.10-7.06 (m, 2H), 7.00-6.98 (m, 2H), 2.04-2.02 (m, 3H), 1.89-1.87 (m, 2H), 1.44-1.30 (m, 4H), 1.22-1.19 (m, 3H) and 0.98-0.88 (m, 5H).

The physical properties of the compound (No. 99) were as follows. Transition temperature: C 69.2 N 144.8 I. $T_{NI}$=94.7° C.; η=63.9 mPa·s; Δn=0.137; and Δn=32.2. Incidentally, the sample for measurement was prepared from 10% by weight of the compound (No. 99) and 90% by weight of the mother liquid crystals (i). This is because crystals deposited at the normal ratio (15% by weight:85% by weight).

Example 8

Preparation of the Compound (No. 172)

(e-27)

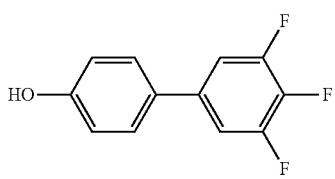

(No. 172)

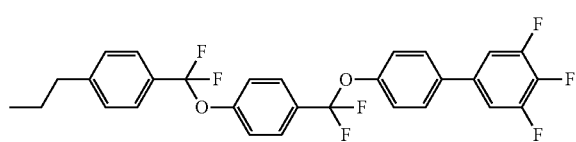

The compound (No. 172) was obtained using the compound (e-23) instead of the compound (e-3) and using the compound (e-27) instead of the compound (e-7) in the procedure of Example 3.

$^1$H-NMR (δ ppm; CDCl$_3$): 7.78 (d, 2H), 7.67 (d, 2H), 7.54-7.51 (m, 2H), 7.41-7.37 (m, 4H), 7.32 (d, 2H), 7.22-7.19 (m, 2H), 2.68 (t, 2H), 1.74-1.66 (m, 2H) and 0.99 (t, 3H).

The physical properties of the compound (No. 172) were as follows. Transition temperature: C 80.0 N 120.5 I. $T_{NI}$=84.4° C.; η=46.7 mPa·s; Δn=0.157; and Δ∈=22.9.

Example 9

Preparation of the Compound (No. 183)

(e-28)

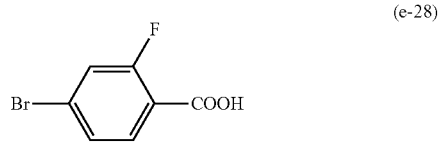

(e-29)

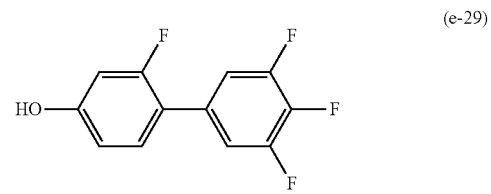

(e-30)

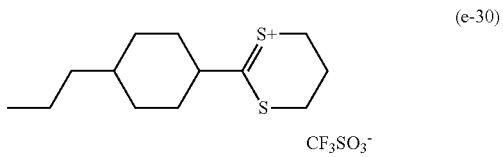

(No. 183)

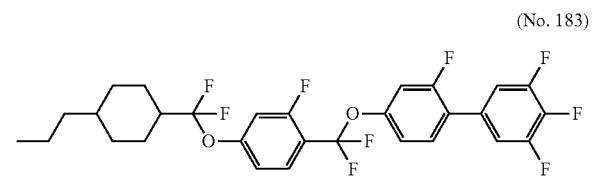

The compound (No. 183) was obtained using the compound (e-30) instead of the compound (e-3), using the compound (e-28) instead of the compound (e-13), and using the compound (e-29) instead of the compound (e-7) in the procedure of Example 3.

$^1$H-NMR (δ ppm; CDCl$_3$): 7.67 (dd, 1H), 7.37 (dd, 1H), 7.19-7.13 (m, 4H), 7.06 (d, 2H), 2.08-2.01 (m, 3H), 1.89-1.86 (m, 2H), 1.42-1.18 (m, 7H) and 0.98-0.88 (m, 2H).

The physical properties of the compound (No. 183) were as follows. Transition temperature: C 43.8 N 140.6 I. $T_{NI}$=96.4° C.; η=81.0 mPa·s; Δn=0.130; and Δ∈=26.1.

The compounds (No. 1) to (No. 252) shown below can be prepared by synthetic methods similar to those described in Examples 1 to 9. Appended data were obtained according to the methods described above. A compound itself was used as a sample when the transition temperature was measured. A mixture of the compound (15% by weight) and the mother liquid crystals (i) (85% by weight) was used as a sample when maximum temperature ($T_{NI}$), viscosity (r), optical anisotropy (Δn) and dielectric anisotropy (Δ∈) were measured. The extrapolated values calculated from these measured values according to the extrapolation described above were reported herein. Incidentally, in the compound (No. 1), the sample for measurement was prepared from 5% by weight of the compound (No. 1) and 95% by weight of the mother liquid crystals (i). In the compound (No. 90) and the compound (No. 99), the sample for measurement was prepared from 10% by weight of the compound (No. 90 or No. 99) and 90% by weight of the mother liquid crystals (i). This is because crystals deposited at the normal ratio (15% by weight:85% by weight).

| No. | |
|---|---|
| 1 | 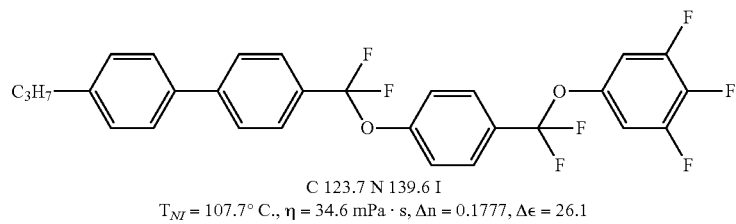<br>C 123.7 N 139.6 I<br>$T_{NI}$ = 107.7° C., η = 34.6 mPa·s, Δn = 0.1777, Δε = 26.1 |
| 2 | 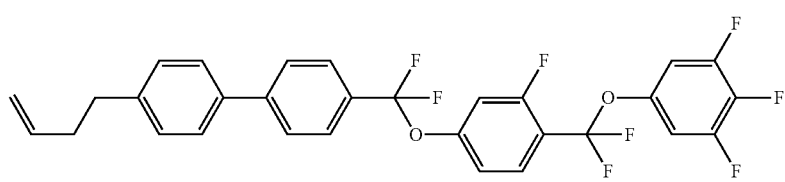 [SMILES: C=CCCc1ccc(-c2ccc(C(F)(F)Oc3ccc(C(F)(F)Oc4cc(F)c(F)c(F)c4)c(F)c3)cc2)cc1] |
| 3 | 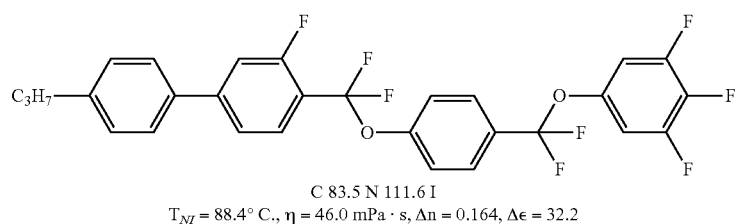<br>C 83.5 N 111.6 I<br>$T_{NI}$ = 88.4° C., η = 46.0 mPa·s, Δn = 0.164, Δε = 32.2 |
| 4 | 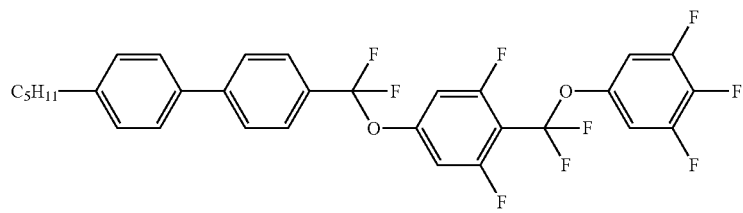 |
| 5 | 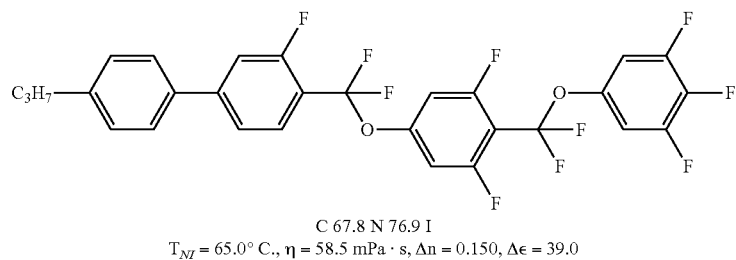<br>C 67.8 N 76.9 I<br>$T_{NI}$ = 65.0° C., η = 58.5 mPa·s, Δn = 0.150, Δε = 39.0 |
| 6 | 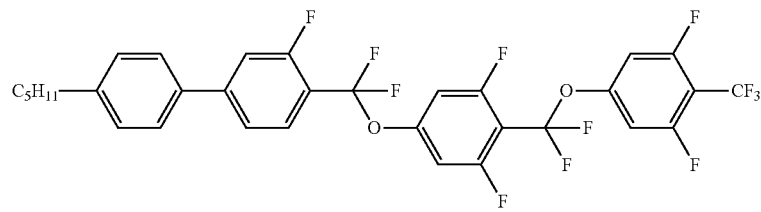 |
| 7 | 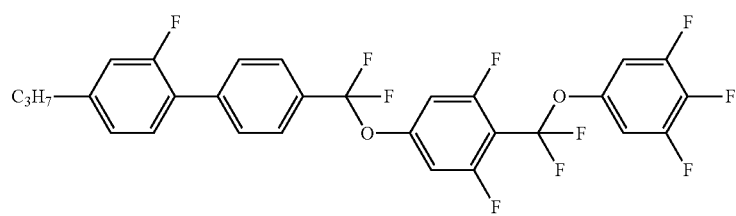 |

-continued
| No. | |
|---|---|
| 8 | 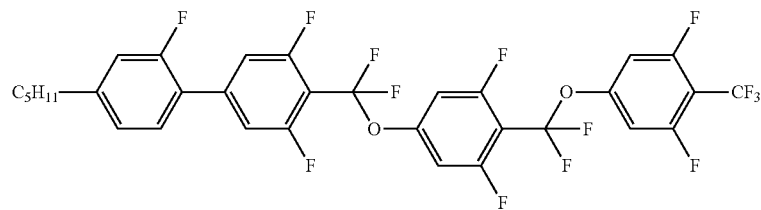 |
| 9 | 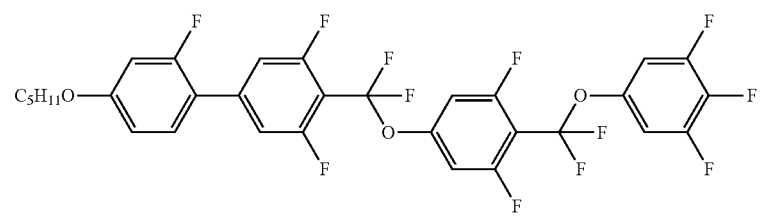 |
| 10 | 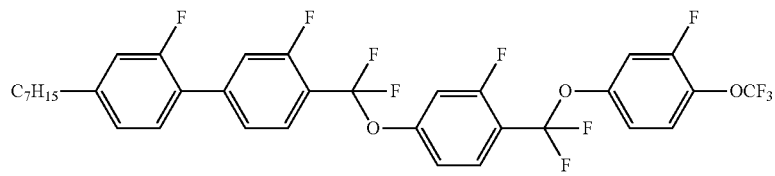 |
| 11 | 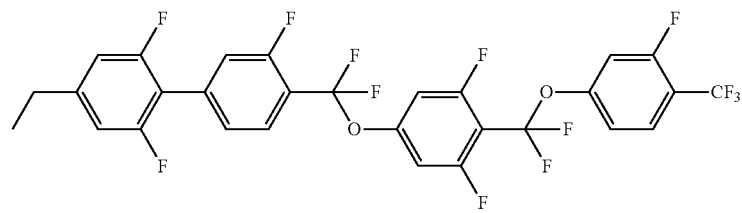 [SMILES: CCc1cc(F)c(-c2ccc(C(F)(F)Oc3cc(F)c(C(F)(F)Oc4ccc(C(F)(F)F)c(F)c4)c(F)c3)c(F)c2)c(F)c1] |
| 12 | 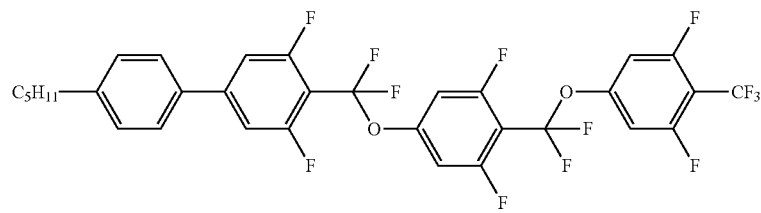 |
| 13 | 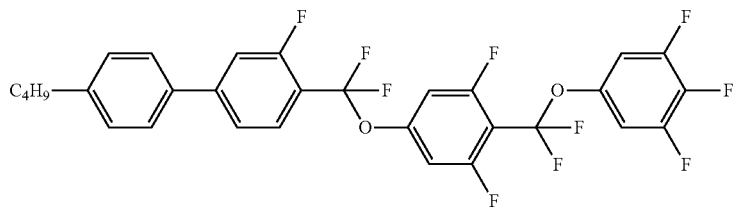 |
| 14 | 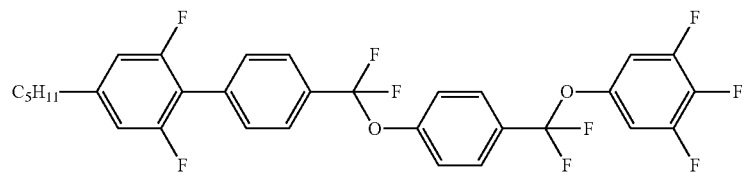 |

-continued
| No. |  |
|---|---|
| 15 | 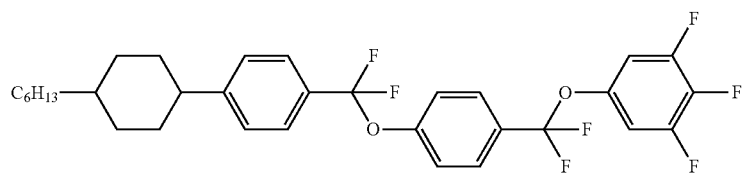 |
| 16 | 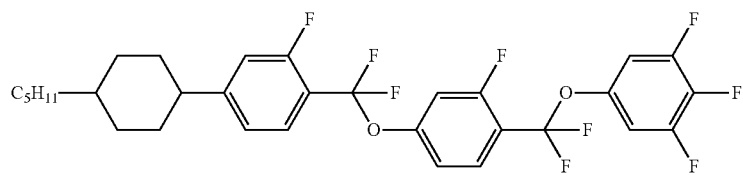 |
| 17 | 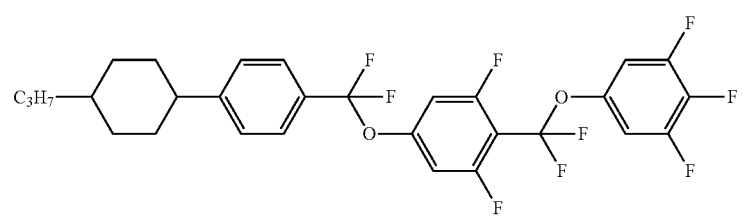 |
| 18 | 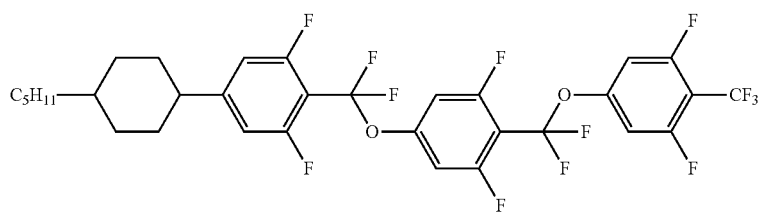 |
| 19 | 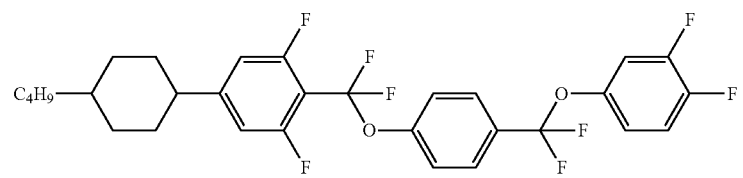 |
| 20 | 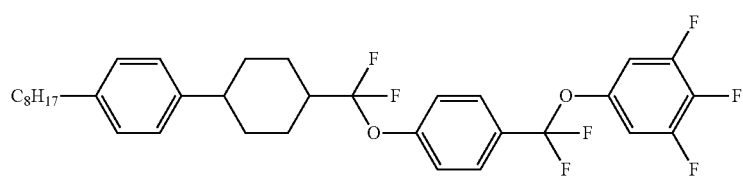 |
| 21 | 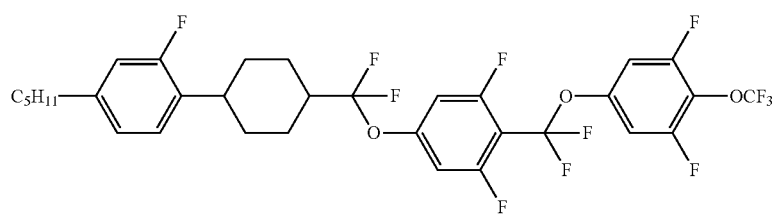 |
| 22 | 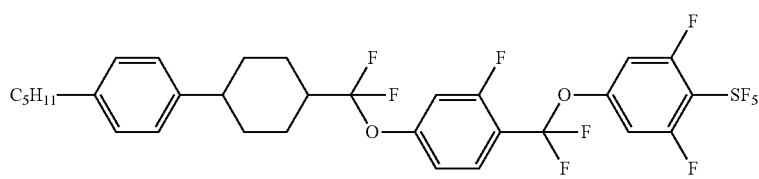 |

-continued
| No. | |
|---|---|
| 23 | 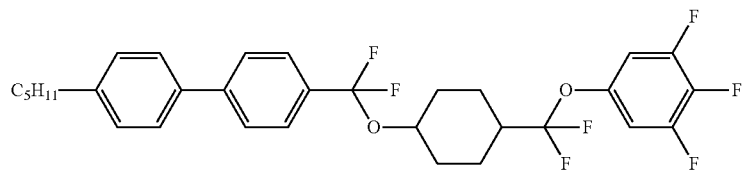 |
| 24 | 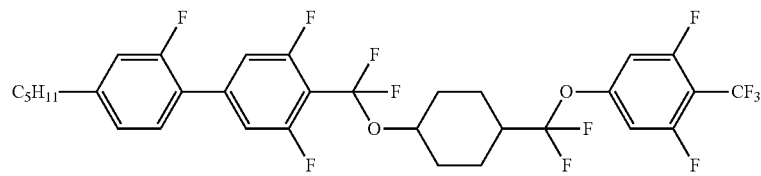 |
| 25 | 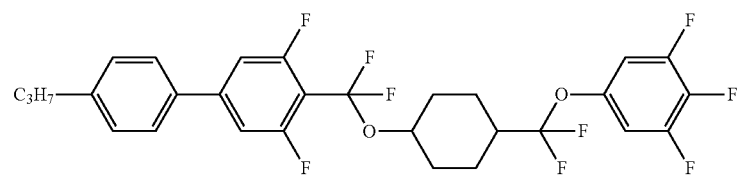 |
| 26 | 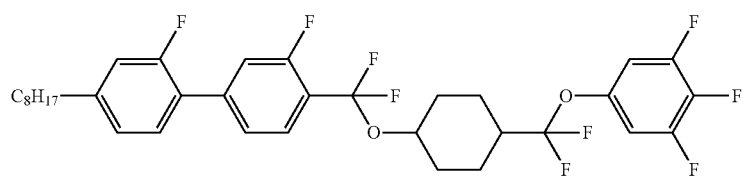 |
| 27 | 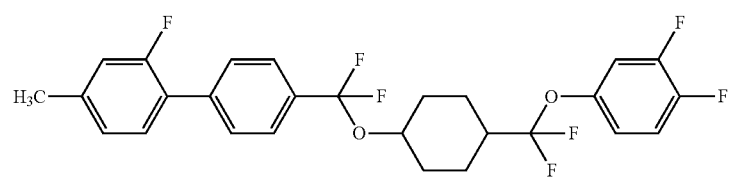 |
| 28 | 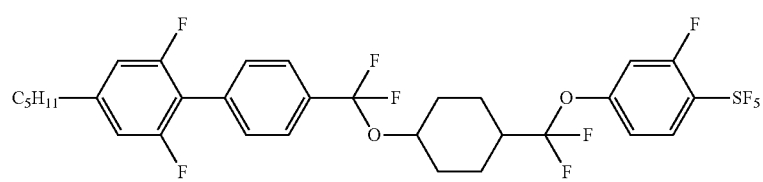 |
| 29 | 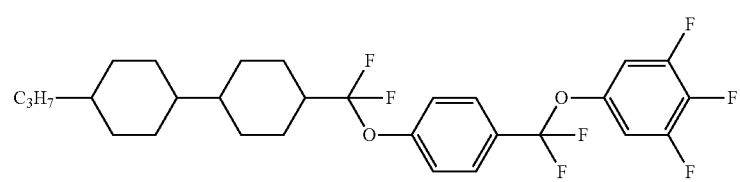  C 68.3 N 190.0 I  $T_{NI} = 147.7°$ C., $\eta = 50.2$ mPa·s, $\Delta n = 0.117$, $\Delta\epsilon = 17.5$ |
| 30 | 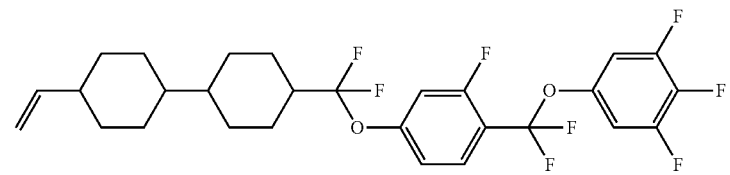 |

-continued
| No. | |
|---|---|
| 31 | 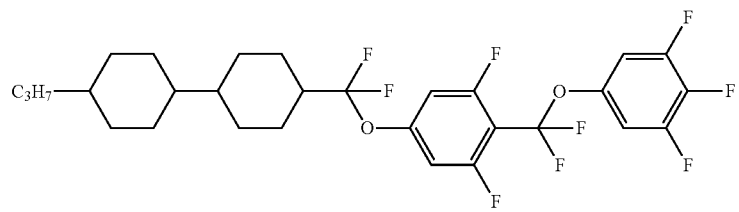 C 76.8 N 168.3 I  $T_{NI}$ = 121.7° C., η = 57.1 mPa·s, Δn = 0.110, Δε = 24.1 |
| 32 | 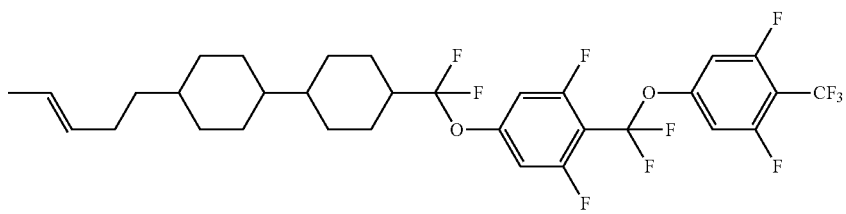 [SMILES: C/C=C/CCC1CCC(C2CCC(C(F)(F)Oc3cc(F)c(C(F)(F)Oc4cc(F)c(C(F)(F)F)c(F)c4)c(F)c3)CC2)CC1] |
| 33 | 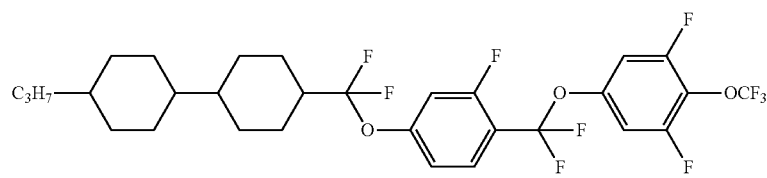 |
| 34 | 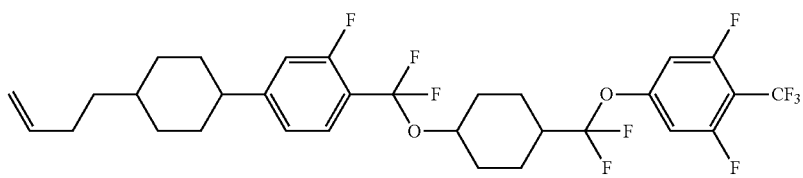 [SMILES: C=CCCC1CCC(c2ccc(C(F)(F)OC3CCC(C(F)(F)Oc4cc(F)c(C(F)(F)F)c(F)c4)CC3)c(F)c2)CC1] |
| 35 | 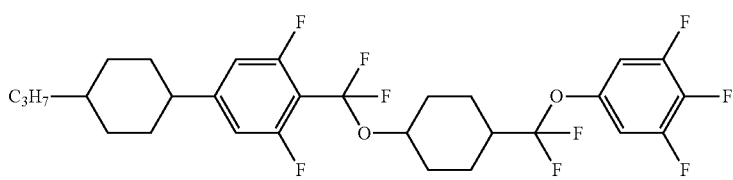 |
| 36 | 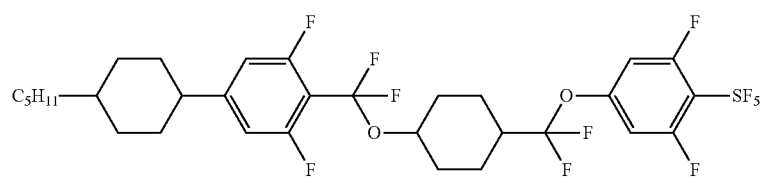 |
| 37 | 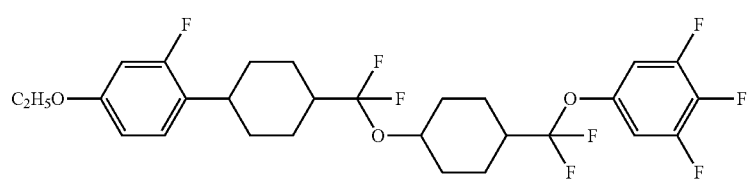 |
| 38 | 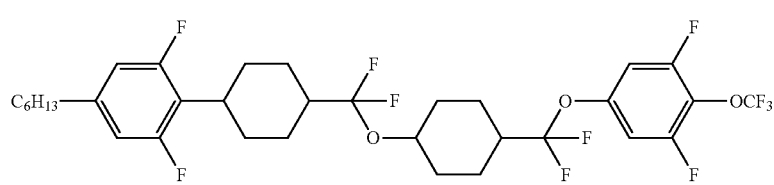 |

-continued
| No. | |
|---|---|
| 39 | 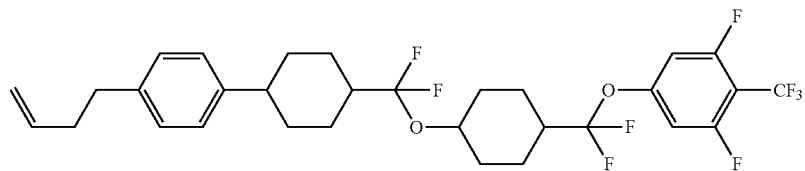 [SMILES: C=CCCc1ccc(C2CCC(C(F)(F)OC3CCC(C(F)(F)Oc4cc(F)c(C(F)(F)F)c(F)c4)CC3)CC2)cc1] |
| 40 | 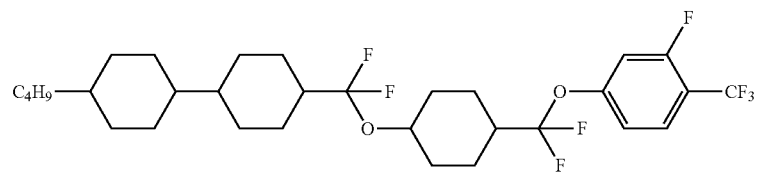 |
| 41 | 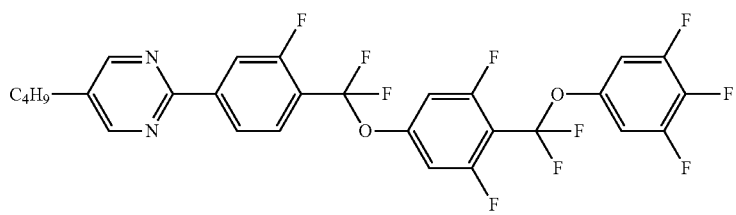 |
| 42 | 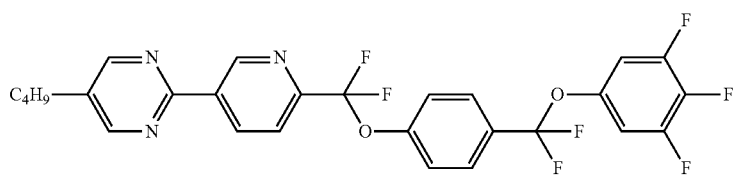 |
| 43 | 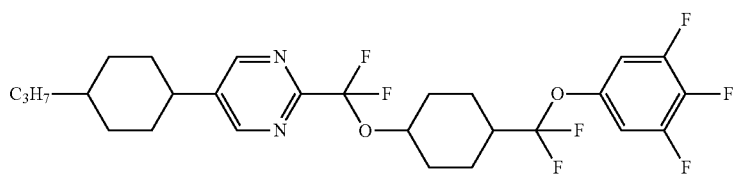 |
| 44 | 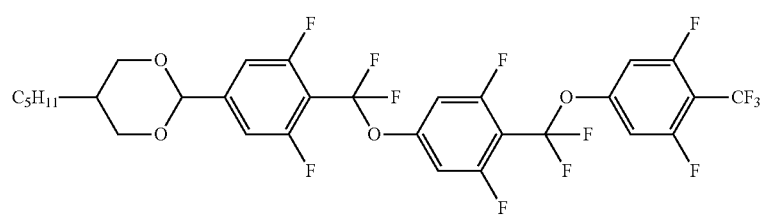 |
| 45 | 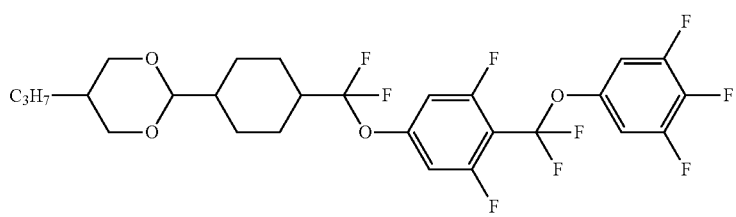 |
| 46 | 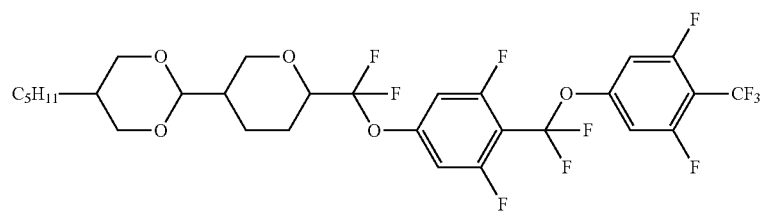 |

-continued
| No. | |
|---|---|
| 47 | 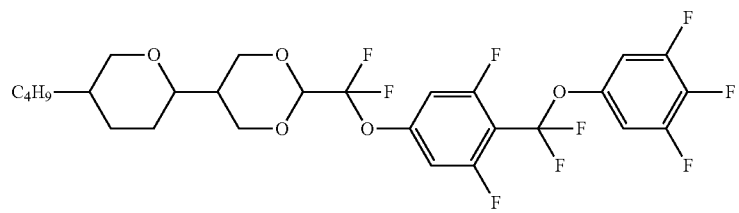 |
| 48 | 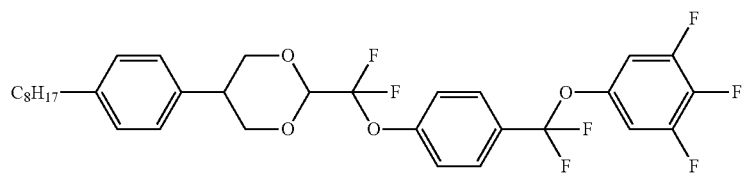 |
| 49 | 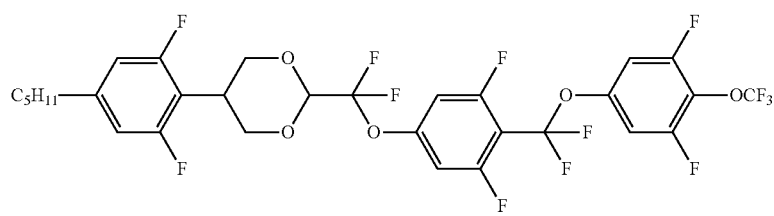 |
| 50 | 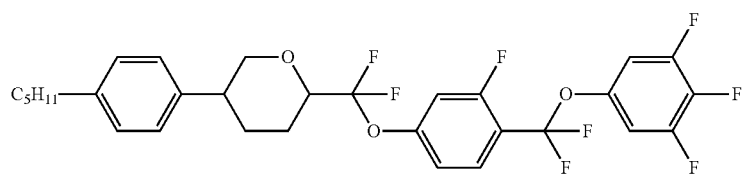 |
| 51 | 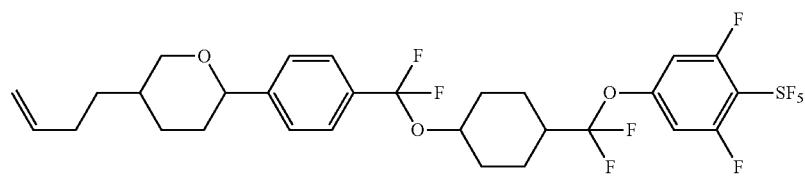 |
| 52 | 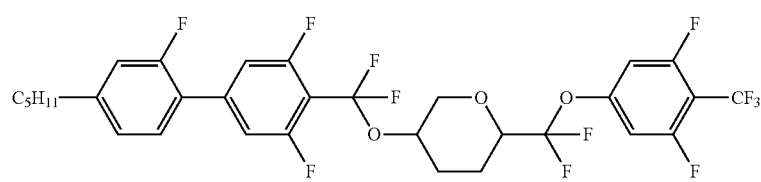 |
| 53 | 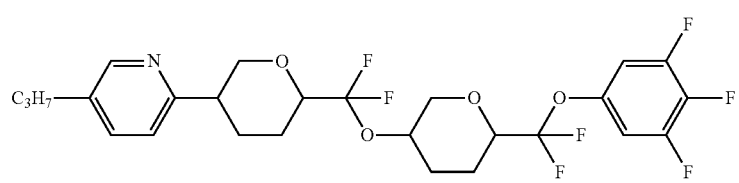 |
| 54 | 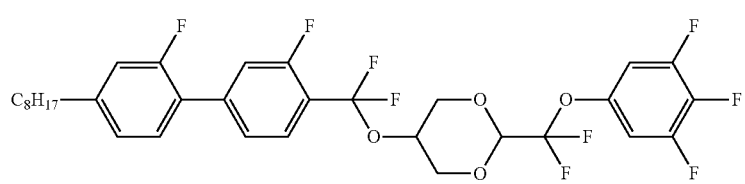 |

| No. | |
|---|---|
| 55 | 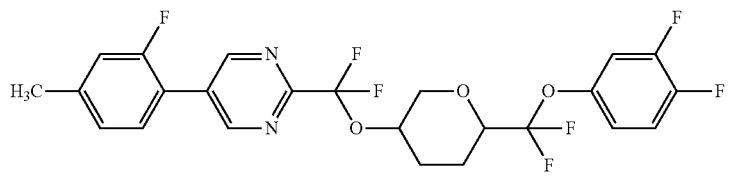 |
| 56 | 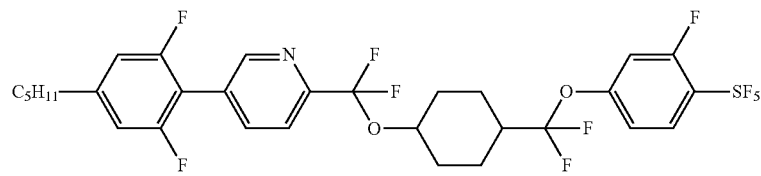 |
| 57 | 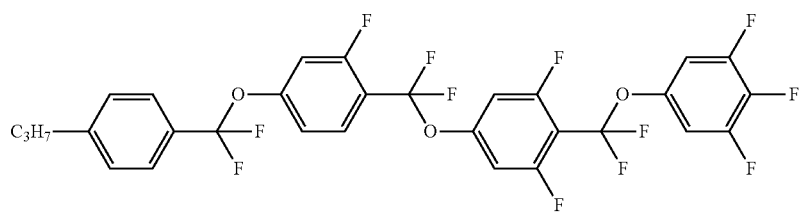 |
| 58 | 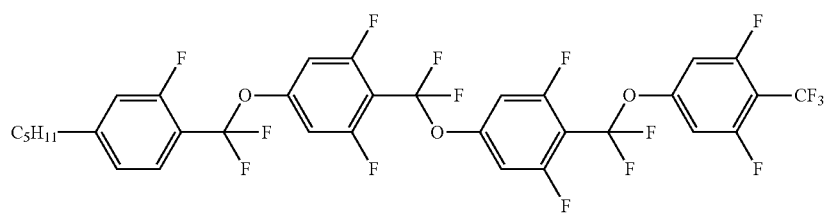 |
| 59 | 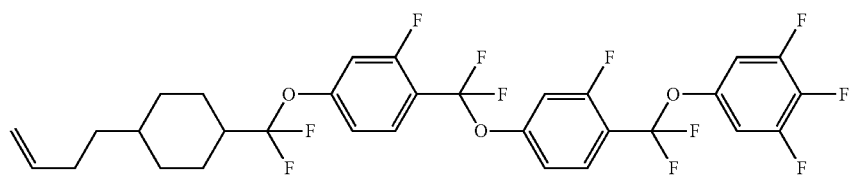 [SMILES: C=CCCC1CCC(C(F)(F)Oc2ccc(C(F)(F)Oc3ccc(C(F)(F)Oc4cc(F)c(F)c(F)c4)c(F)c3)c(F)c2)CC1] |
| 60 | 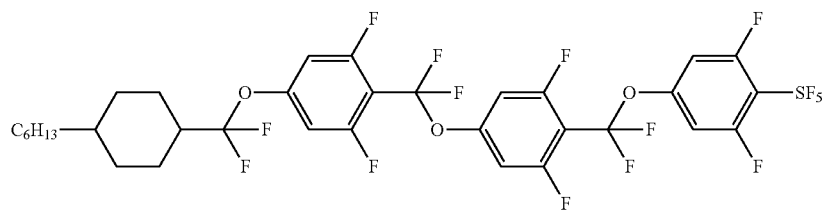 |
| 61 | 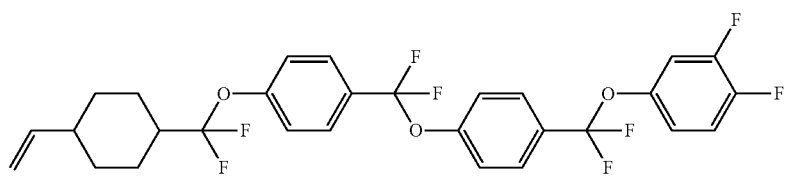 [SMILES: C=CC1CCC(C(F)(F)Oc2ccc(C(F)(F)Oc3ccc(C(F)(F)Oc4ccc(F)c(F)c4)cc3)cc2)CC1] |
| 62 | 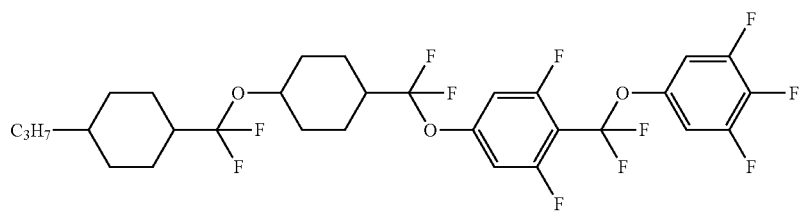 |

| No. | |
|---|---|
| 63 | 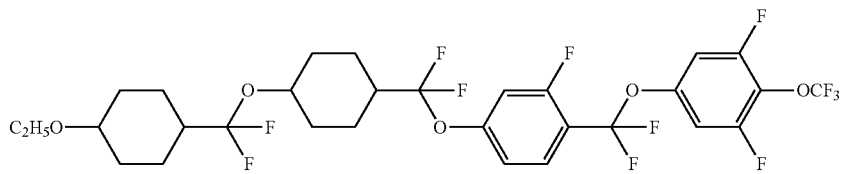 |
| 64 | 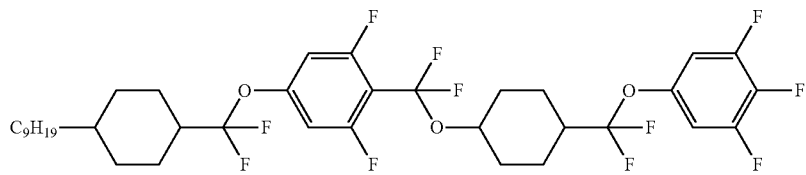 |
| 65 | 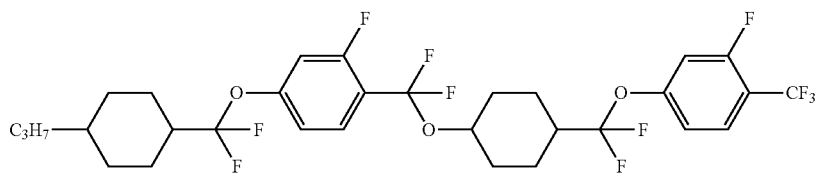 |
| 66 | 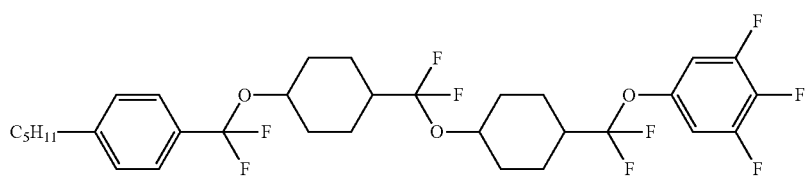 |
| 67 | 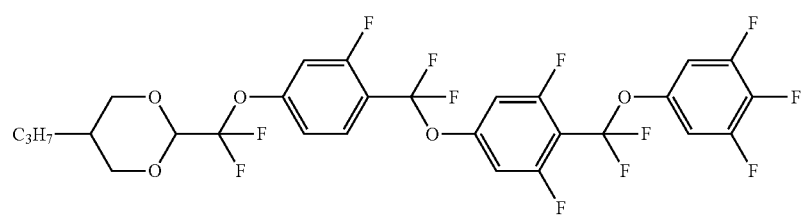 |
| 68 | 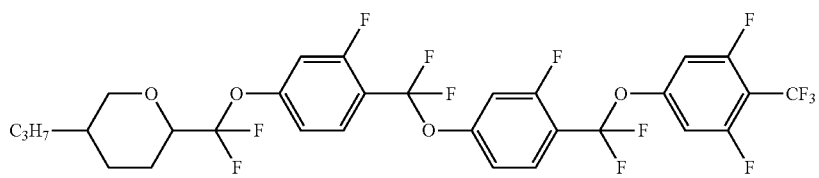 |
| 69 | 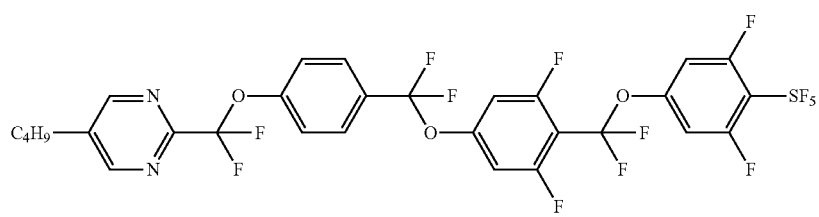 |
| 70 | 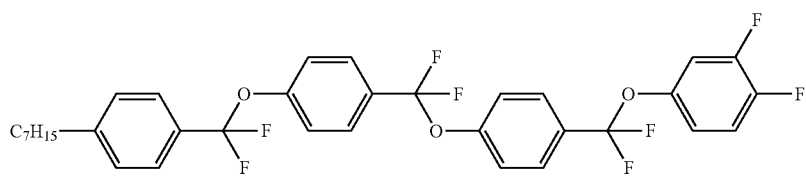 |

| No. |
|---|
| 71 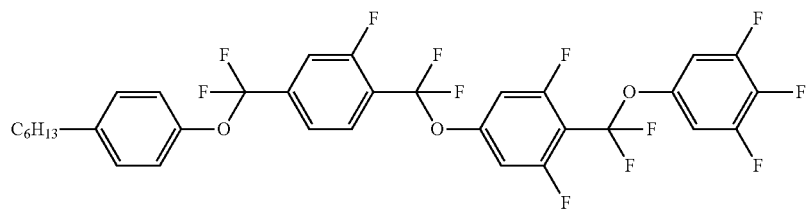 |
| 72 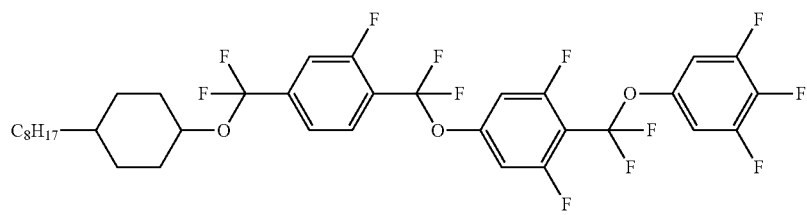 |
| 73 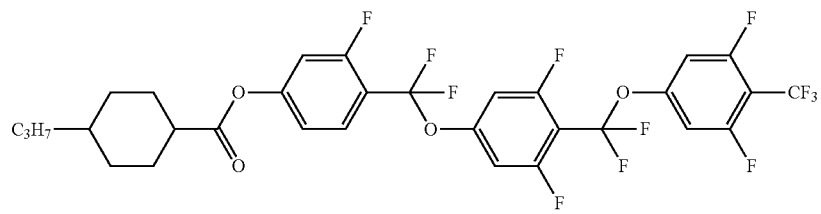 |
| 74 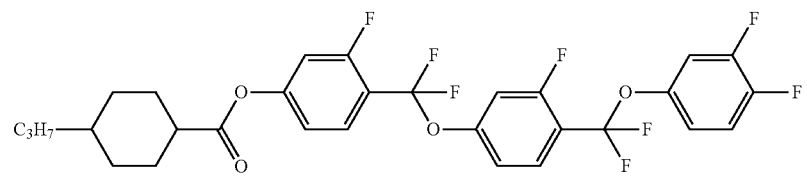 |
| 75 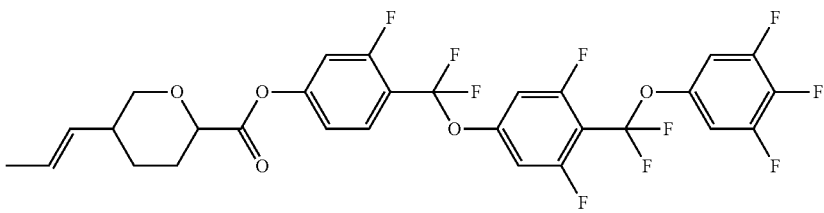 [SMILES: C/C=C/C1CCC(C(=O)Oc2ccc(C(F)(F)Oc3cc(F)c(C(F)(F)Oc4cc(F)c(F)c(F)c4)c(F)c3)c(F)c2)OC1] |
| 76 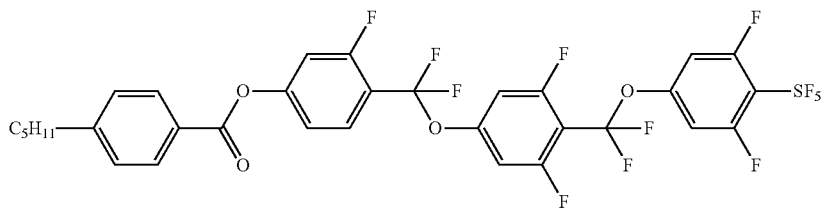 |
| 77 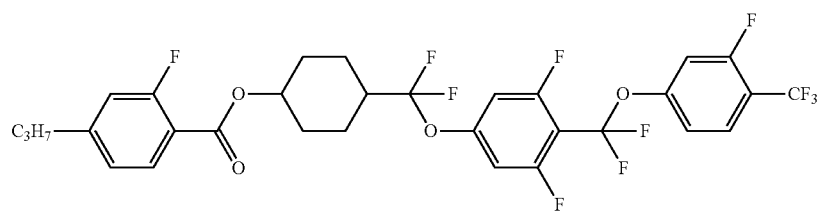 |

| No. | |
|---|---|
| 78 | 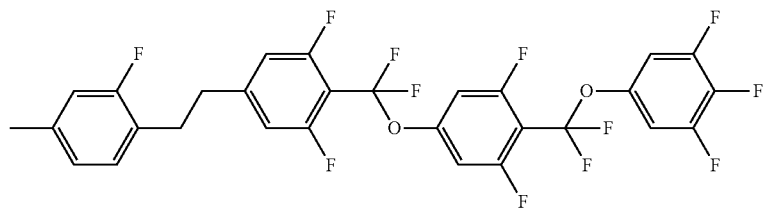 [SMILES: Cc1ccc(CCc2cc(F)c(C(F)(F)Oc3cc(F)c(C(F)(F)Oc4cc(F)c(F)c(F)c4)c(F)c3)c(F)c2)c(F)c1] |
| 79 | 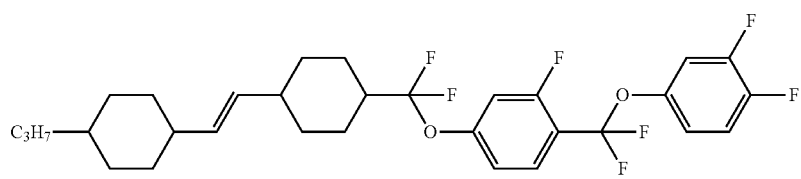 |
| 80 | 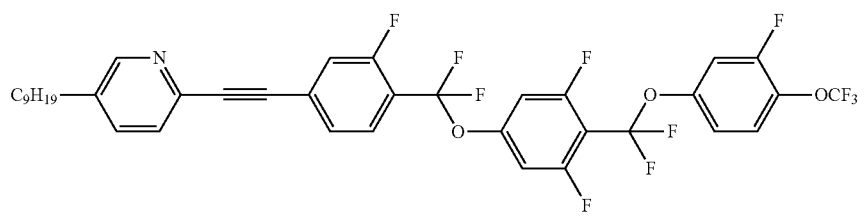 |
| 81 | 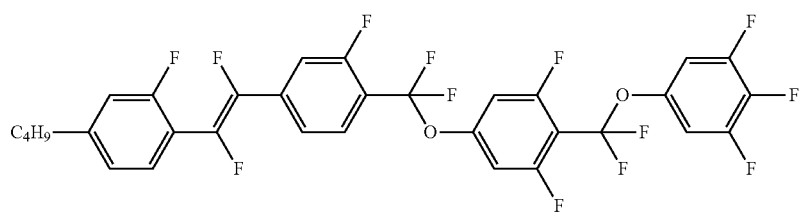 |
| 82 | 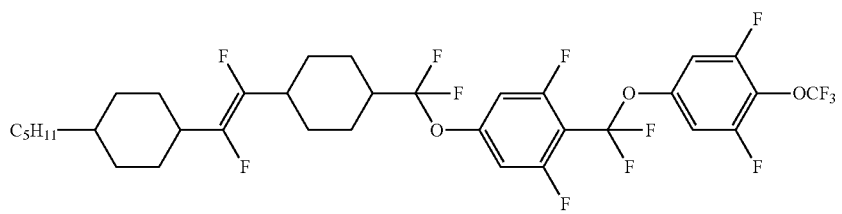 |
| 83 | 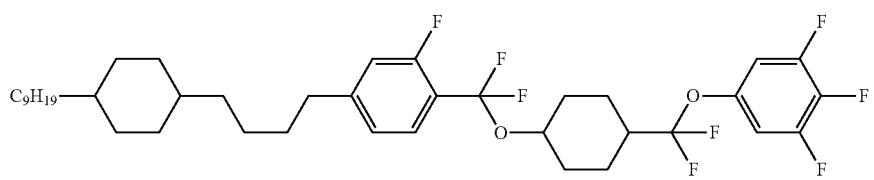 |
| 84 | 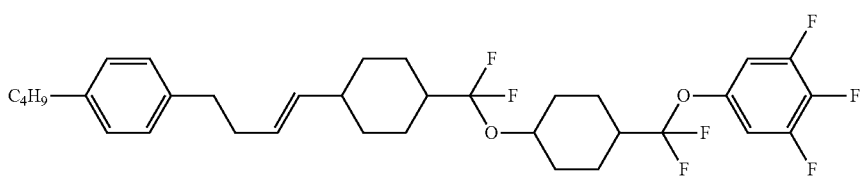 |

| No. | |
|---|---|
| 85 | 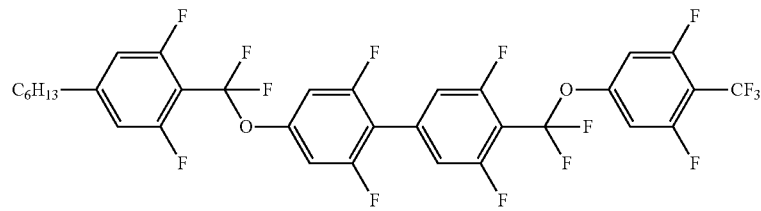 |
| 86 | 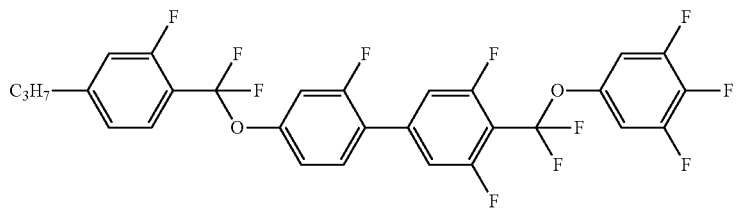 |
| 87 | 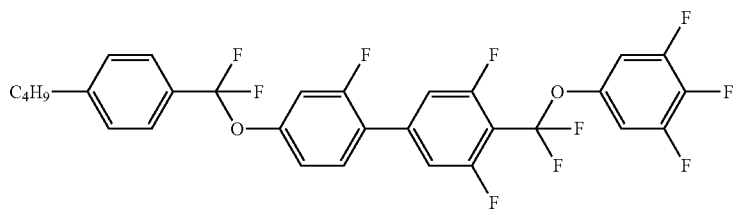 |
| 88 | 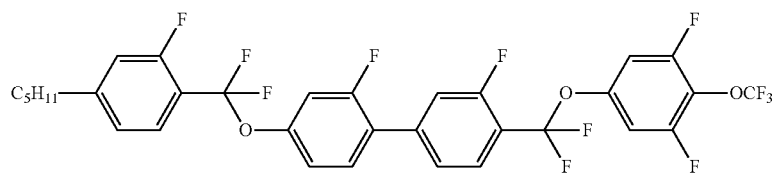 |
| 89 | 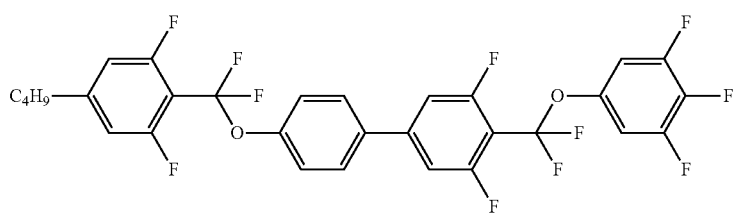 |
| 90 | 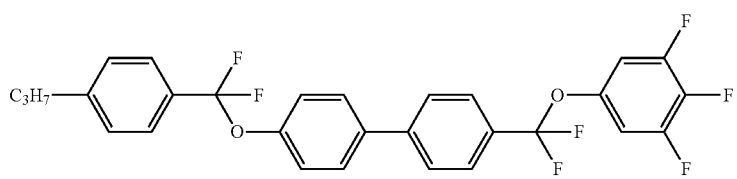 |
| | C 99.4 $S_C$ 117.2 $S_A$ 126.8 N 144.7 I |
| | $T_{NI}$ = 106.7° C., η = 36.6 mPa · s, Δn = 0.177, Δε = 26.1 |
| 91 | 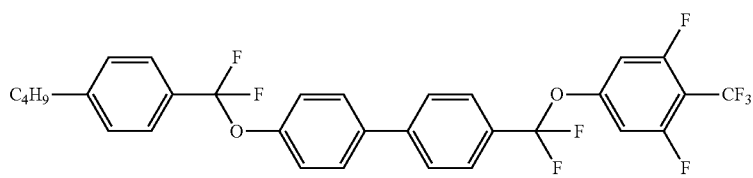 |

| No. |
|---|
| 92 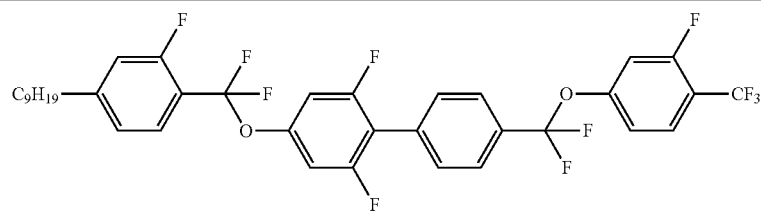 |
| 93 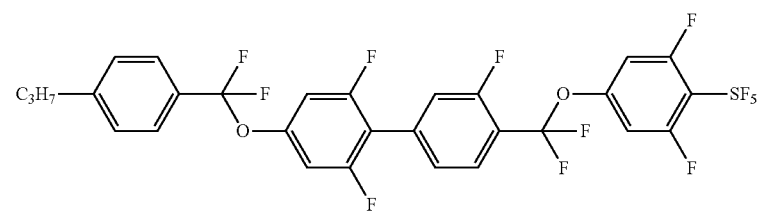 |
| 94 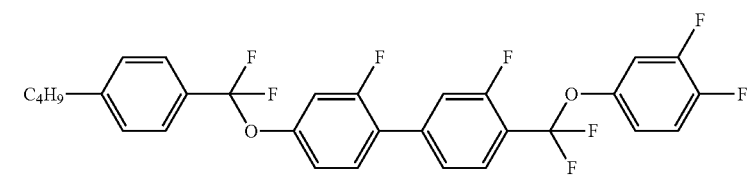 |
| 95 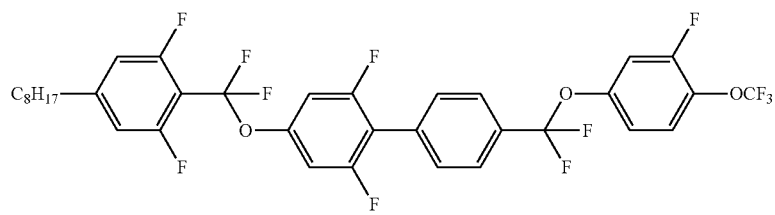 |
| 96 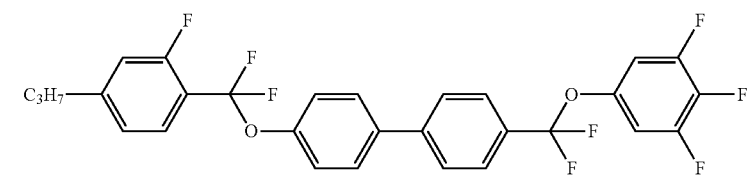 |
| 97 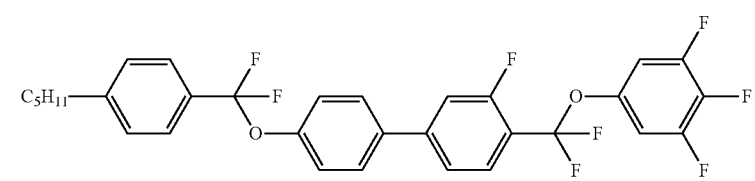 |
| 98 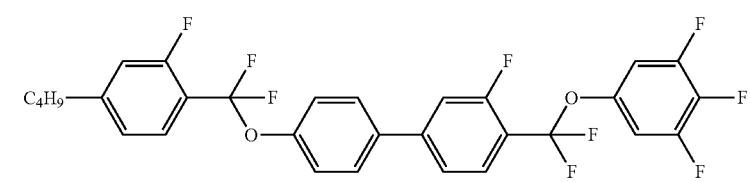 |

| No. | |
|---|---|
| 99 | 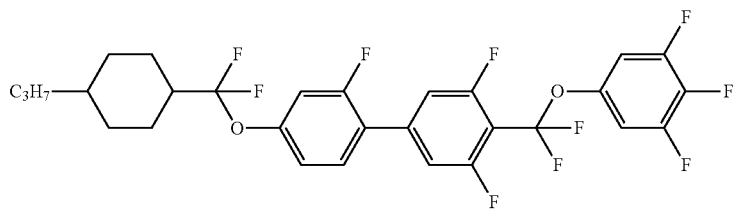<br>C 69.2 N 144.8 I<br>$T_{NI} = 94.7°$ C., $\eta = 63.9$ mPa·s, $\Delta n = 0.137$, $\Delta\epsilon = 332.2$ |
| 100 | 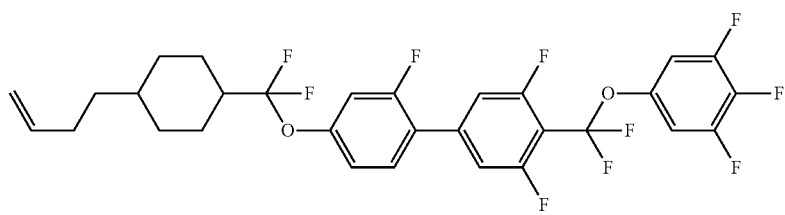 [SMILES: C=CCCC1CCC(C(F)(F)Oc2ccc(-c3cc(F)c(C(F)(F)Oc4cc(F)c(F)c(F)c4)c(F)c3)c(F)c2)CC1] |
| 101 | 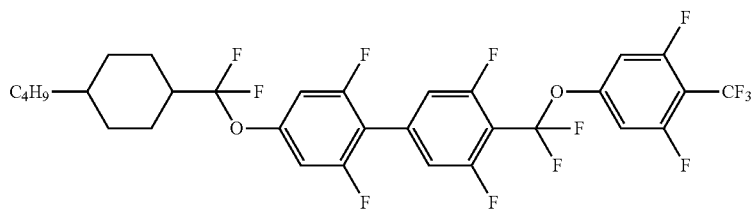 |
| 102 | 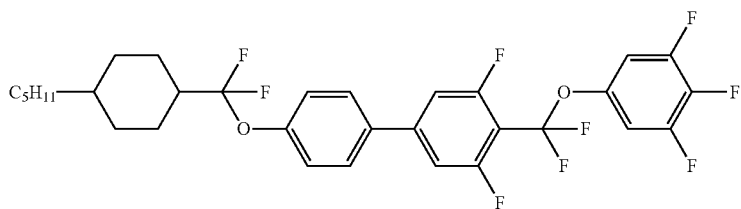 |
| 103 | 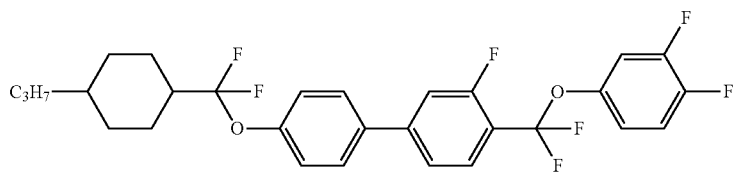 |
| 104 | 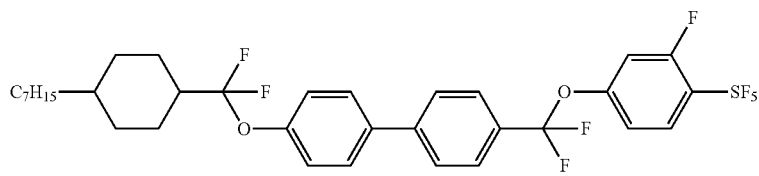 |
| 105 | 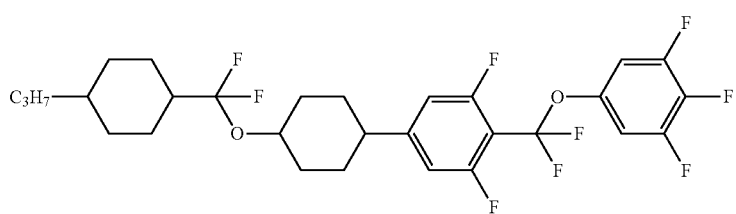 |

-continued
| No. | |
|---|---|
| 106 | 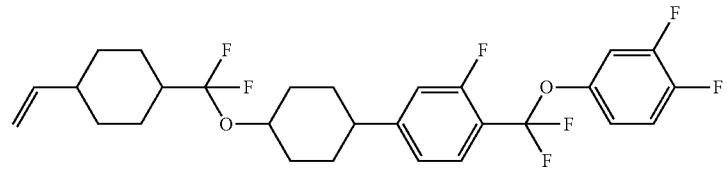 [SMILES: C=CC1CCC(C(F)(F)OC2CCC(c3ccc(C(F)(F)Oc4ccc(F)c(F)c4)c(F)c3)CC2)CC1] |
| 107 | 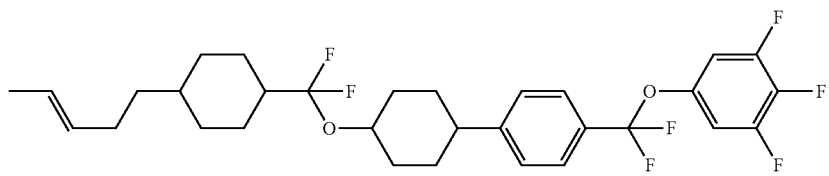 [SMILES: C/C=C/CCC1CCC(C(F)(F)OC2CCC(c3ccc(C(F)(F)Oc4cc(F)c(F)c(F)c4)cc3)CC2)CC1] |
| 108 | 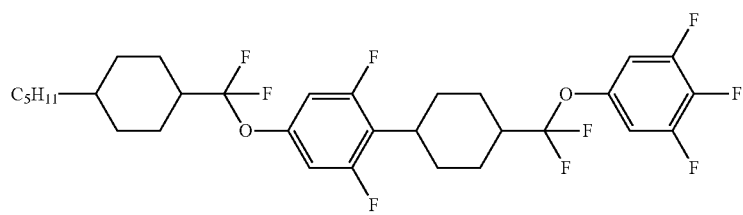 |
| 109 | 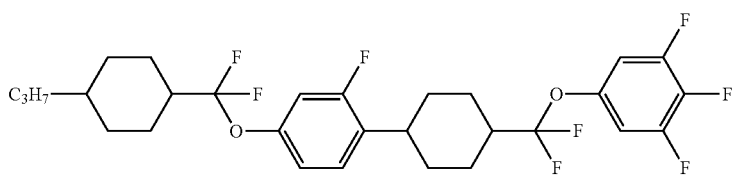 |
| 110 | 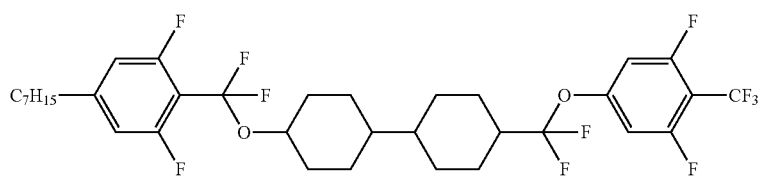 |
| 111 | 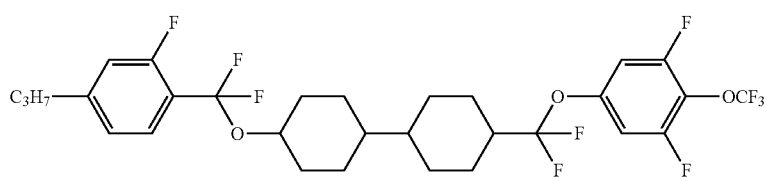 |
| 112 | 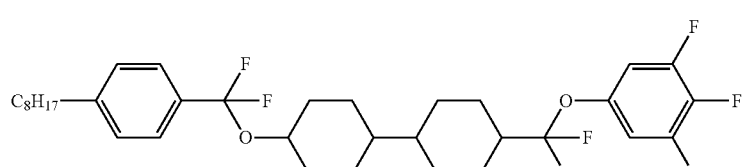 |
| 113 | 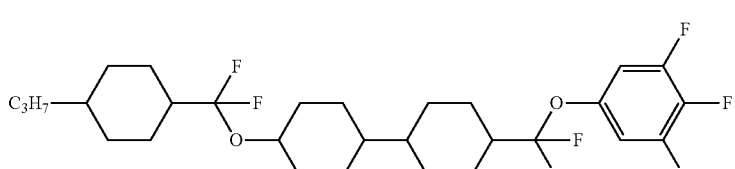 |

-continued
| No. | |
|---|---|
| 114 | 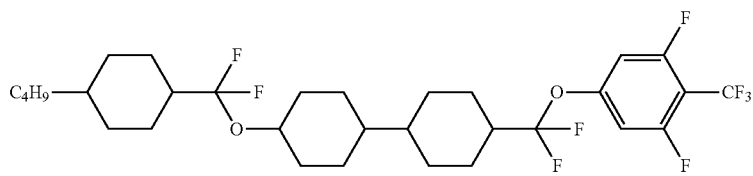 |
| 115 | 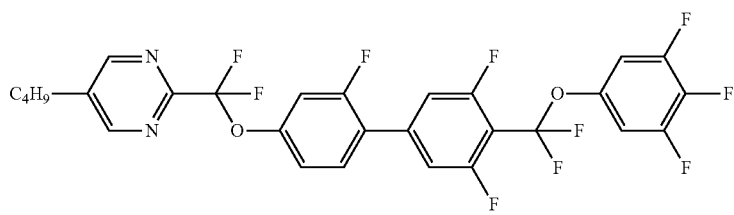 |
| 116 | 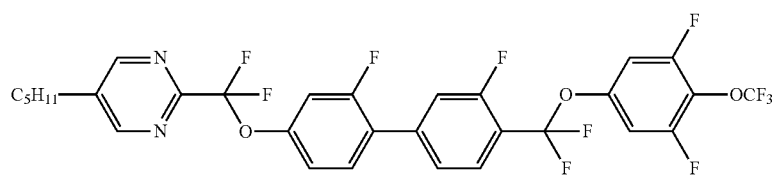 |
| 117 | 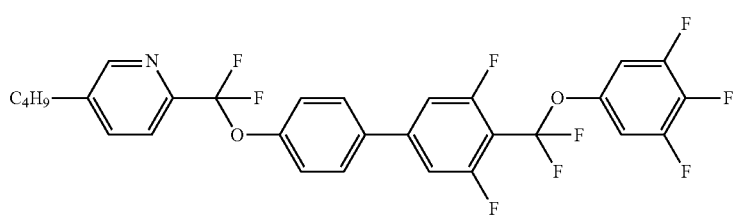 |
| 118 | 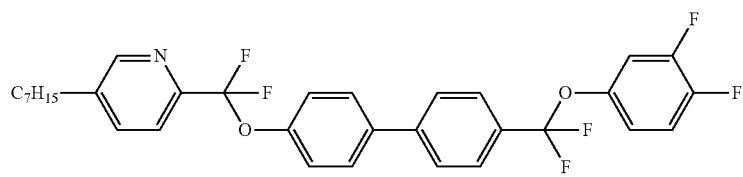 |
| 119 | 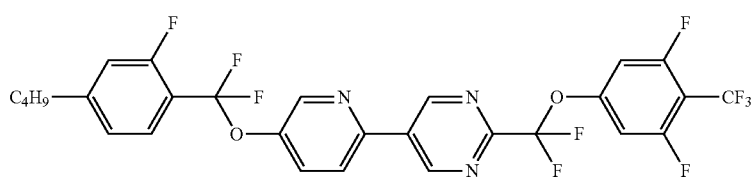 |
| 120 | 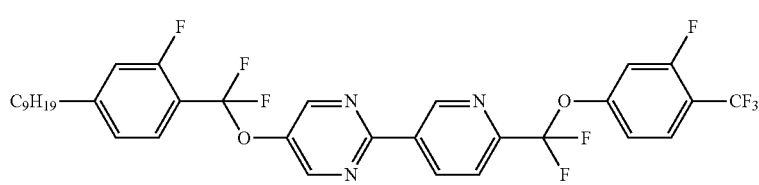 |
| 121 | 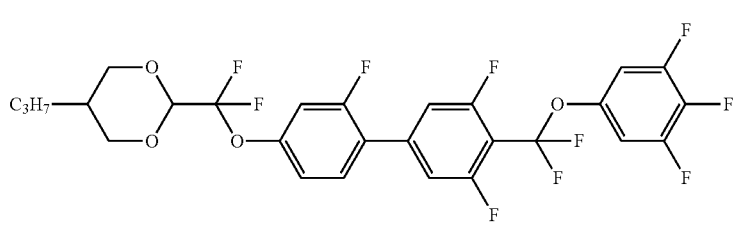 |

-continued
| No. | |
|---|---|
| 122 | 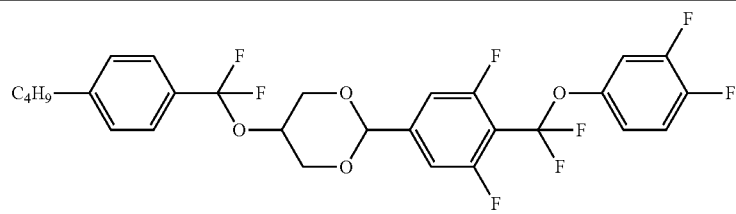 |
| 123 | 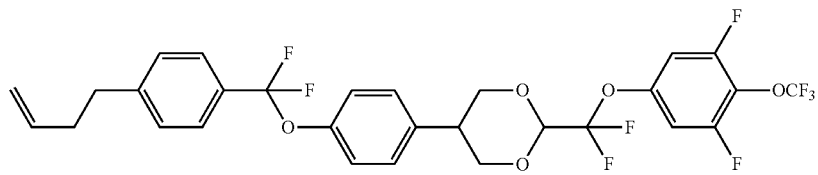 [SMILES: C=CCCc1ccc(C(F)(F)Oc2ccc(C3COC(C(F)(F)Oc4cc(F)c(OC(F)(F)F)c(F)c4)OC3)cc2)cc1] |
| 124 | 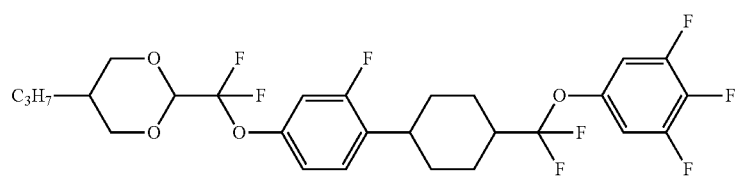 |
| 125 | 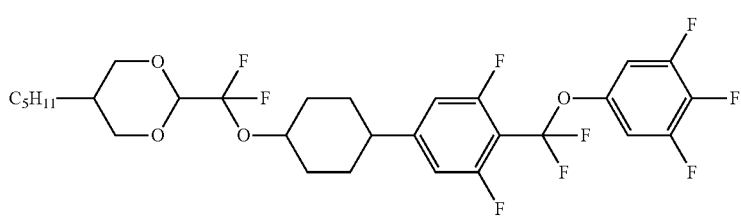 |
| 126 | 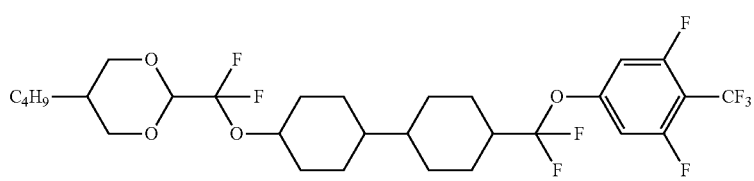 |
| 127 | 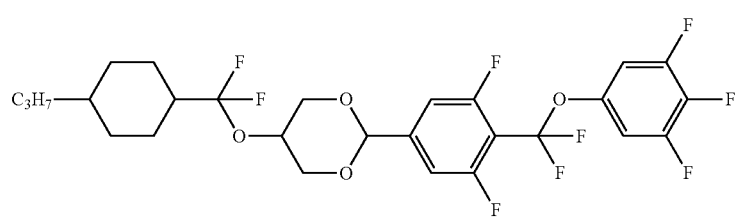 |
| 128 | 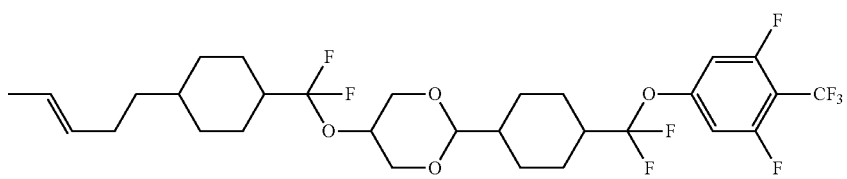 [SMILES: C/C=C/CCC1CCC(C(F)(F)OC2COC(C3CCC(C(F)(F)Oc4cc(F)c(C(F)(F)F)c(F)c4)CC3)OC2)CC1] |
| 129 | 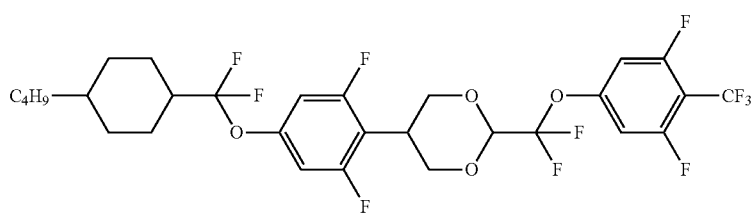 |

| No. | |
|---|---|
| 130 | 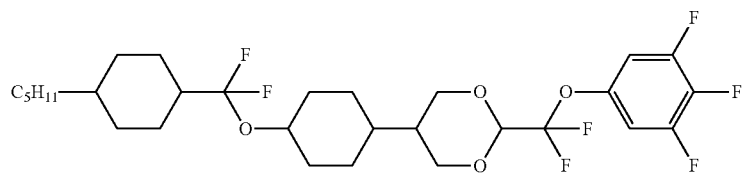 |
| 131 | 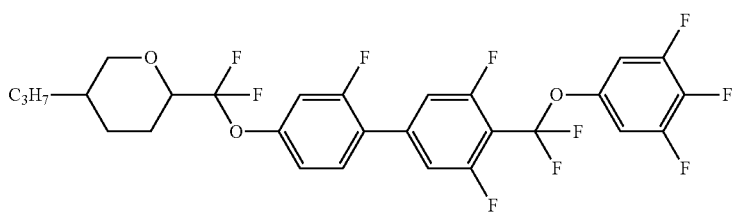 |
| 132 | 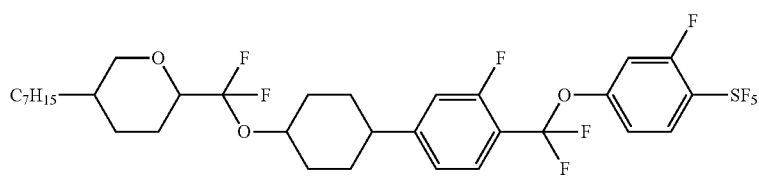 |
| 133 | 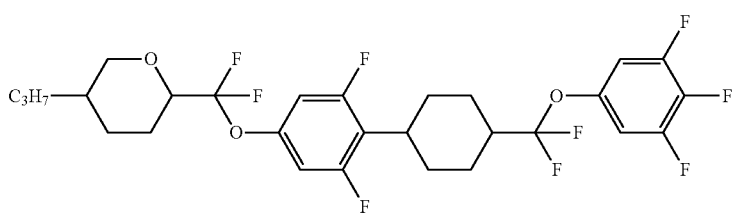 |
| 134 | 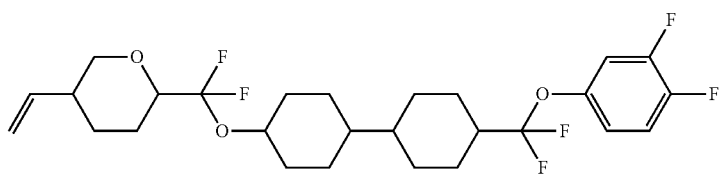 [SMILES: C=CC1CCC(C(F)(F)OC2CCC(C3CCC(C(F)(F)Oc4ccc(F)c(F)c4)CC3)CC2)OC1] |
| 135 | 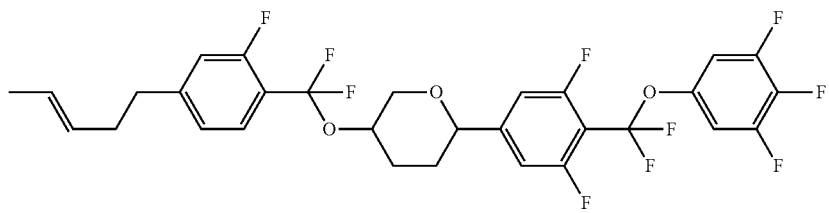 [SMILES: C/C=C/CCc1ccc(C(F)(F)OC2CCC(c3cc(F)c(C(F)(F)Oc4cc(F)c(F)c(F)c4)c(F)c3)OC2)c(F)c1] |
| 136 | 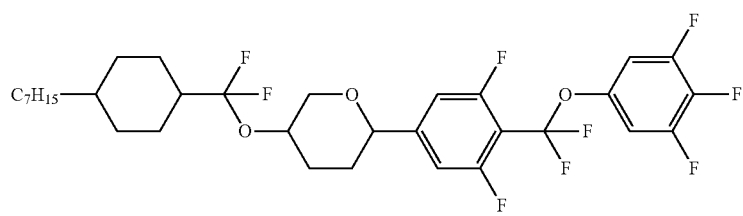 |
| 137 | 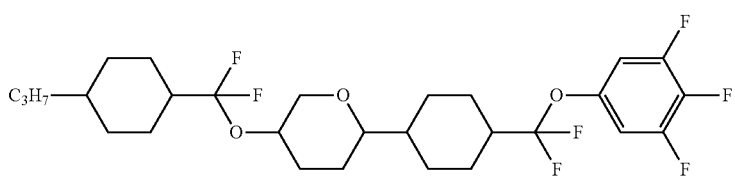 |

-continued
| No. | |
|---|---|
| 138 | 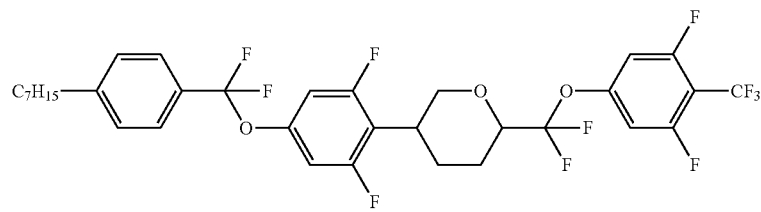 |
| 139 | 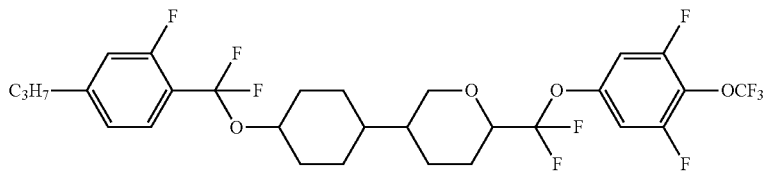 |
| 140 | 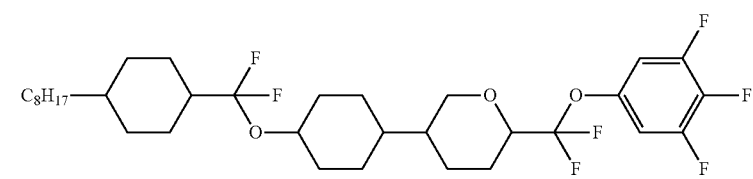 |
| 141 | 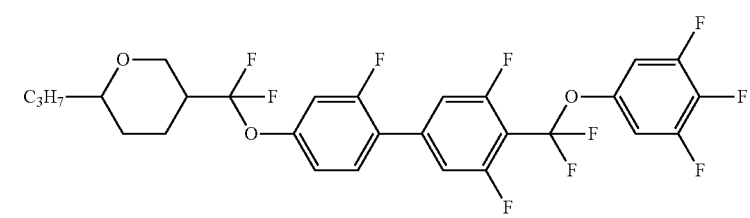 |
| 142 | 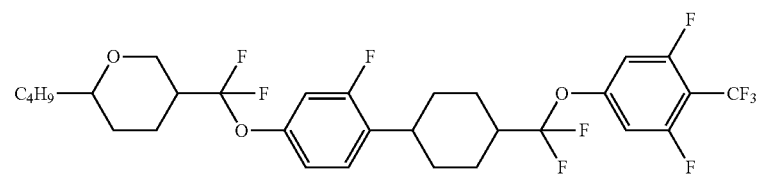 |
| 143 | 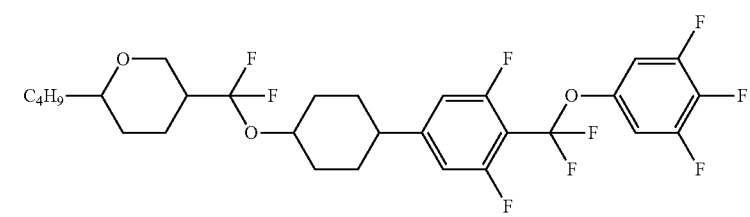 |
| 144 | 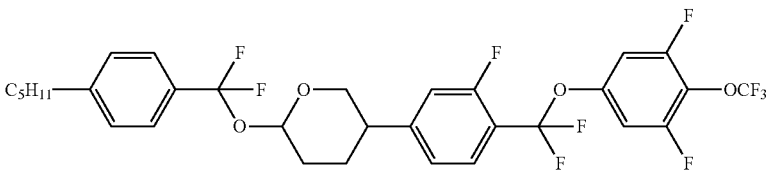 |
| 145 | 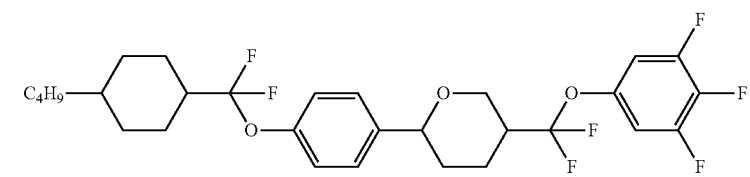 |

| No. | |
|---|---|
| 146 | 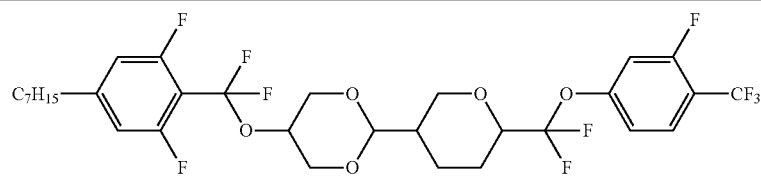 |
| 147 | 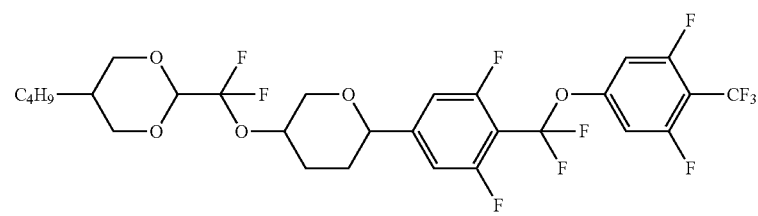 |
| 148 | 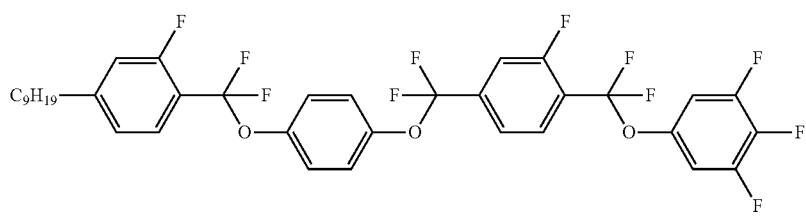 |
| 149 | 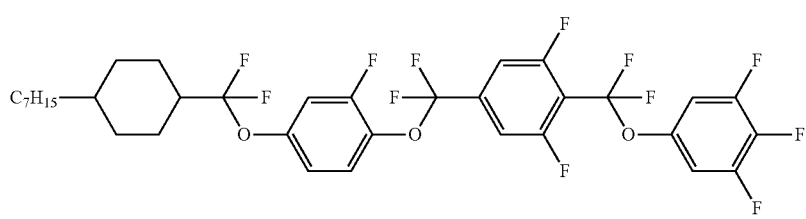 |
| 150 | 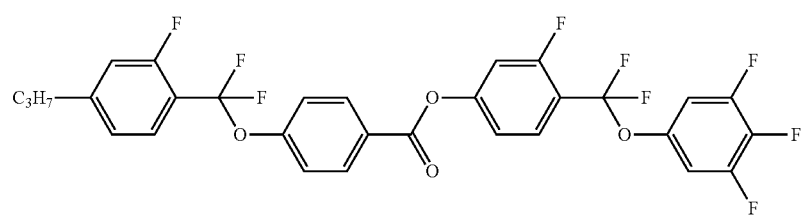 |
| 151 | 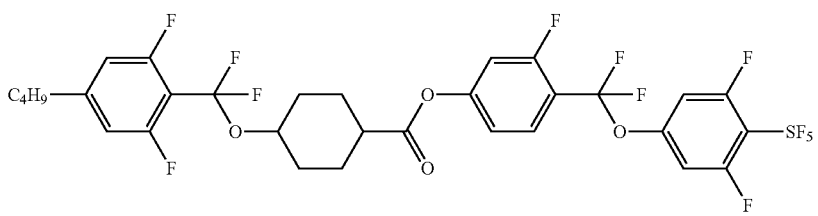 |
| 152 | 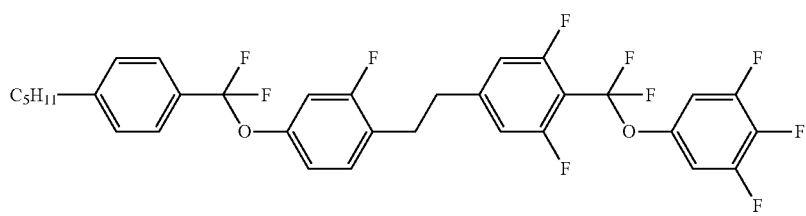 |

-continued
| No. | |
|---|---|
| 153 | 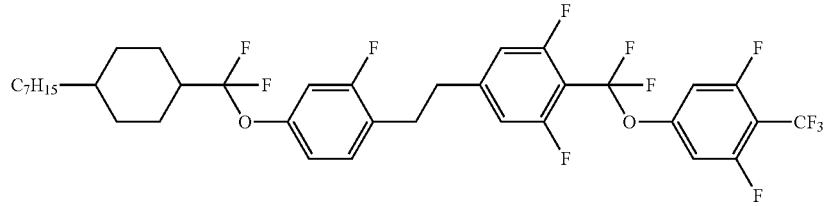 |
| 154 | 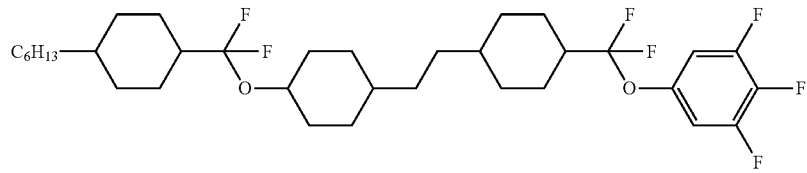 |
| 155 | 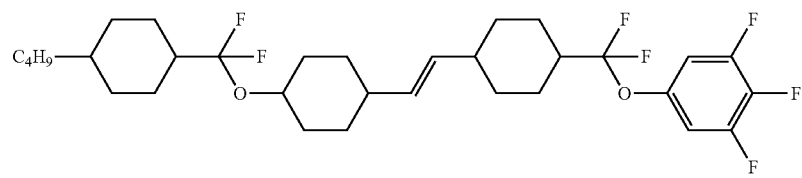 |
| 156 | 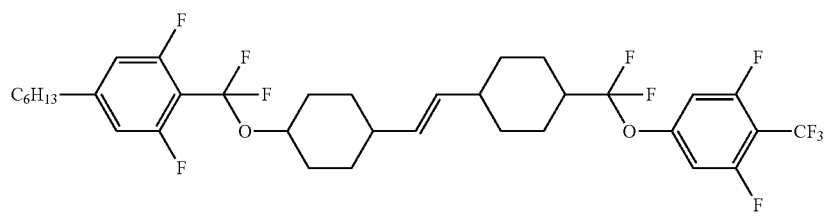 |
| 157 | 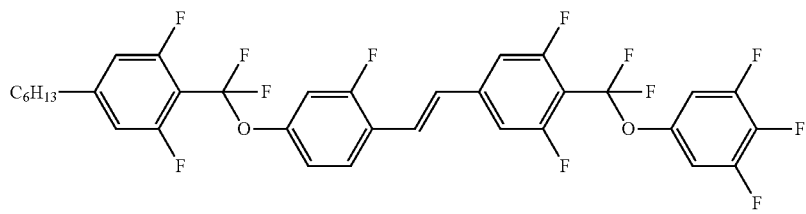 |
| 158 | 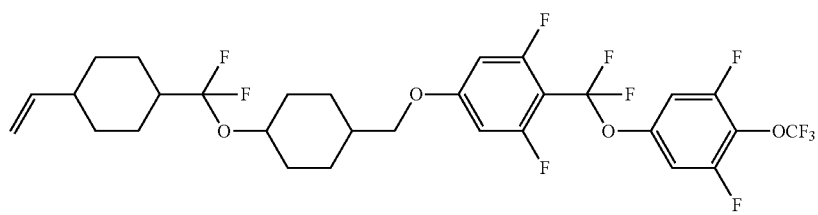 [SMILES: C=CC1CCC(C(F)(F)OC2CCC(COc3cc(F)c(C(F)(F)Oc4cc(F)c(OC(F)(F)F)c(F)c4)c(F)c3)CC2)CC1] |
| 159 | 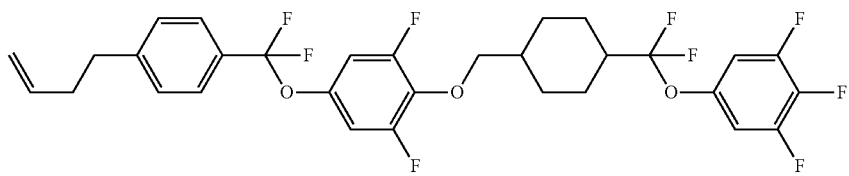 [SMILES: C=CCCc1ccc(C(F)(F)Oc2cc(F)c(OCC3CCC(C(F)(F)Oc4cc(F)c(F)c(F)c4)CC3)c(F)c2)cc1] |
| 160 | 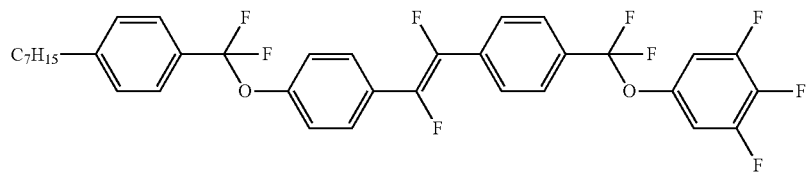 |

-continued
No.
161
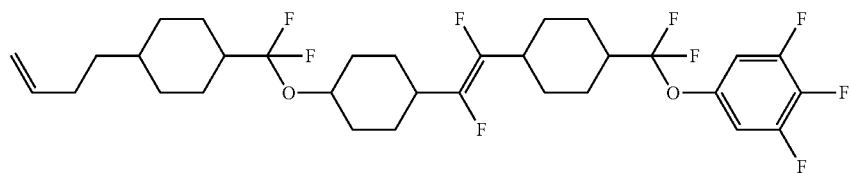
162
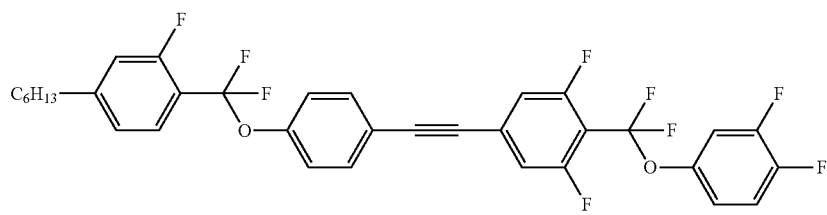
163
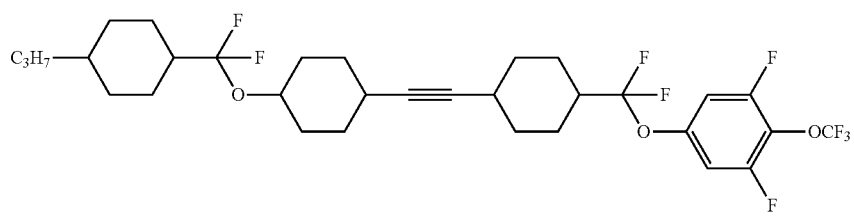
164
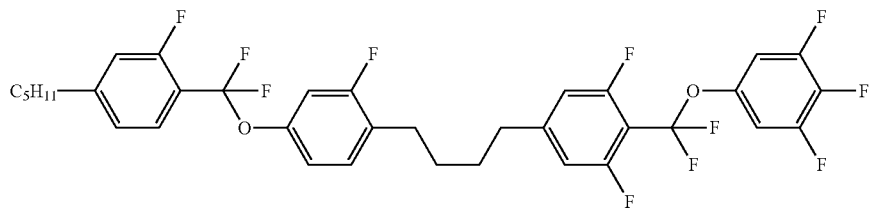
165
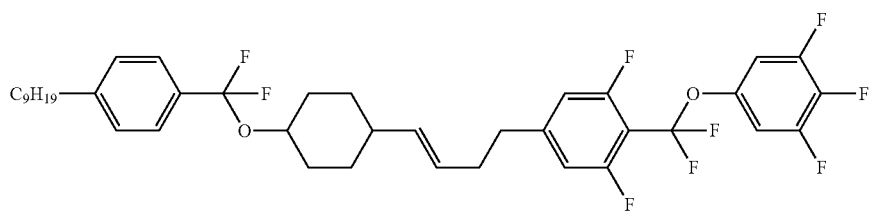
166
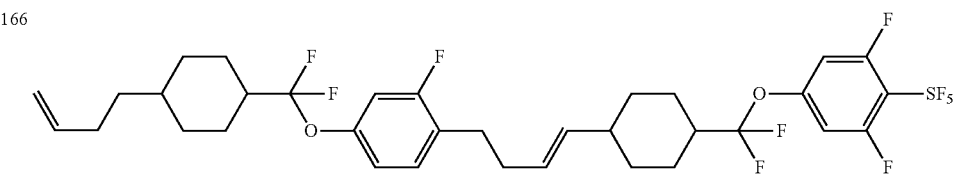
167
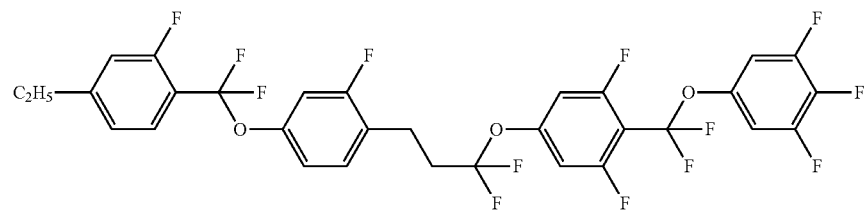 [SMILES: CCc1ccc(C(F)(F)Oc2ccc(CCC(F)(F)Oc3cc(F)c(C(F)(F)Oc4cc(F)c(F)c(F)c4)c(F)c3)c(F)c2)c(F)c1]

| No. | |
|---|---|
| 168 | 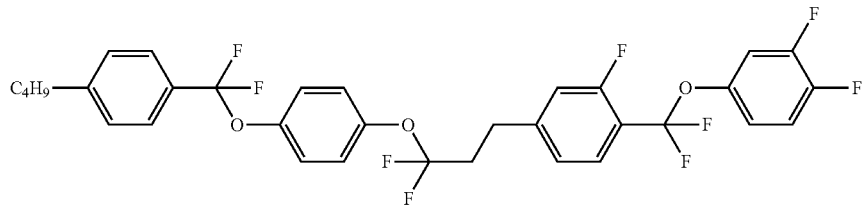 |
| 169 | 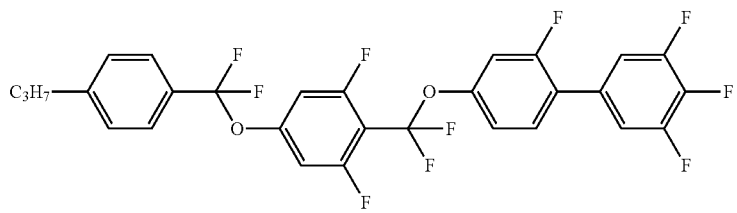 |
| 170 | 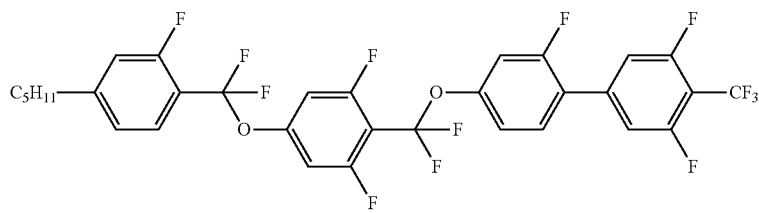 |
| 171 | 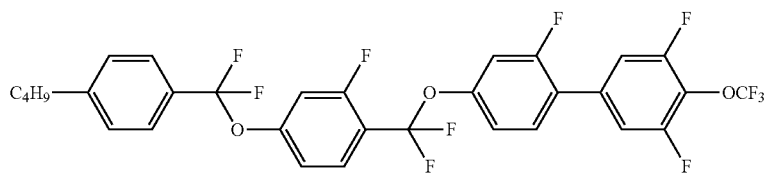 |
| 172 | 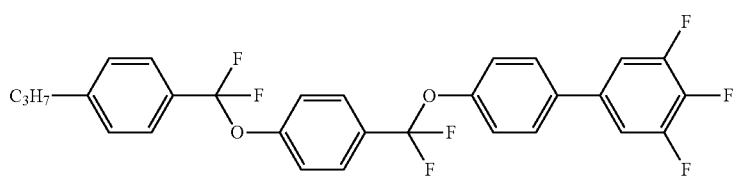<br>C 80.0 N 120.5 I<br>$T_{NI}$ = 84.4° C., η = 46.7 mPa · s, Δn = 0.157, Δε = 22.9 |
| 173 | 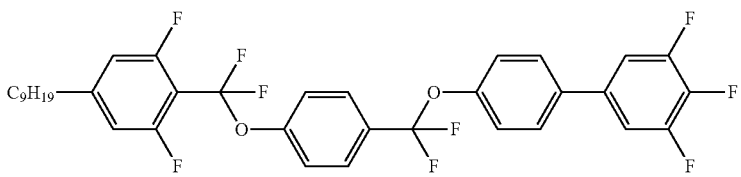 |
| 174 | 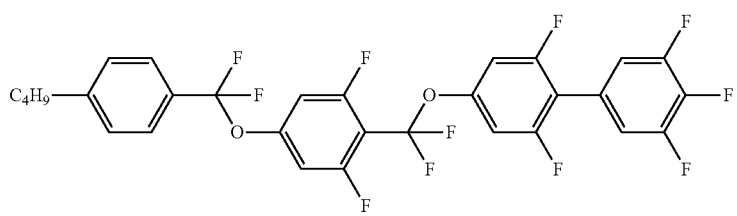 |

| No. | |
|---|---|
| 175 | 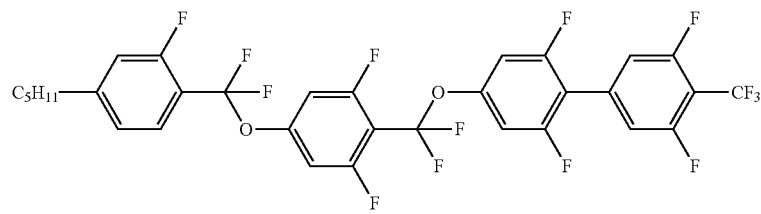 |
| 176 | 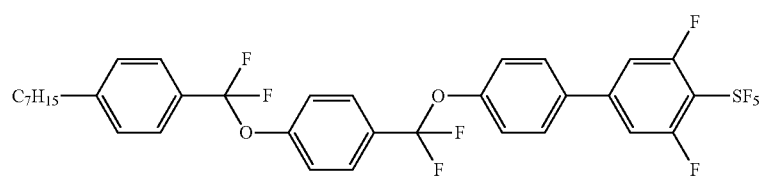 |
| 177 | 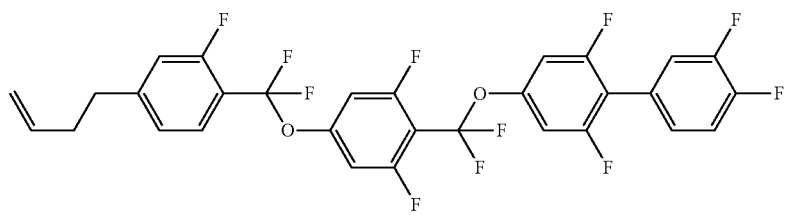 [SMILES: C=CCCc1ccc(C(F)(F)Oc2cc(F)c(C(F)(F)Oc3cc(F)c(-c4ccc(F)c(F)c4)c(F)c3)c(F)c2)c(F)c1] |
| 178 | 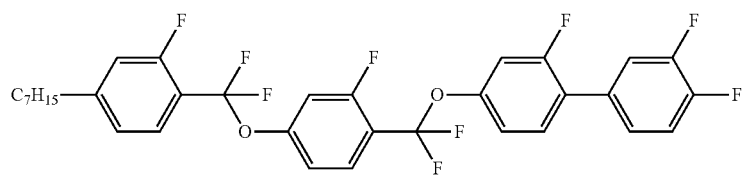 |
| 179 | 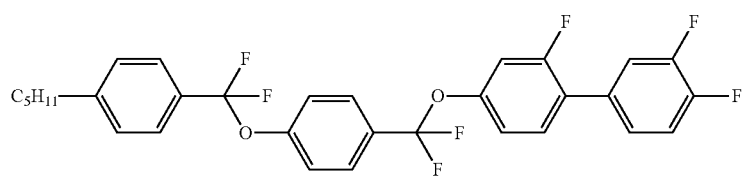 |
| 180 | 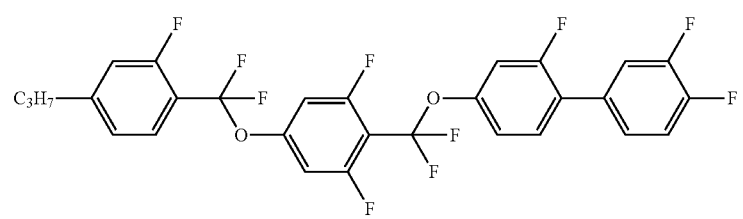 |
| 181 | 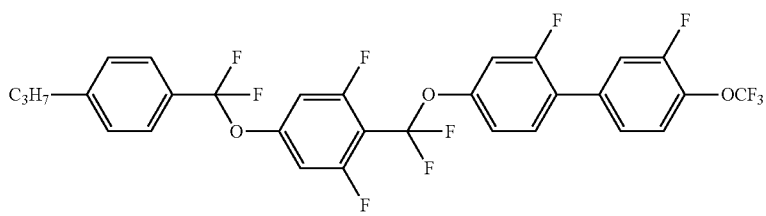 |

-continued
| No. | |
|---|---|
| 182 | 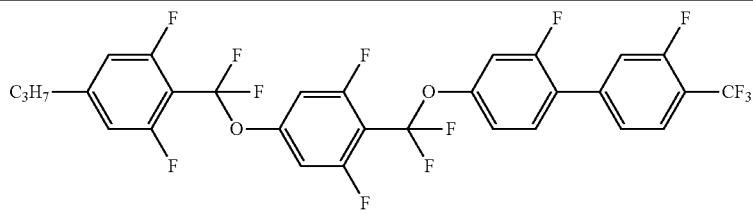 |
| 183 | 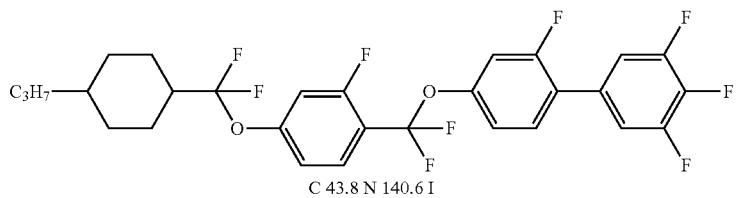<br>C 43.8 N 140.6 I<br>T$_{NI}$ = 96.4° C., η = 81.0 mPa · s, Δn = 0.130, Δε = 26.1 |
| 184 | 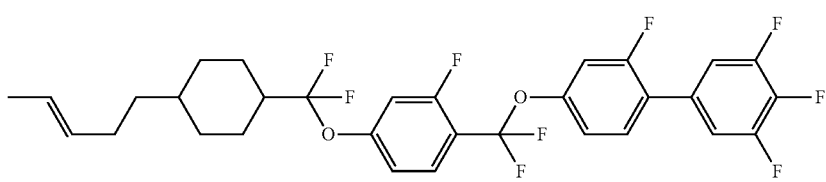 [SMILES: C/C=C/CCC1CCC(C(F)(F)Oc2ccc(C(F)(F)Oc3ccc(-c4cc(F)c(F)c(F)c4)c(F)c3)c(F)c2)CC1] |
| 185 | 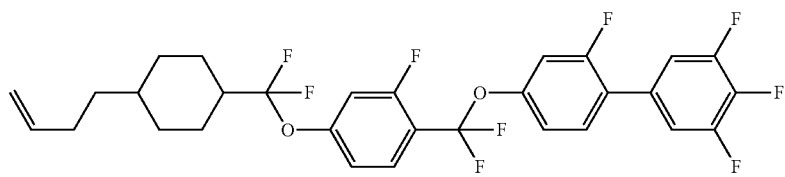 [SMILES: C=CCCC1CCC(C(F)(F)Oc2ccc(C(F)(F)Oc3ccc(-c4cc(F)c(F)c(F)c4)c(F)c3)c(F)c2)CC1] |
| 186 | 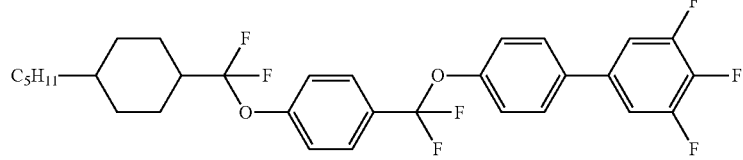 |
| 187 | 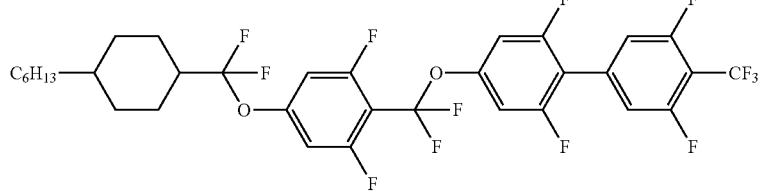 |
| 188 | 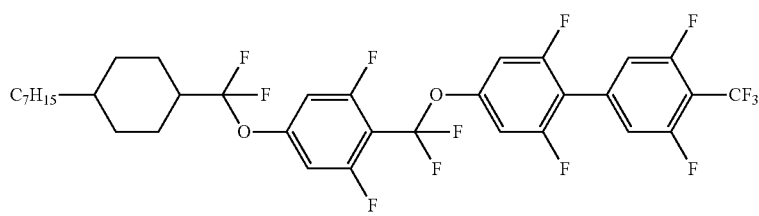 |
| 189 | 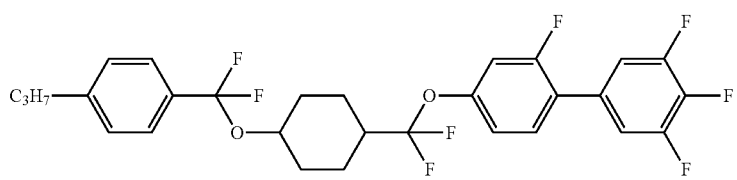 |

-continued
| No. | |
|---|---|
| 190 | 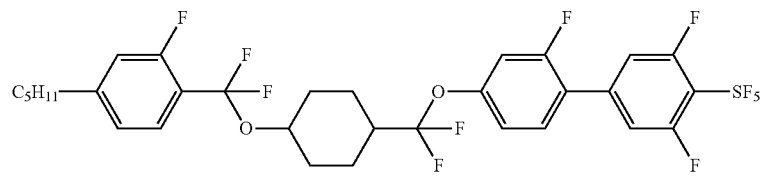 |
| 191 | 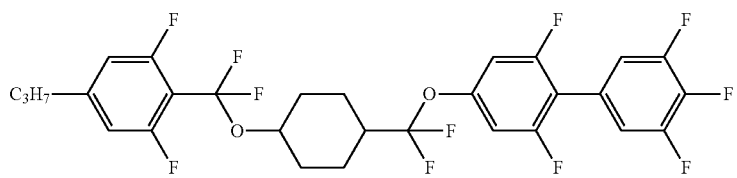 |
| 192 | 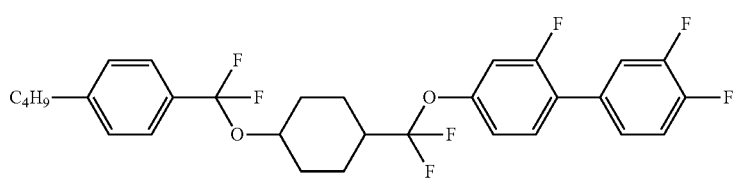 |
| 193 | 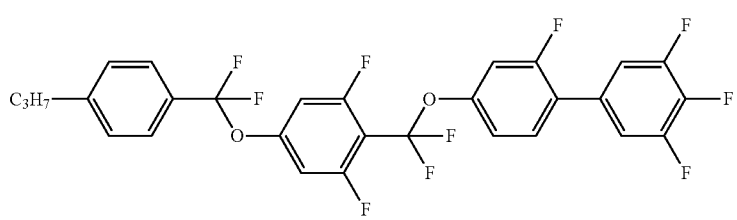 |
| 194 | 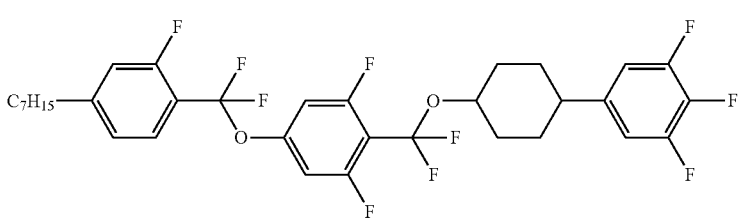 |
| 195 | 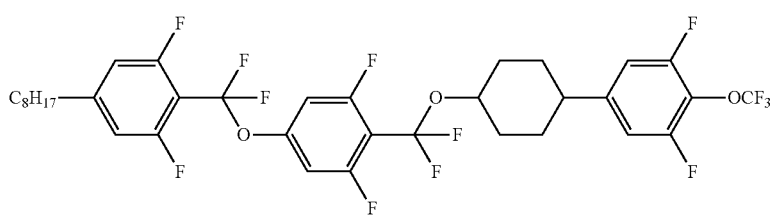 |
| 196 | 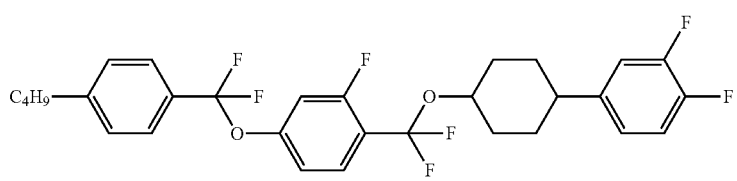 |
| 197 | 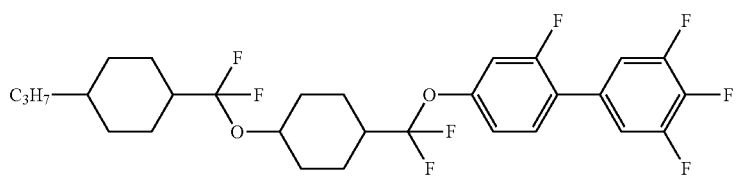 |

| No. |
|---|
| 198 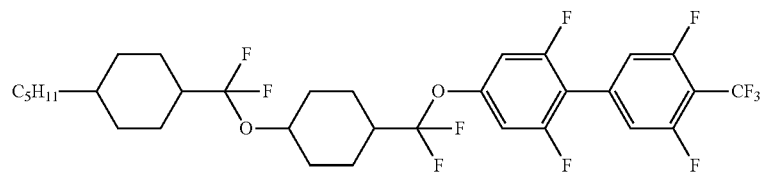 |
| 199 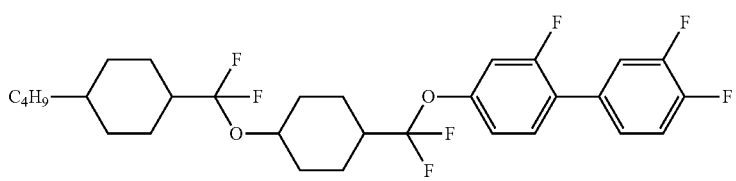 |
| 200 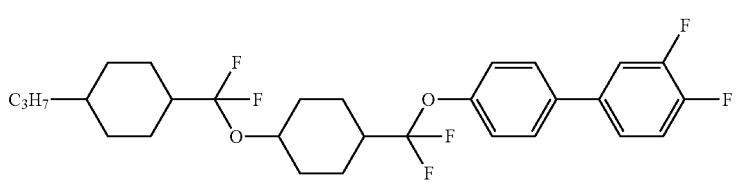 |
| 201 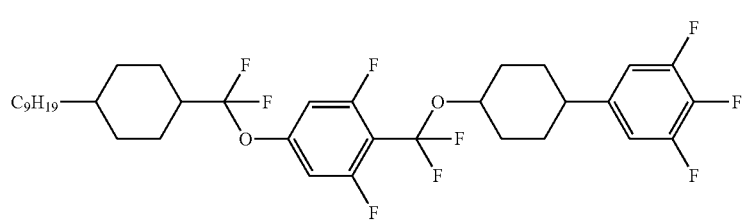 |
| 202 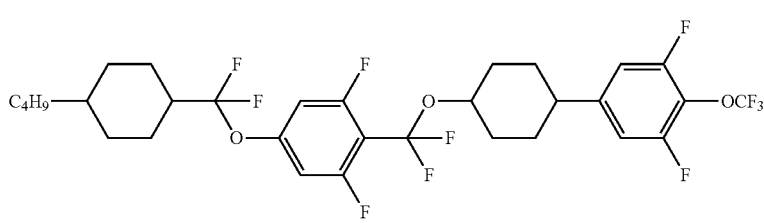 |
| 203 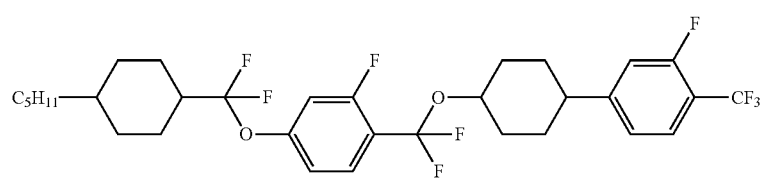 |
| 204 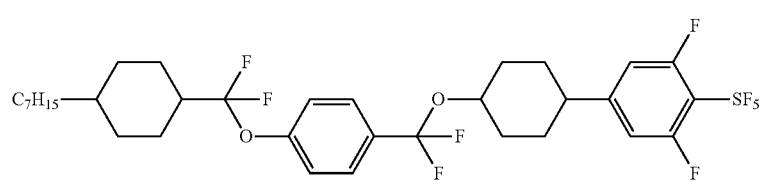 |
| 205 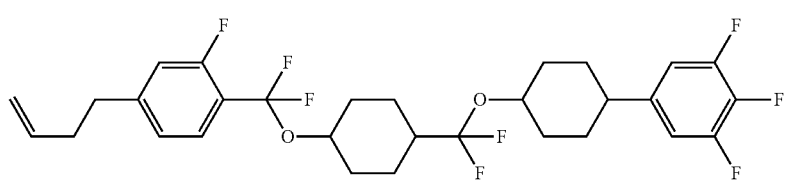 [SMILES: C=CCCc1ccc(C(F)(F)OC2CCC(C(F)(F)OC3CCC(c4cc(F)c(F)c(F)c4)CC3)CC2)c(F)c1] |

-continued
| No. | |
|---|---|
| 206 | 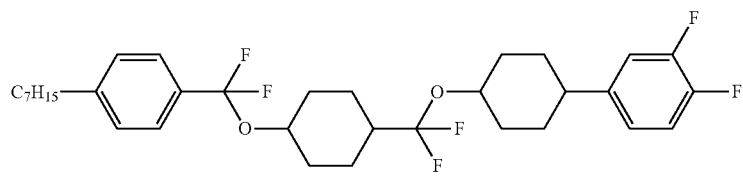 |
| 207 | 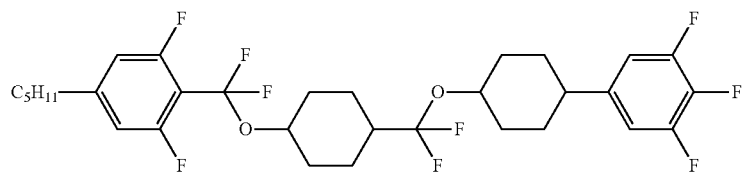 |
| 208 | 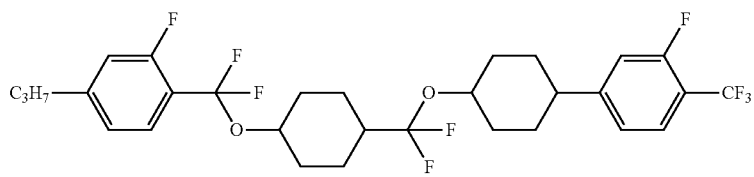 |
| 209 | 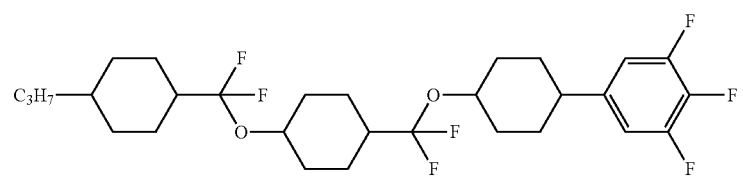 |
| 210 | 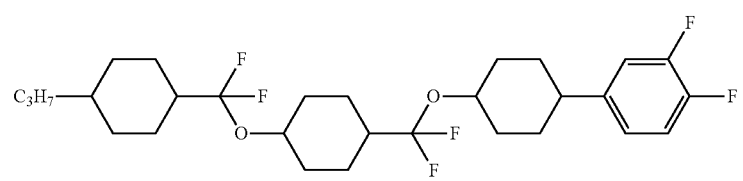 |
| 211 | 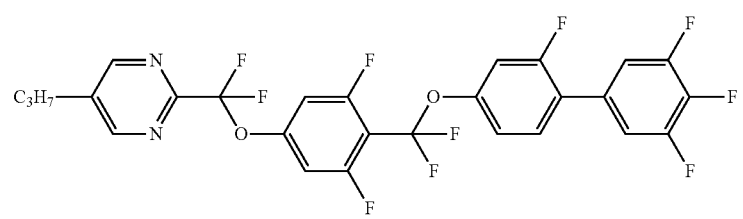 |
| 212 | 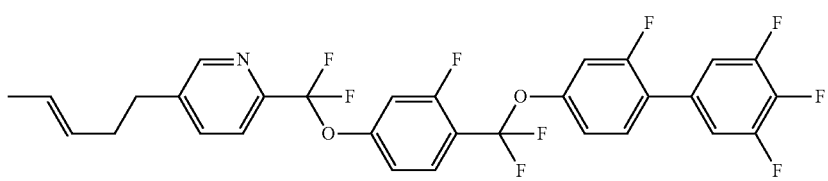 [SMILES: C/C=C/CCc1ccc(C(F)(F)Oc2ccc(C(F)(F)Oc3ccc(-c4cc(F)c(F)c(F)c4)c(F)c3)c(F)c2)nc1] |
| 213 | 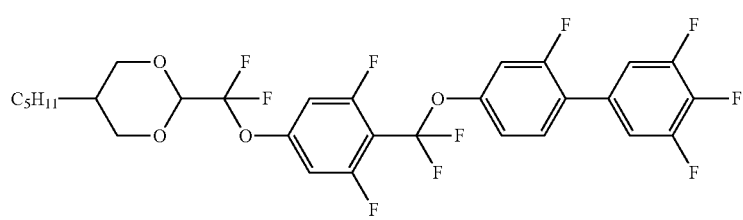 |

-continued
| No. | |
|---|---|
| 214 | 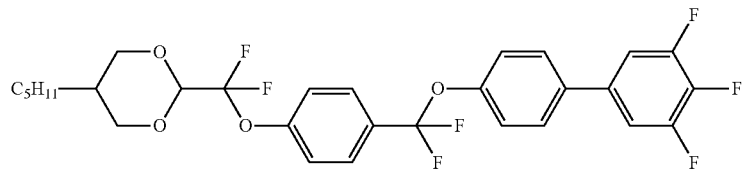 |
| 215 | 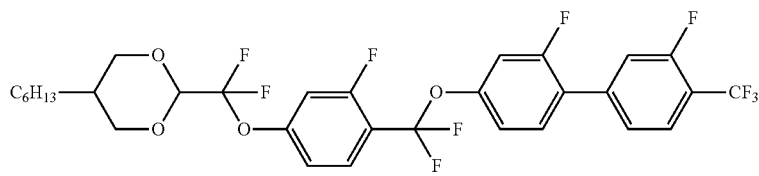 |
| 216 | 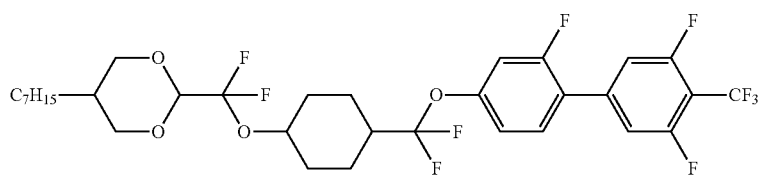 |
| 217 | 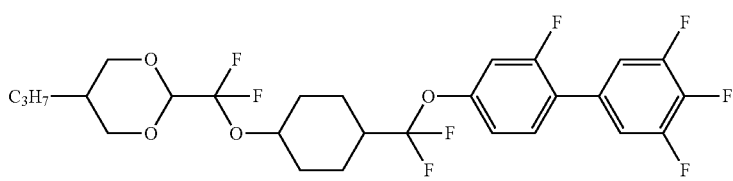 |
| 218 | 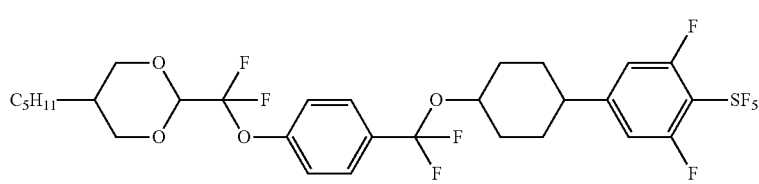 |
| 219 | 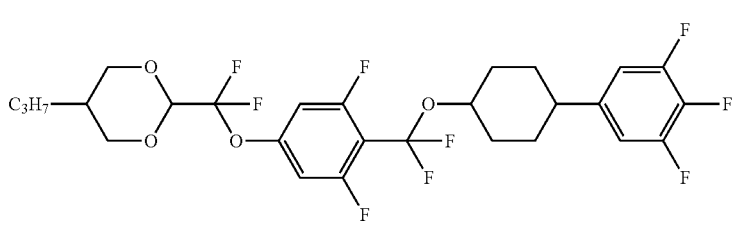 |
| 220 | 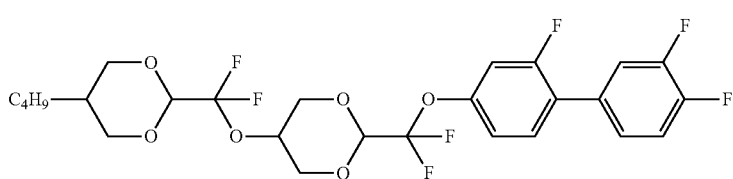 |
| 221 | 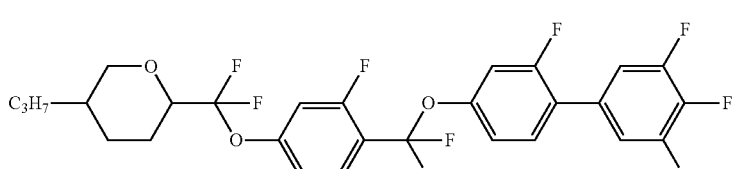 |

-continued
| No. | |
|---|---|
| 222 | 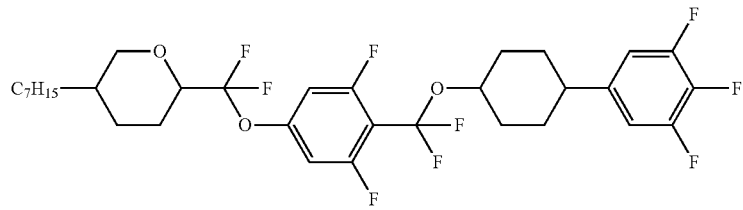 |
| 223 | 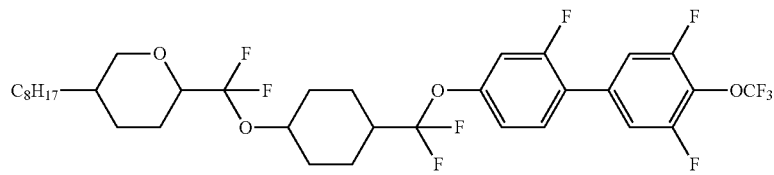 |
| 224 | 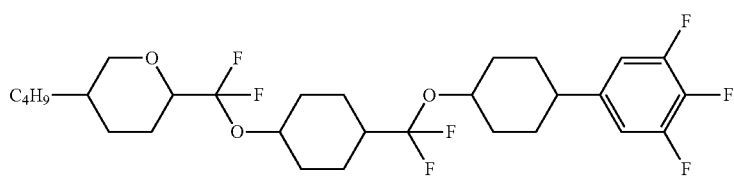 |
| 225 | 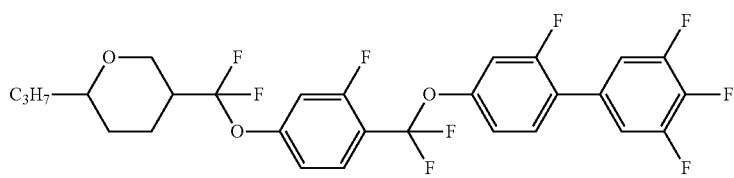 |
| 226 | 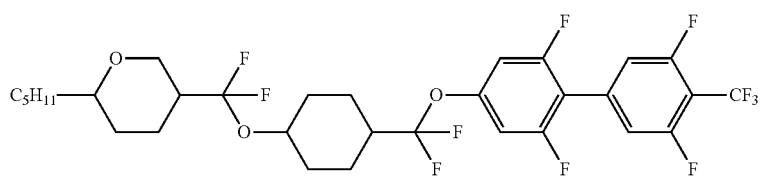 |
| 227 | 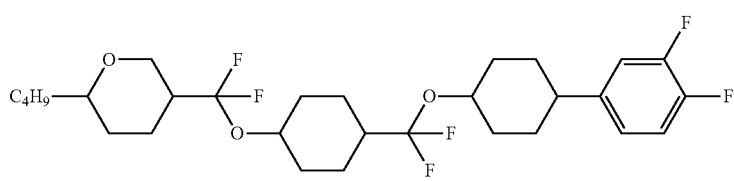 |
| 228 | 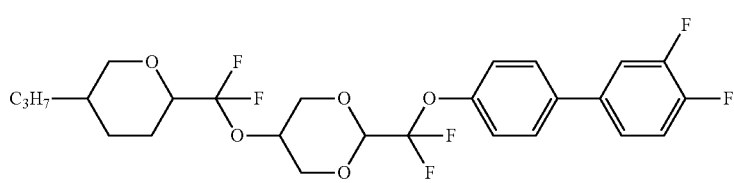 |
| 229 | 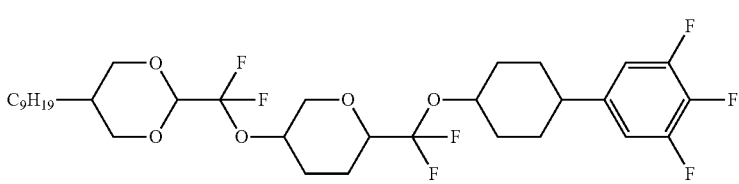 |

-continued
| No. | |
|---|---|
| 230 | 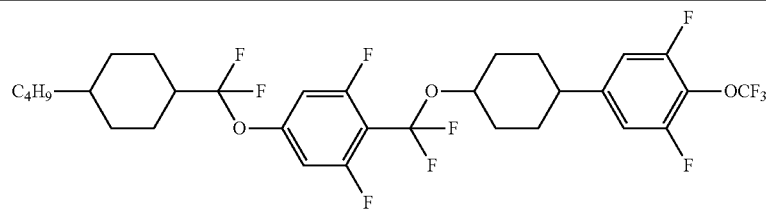 |
| 231 | 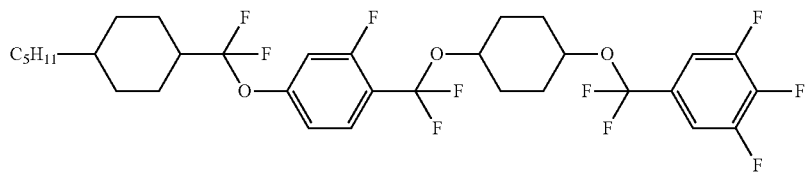 |
| 232 | 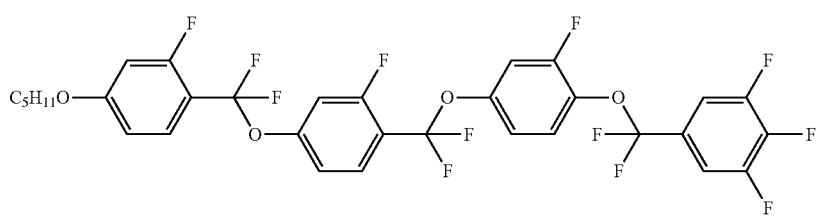 |
| 233 | 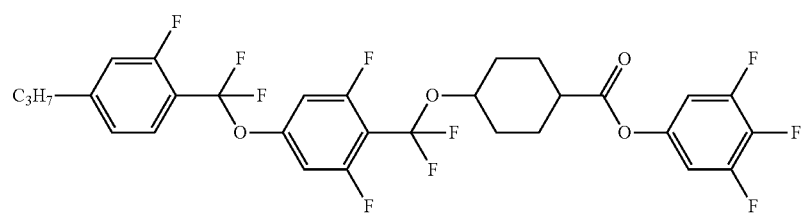 |
| 234 | 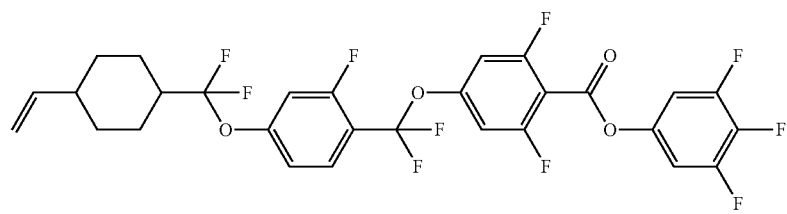 [SMILES: C=CC1CCC(C(F)(F)Oc2ccc(C(F)(F)Oc3cc(F)c(C(=O)Oc4cc(F)c(F)c(F)c4)c(F)c3)c(F)c2)CC1] |
| 235 | 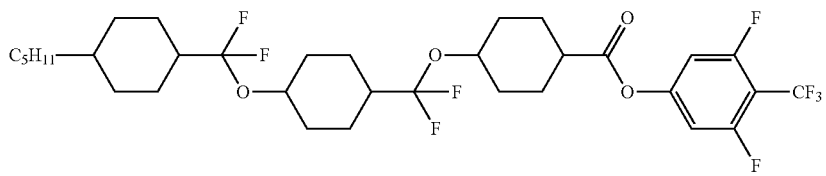 |
| 236 | 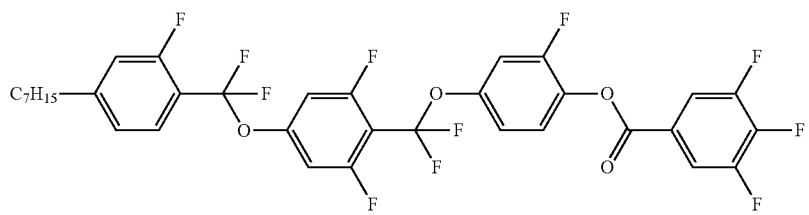 |
| 237 | 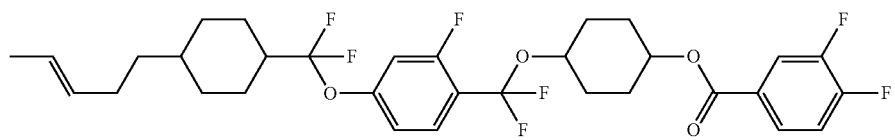 [SMILES: C/C=C/CCC1CCC(C(F)(F)Oc2ccc(C(F)(F)OC3CCC(OC(=O)c4ccc(F)c(F)c4)CC3)c(F)c2)CC1] |

-continued
| No. | |
|---|---|
| 238 | 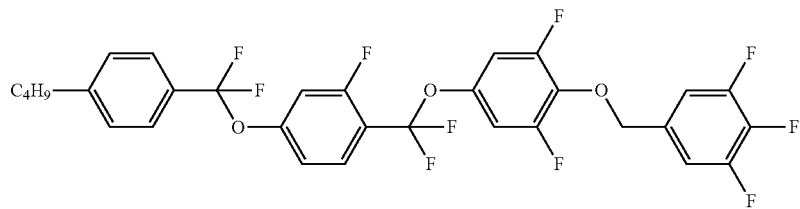 |
| 239 | 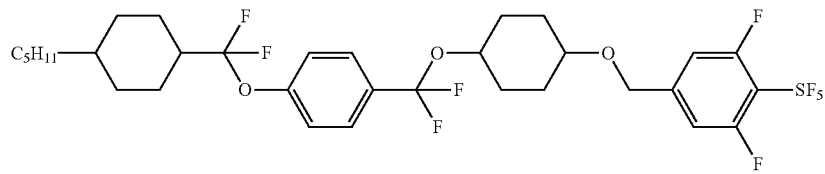 |
| 240 | 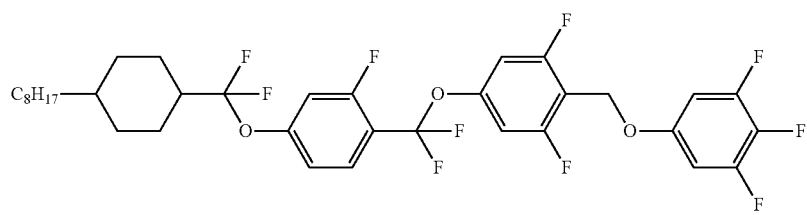 |
| 241 | 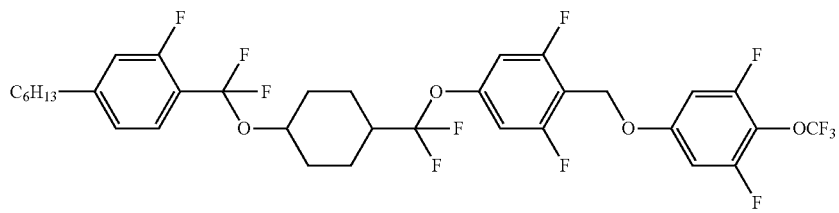 |
| 242 | 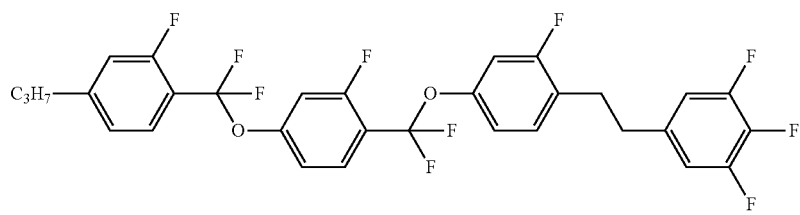 |
| 243 | 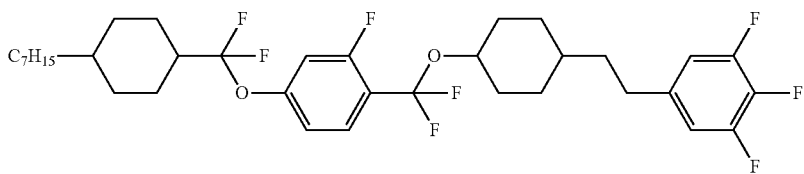 |
| 244 | 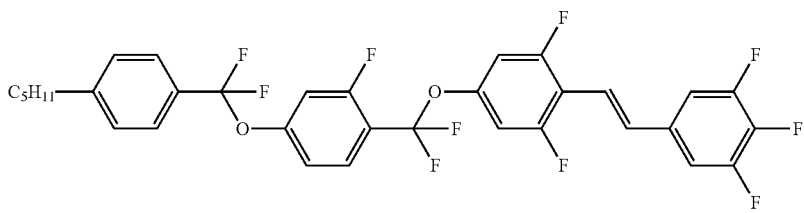 |

-continued
| No. | |
|---|---|
| 245 | 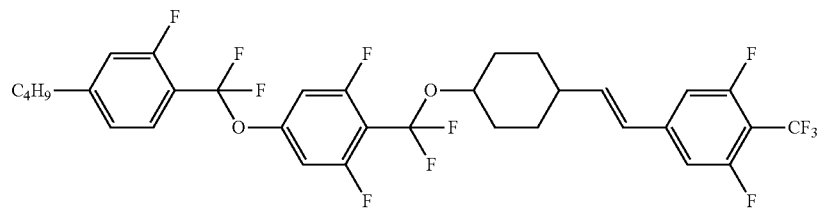 |
| 246 | 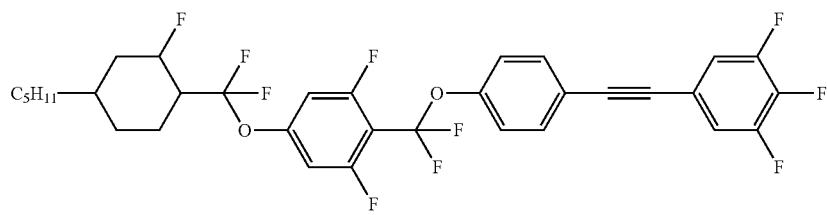 |
| 247 | 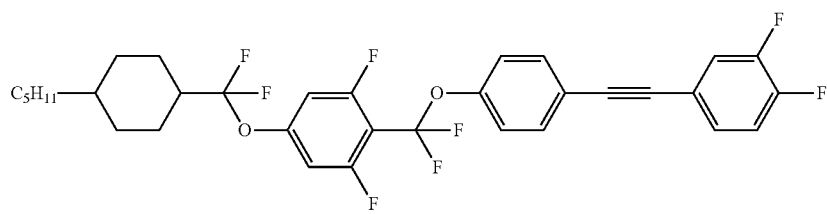 |
| 248 | 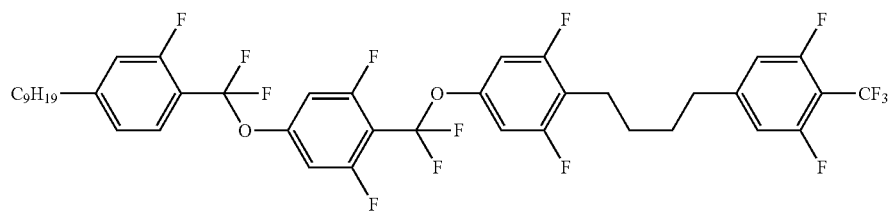 |
| 249 | 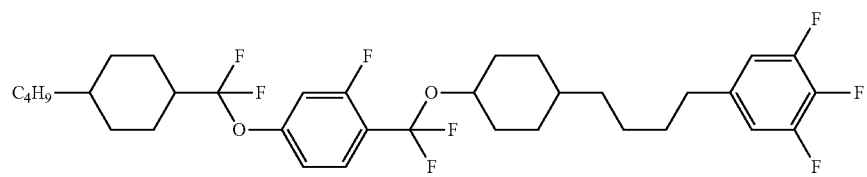 |
| 250 | 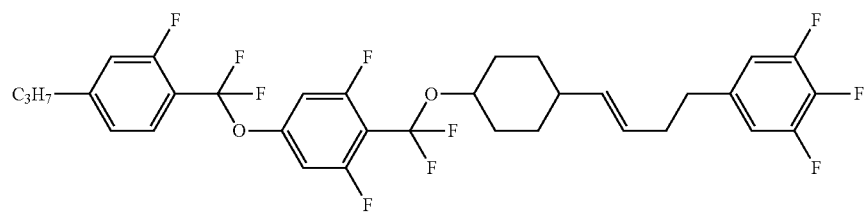 |
| 251 | 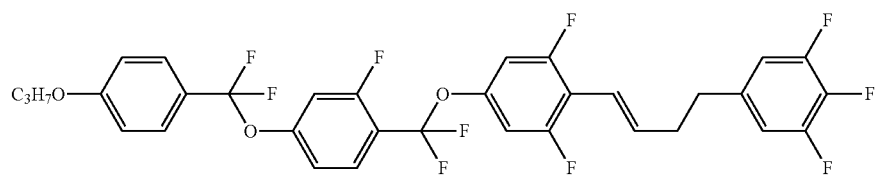 |

| No. | |
|---|---|
| 252 | 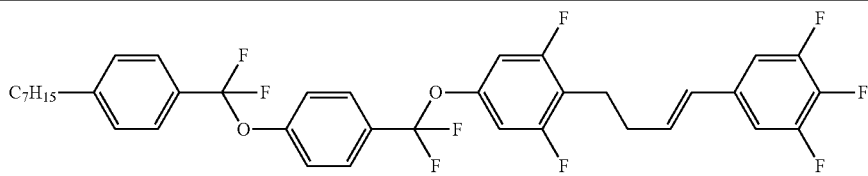 |

Comparative Example 1

The compound (F) was prepared as a comparative compound. This compound is included in the compound (609) described in WO 1996-011897 A, and is similar to the compound of the invention.

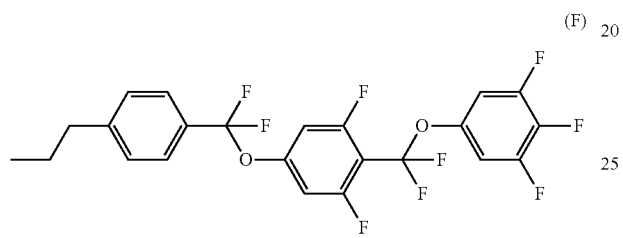

(F)

$^1$H-NMR (δ ppm; CDCl$_3$): 7.59 (d, 2H), 7.30 (d, 2H), 6.99-6.93 (m, 4H), 2.66 (t, 2H), 1.71-1.64 (m, 2H) and 0.96 (t, 3H).

The physical properties of the comparative compound (F) were as follows. Transition temperature: C 40.2 I. $T_{NI}$=−28.3° C.; η=22.4 mPa·s; Δn=0.070; and Δ∈=29.3.

Table 1 summarizes the physical properties of the compound (No. 5) obtained in Example 1 and the comparative compound (F). From Table 1, it was found that the compound (No. 5) was excellent in view of a high maximum temperature and a large dielectric anisotropy.

Comparative Example 2

The compound (G) was prepared as a comparative compound. This compound is included in the compound (1-1-19) described in JP 2001-003053 A, and is similar to the compound of the invention.

(G)

TABLE 1

Physical properties of the compound (No. 5) and the comparative compound (F)

Compound (No. 5)

| | |
|---|---|
| Maximum Temperature ($T_{NI}$) | 65.0° C. |
| Viscosity (η) | 58.5 mPa · s |
| Optical Anisotropy (Δn) | 0.150 |
| Dielectric Anisotropy (Δε) | 39.0 |

Comparative compound (F)

| | |
|---|---|
| Maximum Temperature ($T_{NI}$) | −28.3° C. |
| Viscosity (η) | 22.4 mPa · s |
| Optical Anisotropy (Δn) | 0.070 |
| Dielectric Anisotropy (Δε) | 29.3 |

$^1$H-NMR (δ ppm; CDCl$_3$): 7.55-7.53 (m, 2H), 7.49-7.48 (m, 2H), 7.44-7.41 (m, 1H), 7.30-7.26 (m, 4H), 7.02-6.99 (m, 2H), 2.65 (t, 2H), 1.73-1.66 (m, 2H) and 0.98 (t, 3H).

The physical properties of the comparative compound (G) were as follows. Transition temperature: C 82.3 N 127.7 I. $T_{NI}$=96.4° C.; η=71.1 mPa·s; Δn=0.210; and Δ∈=34.0.

$^1$H-NMR (δ ppm; CDCl$_3$): 7.50-7.48 (m, 2H), 7.44 (dd, 1H), 7.31-7.29 (m, 2H), 7.23-7.19 (m, 6H), 7.02-6.98 (m, 2H), 2.66 (t, 2H), 1.68-1.62 (m, 2H), 1.40-1.31 (m, 4H) and 0.91 (t, 3H).

The physical properties of the comparative compound (H) were as follows. Transition temperature: C 98.4 N 164.6 I.

TABLE 2

Physical properties of the compound (No. 5) and the comparative compound (G)

Compound (No. 5)

| Maximum Temperature ($T_{NI}$) | 65.0° C. |
| Viscosity (η) | 58.5 mPa · s |
| Optical Anisotropy (Δn) | 0.150 |
| Dielectric Anisotropy (Δε) | 39.0 |

Comparative compound (G)

| Maximum Temperature ($T_{NI}$) | 96.4° C. |
| Viscosity (η) | 71.1 mPa · s |
| Optical Anisotropy (Δn) | 0.210 |
| Dielectric Anisotropy (Δε) | 34.0 |

Table 2 summarizes the physical properties of the compound (No. 5) obtained in Example 1 and the comparative compound (G). From Table 2, it was found that the compound (No. 5) was excellent in view of a small viscosity and a large dielectric anisotropy. The difference between the compound (No. 5) and the comparative compound (G) is the number of a single bond and —CF$_2$O— alone. It is worthy to note that the viscosity of the compound (No. 5) which has two —CF$_2$O— is smaller than that of the comparative compound (G) which has one —CF$_2$O—.

Comparative Example 3

The compound (H) was prepared as a comparative compound. This compound is included in the compound (1) described in WO 96-011897 A, and is similar to the compound of the invention.

$T_{NI}$=103.7° C.; η=71.9 mPa·s; Δn=0.177; and Δ∈=47.8. Incidentally, the sample for measurement was prepared from 10% by weight of the comparative compound (H) and 90% by weight of the mother liquid crystals (i).

This is because crystals deposited at the normal ratio (15% by weight:85% by weight).

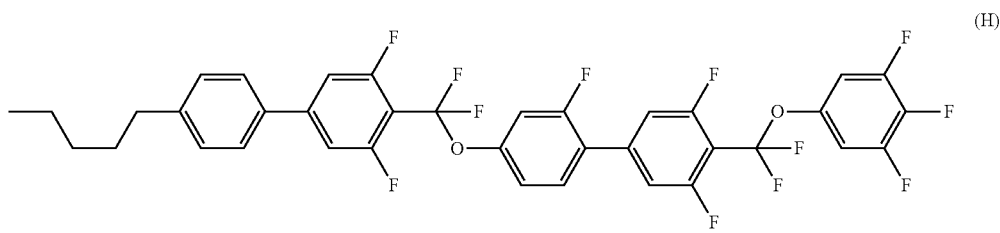 [SMILES: CCCCCc1ccc(-c2cc(F)c(C(F)(F)Oc3ccc(-c4cc(F)c(C(F)(F)Oc5cc(F)c(F)c(F)c5)c(F)c4)c(F)c3)c(F)c2)cc1]
(H)

TABLE 3

Physical properties of the compound (No. 5) and the comparative compound (H)

Compound (No. 5)

| Maximum Temperature ($T_{NI}$) | 65.0° C. |
| --- | --- |
| Viscosity (η) | 58.5 mPa·s |
| Optical Anisotropy (Δn) | 0.150 |
| Dielectric Anisotropy (Δε) | 39.0 |
| Compatibility(Compound/ Mother liquid crystals) | 15% by weight/85% by weight |

Comparative compound (H)

| Maximum Temperature ($T_{NI}$) | 103.7° C. |
| --- | --- |
| Viscosity (η) | 71.9 mPa·s |
| Optical Anisotropy (Δn) | 0.177 |
| Dielectric Anisotropy (Δε) | 47.8 |
| Compatibility(Compound/ Mother liquid crystals) | 10% by weight/90% by weight |

Table 3 summarizes the physical properties of the compound (No. 5) obtained in Example 1 and the comparative compound (H). From Table 3, it was found that the compound (No. 5) was excellent in view of a small viscosity and a large compatibility with other liquid crystal compounds. The difference between the compound (No. 5) and the comparative compound (H) is the number of a single bond and —CF$_2$O— alone. It is worthy to note that the viscosity of the compound (No. 5) which has two —CF$_2$O— is smaller than that of the comparative compound (H) which has one —CF$_2$O—.

Comparative Example 4

The compound (1) was prepared as a comparative compound. This compound is included in the compound (3-2) described in JP H10-204436 A (1998), and is similar to the compound of the invention.

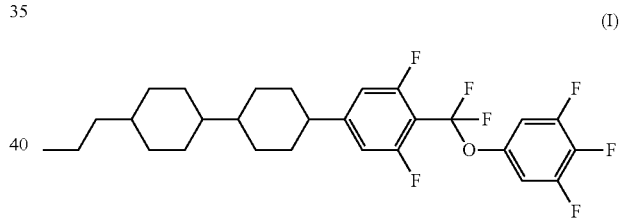

(I)

$^1$H-NMR (δ ppm; CDCl$_3$): 6.95 (dd, 2H), 6.83 (d, 2H), 2.48-2.43 (m, 1H), 1.92-1.85 (m, 4H), 1.78-1.71 (m, 4H), 1.38-1.25 (m, 4H), 1.16-0.95 (m, 9H) and 0.89-0.86 (m, 5H).

The physical properties of the comparative compound (1) were as follows. Transition temperature: C 84.3 N 165.5 I. $T_{NI}$=112.4° C.; η=62.4 mPa·s; Δn=0.112; and Δn=21.2.

TABLE 4

Physical properties of the compound (No. 5) and the comparative compound (1)

Compound (No. 31)

| Maximum Temperature ($T_{NI}$) | 121.7° C. |
| --- | --- |
| Viscosity (η) | 57.1 mPa·s |

TABLE 4-continued

Physical properties of the compound (No. 5) and the comparative compound (1)

| | |
|---|---|
| Optical Anisotropy (Δn) | 0.110 |
| Dielectric Anisotropy (Δε) | 24.1 |

Comparative compound (I)

| | |
|---|---|
| Maximum Temperature (T$_{NI}$) | 112.4° C. |
| Viscosity (η) | 62.4 mPa·s |
| Optical Anisotropy (Δn) | 0.112 |
| Dielectric Anisotropy (Δε) | 21.2 |

Table 4 summarized the physical properties of the compound (No. 31) obtained in Example 2 and the comparative compound (I). From Table 4, it was found that the compound (No. 31) was excellent in view of a high maximum temperature, a small viscosity and a large dielectric anisotropy.

1-2. Examples of the Composition (1)

The liquid crystal composition (1) of the invention will be explained in detail by way of Examples. The invention is not limited by Examples described below. The compounds described in Examples were expressed in terms of symbols according to the definition in the following table. In the table, the configuration of 1,4-cyclohexylene is trans. The parenthesized number next to a symbolized compound in Example indicates the number of the compound. The symbol (-) means any other liquid crystal compound. The ratios (percentage) of liquid crystal compounds mean the percentages by weight (% by weight) based on the total weight of the liquid crystal composition. Last, the values of physical properties of the composition were summarized. The physical properties were measured according to the method described above, and measured values were reported without extrapolation.

TABLE

Method of Description of Compounds using Symbols
R—(A$_1$)—Z$_1$—...—Z$_n$—(A$_n$)—R'

| | Symbol |
|---|---|
| 1) Left-terminal Group R— | |
| C$_n$H$_{2n+1}$— | n- |
| C$_n$H$_{2n+1}$O— | nO— |
| C$_m$H$_{2m+1}$OC$_n$H$_{2n}$— | mOn— |
| CH$_2$=CH— | V— |
| C$_n$H$_{2n+1}$—CH=CH— | nV— |
| CH$_2$=CH—C$_n$H$_{2n}$— | Vn— |
| C$_m$H$_{2m+1}$—CH=CH—C$_n$H$_{2n}$— | mVn— |
| CF$_2$=CH— | VFF— |
| CF$_2$=CH—C$_n$H$_{2n}$— | VFFn— |
| 2) Right-terminal Group —R' | |
| —C$_n$H$_{2n+1}$ | -n |
| —OC$_n$H$_{2n+1}$ | —On |
| —COOCH$_3$ | —EMe |
| —CH=CH$_2$ | —V |
| —CH=CH—C$_n$H$_{2n+1}$ | —Vn |
| —C$_n$H$_{2n}$—CH=CH$_2$ | —nV |
| —C$_m$H$_{2m}$—CH=CH—CnH2n+1 | —mVn |
| —CH=CF$_2$ | —VFF |
| —F | —F |

TABLE-continued

Method of Description of Compounds using Symbols
R—(A$_1$)—Z$_1$—...—Z$_n$—(A$_n$)—R'

| | Symbol |
|---|---|
| —Cl | —CL |
| —OCF$_3$ | —OCF3 |
| —OHCF$_2$ | —OHCF2 |
| —CF$_3$ | —CF3 |
| 3) Bonding Group —Z$_n$— | |
| —C$_n$H$_{2n}$— | n |
| —COO— | E |
| —CH=CH— | V |
| —CH$_2$O— | 1O |
| —OCH$_2$— | O1 |
| —CF$_2$O— | X |
| —C≡C— | T |
| 4) Ring Structure —A$_n$— | |
| (cyclohexane) | H |
| (benzene) | B |
| (fluorobenzene) | B(F) |
| (fluorobenzene, 2F) | B(2F) |
| (difluorobenzene) | B(F,F) |

TABLE-continued

Method of Description of Compounds using Symbols
R—(A₁)—Z₁— . . . —Zₙ—(Aₙ)—R'

| Structure | Symbol |
|---|---|
| (2,5-difluoro-1,3-phenylene) | B(2F,5F) |
| (2,3-difluoro-1,4-phenylene) | B(2F,3F) |
| pyrimidine-2,5-diyl | Py |
| 1,3-dioxane-2,5-diyl | G |

5) Examples of Description

Example 1. 3-BB(F)XB(F,F)XB(F,F)-F

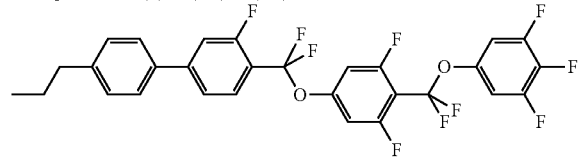

Example 2. 3-HHXB(F,F)XB(F,F)-F

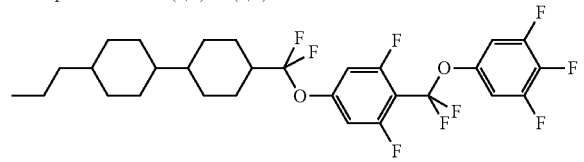

Example 3. 3-HB-O2

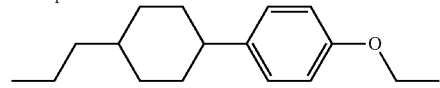

Example 4. V2-BB-1

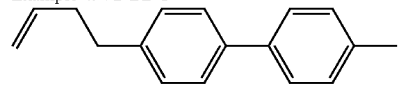

Example 10

| | | |
|---|---|---|
| 3-BB(F)XB(F,F)XB(F,F)-F | (No. 5) | 4% |
| 3-HHXB(F,F)XB(F,F)-F | (No. 31) | 3% |
| 5-HB-CL | (2-2) | 16% |
| 3-HB-O2 | (12-5) | 10% |
| 5-HB-O2 | (12-5) | 6% |
| 3-HHB-F | (3-1) | 4% |
| 3-HHB-CL | (3-1) | 3% |
| 4-HHB-CL | (3-1) | 4% |
| 3-HHB(F)-F | (3-2) | 10% |
| 4-HHB(F)-F | (3-2) | 9% |
| 5-HHB(F)-F | (3-2) | 9% |
| 7-HHB(F)-F | (3-2) | 5% |
| 1O1-HBBH-5 | (14-1) | 3% |
| 3-HHBB(F,F)-F | (4-6) | 2% |
| 4-HHBB(F,F)-F | (4-6) | 3% |
| 5-HHBB(F,F)-F | (4-6) | 3% |
| 3-HH2BB(F,F)-F | (4-15) | 3% |
| 4-HH2BB(F,F)-F | (4-15) | 3% |

NI = 107.7° C.;
Δn = 0.099;
Δε = 6.1;
Vth = 1.88 V;
η = 21.8 mPa · s.

Example 11

| | | |
|---|---|---|
| 3-BB(F)XB(F,F)XB(F,F)-F | (No. 5) | 5% |
| 3-HHXB(F,F)XB(F,F)-F | (No. 31) | 4% |
| 3-HHB(F,F)-F | (3-3) | 9% |
| 3-H2HB(F,F)-F | (3-15) | 8% |
| 4-H2HB(F,F)-F | (3-15) | 8% |
| 5-H2HB(F,F)-F | (3-15) | 8% |
| 3-HBB(F,F)-F | (3-24) | 21% |
| 5-HBB(F,F)-F | (3-24) | 20% |
| 3-H2BB(F,F)-F | (3-27) | 8% |
| 5-HHBB(F,F)-F | (4-6) | 3% |
| 5-HHEBB-F | (4-17) | 2% |
| 1O1-HBBH-5 | (14-1) | 4% |

NI = 89.7° C.;
Δn = 0.114;
Δε = 11.2;
Vth = 1.41 V;
η = 35.0 mPa · s.

Example 12

| | | |
|---|---|---|
| 3-HHXBXB(F,F)-F | (No. 29) | 3% |
| 3-BB(F)XBXB(F,F)-F | (No. 3) | 3% |
| 5-HB-F | (2-2) | 12% |
| 6-HB-F | (2-2) | 9% |
| 7-HB-F | (2-2) | 7% |
| 2-HHB-OCF3 | (3-1) | 7% |
| 3-HHB-OCF3 | (3-1) | 7% |
| 4-HHB-OCF3 | (3-1) | 7% |
| 5-HHB-OCF3 | (3-1) | 5% |
| 3-HH2B-OCF3 | (3-4) | 4% |
| 5-HH2B-OCF3 | (3-4) | 4% |
| 3-HHB(F,F)-OHCF2 | (3-3) | 4% |
| 3-HHB(F,F)-OCF3 | (3-3) | 5% |
| 3-HH2B(F)-F | (3-5) | 3% |
| 3-HBB(F)-F | (3-23) | 7% |
| 5-HBB(F)-F | (3-23) | 7% |
| 5-HBBH-3 | (14-1) | 3% |
| 3-HB(F)BH-3 | (14-2) | 3% |

NI = 87.2° C.;
Δn = 0.092;
Δε = 5.5;
Vth = 2.21 V;
η = 15.9 mPa · s.

The helical pitch was 59.8 μm when 0.25 part by weight of the optically active compound (Op-5) was added to 100 parts by weight of the preceding composition.

Example 13

| | | |
|---|---|---|
| 3-BB(F)XBXB(F,F)-F | (No. 3) | 4% |
| 3-BBXBXB(F,F)-F | (No. 1) | 4% |
| 5-HB-CL | (2-2) | 8% |
| 3-HB-O2 | (12-5) | 4% |
| 5-HB-O2 | (12-5) | 4% |
| 3-HHB-1 | (13-1) | 2% |
| 3-HHB(F,F)-F | (3-3) | 8% |
| 3-HBB(F,F)-F | (3-24) | 20% |
| 5-HBB(F,F)-F | (3-24) | 15% |
| 3-HHEB(F,F)-F | (3-12) | 8% |
| 4-HHEB(F,F)-F | (3-12) | 3% |
| 5-HHEB(F,F)-F | (3-12) | 3% |
| 2-HBEB(F,F)-F | (3-39) | 3% |
| 3-HBEB(F,F)-F | (3-39) | 5% |
| 5-HBEB(F,F)-F | (3-39) | 3% |
| 3-HHBB(F,F)-F | (4-6) | 6% |

NI = 78.3° C.;
Δn = 0.113;
Δε = 10.9;
Vth = 1.32 V;
η = 24.7 mPa·s.

Example 14

| | | |
|---|---|---|
| 3-HXB(F)B(F,F)XB(F,F)-F | (No. 99) | 4% |
| 3-BXBBXB(F,F)-F | (No. 90) | 4% |
| 3-HB-CL | (2-2) | 3% |
| 5-HB-CL | (2-2) | 4% |
| 3-HHB-OCF3 | (3-1) | 5% |
| 3-H2HB-OCF3 | (3-13) | 5% |
| 5-H4HB-OCF3 | (3-19) | 15% |
| V-HHB(F)-F | (3-2) | 5% |
| 3-HHB(F)-F | (3-2) | 5% |
| 5-HHB(F)-F | (3-2) | 5% |
| 3-H4HB(F,F)-CF3 | (3-21) | 8% |
| 5-H4HB(F,F)-CF3 | (3-21) | 10% |
| 5-H2HB(F,F)-F | (3-15) | 5% |
| 5-H4HB(F,F)-F | (3-21) | 7% |
| 2-H2BB(F)-F | (3-26) | 5% |
| 3-H2BB(F)-F | (3-26) | 5% |
| 3-HBEB(F,F)-F | (3-39) | 5% |

NI = 73.8° C.;
Δn = 0.101;
Δε = 10.1;
Vth = 1.67 V;
η = 28.1 mPa·s.

Example 15

| | | |
|---|---|---|
| 3-HXB(F)XB(F)B(F,F)-F | (No. 183) | 5% |
| 3-BXBXBB(F,F)-F | (No. 172) | 5% |
| 5-HB-CL | (2-2) | 7% |
| 7-HB(F,F)-F | (2-4) | 3% |
| 7-HB-1 | (12-5) | 5% |
| 3-HB-O2 | (12-5) | 15% |
| V2-BB-1 | (12-8) | 5% |
| 3-HHB-1 | (13-1) | 8% |
| 3-HHB-3 | (13-1) | 5% |
| 3-HHB-O1 | (13-1) | 5% |
| 2-HHB(F)-F | (3-2) | 7% |
| 3-HHB(F)-F | (3-2) | 7% |
| 5-HHB(F)-F | (3-2) | 7% |
| 3-HHB(F,F)-F | (3-3) | 6% |
| 3-H2HB(F,F)-F | (3-15) | 5% |
| 4-H2HB(F,F)-F | (3-15) | 5% |

NI = 77.3° C.;
Δn = 0.089;
Δε = 4.9;
Vth = 1.64 V;
η = 21.8 mPa·s.

Example 16

| | | |
|---|---|---|
| 3-HHXBXB(F,F)-F | (No. 29) | 5% |
| 3-BBXBXB(F,F)-F | (No. 1) | 5% |
| 5-HB-CL | (2-2) | 3% |
| 7-HB(F)-F | (2-3) | 7% |
| 3-HB-O2 | (12-5) | 9% |
| 3-HH-EMe | (12-2) | 23% |
| 3-HHEB-F | (3-10) | 8% |
| 5-HHEB-F | (3-10) | 8% |
| 3-HHEB(F,F)-F | (3-12) | 10% |
| 4-HHEB(F,F)-F | (3-12) | 5% |
| 5-HGB(F,F)-F | (3-103) | 6% |
| 2-H2GB(F,F)-F | (3-106) | 4% |
| 5-GHB(F,F)-F | (3-109) | 7% |

NI = 83.0° C.;
Δn = 0.076;
Δε = 6.7;
Vth = 1.45 V;
η = 20.5 mPa·s.

Example 17

| | | |
|---|---|---|
| 3-HXB(F)B(F,F)XB(F,F)-F | (No. 99) | 5% |
| 3-BXBBXB(F,F)-F | (No. 90) | 5% |
| 3-HB-O2 | (12-5) | 10% |
| 5-HB-CL | (2-2) | 13% |
| 3-HBB(F,F)-F | (3-24) | 7% |
| 3-PyB(F)-F | (2-15) | 10% |
| 5-PyB(F)-F | (2-15) | 10% |
| 3-PyBB-F | (3-80) | 10% |
| 4-PyBB-F | (3-80) | 10% |
| 5-PyBB-F | (3-80) | 10% |
| 5-HBB(F)B-3 | (14-5) | 10% |

NI = 86.1° C.;
Δn = 0.181;
Δε = 10.5;
Vth = 1.46 V;
η = 38.9 mPa·s.

Example 18

| | | |
|---|---|---|
| 3-HXB(F)XB(F)B(F,F)-F | (No. 183) | 4% |
| 3-BXBXBB(F,F)-F | (No. 172) | 4% |
| 3-HB-O1 | (12-5) | 10% |
| 3-HB-O2 | (12-5) | 10% |
| 3-HB(2F,3F)-O2 | (6-1) | 12% |
| 5-HB(2F,3F)-O2 | (6-1) | 12% |
| 2-HHB(2F,3F)-1 | (7-1) | 12% |
| 3-HHB(2F,3F)-1 | (7-1) | 10% |
| 3-HHB(2F,3F)-O2 | (7-1) | 7% |
| 5-HHB(2F,3F)-O2 | (7-1) | 13% |
| 3-HHB-1 | (13-1) | 6% |

NI = 80.3° C.;
Δn = 0.095;
Δε = −0.9;
η = 36.9 mPa·s.

Industrial Applicability

The liquid crystal compound of the invention has a high stability to heat, light or the like, a high clearing point, a low minimum temperature of a liquid crystal phase, a small viscosity, a suitable optical anisotropy, a large dielectric anisotropy, a suitable elastic constant and an excellent compatibility with other liquid crystal compounds. The liquid crystal composition of the invention includes this compound and has a high maximum temperature of a nematic phase, a low minimum temperature of a nematic phase, a small viscosity, a suitable optical anisotropy, a large dielectric anisotropy and a suitable elastic constant. The composition has a suitable balance regarding at least two of the physical properties. The liquid crystal display device of the invention contains this composition and has a wide temperature range in which the device can be used, a short response time, a large voltage

What is claimed is:

1. A compound represented by formula (1):

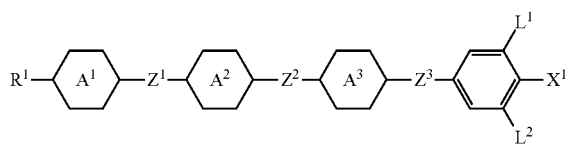

(1)

wherein
- $R^1$ is hydrogen, halogen or alkyl having 1 to 20 carbons, and in the alkyl, at least one of —$CH_2$— may be replaced by —O— or —S—, and at least one of —$(CH_2)_2$— may be replaced by —CH=CH—, and in the groups, at least one of hydrogen may be replaced by halogen;
- ring $A^1$, ring $A^2$ and ring $A^3$ are independently 1,4-cyclohexylene, 1,4-phenylene, 1,4-phenylene in which at least one of hydrogen has been replaced by halogen, tetrahydropyran-2,5-diyl, 1,3-dioxane-2,5-diyl, pyrimidine-2,5-diyl or pyridine-2,5-diyl;
- $Z^1$, $Z^2$ and $Z^3$ are independently a single bond, —$(CH_2)_2$—, —CH=CH—, —CF=CF—, —C≡C—, —COO—, —OCO—, —$CF_2O$—, —$OCF_2$—, —$CH_2O$—, —$OCH_2$—, —$(CH_2)_4$—, —$(CH_2)_2CF_2O$—, —$(CH_2)_2OCF_2$—, —$CF_2O(CH_2)_2$—, —$OCF_2(CH_2)_2$—, —CH=CH—$(CH_2)_2$— or —$(CH_2)_2$—CH=CH—, and at least two of $Z^1$, $Z^2$ and $Z^3$ are —$CF_2O$— or —$OCF_2$—;
- $L^1$ and $L^2$ are independently hydrogen or halogen, and at least one of $L^1$ and $L^2$ is halogen; and
- $X^1$ is hydrogen, halogen, —C≡N, —N=C=S, —$SF_5$ or alkyl having 1 to 10 carbons, and in the alkyl, at least one of —$CH_2$— may be replaced by —O— or —S—, and at least one of —$(CH_2)_2$— may be replaced by —CH=CH—, and in the groups, at least one of hydrogen may be replaced by halogen.

2. The compound according to claim 1, wherein any one of $Z^1$, $Z^2$ and $Z^3$ is a single bond.

3. The compound according to claim 1, wherein the compound is represented by any one of formulas (1-2) to (1-4):

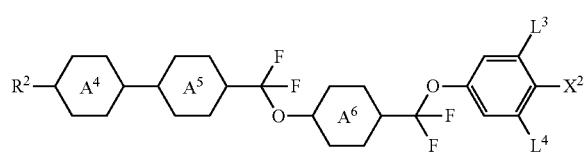

(1-2)

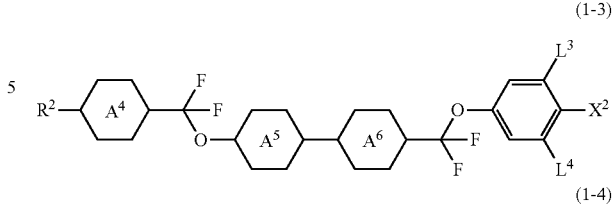

(1-3)

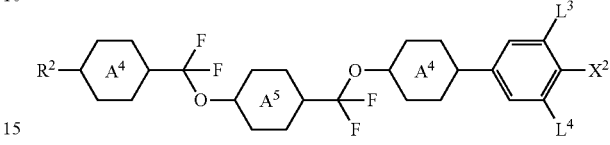

(1-4)

wherein $R^2$ is alkyl having 1 to 15 carbons, and in the alkyl, at least one of —$CH_2$— may be replaced by —O— or —S—, and at least one of —$(CH_2)_2$— may be replaced by —CH=CH—, and in the groups, at least one of hydrogen may be replaced by fluorine; ring $A^4$, ring $A^5$ and ring $A^6$ are independently 1,4-cyclohexylene, 1,4-phenylene, 1,4-phenylene in which at least one of hydrogen has been replaced by halogen, tetrahydropyran-2,5-diyl or 1,3-dioxane-2,5-diyl; $L^3$ and $L^4$ are independently hydrogen or fluorine, and at least one of $L^3$ and $L^4$ is fluorine; and $X^2$ is fluorine or alkyl having 1 to 10 carbons, and in the alkyl, at least one of —$CH_2$— may be replaced by —O— or —S—, and at least one of —$(CH_2)_2$— may be replaced by —CH=CH—, and in the groups, at least one of hydrogen may be replaced by fluorine.

4. The compound according to claim 1, wherein the compound is represented by any one of formulas (1-2-1) to (1-4-1):

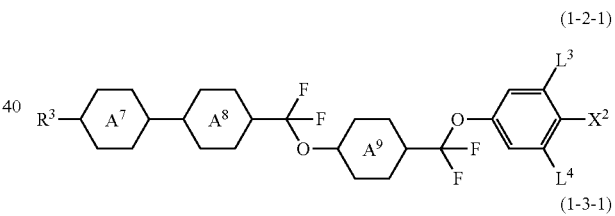

(1-2-1)

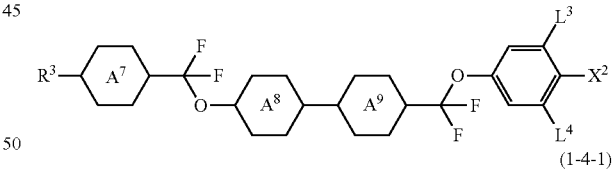

(1-3-1)

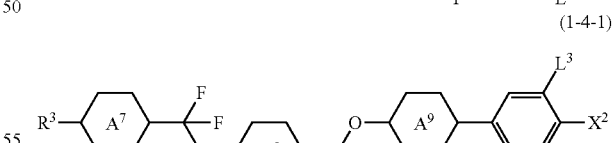

(1-4-1)

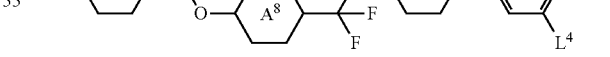

wherein $R^3$ is alkyl having 1 to 10 carbons, and in the alkyl, at least one of —$CH_2$— may be replaced by —O—, and at least one of —$(CH_2)_2$— may be replaced by —CH=CH—; ring $A^7$, ring $A^8$ and ring $A^9$ are independently 1,4-cyclohexylene, 1,4-phenylene, 2-fluoro-1,4-phenylene, 2,6-difluoro-1,4-phenylene, tetrahydropyran-2,5-diyl or 1,3-dioxane-2,5-diyl; $L^3$ and $L^4$ are independently hydrogen or fluorine, and at least one of $L^3$ and $L^4$ is fluorine; and $X^3$ is fluorine, —$CF_3$ or —$OCF_3$.

5. The compound according to claim 1, wherein the compound is represented by any one of formulas (1-2-1-1) to (1-2-1-8), formulas (1-3-1-1) to (1-3-1-8) and formulas (1-4-1-1) to (1-4-1-8):
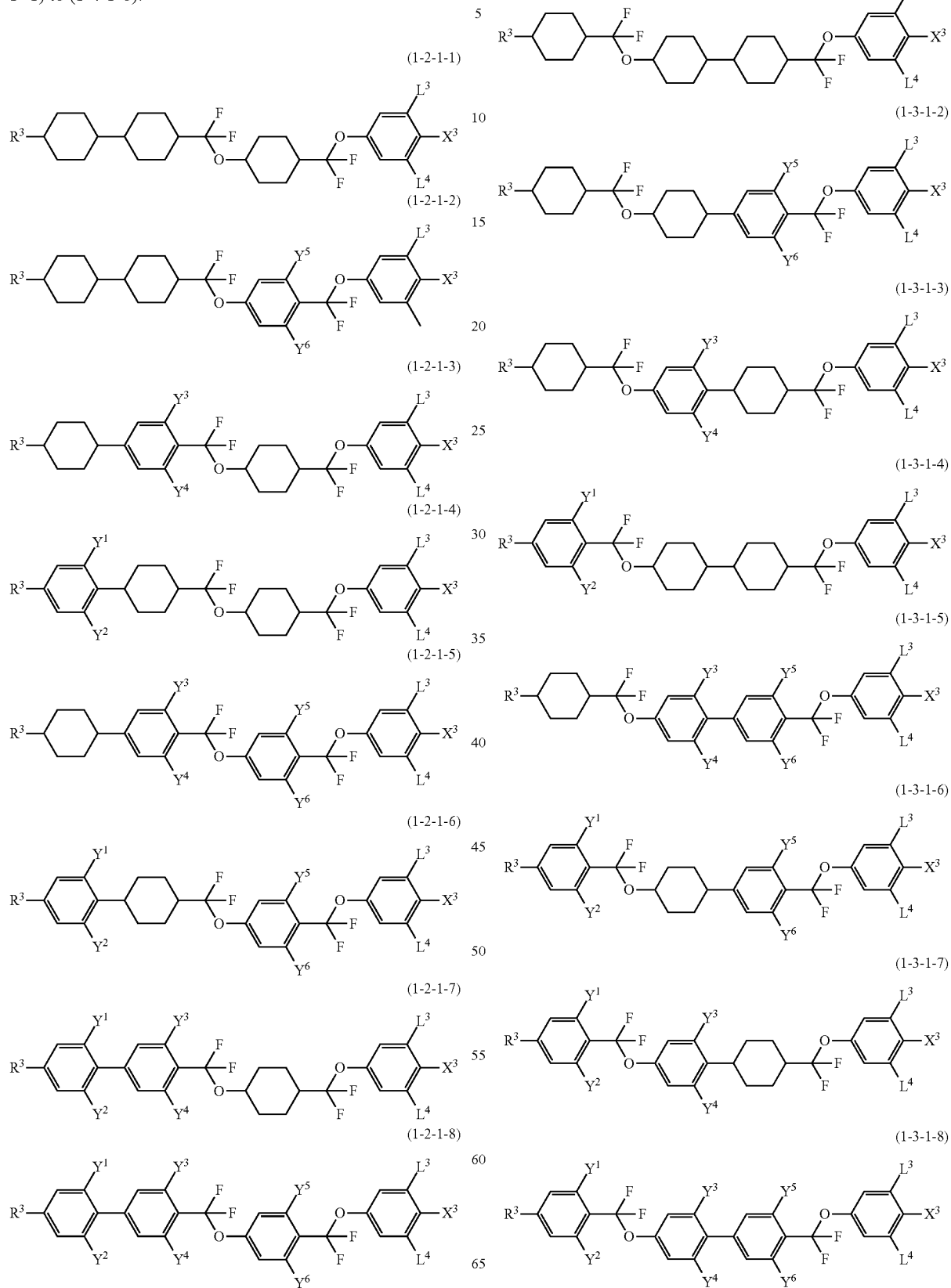

-continued (1-4-1-1)
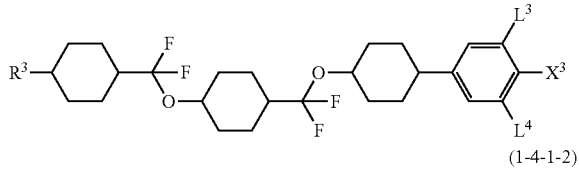

(1-4-1-2)
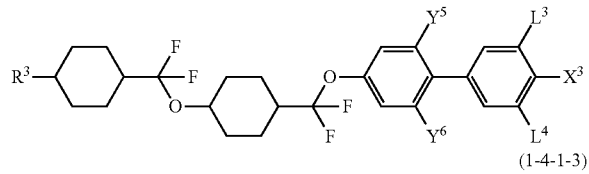

(1-4-1-3)
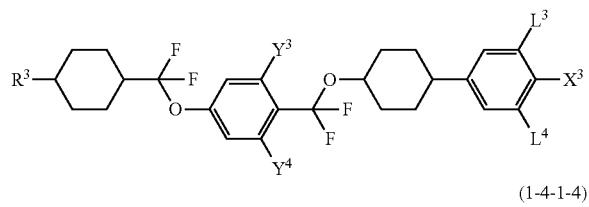

(1-4-1-4)
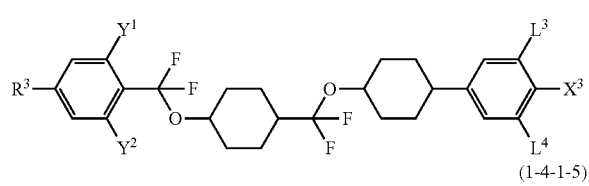

(1-4-1-5)
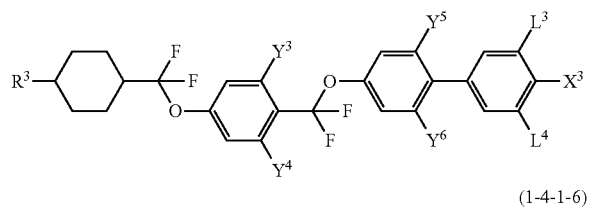

(1-4-1-6)
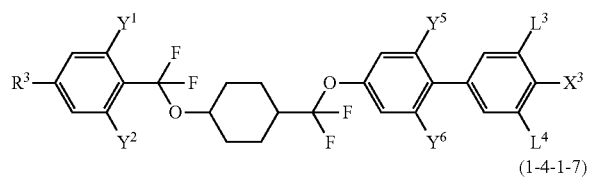

(1-4-1-7)
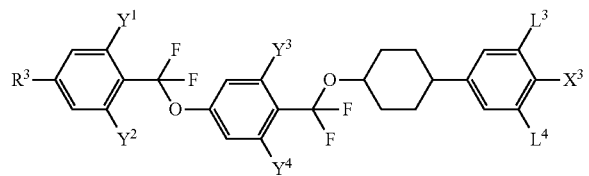

(1-4-1-8)
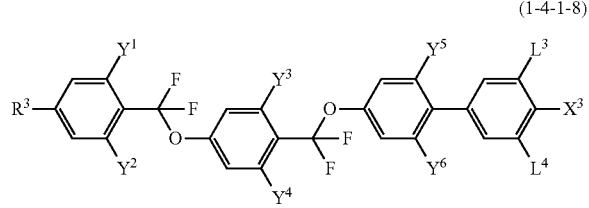

wherein $R^3$ is alkyl having 1 to 10 carbons, and in the alkyl, at least one of —$CH_2$— may be replaced by —O—, and at least one of —$(CH_2)_2$— may be replaced by —CH=CH—; $Y^1$, $Y^2$, $Y^3$, $Y^4$, $Y^5$ and $Y^6$ are independently hydrogen or fluorine; $L^3$ and $L^4$ are independently hydrogen or fluorine, and at least one of $L^3$ and $L^4$ is fluorine; and $X^3$ is fluorine, —$CF_3$ or —$OCF_3$.

6. The compound according to claim 5, wherein in formulas (1-2-1-1) to (1-2-1-8), $R^3$ is alkyl having 1 to 10 carbons, alkoxy having 1 to 9 carbons or alkenyl having 2 to 10 carbons; $Y^1$, $Y^2$, $Y^3$, $Y^4$, $Y^5$ and $Y^6$ independently independently hydrogen or fluorine; $L^3$ and $L^4$ are independently hydrogen or fluorine, and at least one of $L^3$ and $L^4$ is fluorine; and $X^3$ is fluorine, —$CF_3$ or —$OCF_3$.

7. The compound according to claim 5, wherein in formulas (1-3-1-1) to (1-3-1-8), $R^3$ is alkyl having 1 to 10 carbons, alkoxy having 1 to 9 carbons or alkenyl having 2 to 10 carbons; $Y^1$, $Y^2$, $Y^3$, $Y^4$, $Y^5$ and $Y^6$ independently hydrogen or fluorine; $L^3$ and $L^4$ are independently hydrogen or fluorine, and at least one of $L^3$ and $L^4$ is fluorine; and $X^3$ is fluorine, —$CF_3$ or —$OCF_3$.

8. The compound according to claim 5, wherein in formulas (1-4-1-1) to (1-4-1-8), $R^3$ is alkyl having 1 to 10 carbons, alkoxy having 1 to 9 carbons or alkenyl having 2 to 10 carbons; $Y^1$, $Y^2$, $Y^3$, $Y^4$, $Y^5$ and $Y^6$ are independently hydrogen or fluorine; $L^3$ and $L^4$ are independently hydrogen or fluorine, and at least one of $L^3$ and $L^4$ is fluorine; and $X^3$ is fluorine, —$CF_3$ or —$OCF_3$.

9. The compound according to claim 1, wherein the compound is represented by any one of formulas (1-2-1-8-1) and (1-2-1-2-1):

(1-2-1-8-1)
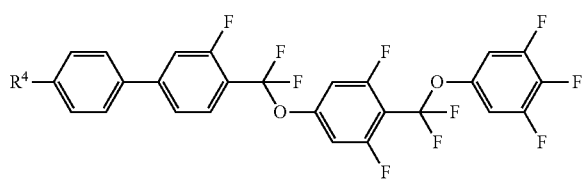

(1-2-1-2-1)
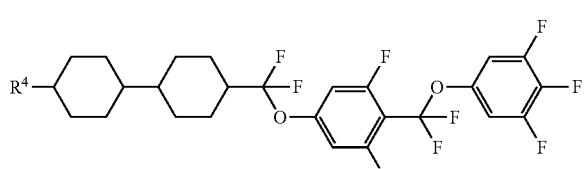

wherein $R^4$ is alkyl having 1 to 10 carbons.

10. A liquid crystal composition comprising at least one compound according to claim 1.

11. The liquid crystal composition according to claim 10, further comprising at least one compound selected from the group consisting of compounds represented by formulas (2) to (4):

(2)
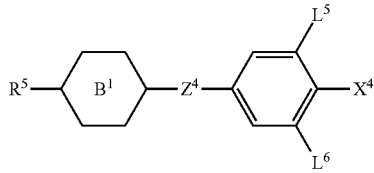

-continued

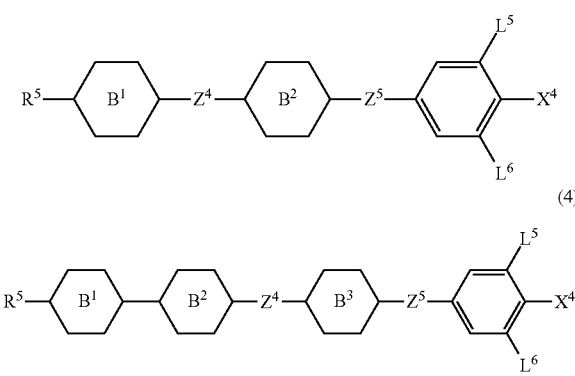
(3)

(4)

wherein
- $R^5$ is alkyl having 1 to 10 carbons or alkenyl having 2 to 10 carbons, and in the alkyl and the alkenyl, at least one of hydrogen may be replaced by fluorine, and at least one of —$CH_2$— may be replaced by —O—;
- $X^4$ is fluorine, chlorine, —$OCF_3$, —$OCHF_2$, —$CF_3$, —$CHF_2$, —$CH_2F$, —$CF=F_2$, —$OCF_2CHF_2$ or —$OCF_2CHFCF_3$;
- ring $B^1$, ring $B^2$ and ring $B^3$ are independently 1,4-cyclohexylene, 1,4-phenylene, 2-fluoro-1,4-phenylene, 2,6-difluoro-1,4-phenylene, tetrahydropyran-2,5-diyl, 1,3-dioxane-2,5-diyl or pyrimidine-2,5-diyl;
- $Z^4$ and $Z^5$ are independently a single bond, —$(CH_2)_2$—, —CH=CH—, —C≡C—, —COO—, —$CF_2O$—, —$OCF_2$—, —$CH_2O$— or —$(CH_2)_4$—, and $Z^4$ and $Z^5$ are not simultaneously —$CF_2O$— or —$OCF_2$—; and
- $L^5$ and $L^6$ are independently hydrogen or fluorine.

12. The liquid crystal composition according to claim 10, further comprising at least one compound selected from the group consisting of compounds represented by formula (5):

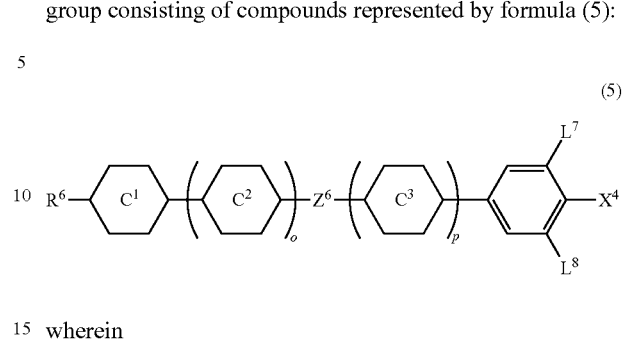
(5)

wherein
- $R^6$ is alkyl having 1 to 10 carbons or alkenyl having 2 to 10 carbons, and in the alkyl and the alkenyl, at least one of hydrogen may be replaced by fluorine, and at least one of —$CH_2$— may be replaced by —O—;
- $X^5$ is —C≡N or —C≡C—C≡N;
- ring $C^1$, ring $C^2$ and ring $C^3$ are independently 1,4-cyclohexylene, 1,4-phenylene in which at least one of hydrogen may be replaced by fluorine, tetrahydropyran-2,5-diyl, 1,3-dioxane-2,5-diyl or pyrimidine-2,5-diyl;
- $Z^6$ is a single bond, —$(CH_2)_2$—, —C≡C—, —COO—, —$CF_2O$—, —$OCF_2$— or —$CH_2O$—;
- $L^7$ and $L^8$ are independently hydrogen or fluorine; and
- o is 0, 1 or 2, p is 0 or 1, the sum of o and p is 0, 1, 2 or 3.

13. The liquid crystal composition according to claim 10, further comprising at least one compound selected from the group consisting of compounds represented by formulas (6) to (11):

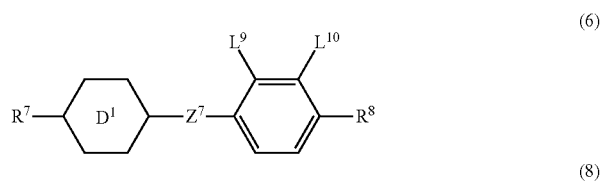
(6)

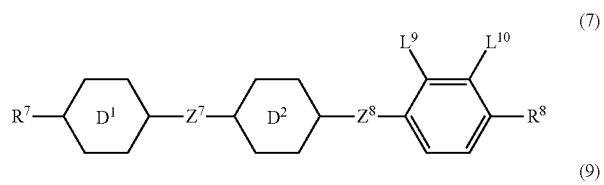
(7)

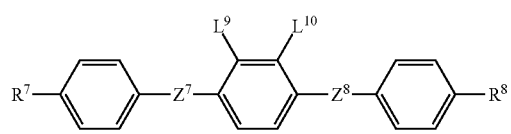
(8)

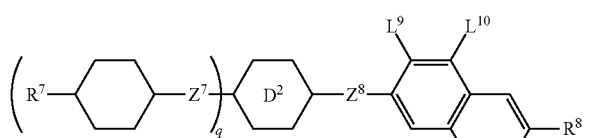
(9)

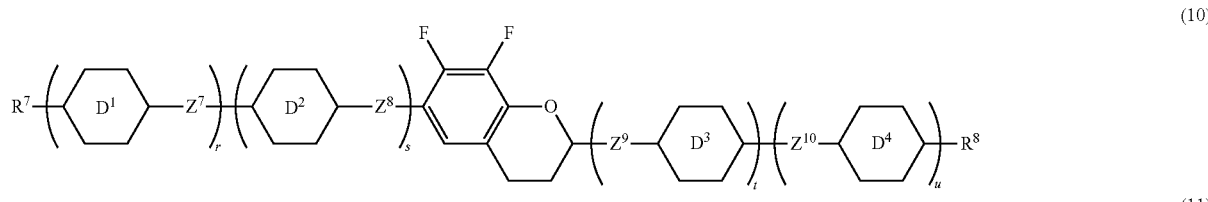
(10)

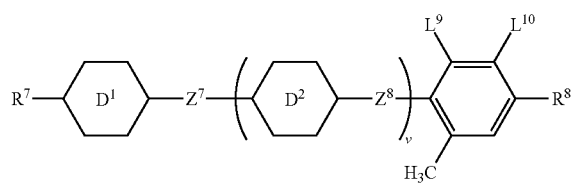
(11)

wherein
$R^7$ and $R^8$ are independently alkyl having 1 to 10 carbons or alkenyl having 2 to 10 carbons, and in the alkyl and the alkenyl, at least one of hydrogen may be replaced by fluorine, and at least one of —CH$_2$— may be replaced by —O—;

ring D$^1$, ring D$^2$, ring D$^3$ and ring D$^4$ are independently 1,4-cyclohexylene, 1,4-cyclohexenylene, 1,4-phenylene in which at least one of hydrogen may be replaced by fluorine, tetrahydropyran-2,5-diyl or decahydronaphthalene-2,6-diyl;

Z$^7$, Z$^8$, Z$^9$ and Z$^{10}$ are independently a single bond, —(CH$_2$)$_2$—, —COO—, —CH$_2$O—, —OCF$_2$— or —OCF$_2$(CH$_2$)$_2$—;

L$^9$ and L$^{10}$ are independently fluorine or chlorine; and q, r, s, t, u and v are independently 0 or 1, and the sum of r, s, t and u is 1 or 2.

14. The liquid crystal composition according to claim 10, further comprising at least one compound selected from the group consisting of compounds represented by formulas (12) to (14):

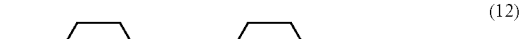
(12)

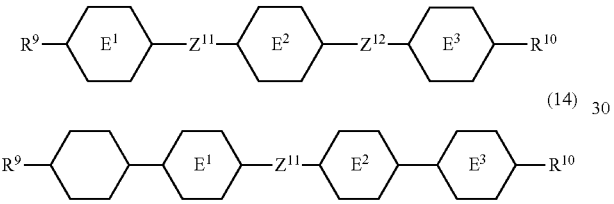
(13)

(14)

wherein
R$^9$ and R$^{10}$ are independently alkyl having 1 to 10 carbons or alkenyl having 2 to 10 carbons, and in the alkyl and the alkenyl, at least one of —CH$_2$— may be replaced by —O—;

ring E$^1$, ring E$^2$ and ring E$^3$ are independently 1,4-cyclohexylene, 1,4-phenylene, 2-fluoro-1,4-phenylene, 2,5-difluoro- 1,4-phenylene or pyrimidine-2,5-diyl; and Z$^{11}$ and Z$^{12}$ are independently a single bond, —(CH$_2$)$_2$, —CH=CH—, —C≡C— or —COO—.

15. The liquid crystal composition according to claim 11, further comprising at least one compound selected from the group consisting of compounds represented by formulas (12) to (14)

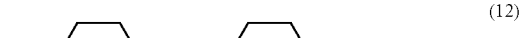
(12)

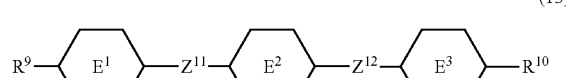
(13)

(14)
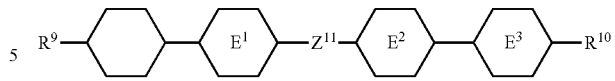

wherein
R$^9$ and R$^{10}$ are independently alkyl having 1 to 10 carbons or alkenyl having 2 to 10 carbons, and in the alkyl and the alkenyl, at least one of —CH$_2$— may be replaced by —O—;

ring E$^1$, ring E$^2$ and ring E$^3$ are independently 1,4-cyclohexylene, 1,4-phenylene, 2-fluoro-1,4-phenylene, 2,5-difluoro-1,4-phenylene or pyrimidine-2,5-diyl; and Z$^{11}$ and Z$^{12}$ are independently a single bond, —(CH$_2$)$_2$, —CH=CH—, —C≡C— or —COO—.

16. The liquid crystal composition according to claim 13, further comprising at least one compound selected from the group consisting of compounds represented by formulas (12) to (14)

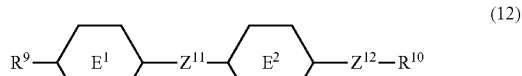
(12)

(13)

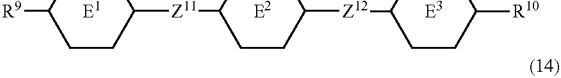
(14)

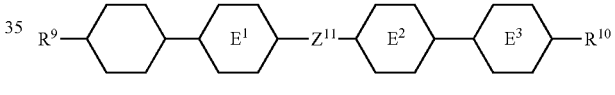

wherein
R$^9$ and R$^{10}$ are independently alkyl having 1 to 10 carbons or alkenyl having 2 to 10 carbons, and in the alkyl and the alkenyl, at least one of —CH$_2$— may be replaced by —O—;

ring E$^1$, ring E$^2$ and ring E$^3$ are independently 1,4-cyclohexylene, 1,4-phenylene, 2-fluoro-1,4-phenylene, 2,5-difluoro-1,4-phenylene or pyrimidine-2,5-diyl; and Z$^{11}$ and Z$^{12}$ are independently a single bond, —(CH$_2$)$_2$—, —CH=CH—, —C≡C— or —COO—.

17. The liquid crystal composition according to claim 10, further comprising at least one selected from the group consisting of an optically active compound, a polymerizable compound, and an optically active compound and a polymerizable compound.

18. The liquid crystal composition according to claim 10, further comprising at least one selected from the group consisting of an antioxidant, an ultraviolet light absorber, and an antioxidant and an ultraviolet light absorber.

19. A liquid crystal display device containing the liquid crystal composition according to claim 10.

* * * * *